US011440922B2

(12) United States Patent
Riva et al.

(10) Patent No.: US 11,440,922 B2
(45) Date of Patent: Sep. 13, 2022

(54) HETEROCYCLYLMETHYLIDENE DERIVATIVES AND THEIR USE AS MODULATORS OF MGLUR5 RECEPTORS

(71) Applicant: Recordati Industria Chimica e Farmaceutica S.p.A., Milan (IT)

(72) Inventors: Carlo Riva, Milan (IT); Davide Graziani, Milan (IT); Matteo Longhi, Milan (IT); Elisa Callegari, Milan (IT); Fabio Frigerio, Milan (IT); Patrizia Angelico, Milan (IT)

(73) Assignee: Recordati Industria Chimica e Farmacentica S.p.A., Milan (IT)

( * ) Notice: Subject to any disclaimer, the term of this patent is extended or adjusted under 35 U.S.C. 154(b) by 0 days.

(21) Appl. No.: 16/500,128

(22) PCT Filed: Jun. 29, 2018

(86) PCT No.: PCT/EP2018/067628
§ 371 (c)(1),
(2) Date: Oct. 2, 2019

(87) PCT Pub. No.: WO2019/002571
PCT Pub. Date: Jan. 3, 2019

(65) Prior Publication Data
US 2020/0347078 A1 Nov. 5, 2020

Related U.S. Application Data

(60) Provisional application No. 62/526,762, filed on Jun. 29, 2017.

(51) Int. Cl.
| | | |
|---|---|---|
| C07D 211/70 | (2006.01) |
| A61K 31/445 | (2006.01) |
| C07D 498/04 | (2006.01) |
| A61P 25/28 | (2006.01) |
| C07D 207/20 | (2006.01) |
| C07D 401/06 | (2006.01) |
| C07D 401/14 | (2006.01) |
| C07D 405/06 | (2006.01) |
| C07D 405/12 | (2006.01) |
| C07D 405/14 | (2006.01) |
| C07D 413/12 | (2006.01) |
| C07D 471/04 | (2006.01) |
| C07D 471/08 | (2006.01) |
| C07D 487/04 | (2006.01) |

(52) U.S. Cl.
CPC .......... *C07D 498/04* (2013.01); *A61P 25/28* (2018.01); *C07D 207/20* (2013.01); *C07D 211/70* (2013.01); *C07D 401/06* (2013.01); *C07D 401/14* (2013.01); *C07D 405/06* (2013.01); *C07D 405/12* (2013.01); *C07D 405/14* (2013.01); *C07D 413/12* (2013.01); *C07D 471/04* (2013.01); *C07D 471/08* (2013.01); *C07D 487/04* (2013.01)

(58) Field of Classification Search
CPC .. C07D 211/70; C07D 401/06; A61K 31/445; A61K 31/4545; A61P 25/00
USPC .......................... 546/226, 194; 514/330, 318
See application file for complete search history.

(56) References Cited

FOREIGN PATENT DOCUMENTS

WO    WO2009/015897    2/2009

OTHER PUBLICATIONS

Beniazza, Redouane, et al., "Zinc radical transfer based modular approach to enantiopure alkylidene-ß-prolines from N-(tert-butylsulfinyl)-α-(aminomethyl)acrylates", Eur. J. Org. Chem., 2015, pp. 7661-7665.
International Search Report for PCT/EP2018/067628 dated Jul. 26, 2018.
Lin, Aijun, et al., "Iron-catalyzed reductive cyclization of 1,6-enynes", Org. Lett., 16, 2014, pp. 386-389.
Bear, et al. (TRENDS in Neurosciences, 2004, 27, 370-377).
Berry-Kravis, E.M., et al, Nat Rev Drug Discov. Apr. 2018; 17(4): 280-299. doi:10.1038/nrd.2017.221.
Bozdagi, et al. (Molecular Autism, 2010, 1:15).
Chan et al., Psychopharma. (2008), vol. 198, pp. 141-148.
Dolen, et al. (J. Physiol, 586.6 (2008), 1503-1508).
Foster, et al. (Neuron, 2017, 431-446).
Gogliotti, et al. (Human Molecular Genetics, 2016, 1-15).
Kelly,E. et al. (Neuropsychopharmacology (2018) 43, 1457-1465).
Lujan et al., Eur. J. Neurosci. (1996), vol. 8, pp. 1488-1500.
Maksymetz, et al. (Molecular Brain, 2017, 10:15).
Mannaioni et al., NeuroSci., (2001), vol. 21, pp. 5925-5924.
(Continued)

*Primary Examiner* — Charanjit Aulakh
(74) *Attorney, Agent, or Firm* — Hueschen and Sage

(57) ABSTRACT

This invention relates to compounds of formula (I) and their use as allosteric modulators of mGluR5 receptor activity, pharmaceutical compositions containing the same, and methods of using the same as agents for the treatment and/or prevention of neurological and psychiatric disorders associated with glutamate dysfunction, such as schizophrenia or cognitive decline, dementia or cognitive impairment, or other pathologies that can be related directly or indirectly to glutamate dysfunction.

18 Claims, No Drawings

(56) References Cited

OTHER PUBLICATIONS

Rosenbrock et al., Eur. J. Pharma., (2010), vol. 639, pp. 40-46).
Verpelli, et al. (Journal of Biological Chemistry, 2011, 286, 34839-34850).
Vicidomini, et al. (Molecular Psychiatry, 2016, 1-14).

HETEROCYCLYLMETHYLIDENE DERIVATIVES AND THEIR USE AS MODULATORS OF MGLUR5 RECEPTORS

FIELD OF THE INVENTION

This invention relates to heterocyclylmethylidene derivatives and their use as allosteric modulators of mGluR5 receptor activity, pharmaceutical compositions comprising such compounds, and methods of treatment therewith.

BACKGROUND TO THE INVENTION

Glutamate is the primary excitatory amino acid in the mammalian central nervous system, exerting its effects through both ionotropic and metabotropic glutamate receptors. Neurotransmission mediated by glutamate has been demonstrated to be critical in many physiological processes, such as synaptic plasticity, long-term potentiation involved in both learning and memory as well as sensory perception (Riedel et al., *Behav. Brain Res.* (2003), Vol. 140, pp. 1-47, Rose et al. *J. Neurosci.*, (2006), Vol. 26(45), pp. 11582-11587. Furthermore, it has been demonstrated that an imbalance of glutamate neurotransmission plays a critical role in the pathophysiology of various neurological and psychiatric diseases.

The excitatory neurotransmission of glutamate is mediated through at least two different classes of receptors: ionotropic glutamate receptors such as the N-methyl-D-aspartate receptor (NMDA), α-amino-3-hydroxy-5-methyl-4-isoxazolepropionic acid receptor (AMPA) or kainate; and the metabotropic glutamate receptors (mGluR) and metabotropic glutamate receptors. The ionotropic receptors are ligand gated ion channels and are thought to be responsible for regulating the rapid neuronal transmission between two neurons. The metabotropic glutamate receptors are G-protein coupled receptors (GPCRs) which appear to mediate not only synaptic transmission, but also to regulate the extent of neurotransmitter release as well as post synaptic receptor activation. The metabotropic glutamate receptors (mGluRs) belong to family C (also known as family 3) of the g-protein-coupled receptors (GPCRs). They are characterized by a seven transmembrane (7TM) a-helical domain connected via a cysteine rich-region to a large bi-lobed extracellular amino-terminal domain where the glutamate ligand binds. The mGluR family comprises eight known mGluRs receptor types (designated as mGluR1 through mGluR8). Several of the receptor types are expressed as specific splice variants, e.g. mGluR5a and mGluR5b or mGluR8a, mGluR8b and mGluR8c. This superfamily is further divided into three groups (Groups I, II and III) based on amino acid homology as well as the intracellular signalling cascades they regulate (Schoepp et al., *Neuropharma*, (1999), Vol. 38, pp. 1431-1476) and pharmacological profile. Group I receptors (mGluR1 and mGluR5) are coupled to $G_{\alpha q}$, a process that results in stimulation of phospholipase C and an increase in intracellular calcium and inositol phosphate levels. Group II receptors (mGluR2 and mGluR3) and group III receptors (mGluR4, mGluR6, mGluR7, and mGluR8) are coupled to $G_{\alpha i}$, which leads to decreases in cyclic adenosine monophosphate (cAMP) levels. While the group I receptors are predominately located postsynaptically and typically enhance postsynaptic signaling, the group II and III receptors are located presynaptically and typically have inhibitory effects on neurotransmitter release.

Dysregulation in glutamatergic neurotransmission, for example through altered glutamate release or post-synaptic receptor activation, has been demonstrated in a variety of neurological as well as psychiatric disorders. Hypofunction of the NMDA receptor has not only been demonstrated in Alzheimer's patients, but is increasingly accepted as the putative cause of schizophrenia (Farber et al., *Prog. Brain Res.*, (1998), Vol. 116, pp. 421-437, Coyle et al., *Cell. and Mol. Neurobiol.*, (2006), Vol. 26, pp. 365-384). This is supported by clinical studies showing that antagonists of the NMDA receptor induce symptoms indistinguishable to those suffered by schizophrenia patients (Javitt et al., *Am J. Psychiatry*, (1991), Vol. 148, pp. 1301-1308; Meltzer H Y, *Biol. Psychiatry*, (1999), Vol. 46(10), pp. 1321-1327). Therefore, approaches that could potentiate or normalize NMDA receptor signaling have the potential to treat neurological and psychiatric disorders.

mGluR5, encoded by the GRM5 gene, has been demonstrated to be expressed in the central nervous system (CNS), mainly in the cortex, hippocampus, nucleus accumbens and the caudate-putamen. These brain regions are known to be involved in memory formation and cognitive function as well as emotional response. mGluR5 has been shown to be localized post-synaptically, adjacent to the post-synaptic density (Lujan et al., *Eur. J. Neurosci.* (1996), Vol. 8, pp. 1488-1500). A functional interaction between mGluR5 and the NMDA receptor has also been demonstrated, where activation of mGluR5 potentiates the activation state of the NMDA receptor (Mannaioni et al., *NeuroSci.*, (2001), Vol. 21, pp. 5925-5924, Rosenbrock et al., *Eur. J. Pharma.*, (2010), Vol. 639, pp. 40-46). Furthermore, activation of mGluR5 has been demonstrated in pre-clinical in vivo models to rescue cognitive impairment as well as psychotic disturbance induced by NMDA receptor antagonists (Chan et al., *Psychopharma.* (2008), Vol. 198, pp. 141-148). Therefore, activation of mGluR5, and thereby potentiation or normalization of the NMDA receptor signaling, is a potential mechanism for the treatment of psychiatric and neurological disorders.

Most agonists of mGluR5 bind the orthosteric glutamate binding site. Since the glutamate binding site between the mGluR family members is highly conserved, it has been challenging to develop selective mGluR5 agonists which have acceptable CNS penetration and demonstrate in vivo activity.

An alternative approach to achieve selectivity between the mGluR family members is to develop compounds which bind to an allosteric site, which is not as highly conserved between the family members. These allosteric binding compounds would not interfere with the natural glutamate binding and signaling, but modulate the receptor activation state. Allosteric ligands that have agonistic or inverse agonistic activity in the absence of orthosteric ligands are termed allosteric agonists or antagonists, respectively. Allosteric ligands lacking effect in the absence of orthosteric ligands are termed modulators (negative or positive).

Positive allosteric modulators of mGluR5 have recently been identified (O'Brien et al., *Mol. Pharma.* (2003), Vol. 64, pp. 731-740, Lindsley et al., *J. Med. Chem.* (2004), Vol. 47, pp. 5825-5828), where it has been determined that these compounds potentiate mGluR5 activity in the presence of bound glutamate. In the absence of bound glutamate, the mGluR5 positive modulators do not demonstrate any intrinsic activity.

Therefore, these compounds potentiate the natural signaling of mGluR5 as opposed to agonists which activate the receptor in a permanent, unnatural manner. mGluR5 positive allosteric modulators therefore represent an approach to potentiate mGluR5 signaling which in turn potentiates and normalizes the NMDA receptor hypofunction detected in neurological and psychiatric disorders. mGluR5 negative allosteric modulators are useful to depress the mGluR5 signaling which in turn decreases and normalizes the NMDA receptor hyperfunction detected in some neurological, psychiatric disorders and in more general CNS disorders. Without wishing to be bound by a particular theory, metabotropic glutamate receptors, including mglur5, have been implicated in a wide range of biological functions, indicating a potential role for the mGluR5 receptor in a variety of disease processes in mammals. Ligands of metabotropic glutamate receptors can be used for the treatment or prevention of acute and/or chronic neurological and/or psychiatric disorders associated with glutamate dysfunction, such as psychosis, schizophrenia, age-related cognitive decline, and the like. Further, without wishing to be bound by theory, increasing evidence indicates mGlu receptors play an important role in lasting changes in synaptic transmission, and studies of synaptic plasticity in the FMR1 knockout mouse have identified a connection between the Fragile X phenotype and mGluR signaling. Both types of allosteric modulator can also be related to some rare disease e.g. without any kind of limitation, Fragile-X syndrome, Rett syndrome, Phelan-McDermid syndrome or tuberous sclerosis.

The identification of small molecule mGluR agonists that bind at the orthosteric site has greatly increased the understanding of the roles played by these receptors and their corresponding relation to disease. Because the majority of these agonists were designed as analogs of glutamate, they typically lack the desired characteristics for drugs targeting mGluR such as oral bioavailability and/or distribution to the central nervous system (CNS). Moreover, because of the highly-conserved nature of the glutamate binding site, most orthosteric agonists lack selectivity among the various mGluRs.

Allosteric binding sites are topographically distinct from the endogenous ligand (orthosteric) binding site. The contemporary occupation into the receptor by the endogenous ligand and an allosteric modulator on both sites may result in different outcomes. Allosteric ligands potentiating the effect of the endogenous ligand (positive cooperativity) are defined "positive allosteric modulators" (PAMs), while allosteric ligands decreasing or blocking the effect of the endogenous ligand (negative cooperativity) are defined negative allosteric modulators (NAMs) (Christopoulos A, *Advances in G protein-coupled receptor allostery: from function to structure, Mol Pharmacol.* (2014), Vol. 86 (5), pp. 463-78.).

Both PAMs and NAMs are thus an attractive mechanism for modulating appropriate physiological receptor responses.

Unfortunately, there is a scarcity of selective positive allosteric modulators for the mGluR5 receptor. Further, conventional mGluR5 receptor modulators typically lack satisfactory aqueous solubility and exhibit poor oral bioavailability. Therefore, there remains a need for methods and compositions that overcome these deficiencies and that effectively provide selective positive, but also negative, allosteric modulators for the mGluR5 receptor.

SUMMARY OF THE INVENTION

The invention provides a compound having the general formula I:

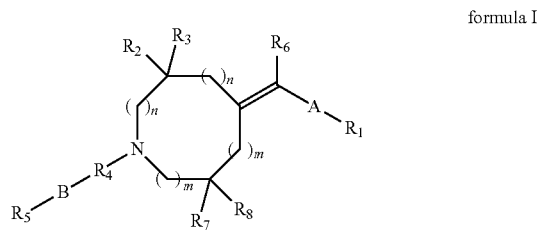

formula I or an enantiomer, diastereomer, N-oxide, or a pharmaceutically acceptable salt or combinations thereof, wherein:
$R_1$ is an optionally substituted mono-, bi- or tricyclic $C_6$-$C_{14}$ aryl group, an optionally substituted mono-, bi- or tricyclic $C_1$-$C_{13}$ heterocyclic group containing from 1 to 5 heteroatoms selected from N, O and S, an optionally substituted $C_3$-$C_6$ cycloalkyl group, an optionally substituted $C_3$-$C_6$ cycloalkenyl group or an optionally substituted $C_1$-$C_6$ alkyl group;
A is a carbon-carbon triple bond, a carbon-carbon double bond or A represents a five- or six-membered heterocyclic group containing from 1 to 4 heteroatoms selected from N, S and O;
$R_2$ and $R_3$ are each independently hydrogen, an alkyl group or a fluorine atom, or $R_2$ and $R_3$ are linked to each other to form a $C_3$-$C_6$ cycloalkyl or a $C_3$-$C_6$ heterocyclic ring (e.g. cyclopropyl or cyclobutyl or oxetanyl) while simultaneously $R_7$ and $R_8$ are each independently an alkyl group, or a fluorine atom, or alternatively $R_2$ or $R_3$ are bonded to $R_7$ or $R_8$ to form a condensed cycloalkyl ring (e.g. 8-azabicyclo[3.2.1]octane or 6-azabicyclo[3.1.1]heptane or 9-azabicyclo[3.3.1]nonane);
n and m are each independently an integer selected from 0-2;
$R_4$ is a carbonyl, a thiocarbonyl, or a sulphonyl group, or a bond;
B is an oxygen or sulphur atom, a nitrogen atom optionally substituted by a $C_1$-$C_5$ alkyl group or a methoxy group, or B is absent;
$R_5$ is an optionally substituted mono-, bi- or tricyclic $C_6$-$C_{14}$ aryl group, an optionally substituted mono-, bi- or tricyclic $C_1$-$C_{13}$ heterocyclic group containing from 1 to 5 heteroatoms selected from N, O and S, an optionally substituted $C_3$-$C_6$ cycloalkyl group, an optionally substituted $C_3$-$C_6$ cycloalkenyl group or an optionally substituted $C_1$-$C_6$ alkyl group; and
$R_6$ is a hydrogen atom, an optionally substituted $C_1$-$C_4$ alkyl group, or a fluorine atom.

Compounds of the invention can be used for the treatment and/or prevention of neurological and psychiatric disorders associated with glutamate dysfunction such as schizophrenia or cognitive decline, dementia or cognitive impairment, or other pathologies that can be related either directly or indirectly to glutamate dysfunction, i.e. disorders treatable by positive allosteric modulation (PAM) or by negative allosteric modulation (NAM) of mGluR5.

The optional substituents are independently selected from the group consisting of halogen atoms and $C_1$-$C_6$ alkyl, $C_1$-$C_6$ alkoxy, hydroxy, mercapto, nitro, cyano, oxo, halo($C_1$-$C_6$)alkyl, halo($C_1$-$C_6$)alkoxy, $C_1$-$C_6$ alkylthio, $C_1$-$C_6$ alkylsulphonyl, $C_1$-$C_6$ alkylcarbonyl, sulphamoyl, $C_1$-$C_6$ alkylsulphamoyl, di($C_1$-$C_6$)alkylsulphamoyl, ($C_1$-$C_6$) alkoxycarbonyl and ($C_1$-$C_6$)alkylcarbonyl($C_1$-$C_6$)alkyl groups, and from groups of the formulae —NR*R*, —C(=O)—NR*R*, -A, —O-A, —C(=O)-A, —($CH_2$)q-A, —NR-A, —C(=O)—NR-A, —NR**C(=O)-A and —O—C(=O)-A wherein each R* independently represents a hydrogen atom or a $C_1$-$C_6$ alkyl, $C_1$-$C_6$ alkoxy, $C_1$-$C_6$ alkylcarbonyl, phenyl or benzyl group, R** represents a hydrogen atom or a $C_1$-$C_6$ alkyl group, q is an integer from 1 to 6 and A represents a phenyl group or a $C_1$-$C_6$ heterocyclic group containing from 1 to 3 heteroatoms selected from N, O and S; a $C_1$-$C_6$ cycloalkyl group; each group A being optionally substituted with from 1 to 3 groups independently selected from halo, hydroxy, cyano, nitro and $C_1$-$C_6$ alkyl, preferably wherein the optional substituents are selected from the groups consisting of halogen atoms and $C_1$-$C_6$ alkyl groups.

Preferred compounds according to the invention are those in which $R_1$ is selected from the group consisting of an optionally substituted phenyl, pyridinyl or pyrimidinyl moiety or derivative thereof. Highly preferred compounds according to the invention are those in which $R_1$ is selected from the group consisting of an optionally substituted pyridin-2-yl, pyridin-3-yl, pyridin-4-yl or pyrimidin-2-yl moiety or derivative thereof.

Preferred compounds according to the invention are those in which A is a carbon-carbon triple bond or A is selected from the group consisting of a 1,3-oxazolyl, isoxazolyl, 1,2,4-oxadiazolyl, 1,3,4-oxadiazolyl or pyrazolyl moiety or derivative thereof. Highly preferred compounds according to the invention are those in which A is a carbon-carbon triple bond or A is selected from the group consisting of a 1,3-oxazol-2-yl, isoxazol-3-yl, 1,2,4-oxadiazol-3-yl, 1,3,4-oxadiazol-2-yl, 1H-pyrazol-3-yl or 1H-pyrazol-5-yl moiety or derivative thereof.

Preferred compounds according to the invention are those in which $R_5$ is selected from the group consisting of an, optionally substituted, methyl, ethyl, propyl, iso-propyl, tertiary-butyl, methoxyethyl, N,N-dimethyl, N-methoxy-N-methyl, N,N-diethyl, N-ethyl-N-isopropyl, cyclohexyl, benzotriazolyl, furanyl, isoxazolyl, morpholinyl, oxazolyl, phenyl, piperidinyl, pyranyl, pyrazolyl, pyridinyl, pyrimidinyl, pyrrolidinyl, triazinyl or triazolyl moiety or derivative thereof. Highly preferred compounds according to the invention are those in which $R_5$ is selected from the group consisting of an, optionally substituted, methyl, ethyl, propyl, iso-propyl, tertiary-butyl, methoxyethyl, N,N-dimethyl, N-methoxy-N-methyl, N,N-diethyl, N-ethyl-N-isopropyl, cyclohexyl, benzotriazole-4-yl, furan-2-yl, furan-3-yl, isoxazol-5-yl, isoxazol[5,4-b]pyridin-5-yl, morpholin-4-yl, oxazol-4-yl, phenyl, piperidin-4-yl, pyran-2-yl, pyran-3-yl, pyran-4-yl, pyrazol-4-yl, pyrazol-5-yl, pyrazolo[2,1-c][1,4]oxazin-3-yl, pyrazolo[5,1-b][1,3]oxazin-3-yl, pyrazolo[1,5-a]pyrimidin-6-yl, pyridin-2-yl, pyridin-3-yl, pyridin-4-yl, pyrimidin-2-yl, pyrimidin-4-yl, pyrrolidinyl, triazin-4-yl, triazol-4-yl or triazolo[1,5-a]pyridin-2-yl moiety or derivative thereof.

Preferred compounds according to the invention are those in which $R_4$ is a carbonyl or sulphonyl group, B is absent and $R_5$ is an optionally substituted bicyclic $C_1$-$C_{13}$ heterocyclic group containing from 1 to 5 heteroatoms selected from N, O and S. Highly preferred compounds according to the invention are those in which $R_4$ is a carbonyl or sulphonyl group, B is absent and $R_5$ is selected from the group consisting of an, optionally substituted, isoxazol[5,4-b]pyridin-5-yl, pyrazolo[2,1-c][1,4]oxazin-3-yl, pyrazolo[5,1-b] [1,3]oxazin-3-yl, pyrazolo[1,5-a]pyrimidin-6-yl, or triazolo [1,5-a]pyridin-2-yl moiety or derivative thereof.

Preferred compounds according to the invention are those in which B is an oxygen or nitrogen atom optionally substituted by a $C_1$-$C_5$ alkyl group or a methoxy group and $R_5$ is selected from the group consisting of an optionally substituted methyl, ethyl, propyl, iso-propyl, tertiary-butyl or methoxyethyl moiety or derivative thereof.

Highly preferred compounds according to the invention are those in which $R_1$ is an optionally substituted mono-, bi- or tricyclic $C_6$-$C_{14}$ aryl group, an optionally substituted mono-, bi- or tricyclic $C_1$-$C_{13}$ heterocyclic group containing from 1 to 5 heteroatoms selected from N, O and S, A is a carbon-carbon triple bond, $R_4$ represents a CO group, n is 1, $R_2$ and $R_3$ are both methyl groups or both fluorine atoms and B is absent.

Preferred compounds according to the invention are those in which $R_1$ and $R_5$ are optionally substituted mono-, bi- or tricyclic $C_6$-$C_{14}$ aryl groups or optionally substituted mono-, bi- or tricyclic $C_1$-$C_{13}$ heterocyclic groups containing from 1 to 5 heteroatoms selected from N, O and S, A is a carbon-carbon triple bond, $R_2$ and $R_3$ are both methyl groups and B is absent.

Preferred compounds according to the invention are those in which $R_1$ and $R_5$ are optionally substituted mono-, bi- or tricyclic $C_6$-$C_{14}$ aryl groups, optionally substituted mono-, bi- or tricyclic $C_1$-$C_{13}$ heterocyclic groups containing from 1 to 5 heteroatoms selected from N, O and S, optionally substituted $C_1$-$C_6$ alkyl, $C_3$-$C_6$ cycloalkyl or $C_3$-$C_6$ cycloalkenyl groups, $R_2$ and $R_3$ are both methyl groups, A is a carbon-carbon triple bond or a 5-membered heterocyclic group, wherein the heteroatoms are as defined in the immediately preceding paragraph, and B is absent.

Preferred compounds according to the invention are those in which $R_1$ and $R_5$ are optionally substituted monocyclic aryl groups or optionally substituted monocyclic heterocyclic groups containing from 1 to 5 heteroatoms selected from N, O S, or optionally substituted alkyl, cycloalkyl or cycloalkenyl groups, $R_2$ and $R_3$ are both methyl groups, A is a carbon-carbon triple bond, B is absent and $R_4$ is a CO group.

Preferred compounds according to the invention are those in which $R_1$ and $R_5$ are optionally substituted monocyclic aryl groups, optionally substituted monocyclic heterocyclic groups containing from 1 to 5 heteroatoms selected from N, O and S, or optionally substituted alkyl, cycloalkyl or cycloalkenyl groups, $R_2$ and $R_3$ are both methyl groups, A is a carbon-carbon triple bond and B is oxygen or an optionally substituted nitrogen atom where $R_4$ is a CO group.

Preferred compounds according to the invention are those in which A is a five- or six-membered heterocyclic ring or a carbon-carbon double bond.

Preferred compounds according to the invention are those in which $R_6$ is a hydrogen atom.

Preferred compounds according to the invention are those in which $R_6$ is an optionally substituted $C_1$-$C_4$ alkyl group, or a fluorine atom.

Preferred compounds according to the invention are those in which $R_4$ is a CO group and $R_1$ represents an optionally substituted mono- or bicyclic $C_1$-$C_9$ heterocyclic group containing from 1 to 3 heteroatoms selected from nitrogen, oxygen and sulfur, and $R_5$ is preferably without any limitation a 2-furyl, 3-methylphenyl, 3-chlorophenyl, 5-methyl-2-furyl, 3-furyl, 2,5-dimethyl-3-furyl, 4-morpholinyl, piperidinyl or pyrrolidinyl group.

Preferred compounds according to the invention are those in which $R_4$ is a CO group, B is oxygen and $R_1$ represents an optionally substituted mono- or bicyclic $C_1$-$C_9$ heterocyclic group containing from 1 to 3 heteroatoms selected from nitrogen, oxygen and sulfur, n is 0 or 1 and $R_5$ is preferably without any limitation an optionally substituted alkyl group chosen from methyl, ethyl, isopropyl, propyl, tert-butyl, butyl and isobutyl compounds which are typically and preferentially negative allosteric modulators.

Preferred compounds according to the invention are those in which $R_4$ is a CO group, B is nitrogen or N-alkyl group substituted by methyl, ethyl, isopropyl, propyl, tert-butyl, butyl, isobutyl or methoxy groups, and $R_1$ represents an optionally substituted mono- or bicyclic $C_1$-$C_9$ heterocyclic group containing from 1 to 3 heteroatoms selected from nitrogen, oxygen and sulfur.

Preferred compounds according to the invention are those in which $R_4$ is a CO group, B is absent and $R_1$ represents an optionally substituted mono-, bi- or tricyclic $C_6$-$C_{14}$ aryl group, n is 1 and $R_5$ is preferably without any limitation an optionally substituted monocyclic aryl group or optionally substituted monocyclic heterocyclic group containing from 1 to 5 heteroatoms selected from N, O and S which are typically and preferentially positive allosteric modulators.

A non-limiting example of a compound according to the invention is (3-chlorophenyl)-[(4E)-4-[3-(3-chlorophenyl)prop-2-ynylidene]-3,3-dimethyl-1-piperidyl]methanone. In this compound, $R_1$ and $R_5$ are 3-chlorophenyl, $R_2$ and $R_3$ are methyl groups, B is a null, $R_4$ is carbonyl, n is 1, m is 1, $R_6$ is hydrogen and A is a carbon-carbon triple bond.

Preferred compounds according to the invention are those in which $R_4$ is a CO group, B is nitrogen or N-alkyl chosen from methyl, ethyl, isopropyl, propyl, tert-butyl, butyl, isobutyl or methoxy and $R_1$ represents an optionally substituted mono- or bicyclic $C_1$-$C_9$ heterocyclic group containing from 1 to 3 heteroatoms selected from nitrogen, oxygen and sulfur, $R_5$ is preferably without any limitation an optionally substituted alkyl group chosen from methyl, ethyl, isopropyl, propyl, tert-butyl, butyl or isobutyl groups.

Preferred compounds according to the invention are those in which $R_4$ is a CO group, A is a five- or six-membered heterocyclic group containing from 1 to 4 heteroatoms selected from N, S or O, $R_1$ represents an optionally substituted mono-, bi- or tricyclic $C_6$-$C_{14}$ aryl group, and $R_5$ is preferably without any limitation a 2-furyl, 3-methylphenyl, 3-chlorophenyl, 5-methyl-2-furyl, 3-furyl, 2,5-dimethyl-3-furyl, 4-morpholinyl, piperidinyl, pyrrolidinyl group. A non-limiting example is (3-chlorophenyl)[(4E)-4-{[5-(3-chlorophenyl)-1H-pyrazol-3-yl]methylidene}-3,3-dimethylpiperidin-1-yl]methanone. In this compound, $R_1$ and $R_5$ are 3-chlorophenyl, B is absent, $R_2$ and $R_3$ are methyl groups, $R_4$ is carbonyl, n is 1, m is 1, $R_6$ is hydrogen and A is a pyrazole group.

Preferred compounds according to the invention are those in which there is only one possible group n (=0 to 2) and one possible group m (=0 to 2), each respectively flanking the ring nitrogen atom of formula I, yielding a structure according to formula IA:

formula IA

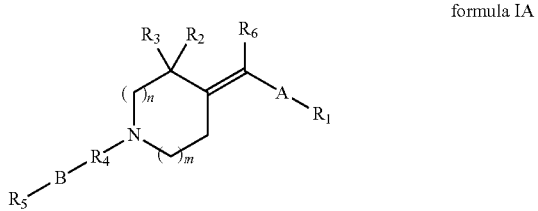

wherein A, B, and $R_1$ through $R_6$ have the meanings ascribed to them in connection with formula I above. Preferably the invention relates to compounds of formula IA, wherein $R_1$ represents an optionally substituted monocyclic aryl group or optionally substituted monocyclic heterocyclic group containing from 1 to 5 heteroatoms selected from N, O, and S.

Preferred compounds according to the invention are those in which A represents a carbon-carbon triple bond.

Preferred compounds according to the invention are compounds of formula IA, wherein n is 0 or 1.

Preferred compounds according to the invention are compounds of formula IA, wherein m is 1.

Preferred compounds according to the invention are compounds of formula IA, wherein $R_2$ and $R_3$ each represent an alkyl group or $R_2$ and $R_3$ each represent a fluorine atom.

Preferred compounds according to the invention are compounds of formula IA, wherein $R_4$ represents a carbonyl group or a bond.

Preferred compounds according to the invention are compounds of formula IA, wherein B represents an oxygen atom or a nitrogen atom optionally substituted by a $C_1$-$C_5$ alkyl or methoxy group, or a bond.

Preferred compounds according to the invention are compounds of formula IA, wherein $R_5$ represents an optionally substituted monocyclic aryl group, an optionally substituted monocyclic heterocyclic group containing from 1 to 5 heteroatoms selected from N, O and S or an optionally substituted alkyl.

Preferred compounds according to the invention are compounds of formula IA, wherein $R_6$ represents hydrogen.

Preferred compounds according to the invention are compounds of formula IA, wherein $R_1$ represents an optionally substituted monocyclic aryl group or an optionally substituted monocyclic heterocyclic group containing from 1 to 5 heteroatoms selected from N, O and S; A represents a carbon-carbon triple bond; $R_2$ and $R_3$ each represent an alkyl group; m represents 1; n represents 0 or 1; $R_4$ represents carbonyl; B represents oxygen; $R_5$ represents an optionally substituted alkyl group; and $R_6$ represents hydrogen.

Preferred compounds according to the invention are compounds of formula IA, wherein $R_1$ represents an optionally substituted monocyclic aryl group or optionally substituted monocyclic heterocyclic group containing from 1 to 5 heteroatoms selected from N, O and S; A represents a carbon-carbon triple bond; $R_2$ and $R_3$ each represent an alkyl group; m represents 1; n represents 0 or 1; $R_4$ represents carbonyl; B is absent; $R_5$ represents an optionally substituted monocyclic aryl group or optionally substituted monocyclic heterocyclic group containing from 1 to 5 heteroatoms selected from N, O and S; and $R_6$ represents hydrogen.

Preferred compounds according to the invention are compounds of formula IA, wherein $R_1$ represents an optionally substituted monocyclic aryl group; A represents a carbon-carbon triple bond; $R_2$ and $R_3$ each represent an alkyl group; m represents 1; n represents 0 or 1; $R_4$ represents carbonyl; B represents a nitrogen atom substituted by a $C_1$-$C_5$ alkyl or methoxy group; $R_5$ represents an optionally substituted alkyl group; and $R_6$ represents hydrogen.

Preferred compounds according to the invention are compounds of formula IA, wherein $R_1$ represents an optionally substituted monocyclic aryl group or optionally substituted monocyclic heterocyclic group containing from 1 to 5 heteroatoms selected from N, O and S; A represents a carbon-carbon triple bond; $R_2$ and $R_3$ each represent fluorine; m represents 1; n represents 1; $R_4$ represents carbonyl;

B represents oxygen; $R_5$ represents optionally substituted alkyl group; and $R_6$ represents hydrogen.

Preferred compounds according to the invention are compounds of formula IA, wherein $R_1$ represents an optionally substituted monocyclic heterocyclic group containing from 1 to 5 heteroatoms selected from N, O and S; A represents a carbon-carbon triple bond; $R_2$ and $R_3$ each represent alkyl; m represents 1; n represents 1; $R_4$ represents a bond; B is absent; $R_5$ represents an optionally substituted monocyclic heterocyclic group containing from 1 to 5 heteroatoms selected from N, O and S; and $R_6$ represents hydrogen.

Preferred compounds according to the invention are compounds of formula I which may be represented by compounds according to formula IB:

IB

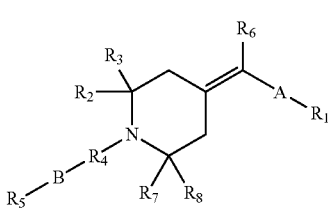

formula IB wherein A, B, and $R_1$ through $R_8$ have the meanings ascribed to them in connection with formula I above, with the proviso that, in addition to the meanings ascribed to $R_5$ in connection with formula I, $R_5$ may also represent hydrogen.

Preferred compounds according to the invention are compounds of formula IB, wherein $R_1$ represents an optionally substituted monocyclic aryl group or optionally substituted monocyclic heterocyclic group containing from 1 to 5 heteroatoms selected from N, O and S.

Preferred compounds according to the invention are compounds of formula IB, wherein A represents a carbon-carbon triple bond.

Preferred compounds according to the invention are compounds of formula IB, wherein $R_2$, $R_3$, $R_7$, and $R_8$ each represent an alkyl group.

Preferred compounds according to the invention are compounds of formula IB, wherein $R_2$ and $R_3$ each represent hydrogen and $R_7$ and $R_8$, together with the carbon atom to which they are attached, form a cycloalkyl ring.

Preferred compounds according to the invention are compounds of formula IB, wherein $R_2$, $R_3$, $R_7$, and $R_8$, together with the carbon atoms to which they are attached, form a condensed cycloalkyl ring.

Preferred compounds according to the invention are compounds of formula IB, wherein $R_4$ represents carbonyl or a bond.

Preferred compounds according to the invention are compounds of formula IB, wherein B represents oxygen or is absent.

Preferred compounds according to the invention are compounds of formula IB, wherein $R_5$ represents hydrogen, an optionally substituted alkyl group, or an optionally substituted monocyclic heterocyclic group containing from 1 to 5 heteroatoms selected from N, O and S.

Preferred compounds according to the invention are compounds of formula IB, wherein $R_6$ represents hydrogen.

Preferred compounds according to the invention are compounds of formula IB, wherein $R_1$ represents an optionally substituted monocyclic aryl group or optionally substituted monocyclic heterocyclic group containing from 1 to 5 heteroatoms selected from N, O and S; A represents a carbon-carbon triple bond; $R_2$, $R_3$, $R_7$, and $R_8$ each represent an alkyl group; $R_4$ represents carbonyl or a bond; B represents oxygen or is absent; and $R_5$ represents hydrogen or an optionally substituted alkyl group.

Preferred compounds according to the invention are compounds of formula IB, wherein $R_1$ represents an optionally substituted monocyclic heterocyclic group containing from 1 to 5 heteroatoms selected from N, O and S; A represents a carbon-carbon triple bond; $R_2$ and $R_3$ each represent hydrogen and $R_7$ and $R_8$, together with the carbon atom to which they are attached, form a cycloalkyl ring; $R_4$ represents carbonyl; B represents oxygen; and $R_5$ represents an optionally substituted alkyl group.

Preferred compounds according to the invention are compounds of formula IB, wherein $R_1$ represents an optionally substituted monocyclic heterocyclic group containing from 1 to 5 heteroatoms selected from N, O and S; A represents a carbon-carbon triple bond; $R_2$, $R_3$, $R_7$, and $R_8$, together with the carbon atoms to which they are attached, form a condensed cycloalkyl ring; $R_4$ represents carbonyl or a bond; B represents oxygen or is absent; and $R_5$ represents an optionally substituted alkyl or optionally substituted monocyclic heterocyclic group containing from 1 to 5 heteroatoms selected from N, O and S.

Preferred compounds according to the invention are compounds, or an enantiomer, diastereomer, N-oxide, or a pharmaceutically acceptable salt or combinations thereof, which are provided according to general formula I, formula IA or formula IB and selected from the compounds in Table 1 below:

TABLE 1

Selected compounds of the invention.

| Example | Compound | Chemical Name |
|---|---|---|
| 1 | | tert-butyl (4E)-3,3-dimethyl-4-[3-(6-methylpyridin-2-yl)prop-2-yn-1-ylidene]piperidine-1-carboxylate |

TABLE 1-continued

Selected compounds of the invention.

| Example | Compound | Chemical Name |
|---|---|---|
| 2 | | tert-butyl (4E)-4-[3-(3-chlorophenyl)prop-2-yn-1-ylidene]-3,3-dimethylpiperidine-1-carboxylate |
| 3 | | ethyl (4E)-3,3-dimethyl-4-[3-(6-methylpyridin-2-yl)prop-2-yn-1-ylidene]piperidine-1-carboxylate |
| 4 | | ethyl (4E)-4-[3-(3-chlorophenyl)prop-2-yn-1-ylidene]-3,3-dimethylpiperidine-1-carboxylate |
| 5 | | tert-butyl (4E)-4-[3-(2-chloropyridin-4-yl)prop-2-yn-1-ylidene]-3,3-dimethylpiperidine-1-carboxylate |
| 6 | | tert-butyl (4E)-3,3-dimethyl-4-[3-(3-methylphenyl)prop-2-yn-1-ylidene]piperidine-1-carboxylate |
| 7 | | tert-butyl (4E)-3,3-difluoro-4-[3-(6-methylpyridin-2-yl)prop-2-yn-1-ylidene]piperidine-1-carboxylate |
| 8 | | tert-butyl (4E)-4-[3-(3-chlorophenyl)prop-2-yn-1-ylidene]-3,3-difluoropiperidine-1-carboxylate |

TABLE 1-continued

Selected compounds of the invention.

| Example | Compound | Chemical Name |
|---|---|---|
| 9 | | tert-butyl (4E)-4-[3-(4-chloropyridin-2-yl)prop-2-yn-1-ylidene]-3,3-difluoropiperidine-1-carboxylate |
| 10 | | tert-butyl (4E)-3,3-difluoro-4-[3-(3-methylphenyl)prop-2-yn-1-ylidene]piperidine-1-carboxylate |
| 11 | | ethyl (4E)-3,3-difluoro-4-[3-(6-methylpyridin-2-yl)prop-2-yn-1-ylidene]piperidine-1-carboxylate |
| 12 | | ethyl (4E)-4-[3-(3-chlorophenyl)prop-2-yn-1-ylidene]-3,3-difluoropiperidine-1-carboxylate |
| 13 | | ethyl (4E)-4-[3-(4-chloropyridin-2-yl)prop-2-yn-1-ylidene]-3,3-difluoropiperidine-1-carboxylate |
| 14 | | ethyl (4E)-3,3-difluoro-4-[3-(3-methylphenyl)prop-2-yn-1-ylidene]piperidine-1-carboxylate |
| 15 | | ethyl (4E)-4-[3-(2-chloropyridin-4-yl)prop-2-yn-1-ylidene]-3,3-dimethylpiperidine-1-carboxylate |

TABLE 1-continued

Selected compounds of the invention.

| Example | Compound | Chemical Name |
|---|---|---|
| 16 | | ethyl (4E)-3,3-dimethyl-4-[3-(3-methylphenyl)prop-2-yn-1-ylidene]piperidine-1-carboxylate |
| 17 | | ethyl (4E)-3,3-dimethyl-4-(3-phenylprop-2-yn-1-ylidene)piperidine-1-carboxylate |
| 18 | | ethyl (4E)-4-[3-(4-chloropyridin-2-yl)prop-2-yn-1-ylidene]-3,3-dimethylpiperidine-1-carboxylate |
| 19 | | ethyl (4E)-4-[3-(2,5-difluorophenyl)prop-2-yn-1-ylidene]-3,3-dimethylpiperidine-1-carboxylate |
| 20 | | ethyl (4E)-3,3-dimethyl-4-{3-[6-(trifluoromethyl)pyridin-2-yl]prop-2-yn-1-ylidene}piperidine-1-carboxylate |
| 21 | | ethyl (4E)-4-[3-(3-fluorophenyl)prop-2-yn-1-ylidene]-3,3-dimethylpiperidine-1-carboxylate |

TABLE 1-continued

Selected compounds of the invention.

| Example | Compound | Chemical Name |
|---|---|---|
| 22 | 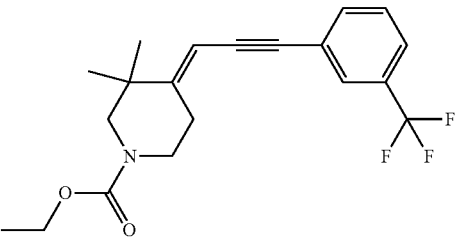 [SMILES: CCOC(=O)N1CC/C(=C\C#Cc2cccc(C(F)(F)F)c2)C(C)(C)C1] | ethyl (4E)-3,3-dimethyl-4-{3-[3-(trifluoromethyl)phenyl]prop-2-yn-1-ylidene}piperidine-1-carboxylate |
| 23 | 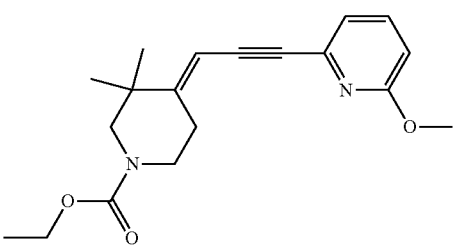 [SMILES: CCOC(=O)N1CC/C(=C\C#Cc2cccc(OC)n2)C(C)(C)C1] | ethyl (4E)-4-[3-(6-methoxypyridin-2-yl)prop-2-yn-1-ylidene]-3,3-dimethylpiperidine-1-carboxylate |
| 24 | 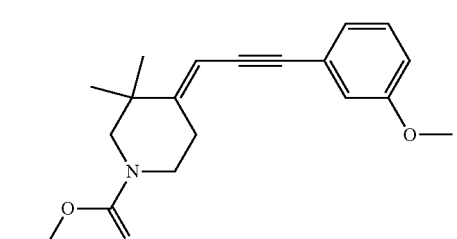 | ethyl (4E)-4-[3-(3-methoxyphenyl)prop-2-yn-1-ylidene]-3,3-dimethylpiperidine-1-carboxylate |
| 25 | 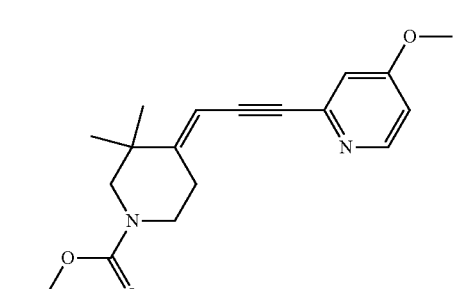 | ethyl (4E)-4-[3-(4-methoxypyridin-2-yl)prop-2-yn-1-ylidene]-3,3-dimethylpiperidine-1-carboxylate |
| 26 | 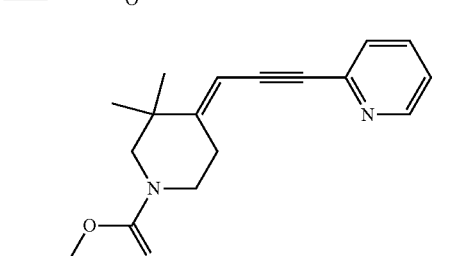 | ethyl (4E)-3,3-dimethyl-4-[3-(pyridin-2-yl)prop-2-yn-1-ylidene]piperidine-1-carboxylate |
| 27 | 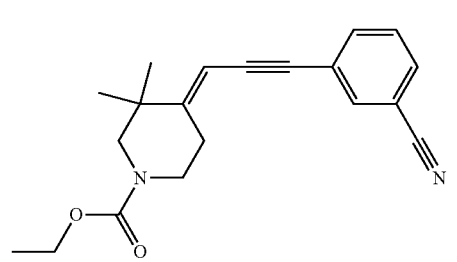 [SMILES: CCOC(=O)N1CC/C(=C\C#Cc2cccc(C#N)c2)C(C)(C)C1] | ethyl (4E)-4-[3-(3-cyanophenyl)prop-2-yn-1-ylidene]-3,3-dimethylpiperidine-1-carboxylate |

TABLE 1-continued

Selected compounds of the invention.

| Example | Compound | Chemical Name |
|---|---|---|
| 28 | | ethyl (4E)-4-{3-[3-(cyanomethyl)phenyl]prop-2-yn-1-ylidene}-3,3-dimethylpiperidine-1-carboxylate |
| 29 | | ethyl (4E)-4-[3-(6-methoxypyridin-3-yl)prop-2-yn-1-ylidene]-3,3-dimethylpiperidine-1-carboxylate |
| 30 | | ethyl (4E)-3,3-dimethyl-4-{3-[6-(methylamino)pyridin-2-yl]prop-2-yn-1-ylidene}piperidine-1-carboxylate |
| 31 | | ethyl (4E)-4-[3-(4-cyanopyridin-2-yl)prop-2-yn-1-ylidene]-3,3-dimethylpiperidine-1-carboxylate |
| 32 | | ethyl (4E)-4-[3-(3-cyano-5-fluorophenyl)prop-2-yn-1-ylidene]-3,3-dimethylpiperidine-1-carboxylate |

TABLE 1-continued

Selected compounds of the invention.

| Example | Compound | Chemical Name |
|---|---|---|
| 33 | | 2-{(4E)-3,3-dimethyl-4-[3-(6-methylpyridin-2-yl)prop-2-yn-1-ylidene]piperidin-1-yl}-6-methyl-3-nitropyridine |
| 34 | | (3-chlorophenyl){(4E)-4-[3-(3-chlorophenyl)prop-2-yn-1-ylidene]-3,3-dimethylpiperidin-1-yl}methanone |
| 35 | | {(4E)-4-[3-(3-chlorophenyl)prop-2-yn-1-ylidene]-3,3-dimethylpiperidin-1-yl}(piperidin-1-yl)methanone |
| 36 | | {(4E)-4-[3-(3-chlorophenyl)prop-2-yn-1-ylidene]-3,3-dimethylpiperidin-1-yl}(pyrrolidin-1-yl)methanone |
| 37 | | (4E)-4-[3-(3-chlorophenyl)prop-2-yn-1-ylidene]-N,N,3,3-tetramethylpiperidine-1-carboxamide |
| 38 | | (4E)-4-[3-(3-chlorophenyl)prop-2-yn-1-ylidene]-N,N-diethyl-3,3-dimethylpiperidine-1-carboxamide |
| 39 | | {(4E)-4-[3-(3-chlorophenyl)prop-2-yn-1-ylidene]-3,3-dimethylpiperidin-1-yl}(furan-2-yl)methanone |

TABLE 1-continued

Selected compounds of the invention.

| Example | Compound | Chemical Name |
|---|---|---|
| 40 | | methyl (4E)-4-[3-(3-chlorophenyl)prop-2-yn-1-ylidene]-3,3-dimethylpiperidine-1-carboxylate |
| 41 | | {(4E)-4-[3-(3-chlorophenyl)prop-2-yn-1-ylidene]-3,3-dimethylpiperidin-1-yl}(morpholin-4-yl)methanone |
| 42 | | (4E)-4-[3-(3-chlorophenyl)prop-2-yn-1-ylidene]-N-methoxy-N,3,3-trimethylpiperidine-1-carboxamide |
| 43 | | {(4E)-4-[3-(3-chlorophenyl)prop-2-yn-1-ylidene]-3,3-dimethylpiperidin-1-yl}(3-methylphenyl)methanone |
| 44 | | 2-{(3E)-3-[1-(3-chlorobenzoyl)-3,3-dimethylpiperidin-4-ylidene]prop-1-yn-1-yl}pyridine-4-carbonitrile |
| 45 | | (3-chlorophenyl){(4E)-3,3-dimethyl-4-[3-(3-methylphenyl)prop-2-yn-1-ylidene]piperidine-1-yl}methanone |
| 46 | | (2,5-dimethylfuran-3-yl)[(4E)-4-{3-[3-(hydroxymethyl)phenyl]prop-2-yn-1-ylidene}-3,3-dimethylpiperidin-1-yl]methanone |

TABLE 1-continued

Selected compounds of the invention.

| Example | Compound | Chemical Name |
|---|---|---|
| 47 | | [(4E)-3,3-dimethyl-4-(3-{3-[(pyrrolidin-1-yl)methyl]phenyl}prop-2-yn-1-ylidene)piperidin-1-yl](5-methylfuran-2-yl)methanone |
| 48 | | ethyl (3E)-2,2-dimethyl-3-[3-(6-methylpyridin-2-yl)prop-2-yn-1-ylidene]pyrrolidine-1-carboxylate |
| 49 | | tert-butyl (3E)-2,2-dimethyl-3-[3-(6-methylpyridin-2-yl)prop-2-yn-1-ylidene]pyrrolidine-1-carboxylate |
| 50 | | propyl (3E)-2,2-dimethyl-3-[3-(6-methylpyridin-2-yl)prop-2-yn-1-ylidene]pyrrolidine-1-carboxylate |
| 51 | | 2-methoxyethyl (3E)-2,2-dimethyl-3-[3-(6-methylpyridin-2-yl)prop-2-yn-1-ylidene]pyrrolidine-1-carboxylate |
| 52 | | 2-methylpropyl (3E)-2,2-dimethyl-3-[3-(6-methylpyridin-2-yl)prop-2-yn-1-ylidene]pyrrolidine-1-carboxylate |

TABLE 1-continued

Selected compounds of the invention.

| Example | Compound | Chemical Name |
|---|---|---|
| 53 | | propan-2-yl (3E)-2,2-dimethyl-3-[3-(6-methylpyridin-2-yl)prop-2-yn-1-ylidene]pyrrolidine-1-carboxylate |
| 54 | | (3E)-N,N,2,2-tetramethyl-3-[3-(6-methylpyridin-2-yl)prop-2-yn-1-ylidene]pyrrolidine-1-carboxamide |
| 55 | | {(3E)-2,2-dimethyl-3-[3-(6-methylpyridin-2-yl)prop-2-yn-1-ylidene]pyrrolidin-1-yl}(furan-2-yl)methanone |
| 56 | | (3-chlorophenyl){(3E)-2,2-dimethyl-3-[3-(6-methylpyridin-2-yl)prop-2-yn-1-ylidene]pyrrolidin-1-yl}methanone |
| 57 | | {(3E)-2,2-dimethyl-3-[3-(6-methylpyridin-2-yl)prop-2-yn-1-ylidene]pyrrolidin-1-yl}(piperidin-1-yl)methanone |
| 58 | | {(3E)-2,2-dimethyl-3-[3-(6-methylpyridin-2-yl)prop-2-yn-1-ylidene]pyrrolidin-1-yl}(pyrrolidin-1-yl)methanone |

TABLE 1-continued

Selected compounds of the invention.

| Example | Compound | Chemical Name |
|---|---|---|
| 59 | | methyl (3E)-2,2-dimethyl-3-[3-(6-methylpyridin-2-yl)prop-2-yn-1-ylidene]pyrrolidine-1-carboxylate |
| 60 | | tert-butyl (3E)-2,2-dimethyl-3-[3-(4-methylpyrimidin-2-yl)prop-2-yn-1-ylidene]pyrrolidine-1-carboxylate |
| 61 | | ethyl (3E)-2,2-dimethyl-3-[3-(4-methylpyrimidin-2-yl)prop-2-yn-1-ylidene]pyrrolidine-1-carboxylate |
| 62 | | 2-methoxyethyl (3E)-2,2-dimethyl-3-[3-(4-methylpyrimidin-2-yl)prop-2-yn-1-ylidene]pyrrolidine-1-carboxylate |
| 63 | | propan-2-yl (3E)-2,2-dimethyl-3-[3-(4-methylpyrimidin-2-yl)prop-2-yn-1-ylidene]pyrrolidine-1-carboxylate |
| 64 | | methyl (3E)-2,2-dimethyl-3-[3-(4-methylpyrimidin-2-yl)prop-2-yn-1-ylidene]pyrrolidine-1-carboxylate |

TABLE 1-continued

Selected compounds of the invention.

| Example | Compound | Chemical Name |
|---|---|---|
| 65 | | tert-butyl (3E)-2,2-dimethyl-3-{3-[6-(methylamino)pyridin-2-yl]prop-2-yn-1-ylidene}pyrrolidine-1-carboxylate |
| 66 | | ethyl (3E)-2,2-dimethyl-3-{3-[6-(methylamino)pyridin-2-yl]prop-2-yn-1-ylidene}pyrrolidine-1-carboxylate |
| 67 | | propyl (3E)-2,2-dimethyl-3-{3-[6-(methylamino)pyridin-2-yl]prop-2-yn-1-ylidene}pyrrolidine-1-carboxylate |
| 68 | | 2-methoxyethyl (3E)-2,2-dimethyl-3-{3-[6-(methylamino)pyridin-2-yl]prop-2-yn-1-ylidene}pyrrolidine-1-carboxylate |
| 69 | | 2-methylpropyl (3E)-2,2-dimethyl-3-{3-[6-(methylamino)pyridin-2-yl]prop-2-yn-1-ylidene}pyrrolidine-1-carboxylate |
| 70 | | propan-2-yl (3E)-2,2-dimethyl-3-{3-[6-(methylamino)pyridin-2-yl]prop-2-yn-1-ylidene}pyrrolidine-1-carboxylate |
| 71 | | methyl (3E)-2,2-dimethyl-3-{3-[6-(methylamino)pyridin-2-yl]prop-2-yn-1-ylidene}pyrrolidine-1-carboxylate |
| 72 | | tert-butyl (3E)-3-[3-(4-cyanopyridin-2-yl)prop-2-yn-1-ylidene]-2,2-dimethylpyrrolidine-1-carboxylate |

TABLE 1-continued

Selected compounds of the invention.

| Example | Compound | Chemical Name |
|---------|----------|---------------|
| 73 | | ethyl (3E)-3-[3-(4-cyanopyridin-2-yl)prop-2-yn-1-ylidene]-2,2-dimethylpyrrolidine-1-carboxylate |
| 74 | | 2-methoxyethyl (3E)-3-[3-(4-cyanopyridin-2-yl)prop-2-yn-1-ylidene]-2,2-dimethylpyrrolidine-1-carboxylate |
| 75 | | 2-methylpropyl (3E)-3-[3-(4-cyanopyridin-2-yl)prop-2-yn-1-ylidene]-2,2-dimethylpyrrolidine-1-carboxylate |
| 76 | | propan-2-yl (3E)-3-[3-(4-cyanopyridin-2-yl)prop-2-yn-1-ylidene]-2,2-dimethylpyrrolidine-1-carboxylate |
| 77 | | methyl (3E)-3-[3-(4-cyanopyridin-2-yl)prop-2-yn-1-ylidene]-2,2-dimethylpyrrolidine-1-carboxylate |
| 78 | | tert-butyl (3E)-3-[3-(3-cyano-5-fluorophenyl)prop-2-yn-1-ylidene]-2,2-dimethylpyrrolidine-1-carboxylate |

TABLE 1-continued

Selected compounds of the invention.

| Example | Compound | Chemical Name |
|---|---|---|
| 79 | | ethyl (3E)-3-[3-(3-cyano-5-fluorophenyl)prop-2-yn-1-ylidene]-2,2-dimethylpyrrolidine-1-carboxylate |
| 80 | | propyl (3E)-3-[3-(3-cyano-5-fluorophenyl)prop-2-yn-1-ylidene]-2,2-dimethylpyrrolidine-1-carboxylate |
| 81 | | 2-methoxyethyl (3E)-3-[3-(3-cyano-5-fluorophenyl)prop-2-yn-1-ylidene]-2,2-dimethylpyrrolidine-1-carboxylate |
| 82 | | 2-methylpropyl (3E)-3-[3-(3-cyano-5-fluorophenyl)prop-2-yn-1-ylidene]-2,2-dimethylpyrrolidine-1-carboxylate |
| 83 | | propan-2-yl (3E)-3-[3-(3-cyano-5-fluorophenyl)prop-2-yn-1-ylidene]-2,2-dimethylpyrrolidine-1-carboxylate |
| 84 | | methyl (3E)-3-[3-(3-cyano-5-fluorophenyl)prop-2-yn-1-ylidene]-2,2-dimethylpyrrolidine-1-carboxylate |
| 85 | | tert-butyl (3E)-3-[3-(4-chloropyridin-2-yl)prop-2-yn-1-ylidene]-2,2-dimethylpyrrolidine-1-carboxylate |

TABLE 1-continued

Selected compounds of the invention.

| Example | Compound | Chemical Name |
|---|---|---|
| 86 | | {(3E)-3-[3-(4-chloropyridin-2-yl)prop-2-yn-1-ylidene]-2,2-dimethylpyrrolidin-1-yl}(furan-2-yl)methanone |
| 87 | | (3E)-3-[3-(4-chloropyridin-2-yl)prop-2-yn-1-ylidene]-N,N-diethyl-2,2-dimethylpyrrolidine-1-carboxamide |
| 88 | | {(3E)-3-[3-(4-chloropyridin-2-yl)prop-2-yn-1-ylidene]-2,2-dimethylpyrrolidin-1-yl}(pyrrolidin-1-yl)methanone |
| 89 | | {(3E)-3-[3-(4-chloropyridin-2-yl)prop-2-yn-1-ylidene]-2,2-dimethylpyrrolidin-1-yl}(piperidin-1-yl)methanone |
| 90 | | (3E)-3-[3-(4-chloropyridin-2-yl)prop-2-yn-1-ylidene]-N,N,2,2-tetramethylpyrrolidine-1-carboxamide |
| 91 | | ethyl (3E)-3-[3-(4-chloropyridin-2-yl)prop-2-yn-1-ylidene]-2,2-dimethylpyrrolidine-1-carboxylate |
| 92 | | methyl (3E)-3-[3-(4-chloropyridin-2-yl)prop-2-yn-1-ylidene]-2,2-dimethylpyrrolidine-1-carboxylate |
| 93 | | (3-chlorophenyl){(3E)-3-[3-(4-chloropyridin-2-yl)prop-2-yn-1-ylidene]-2,2-dimethylpyrrolidin-1-yl}methanone |

TABLE 1-continued

Selected compounds of the invention.

| Example | Compound | Chemical Name |
|---|---|---|
| 94 | | ethyl (3E)-3-[3-(6-aminopyridin-2-yl)prop-2-yn-1-ylidene]-2,2-dimethylpyrrolidine-1-carboxylate |
| 95 | | (3E)-3-[3-(6-aminopyridin-2-yl)prop-2-yn-1-ylidene]-N,N-diethyl-2,2-dimethylpyrrolidine-1-carboxamide |
| 96 | | methyl (3E)-3-[3-(6-aminopyridin-2-yl)prop-2-yn-1-ylidene]-2,2-dimethylpyrrolidine-1-carboxylate |
| 97 | | (3E)-3-[3-(6-aminopyridin-2-yl)prop-2-yn-1-ylidene]-N,N,2,2-tetramethylpyrrolidine-1-carboxamide |
| 98 | | tert-butyl (3E)-3-[3-(3-chlorophenyl)prop-2-yn-1-ylidene]-2,2-dimethylpyrrolidine-1-carboxylate |
| 99 | | {(3E)-3-[3-(3-chlorophenyl)prop-2-yn-1-ylidene]-2,2-dimethylpyrrolidin-1-yl}(piperidin-1-yl)methanone |
| 100 | | {(3E)-3-[3-(3-chlorophenyl)prop-2-yn-1-ylidene]-2,2-dimethylpyrrolidin-1-yl}(pyrrolidin-1-yl)methanone |

TABLE 1-continued

Selected compounds of the invention.

| Example | Compound | Chemical Name |
|---|---|---|
| 101 | | ethyl (3E)-3-[3-(3-chlorophenyl)prop-2-yn-1-ylidene]-2,2-dimethylpyrrolidine-1-carboxylate |
| 102 | | (3E)-3-[3-(3-chlorophenyl)prop-2-yn-1-ylidene]-N-ethyl-2,2-dimethyl-N-(propan-2-yl)pyrrolidine-1-carboxamide |
| 103 | | (3E)-3-[3-(3-chlorophenyl)prop-2-yn-1-ylidene]-N,N,2,2-tetramethylpyrrolidine-1-carboxamide |
| 104 | | {(3E)-3-[3-(3-chlorophenyl)prop-2-yn-1-ylidene]-2,2-dimethylpyrrolidin-1-yl}(furan-2-yl)methanone |
| 105 | | methyl (3E)-3-[3-(3-chlorophenyl)prop-2-yn-1-ylidene]-2,2-dimethylpyrrolidine-1-carboxylate |
| 106 | | (3-chlorophenyl){(3E)-3-[3-(3-chlorophenyl)prop-2-yn-1-ylidene]-2,2-dimethylpyrrolidin-1-yl}methanone |
| 107 | | (3-chlorophenyl)[(4E)-4-{[5-(3-chlorophenyl)-1H-pyrazol-3-yl]methylidene}-3,3-dimethylpiperidin-1-yl]methanone |
| 108 | | ethyl 2,2,6,6-tetramethyl-4-[3-(6-methylpyridin-2-yl)prop-2-yn-1-ylidene]piperidine-1-carboxylate |

TABLE 1-continued

Selected compounds of the invention.

| Example | Compound | Chemical Name |
|---|---|---|
| 109 | | 2-methyl-6-[3-(2,2,6,6-tetramethylpiperidin-4-ylidene)prop-1-yn-1-yl]pyridine |
| 110 | | tert-butyl 8-[3-(6-methylpyridin-2-yl)prop-2-yn-1-ylidene]-5-azaspiro[3.5]nonane-5-carboxylate |
| 111 | | methyl 8[3-(6-methylpyridin-2-yl)prop-2-yn-1-ylidene]-5-azaspiro[3.5]nonane-5-carboxylate (E:Z mixture) |
| 112 | | 4-[3-(3-chlorophenyl)prop-2-yn-1-ylidene]-1,2,2,6,6-pentamethylpiperidine |
| 113 | | 2-methyl-6-[3-(1,2,2,6,6-pentamethylpiperidin-4-ylidene)prop-1-yn-1-yl]pyridine |
| 114 | | ethyl 3-[3-(6-methylpyridin-2-yl)prop-2-yn-1-ylidene]-8-azabicyclo[3.2.1]octane-8-carboxylate |
| 115 | | 8-(6-methyl-3-nitropyridin-2-yl)-3-[3-(6-methylpyridin-2-yl)prop-2-yn-1-ylidene]-8-azabicyclo[3.2.1]octane |

TABLE 1-continued

Selected compounds of the invention.

| Example | Compound | Chemical Name |
|---|---|---|
| 116 | | 3-{(3E)-3-[1-(3-chlorobenzoyl)-3,3-dimethylpiperidin-4-ylidene]prop-1-yn-1-yl}benzonitrile |
| 117 | | 3-{(3E)-3-[1-(3-chlorobenzoyl)-3,3-dimethylpiperidin-4-ylidene]prop-1-yn-1-yl}-5-fluorobenzonitrile |
| 118 | | (3-chlorophenyl){(4E)-4-[3-(3-methoxyphenyl)prop-2-yn-1-ylidene]-3,3-dimethylpiperidin-1-yl}methanone |
| 119 | | (3-chlorophenyl){(4E)-4-{3-[3-(hydroxymethyl)phenyl]prop-2-yn-1-ylidene}-3,3-dimethylpiperidin-1-yl}methanone |
| 120 | | (3-chlorophenyl){(4E)-4-[3-(4-fluorophenyl)prop-2-yn-1-ylidene]-3,3-dimethylpiperidin-1-yl}methanone |
| 121 | | (3-chlorophenyl)[(4E)-3,3-dimethyl-4-(3-{3-[(pyrrolidin-1-yl)methyl]phenyl}prop-2-yn-1-ylidene)piperidin-1-yl]methanone |

TABLE 1-continued

Selected compounds of the invention.

| Example | Compound | Chemical Name |
|---------|----------|---------------|
| 122 | | (3-chlorophenyl){(4E)-3,3-dimethyl-4-[3-(6-methylpyridin-2-yl)prop-2-yn-1-ylidene]piperidin-1-yl}methanone |
| 123 | | 5-{(3E)-3-[1-(3-chlorobenzoyl)-3,3-dimethylpiperidin-4-ylidene]prop-1-yn-1-yl}pyridine-2-carbonitrile |
| 124 | | (3-chlorophenyl){(4E)-4-[3-(6-methoxypyridin-3-yl)prop-2-yn-1-ylidene]-3,3-dimethylpiperidin-1-yl}methanone |
| 125 | | (3-chlorophenyl){(4E)-4-[3-(3-fluoro-5-hydroxyphenyl)prop-2-yn-1-ylidene]-3,3-dimethylpiperidin-1-yl}methanone |
| 126 | | {(4E)-4-[3-(3-chlorophenyl)prop-2-yn-1-ylidene]-3,3-dimethylpiperidin-1-yl}(3-hydroxyphenyl)methanone |
| 127 | | {(4E)-4-[3-(3-chlorophenyl)prop-2-yn-1-ylidene]-3,3-dimethylpiperidin-1-yl}(4-methoxypyridin-2-yl)methanone |

TABLE 1-continued

Selected compounds of the invention.

| Example | Compound | Chemical Name |
|---|---|---|
| 128 | | {(4E)-4-[3-(3-chlorophenyl)prop-2-yn-1-ylidene]-3,3-dimethylpiperidin-1-yl}(6-methylpyridin-2-yl)methanone |
| 129 | | (4E)-4-[3-(3-chlorophenyl)prop-2-yn-1-ylidene]-3,3-dimethyl-N-(6-methylpyridin-2-yl)piperidine-1-carboxamide |
| 130 | | {(4E)-4-[3-(3-chlorophenyl)prop-2-yn-1-ylidene]-3,3-dimethylpiperidin-1-yl}(2,2-dimethylmorpholin-4-yl)methanone |
| 131 | | (4E)-4-[3-(3-chlorophenyl)prop-2-yn-1-ylidene]-N-(2,2-dimethyltetrahydro-2H-pyran-4-yl)-3,3-dimethylpiperidine-1-carboxamide |
| 132 | | (4E)-4-[3-(3-chlorophenyl)prop-2-yn-1-ylidene]-3,3-dimethyl-N-(pyridin-2-yl)piperidine-1-carboxamide |

TABLE 1-continued
Selected compounds of the invention.
| Example | Compound | Chemical Name |
|---------|----------|---------------|
| 133 | 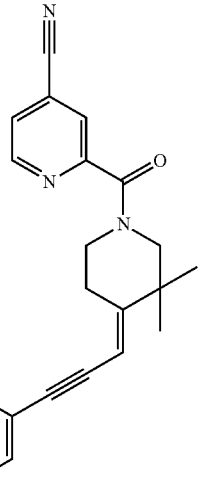 | 2-({(4E)-4-[3-(3-chlorophenyl)prop-2-yn-1-ylidene]-3,3-dimethylpiperidin-1-yl}carbonyl)pyridine-4-carbonitrile |
| 134 | 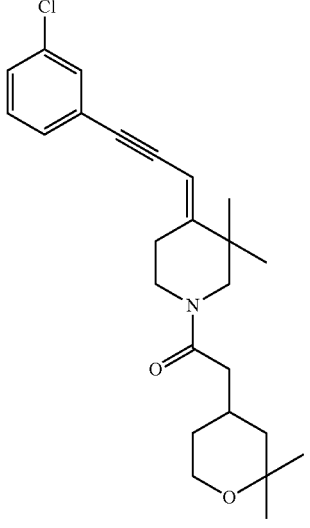 [SMILES: CC1(C)CC(CC(=O)N2CC/C(=C\C#Cc3cccc(Cl)c3)C(C)(C)C2)CCO1] | 1-{(4E)-4-[3-(3-chlorophenyl)prop-2-yn-1-ylidene]-3,3-dimethylpiperidin-1-yl}-2-(2,2-dimethyltetrahydro-2H-pyran-4-yl)ethanone |
| 135 | 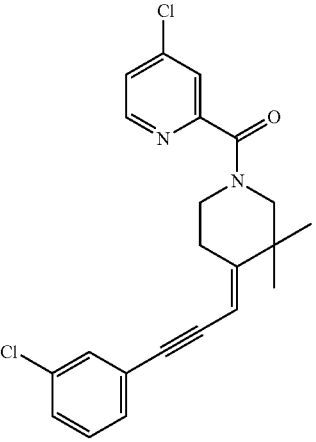 [SMILES: CC1(C)CN(C(=O)c2cc(Cl)ccn2)CC/C1=C\C#Cc1cccc(Cl)c1] | {(4E)-4-[3-(3-Chlorophenyl)prop-2-yn-1-ylidene]-3,3-dimethylpiperidin-1-yl}(4-chloropyridin-2-yl)methanone |

TABLE 1-continued
Selected compounds of the invention.
| Example | Compound | Chemical Name |
|---------|----------|---------------|
| 136 | 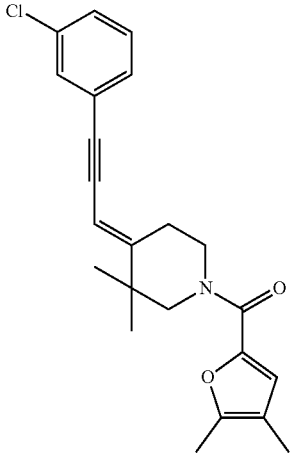 [SMILES: Cc1cc(C(=O)N2CC/C(=C\C#Cc3cccc(Cl)c3)C(C)(C)C2)oc1C] | {(4E)-4-[3-(3-chlorophenyl)prop-2-yn-1-ylidene]-3,3-dimethylpiperidin-1-yl}(4,5-dimethylfuran-2-yl)methanone |
| 137 | 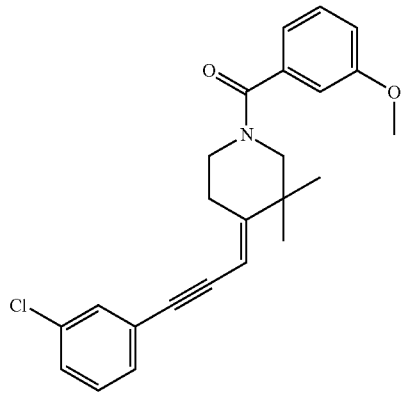 [SMILES: COc1cccc(C(=O)N2CC/C(=C\C#Cc3cccc(Cl)c3)C(C)(C)C2)c1] | {(4E)-4-[3-(3-chlorophenyl)prop-2-yn-1-ylidene]-3,3-dimethylpiperidin-1-yl}(3-methoxyphenyl)methanone |
| 138 | 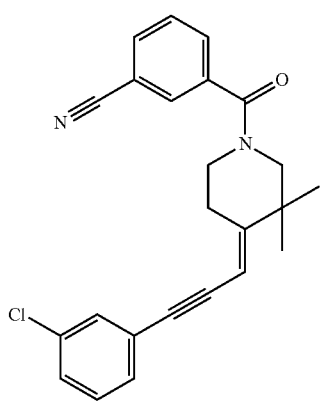 [SMILES: CC1(C)CN(C(=O)c2cccc(C#N)c2)CC/C1=C\C#Cc1cccc(Cl)c1] | 3-({(4E)-4-[3-(3-chlorophenyl)prop-2-yn-1-ylidene]-3,3-dimethylpiperidin-1-yl}carbonyl)benzonitrile |

TABLE 1-continued
Selected compounds of the invention.
| Example | Compound | Chemical Name |
|---|---|---|
| 139 | 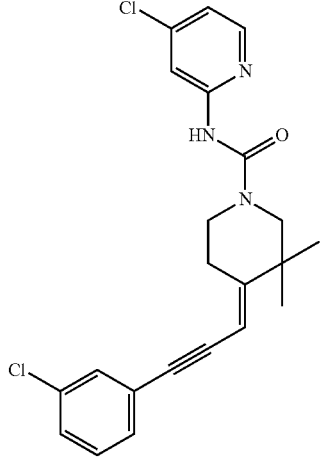 [SMILES: CC1(C)CN(C(=O)Nc2cc(Cl)ccn2)CC/C1=C\C#Cc1cccc(Cl)c1] | (4E)-4-[3-(3-chlorophenyl)prop-2-yn-1-ylidene]-N-(4-chloropyridin-2-yl)-3,3-dimethylpiperidine-1-carboxamide |
| 140 | 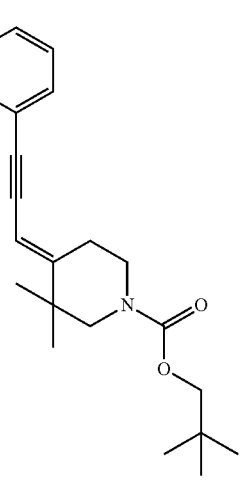 | 2,2-dimethylpropyl (4E)-4-[3-(3-chlorophenyl)prop-2-yn-1-ylidene]-3,3-dimethylpiperidine-1-carboxylate |
| 141 | 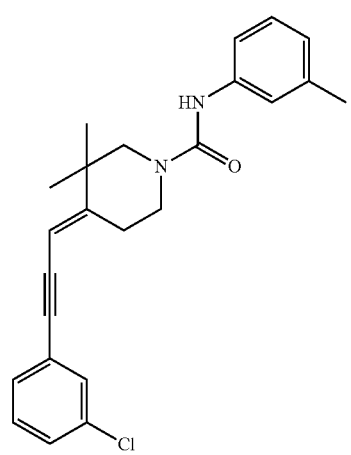 | (4E)-4-[3-(3-chlorophenyl)prop-2-yn-1-ylidene]-3,3-dimethyl-N-(3-methylphenyl)piperidine-1-carboxamide |

TABLE 1-continued
Selected compounds of the invention.
| Example | Compound | Chemical Name |
| --- | --- | --- |
| 142 | 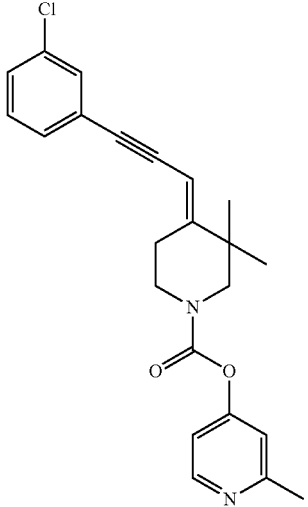 [SMILES: Cc1cc(OC(=O)N2CC/C(=C\C#Cc3cccc(Cl)c3)C(C)(C)C2)ccn1] | 2-methylpyridin-4-yl (4E)-4-[3-(3-chlorophenyl)prop-2-yn-1-ylidene]-3,3-dimethylpiperidine-1-carboxylate |
| 143 | 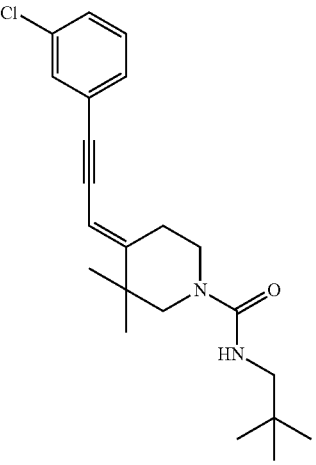 [SMILES: CC(C)(C)CNC(=O)N1CC/C(=C\C#Cc2cccc(Cl)c2)C(C)(C)C1] | (4E)-4-[3-(3-chlorophenyl)prop-2-yn-1-ylidene]-N-(2,2-dimethylpropyl)-3,3-dimethylpiperidine-1-carboxamide |
| 144 | 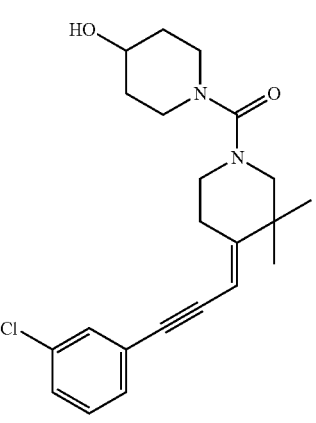 [SMILES: CC1(C)CN(C(=O)N2CCC(O)CC2)CC/C1=C\C#Cc1cccc(Cl)c1] | {(4E)-4-[3-(3-chlorophenyl)prop-2-yn-1-ylidene]-3,3-dimethylpiperidin-1-yl}(4-hydroxypiperidin-1-yl)methanone |

TABLE 1-continued

Selected compounds of the invention.

| Example | Compound | Chemical Name |
|---------|----------|---------------|
| 145 | | ethyl 4-({(4E)-4-[3-(3-chlorophenyl)prop-2-yn-1-ylidene]-3,3-dimethylpiperidin-1-yl}sulfonyl)piperidine-1-carboxylate |
| 146 | | (4E)-4-[3-(3-chlorophenyl)prop-2-yn-1-ylidene]-3,3-dimethyl-1-[(tetrahydro-2H-pyran-2-ylmethyl)sulfonyl]piperidine |
| 147 | | 5-({(4E)-4-[3-(3-chlorophenyl)prop-2-yn-1-ylidene]-3,3-dimethylpiperidin-1-yl}sulfonyl)-3-ethyl[1,2]oxazolo[5,4-b]pyridine |
| 148 | | (4E)-4-[3-(3-chlorophenyl)prop-2-yn-1-ylidene]-3,3-dimethyl-1-{[(3-methyl-1,2-oxazol-5-yl)methyl]sulfonyl}piperidine |
| 149 | | (4E)-4-[3-(3-chlorophenyl)prop-2-yn-1-ylidene]-N,3,3-trimethyl-N-(propan-2-yl)piperidine-1-sulfonamide |
| 150 | | 4-({(4E)-4-[3-(3-chlorophenyl)prop-2-yn-1-ylidene]-3,3-dimethylpiperidin-1-yl}sulfonyl)-2,6-dimethylmorpholine |

TABLE 1-continued

Selected compounds of the invention.

| Example | Compound | Chemical Name |
|---|---|---|
| 151 | | (4E)-4-[3-(3-chlorophenyl)prop-2-yn-1-ylidene]-3,3-dimethyl-1-(phenylsulfonyl)piperidine |
| 152 | | (4E)-N-tert-butyl-4-[3-(3-chlorophenyl)prop-2-yn-1-ylidene]-3,3-dimethylpiperidine-1-sulfonamide |
| 153 | | 4-({(4E)-4-[3-(3-chlorophenyl)prop-2-yn-1-ylidene]-3,3-dimethylpiperidin-1-yl}sulfonyl)morpholine |
| 154 | | 4-({(4E)-4-[3-(3-chlorophenyl)prop-2-yn-1-ylidene]-3,3-dimethylpiperidin-1-yl}sulfonyl)-1-methyl-1H-benzotriazole |
| 155 | | 3-({(4E)-4-[3-(3-chlorophenyl)prop-2-yn-1-ylidene]-3,3-dimethylpiperidin-1-yl}sulfonyl)-5-(propan-2-yloxy)pyridine |
| 156 | | (4E)-4-[3-(3-chlorophenyl)prop-2-yn-1-ylidene]-N-(cyclopropylmethyl)-N,3,3-trimethylpiperidine-1-sulfonamide |

TABLE 1-continued

Selected compounds of the invention.

| Example | Compound | Chemical Name |
|---|---|---|
| 157 | | 5-({(4E)-4-[3-(3-chlorophenyl)prop-2-yn-1-ylidene]-3,3-dimethylpiperidin-1-yl}sulfonyl)-2-methoxypyridine |
| 158 | | 3-({(4E)-4-[3-(3-chlorophenyl)prop-2-yn-1-ylidene]-3,3-dimethylpiperidin-1-yl}sulfonyl)-6,7-dihydro-5H-pyrazolo[5,1-b][1,3]oxazine |
| 159 | | (4E)-4-[3-(3-chlorophenyl)prop-2-yn-1-ylidene]-N-cyclohexyl-N,3,3-trimethylpiperidine-1-sulfonamide |
| 160 | | (4E)-4-[3-(3-chlorophenyl)prop-2-yn-1-ylidene]-3,3-dimethyl-1-[(4-methylpiperidin-1-yl)sulfonyl]piperidine |
| 161 | | (4E)-4-[3-(3-chlorophenyl)prop-2-yn-1-ylidene]-1-[(2,2-dimethylpropyl)sulfonyl]-3,3-dimethylpiperidine |
| 162 | | (4E)-4-[3-(3-chlorophenyl)prop-2-yn-1-ylidene]-3,3-dimethyl-1-[(tetrahydro-2H-pyran-3-ylmethyl)sulfonyl]piperidine |
| 163 | | (4E)-4-[3-(3-chlorophenyl)prop-2-yn-1-ylidene]-1-[(3,5-dimethyl-1,2-oxazol-4-yl)sulfonyl]-3,3-dimethylpiperidine |

TABLE 1-continued

Selected compounds of the invention.

| Example | Compound | Chemical Name |
|---|---|---|
| 164 | 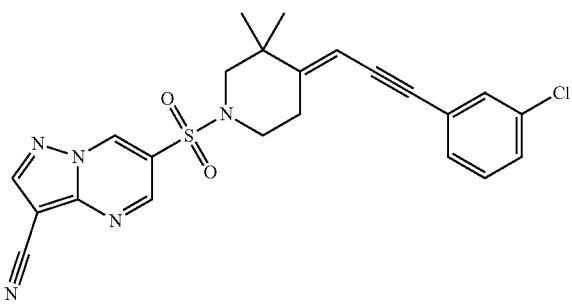 [SMILES: CC1(C)CN(S(=O)(=O)c2cnc3c(C#N)cnn3c2)CC/C1=C\C#Cc1cccc(Cl)c1] | 6-({(4E)-4-[3-(3-chlorophenyl)prop-2-yn-1-ylidene]-3,3-dimethylpiperidin-1-yl}sulfonyl)pyrazolo[1,5-a]pyrimidine-3-carbonitrile |
| 165 | 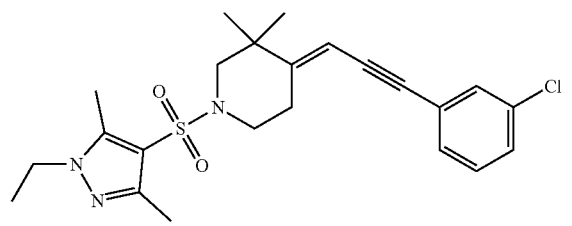 [SMILES: CCn1nc(C)c(S(=O)(=O)N2CC/C(=C\C#Cc3cccc(Cl)c3)C(C)(C)C2)c1C] | (4E)-4-[3-(3-chlorophenyl)prop-2-yn-1-ylidene]-1-[(1-ethyl-3,5-dimethyl-1H-pyrazol-4-yl)sulfonyl]-3,3-dimethylpiperidine |
| 166 | 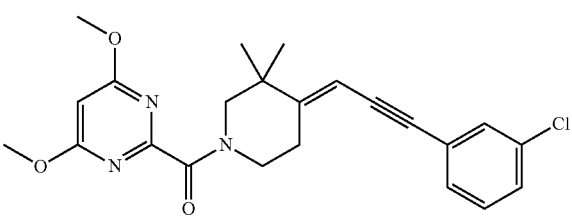 [SMILES: COc1cc(OC)nc(C(=O)N2CC/C(=C\C#Cc3cccc(Cl)c3)C(C)(C)C2)n1] | {(4E)-4-[3-(3-chlorophenyl)prop-2-yn-1-ylidene]-3,3-dimethylpiperidin-1-yl}(4,6-dimethoxypyrimidin-2-yl)methanone |
| 167 | 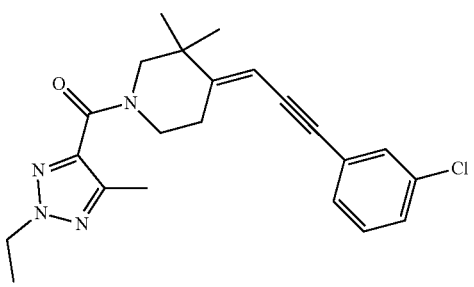 [SMILES: CCn1nc(C)c(C(=O)N2CC/C(=C\C#Cc3cccc(Cl)c3)C(C)(C)C2)n1] | {(4E)-4-[3-(3-chlorophenyl)prop-2-yn-1-ylidene]-3,3-dimethylpiperidin-1-yl}(2-ethyl-5-methyl-2H-1,2,3-triazol-4-yl)methanone |
| 168 | 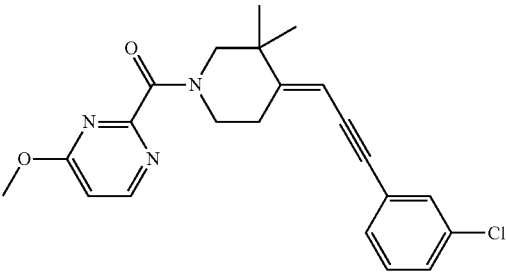 [SMILES: COc1ccnc(C(=O)N2CC/C(=C\C#Cc3cccc(Cl)c3)C(C)(C)C2)n1] | {(4E)-4-[3-(3-chlorophenyl)prop-2-yn-1-ylidene]-3,3-dimethylpiperidin-1-yl}(4-methoxypyrimidin-2-yl)methanone |

TABLE 1-continued

Selected compounds of the invention.

| Example | Compound | Chemical Name |
|---|---|---|
| 169 | | {(4E)-4-[3-(3-chlorophenyl)prop-2-yn-1-ylidene]-3,3-dimethylpiperidin-1-yl}(6,7-dihydro-5H-pyrazolo[5,1-b][1,3]oxazin-3-yl)methanone |
| 170 | | {(4E)-4-[3-(3-chlorophenyl)prop-2-yn-1-ylidene]-3,3-dimethylpiperidin-1-yl}([1,2,4]triazolo[1,5-a]pyridin-2-yl)methanone |
| 171 | | {(4E)-4-[3-(3-chlorophenyl)prop-2-yn-1-ylidene]-3,3-dimethylpiperidin-1-yl}(2,6-dimethoxypyrimidin-4-yl)methanone |
| 172 | | 4-({(4E)-4-[3-(3-chlorophenyl)prop-2-yn-1-ylidene]-3,3-dimethylpiperidin-1-yl}carbonyl)pyridine-2-carbonitrile |
| 173 | | {(4E)-4-[3-(3-chlorophenyl)prop-2-yn-1-ylidene]-3,3-dimethylpiperidin-1-yl}(1,5-dimethyl-1H-1,2,3-triazol-4-yl)methanone |
| 174 | | {(4E)-4-[3-(3-chlorophenyl)prop-2-yn-1-ylidene]-3,3-dimethylpiperidin-1-yl}(5,6-dihydro-8H-imidazo[2,1-c][1,4]oxazin-3-yl)methanone |

TABLE 1-continued

Selected compounds of the invention.

| Example | Compound | Chemical Name |
|---|---|---|
| 175 | | 6-({(4E)-4-[3-(3-chlorophenyl)prop-2-yn-1-ylidene]-3,3-dimethylpiperidin-1-yl}carbonyl)pyridine-2-carbonitrile |
| 176 | | {(4E)-4-[3-(3-chlorophenyl)prop-2-yn-1-ylidene]-3,3-dimethylpiperidin-1-yl}(3-methoxy-1-methyl-1H-pyrazol-5-yl)methanone |
| 177 | | (3-chlorophenyl){(4E)-4-[3-(4-methoxypyridin-2-yl)prop-2-yn-1-ylidene]-3,3-dimethylpiperidin-1-yl}methanone |
| 178 | | (3-chlorophenyl)[(4E)-4-{3-[5-(hydroxymethyl)furan-2-yl]prop-2-yn-1-ylidene}-3,3-dimethylpiperidin-1-yl]methanone |

TABLE 1-continued
Selected compounds of the invention.
| Example | Compound | Chemical Name |
|---|---|---|
| 179 | 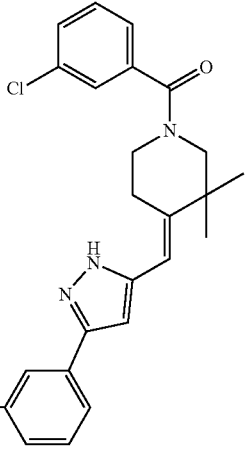 | (3-chlorophenyl)[(4E)-4-({3-[3-(hydroxymethyl)phenyl]-1H-pyrazol-5-yl}methylidene)-3,3-dimethylpiperidin-1-yl]methanone |
| 180 | 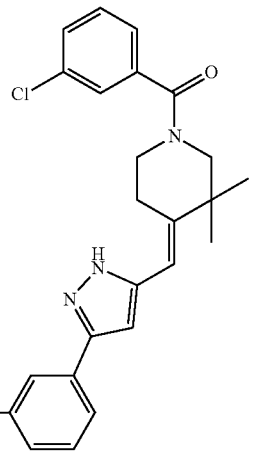 | 3-(5-{(E)-[1-(3-chlorobenzoyl)-3,3-dimethylpiperidin-4-ylidene]methyl}-1H-pyrazol-3-yl)benzonitrile |
| 181 | 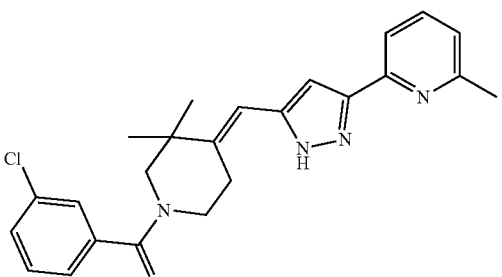 | (3-chlorophenyl)[(4E)-3,3-dimethyl-4-{[3-(6-methylpyridin-2-yl)-1H-pyrazol-5-yl]methylidene}piperidin-1-yl]methanone |

TABLE 1-continued

Selected compounds of the invention.

| Example | Compound | Chemical Name |
|---|---|---|
| 182 | | [(4E)-4-{[5-(3-chlorophenyl)-1H-pyrazol-3-yl]methylidene}-3,3-dimethylpiperidin-1-yl](2,5-dimethylfuran-3-yl)methanone |
| 183 | | (3-chlorophenyl){(4E)-3,3-dimethyl-4-[(5-phenyl-1,2-oxazol-3-yl)methylidene]piperidin-1-yl}methanone |
| 184 | | (3-chlorophenyl)[(4E)-4-{[5-(3-chlorophenyl)-1,3-oxazol-2-yl]methylidene}-3,3-dimethylpiperidin-1-yl]methanone |

TABLE 1-continued

Selected compounds of the invention.

| Example | Compound | Chemical Name |
|---|---|---|
| 185 | 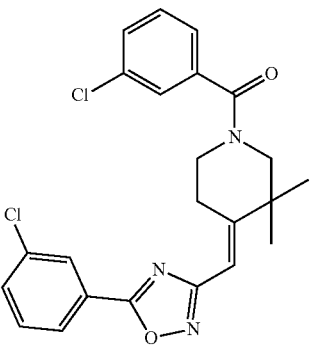 [SMILES: CC1(C)CN(C(=O)c2cccc(Cl)c2)CC/C1=C\c1noc(-c2cccc(Cl)c2)n1] | (3-chlorophenyl)[(4E)-4-{[5-(3-chlorophenyl)-1,2,4-oxadiazol-3-yl]methylidene}-3,3-dimethylpiperidin-1-yl]methanone |
| 186 | 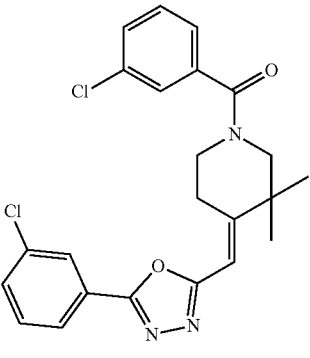 [SMILES: CC1(C)CN(C(=O)c2cccc(Cl)c2)CC/C1=C\c1nnc(-c2cccc(Cl)c2)o1] | (3-chlorophenyl)[(4E)-4-{[5-(3-chlorophenyl)-1,3,4-oxadiazol-2-yl]methylidene}-3,3-dimethylpiperidin-1-yl]methanone |
| 187 | 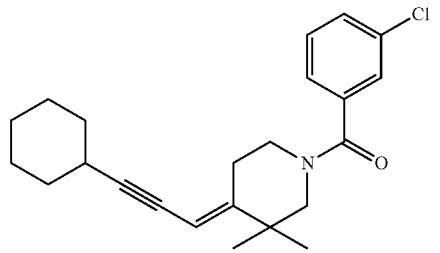 [SMILES: CC1(C)CN(C(=O)c2cccc(Cl)c2)CC/C1=C\C#CC1CCCCC1] | (3-chlorophenyl)[(4E)-4-(3-cyclohexylprop-2-yn-1-ylidene)-3,3-dimethylpiperidin-1-yl]methanone |
| 188 | 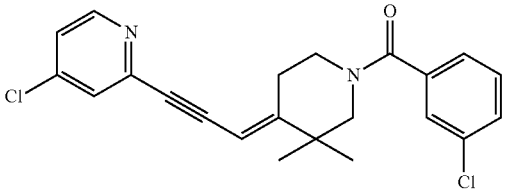 [SMILES: CC1(C)CN(C(=O)c2cccc(Cl)c2)CC/C1=C\C#Cc1cc(Cl)ccn1] | (3-chlorophenyl){(4E)-4-[3-(4-chloropyridin-2-yl)prop-2-yn-1-ylidene]-3,3-dimethylpiperidin-1-yl}methanone |
| 189 | 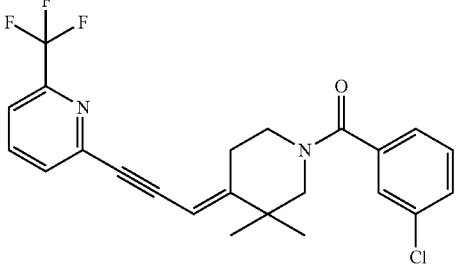 | (3-chlorophenyl)[(4E)-3,3-dimethyl-4-{3-[6-(trifluoromethyl)pyridin-2-yl]prop-2-yn-1-ylidene}piperidin-1-yl]methanone |

TABLE 1-continued

Selected compounds of the invention.

| Example | Compound | Chemical Name |
|---|---|---|
| 190 | | (3-chlorophenyl){(4E)-4-[3-(6-methoxypyridin-2-yl)prop-2-yn-1-ylidene]-3,3-dimethylpiperidin-1-yl}methanone |
| 191 | | (3-chlorophenyl){(4E)-4-[3-(3-hydroxyphenyl)prop-2-yn-1-ylidene]-3,3-dimethylpiperidin-1-yl}methanone |
| 192 | | [(4E)-3,3-dimethyl-4-(3-phenylprop-2-yn-1-ylidene)piperidin-1-yl](phenyl)methanone |
| 193 | | 3-[(3E)-3-{1-[(2,5-dimethylfuran-3-yl)carbonyl]-3,3-dimethylpiperidin-4-ylidene}prop-1-yn-1-yl]benzonitrile |
| 194 | | {(4E)-4-[3-(3-chlorophenyl)prop-2-yn-1-ylidene]-3,3-dimethylpiperidin-1-yl}(phenyl)methanone |
| 195 | | 3-{(3E)-3-[3,3-dimethyl-1-(3-methylbenzoyl)piperidin-4-ylidene]prop-1-yn-1-yl}benzonitrile |
| 196 | | 3-{(3E)-3-[1-(3-methoxybenzoyl)-3,3-dimethylpiperidin-4-ylidene]prop-1-yn-1-yl}benzonitrile |

TABLE 1-continued

Selected compounds of the invention.

| Example | Compound | Chemical Name |
|---------|----------|---------------|
| 197 | | (4E)-4-{3-[3-(hydroxymethyl)phenyl]prop-2-yn-1-ylidene}-3,3-dimethyl-N-(6-methylpyridin-2-yl)piperidine-1-carboxamide |
| 198 | | (3-chlorophenyl){(4E)-4-[4-(3-chlorophenyl)but-3-yn-2-ylidene]-3,3-difluoropiperidin-1-yl}methanone |
| 199 | | (3-chlorophenyl){(4Z)-4-[4-(3-chlorophenyl)but-3-yn-2-ylidene]-3,3-difluoropiperidin-1-yl}methanone |
| 200 | | 3-[(3E)-3-{1-[(2,5-dimethylfuran-3-yl)carbonyl]-3,3-dimethylpiperidin-4-ylidene}prop-1-yn-1-yl]-5-fluorobenzonitrile |
| 201 | | (3-chlorophenyl){(4E)-4-[3-(3-chlorophenyl)prop-2-yn-1-ylidene]-3,3-difluoropiperidin-1-yl}methanone |

TABLE 1-continued

Selected compounds of the invention.

| Example | Compound | Chemical Name |
|---|---|---|
| 202 | 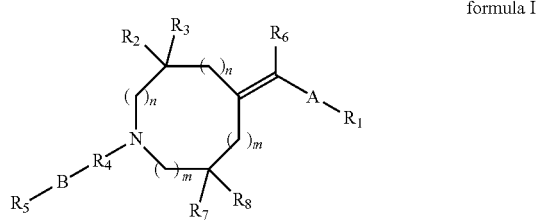 | {(4E)-4-[3-(3-chlorophenyl)prop-2-yn-1-ylidene]-3,3-difluoropiperidin-1-yl}(4-methoxypyridin-2-yl)methanone |

The invention also provides for a pharmaceutical composition comprising a compound of formula I:

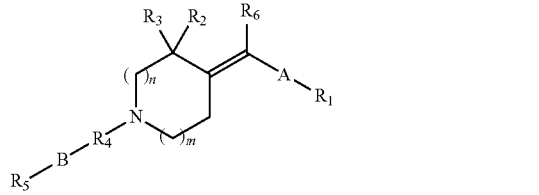

formula I or an enantiomer, diastereomer, N-oxide, or a pharmaceutically acceptable salt or combinations thereof, and a pharmaceutically acceptable carrier, wherein m, n, $R_1$ through $R_6$, A, and B have the meanings ascribed to them above; or, alternatively, a compound of formula IA:

formula IA or formula IB:

IB

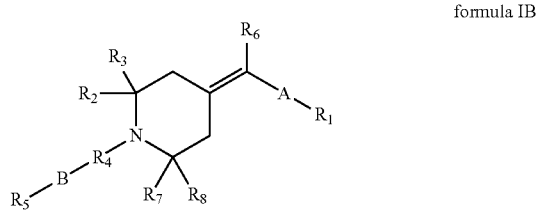

formula IB wherein A, B, m, n and $R_1$ through $R_8$ have the meanings ascribed to them in connection with formula IA or IB above, or an enantiomer, diastereomer, N-oxide, or a pharmaceutically acceptable salt or combinations thereof, for use in the treatment and/or prevention of a neurological disorder, psychotic disorder, pain or a psychiatric disorder associated with glutamate dysfunction is preferably provided.

Preferably according to the invention, a compound according to formula I, IA or IB is used in the treatment and/or prevention of a neurological disorder, psychotic disorder, or a psychiatric disorder associated with glutamate dysfunction including without any limitation for $mGlu_5$ positive allosteric modulators: Rett's syndrome, Phelan-McDermid syndrome, psychosis, schizophrenia, autism cognitive disorders, tuberous sclerosis, cognition disorders, Alzheimer's dementia, and for $mGlu_5$ negative allosteric modulators: addiction, major depressive disorder, anxiety, epilepsy, Fragile X Syndrome, gastroesophageal reflux disease (GERD), substance abuse and dependence, Parkinson's disease and L-Dopa induced dyskinesia, urinary incontinence, irritable bowel syndrome (IBS) and pain.

Preferably the neurological disorder, psychotic disorder, or psychiatric disorder associated with glutamate dysfunction is schizophrenia, schizoaffective disorder, substance induced psychotic disorder, age-associated learning and memory impairments or losses, post stroke dementia, deficits in concentration, mild cognitive impairment, cognitive dysfunction in Alzheimer's disease, cognitive dysfunction of schizophrenia, cognitive decline, dementia or cognitive impairment.

More preferably, the disorder is Fragile-X syndrome, Rett syndrome, Phelan-McDermid syndrome, or tuberous sclerosis.

DETAILED DESCRIPTION OF THE INVENTION

Terms and Definitions Used

Except where stated otherwise, the following definitions apply throughout the present specification and claims. These definitions apply regardless of whether a term is used by itself or in combination with other terms. For example, the definition of "alkyl" applies not only to alkyl groups per se, but also to the alkyl portions of alkoxy, alkylamino, alkylthio or alkylcarbonyl groups etc. Furthermore, all ranges described for a chemical group, for example "from 1 to 13 carbon atoms" or "$C_1$-$C_6$ alkyl" include all combinations and sub-combinations of ranges and specific numbers of carbon atoms therein.

The skilled person will be aware that groups A, B, $R_1$ to $R_8$, m and n all have the meanings given to them as described herein. For example, group B is intended to represent "an oxygen or sulphur atom, a nitrogen atom optionally substituted by a $C_1$-$C_5$ alkyl group or a methoxy group, or B is absent". Group B does not represent a boron atom.

"Alkyl" means a straight chain or branched chain aliphatic hydrocarbon group having from 1 to 20 carbon atoms in the chain. Preferred alkyl groups have from 1 to 12 carbon atoms in the chain. More preferred alkyl groups have from 1 to 6 carbon atoms in the chain. "Lower alkyl" means an alkyl group having about 1 to about 6 carbon atoms in the chain which may be straight or branched. Examples of suitable alkyl groups include methyl, ethyl, n-propyl, isopropyl, sec-butyl, n-butyl, and t-butyl.

"Alkenyl" means a straight chain or branched chain aliphatic hydrocarbon group having at least one carbon-carbon double bond and having from 2 to 15 carbon atoms in the chain. Preferred alkenyl groups have from 2 to 12 carbon atoms in the chain. More preferred alkenyl groups have from 2 to 6 carbon atoms in the chain. "Lower alkenyl" means an alkenyl group having 2 to about 6 carbon atoms in the chain, which may be straight or branched. Examples of suitable alkenyl groups include ethenyl, propenyl, isopropenyl, n-butenyl, 1-hexenyl and 3-methylbut-2-enyl.

"Alkynyl" means a straight chain or branched chain aliphatic hydrocarbon group having at least one carbon-carbon triple bond and having from 2 to 15 carbon atoms in the chain. Preferred alkynyl groups have from 2 to 12 carbon atoms in the chain. More preferred alkynyl groups have from 2 to 6 carbon atoms in the chain. "Lower alkynyl" means an alkynyl group having 2 to about 6 carbon atoms in the chain, which may be straight or branched. Examples of suitable alkynyl groups include ethynyl, propynyl and 2-butynyl.

"Mono-, bi-, or tricyclic heterocyclic" means an aromatic or non-aromatic saturated mono- bi- or tricyclic ring system having from 2 to 14 ring carbon atoms, and containing from 1 to 5 ring atoms selected from N, O and S, alone or in combination. Bi- and tricyclic heterocyclic groups are fused at 2 or 4 points or joined at one point via a bond or a heteroatom linker (O, S, NH, or N($C_1$-$C_6$ alkyl). The "mono- bi- or tricyclic heterocyclic" can be optionally substituted on the ring by replacing an available hydrogen on the ring by one or more substituents which may be the same or different. The nitrogen or sulphur atom of the heterocyclic can be optionally oxidized to the corresponding N-oxide, S-oxide or S-dioxide. Examples of suitable heterocyclics include furanyl, imidazolyl, isoxazolyl, oxadiazolyl, oxazolyl, pyrrolyl, pyridyl, pyrimidyl, pyridazinyl, thiazolyl, triazolyl, tetrazolyl, thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl and benzoisoxazolyl, aziridinyl, piperidinyl, pyrrolidinyl, piperazinyl, tetrahydropyranyl, tetrahydrofuranyl, tetrahydrothiophenyl, morpholinyl and thiomorpholinyl.

Heterocyclics with aromatic characteristics may be referred to as heteroaryls or heteroaromatics. Examples of suitable heteroaromatics include furanyl, imidazolyl, isoxazolyl, oxadiazolyl, oxazolyl, pyrrolyl, pyridyl, pyrimidyl, pyridazinyl, thiazolyl, triazolyl, tetrazolyl, thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisoxazolyl, tetrahydroquinolinyl, tetrahydroisoquinolinyl, 3-phenylpyridine, 3-cyclohexylpyridine, 3-(pyridin-3-yl) morpholine, 3-phenylisoxazole and 2-(piperidin-1-yl)pyrimidine.

"Mono-, bi- or tricyclic aryl" means an aromatic monocyclic, bicyclic or tricyclic ring system comprising 6 to 14 carbon atoms. Bi- and tricyclic aryl groups are fused at 2 or 4 points or joined at one point via a bond or a heteroatom linker (O, S, NH, or N($C_1$-$C_6$ alkyl) (e.g., biphenyl, 1-phenylnapthyl). The aryl group can be optionally substituted on the ring with one or more substituents, preferably 1 to 6 substituents, which may be the same or different. Examples of suitable aryl groups include phenyl and naphthyl.

"Cycloalkyl" means a monocyclic or bicyclic carbon ring system having from 3 to 14 carbon atoms, preferably from 3 to 6 carbon atoms. The cycloalkyl can be optionally substituted on the ring by replacing an available hydrogen on the ring by one or more substituents which may be the same or different. Examples of suitable monocyclic cycloalkyls include cyclopropyl, cyclopentyl, cyclohexyl and cycloheptyl. Examples of suitable multicyclic cycloalkyls include 1-decalinyl, norbornyl and adamantyl.

"Cycloalkenyl" has a meaning corresponding to that of cycloalkyl, but with one or two carbon-carbon double bonds within the ring (e.g., cyclohexenyl, cyclohexadiene).

"Amines" are derivatives of ammonia, wherein one or more hydrogen atoms have been replaced by a substituent such as an alkyl or aryl group. These may respectively be called alkylamines and arylamines; amines in which both types of substituent are attached to one nitrogen atom may be called alkylarylamines.

Amines can be further organized into four sub-categories. Primary amines arise when one of the three hydrogen atoms in ammonia is replaced by an alkyl or aromatic group (an N-alkylamino or N-arylamino respectively). Examples of suitable primary alkyl amines include methylamine or ethanolamine, or aniline (phenylamine) as an example of an aromatic amine. Secondary amines have two organic substituents (independently alkyl or aryl groups) bound to the nitrogen atom together with one hydrogen (or no hydrogen if one of the substituent bonds is double). Examples of suitable secondary amines include dimethylamine and methylethanolamine, while an example of an aromatic amine would be diphenylamine. Such compounds may also be referred to as "N,N-dialkylamino", "N,N-diarylamino" or "N,N-alkylarylamino" groups depending on the nature of the substituents. A secondary amine substituted by an alkoxy group, as defined herein, would be termed an "N-alkyl-N-alkoxyamino" compound for example. In tertiary amines, all three hydrogen atoms are replaced by organic substituents, such as trimethylamine. The final sub-category is cyclic amines which are either secondary or tertiary amines. Examples of suitable cyclic amines include the 3-member ring aziridine and the six-membered ring piperidine. N-methylpiperidine and N-phenylpiperidine are suitable examples of cyclic tertiary amines.

"Amides" are compounds with a nitrogen atom attached to a carbonyl group, thus having the structure R—CO—NR'R", with groups R' and R" being independently selected from alkyl or aromatic groups as defined herein. For example, when R' is hydrogen and R" is a 3-pyridyl group, the resulting amide has a 3-pyridylamino substituent. Alternatively, when R' is hydrogen and R" is a cyclopentyl group, the resulting amide has a cyclopentylamino substituent.

"Halogen", "halide" or "halo" means fluorine, chlorine, bromine or iodine. Preferred halogens are fluorine, chlorine or bromine, and most preferred are fluorine and chlorine.

The term "acyl", whether used alone, or within a term such as "acylamino", denotes a radical provided by the residue after removal of hydroxyl from an organic acid. The term "acylamino" refers to an amino radical substituted with an acyl group. An example of an "acylamino" radical is $CH_3C(=O)-NH-$ where the amine may be further substituted with alkyl, aryl or aralkyl groups.

The term "condensed ring" refers to a polycyclic ring system in a molecule in which two rings share two or more common atoms. Two rings that have only two atoms and one bond in common are said to be ortho-fused, e.g. naphthalene. In a polycyclic compound, a ring ortho-fused to different sides of two other rings that are themselves ortho-fused together (i.e. there are three common atoms between the first ring and the other two) is said to be ortho- and peri-fused to the other two rings. Phenalene is considered as being composed of three benzene rings, each of which is ortho- and peri-fused to the other two.

The term "bridged fused ring system" refers to a polycyclic skeleton which cannot be completely named as a fused ring system, due to the presence of further 'bridging' groups. The skeleton of the portion of the structure which remains after removal of the bridge(s) is named following conventional nomenclature. The maximum number of non-cumulative carbon-carbon double bonds is assigned after insertion of the bridge, hence, in order to allow for the necessary free valences to the bridge, the fused ring system may differ from the isolated fused ring system in the number of non-cumulative carbon-carbon double bonds and/or the need for indicated hydrogen. For example, 4a,8a-propanoquinoline, which is formed from a propyl-bridge extending between the ortho-fused carbon atoms of a quinoline derivative.

The skilled person will be aware that integers m and n, having integer values of between 0 and 2, refer to compounds according to formula I, IA or IB wherein the nitrogen-containing ring comprises 0, 1 or 2 methylene-bridge carbon atoms (as appropriate) and may therefore comprise a piperidine or pyrrolidine moiety or derivative thereof accordingly. For example, when the m and n groups immediately adjacent the ring nitrogen atom in formula 1=0, and the m and n groups immediately flanking the methylidene group in formula 1=1, compounds according to formula I, IA or IB comprise a 6-membered nitrogen-containing ring (piperidine) as exemplified by compounds 108-109 and 112-113 as seen in Table 1 above.

An asterisk may be used in subgeneric-formulae or groups to indicate the bond which is connected to a parent or core molecule as defined herein.

The term "treatment" and the like as used herein encompasses eliminating or alleviating symptoms and/or markers of mGluR5-mediated diseases or disorders or and keeping them from worsening (stabilization) and more generally bringing about a desired physiological or pharmacological effect. The term "prevention" and the like as used herein encompasses inhibiting or retarding the manifestation of symptoms of such diseases or disorders or reducing (or increasing as the case may be) or eliminating abnormal values in markers therefor.

Stereochemistry

Unless specifically indicated, throughout the specification and claims, a given chemical formula or name shall encompass tautomers and all stereo, optical and geometrical isomers (e.g. enantiomers, diastereomers, +/−, R/S, E/Z isomers etc.) racemic mixtures and racemates thereof. This includes mixtures in different proportions of the separate enantiomers, mixtures of diastereomers, or mixtures of any of the foregoing forms where such isomers and enantiomers exist, as well as salts, including pharmaceutically acceptable salts and solvates thereof such as hydrates, solvates of the free compounds or solvates of a salt of the compound.

Derivatives of Compounds of the Invention

The invention further encompasses salts, solvates, hydrates, N-oxides, prodrugs and active metabolites of the compounds of formula I, IA or IB or combinations thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals such as aluminium, calcium, lithium, magnesium, potassium, sodium, zinc and the like (see Pharmaceutical salts, Berge, S. M. et al., *J. Pharm. Sci.*, (1977), Vol. 66, pp. 1-19).

Pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts), also comprise a part of the invention.

Typically, a pharmaceutically acceptable salt of a compound of formula I, IA or IB may be readily prepared by using a desired acid or base as appropriate. The salt may precipitate from solution and be collected by filtration or may be recovered by evaporation of the solvent. For example, an aqueous solution of an acid such as hydrochloric acid may be added to an aqueous suspension of a compound of formula I, IA or IB and the resulting mixture evaporated to dryness (lyophilized) to obtain the acid addition salt as a solid. Alternatively, a compound of formula I, IA or IB may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

The acid addition salts of the compounds of formula I, IA or IB may be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the invention.

Also included are both total and partial salts, that is to say salts with 1, 2 or 3, preferably 2, equivalents of base per mole of acid of formula I, IA or IB or salts with 1, 2 or 3 equivalents, preferably 1 equivalent, of acid per mole of base of formula I, IA or IB.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine.

The base addition salts of said acidic compounds are prepared by contacting the free acid form with a sufficient amount of the desired base to produce the salt in the conventional manner. The free acid form may be regenerated by contacting the salt form with an acid and isolating the free acid.

Compounds of the invention may have both a basic and an acidic centre and may therefore be in the form of zwitterions or internal salts.

Typically, a pharmaceutically acceptable salt of a compound of formula I, IA or IB may be readily prepared by using a desired acid or base as appropriate. The salt may precipitate from solution and be collected by filtration or may be recovered by evaporation of the solvent. For example, an aqueous solution of an acid such as hydrochloric acid may be added to an aqueous suspension of a compound of formula I, IA or IB and the resulting mixture evaporated to dryness (lyophilized) to obtain the acid addition salt as a solid. Alternatively, a compound of formula I, IA or IB may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The salts of the compound of formula I, IA or IB may form solvates (e.g., hydrates) and the invention also includes all such solvates. The meaning of the word "solvates" is well known to those skilled in the art as a compound formed by interaction of a solvent and a solute (i.e., solvation). Techniques for the preparation of solvates are well established in the art (see, for example, Brittain. *Polymorphism in Pharmaceutical solids*. Marcel Decker, New York, 1999.).

The invention also encompasses N-oxides of the compounds of formula I, IA or IB. The term "N-oxide" means that for heterocycles containing an otherwise unsubstituted $sp^2$ N atom, the N atom may bear a covalently bound O atom, i.e., —N→O. Examples of such N-oxide substituted heterocycles include pyridyl N-oxides, pyrimidyl N-oxides, pyrazinyl N-oxides and pyrazolyl N-oxides.

The invention also encompasses prodrugs of the compounds of formula I, IA or IB, i.e., compounds which release an active parent drug according to formula I, IA or IB in vivo when administered to a mammalian subject. A prodrug is a pharmacologically active or more typically an inactive compound that is converted into a pharmacologically active agent by a metabolic transformation. Prodrugs of a compound of formula I, IA or IB are prepared by modifying functional groups present in the compound of formula I, IA or IB in such a way that the modifications may be cleaved in vivo to release the parent compound. In vivo, a prodrug readily undergoes chemical changes under physiological conditions (e.g., are acted on by naturally occurring enzyme(s)) resulting in liberation of the pharmacologically active agent. Prodrugs include compounds of formula I, IA or IB wherein a hydroxy, amino, or carboxy group of a formula I, IA or IB compound is bonded to any group that may be cleaved in vivo to regenerate the free hydroxyl, amino or carboxy group, respectively. Examples of prodrugs include esters (e.g., acetate, formate, and benzoate derivatives) of compounds of formula I, IA or IB or any other derivative which upon being brought to the physiological pH or through enzyme action is converted to the active parent drug. Conventional procedures for the selection and preparation of suitable prodrug derivatives are described in the art (see, for example, Bundgaard. *Design of Prodrugs*. Elsevier, 1985).

Prodrugs may be administered in the same manner as and in effective amounts analogous to the active ingredient to which they convert or they may be delivered in a reservoir form, e.g., a transdermal patch or other reservoir which is adapted to permit (by provision of an enzyme or other appropriate reagent) conversion of a prodrug to the active ingredient slowly over time, and delivery of the active ingredient to the patient.

The invention also encompasses metabolites. A "metabolite" of a compound disclosed herein is a derivative of a compound which is formed when the compound is metabolised. The term "active metabolite" refers to a biologically active derivative of a compound which is formed when the compound is metabolized. The term "metabolized" refers to the sum of the processes by which a particular substance is changed in the living body. In brief, all compounds present in the body are manipulated by enzymes within the body in order to derive energy and/or to remove them from the body. Specific enzymes produce specific structural alterations to the compound. For example, cytochrome P450 catalyses a variety of oxidative and reductive reactions while uridine diphosphate glucuronyltransferases catalyse the transfer of an activated glucuronic-acid molecule to aromatic alcohols, aliphatic alcohols, carboxylic acids, amines and free sulphydryl groups. Further information on metabolism may be obtained from *The Pharmacological Basis of Therapeutics*, 9th Edition, McGraw-Hill (1996), pages 11-17.

Metabolites of the compounds disclosed herein can be identified either by administration of compounds to a host and analysis of tissue samples from the host, or by incubation of compounds with hepatic cells in vitro and analysis of the resulting compounds. Both methods are well known in the art.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

The compounds of the invention may be formulated for administration in any convenient way for use in human or veterinary medicine and the invention therefore includes within its scope pharmaceutical compositions comprising a compound of the invention adapted for use in human or veterinary medicine. Such compositions may be presented for use in a conventional manner with the aid of one or more suitable carriers. Acceptable carriers for therapeutic use are well-known in the pharmaceutical art, and are described, for example, in Remington's Pharmaceutical Sciences, Mack Publishing Co. (A. R. Gennaro edit. 1985). The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

Pharmaceutical Compositions Comprising a Compound of Formula I, IA or IB

While it is possible that a compound I may be administered as the bulk substance, it is preferable to present the active ingredient in a pharmaceutical formulation, e.g., wherein the agent is in admixture with a pharmaceutically acceptable carrier selected with regard to the intended route of administration and standard pharmaceutical practice.

Accordingly, the invention further provides a pharmaceutical composition comprising a compound of formula I, IA or IB or a solvate, hydrate, isomer (e.g., enantiomer, diastereomer, etc.), N-oxide or pharmaceutically acceptable salt or combinations thereof in admixture with a pharmaceutically acceptable carrier. The term "carrier" refers to a diluent, excipient, and/or vehicle with which an active compound is administered.

A compound of formula I, IA or IB may be used in combination with other therapies and/or active agents. Accordingly, the invention provides, in a further aspect, a pharmaceutical composition comprising a compound of formula I, IA or IB or a solvate, hydrate, isomer (e.g., enantiomer, diastereomer, etc.), N-oxide or pharmaceutically acceptable salt or combinations thereof, a second active agent, and a pharmaceutically acceptable carrier.

The pharmaceutical compositions may comprise as, in addition to, the carrier any suitable binder, lubricant, suspending agent, coating agent and/or solubilizing agent.

Preservatives, stabilizers, dyes and flavouring agents also may be provided in the pharmaceutical composition. Antioxidants and suspending agents may be also used.

The compounds of the invention may be reduced to fine particulate form (e.g., milled using known milling procedures such as wet milling) to obtain a particle size appropriate for tablet formation and for other formulation types. Finely divided (nanoparticulate) preparations of the compounds of the invention may be prepared by processes known in the art, for example see the disclosure of WO02/00196.

Routes of Administration and Unit Dosage Forms

The routes for administration include oral (e.g., as a tablet, capsule, or as an ingestible solution), topical, mucosal (e.g., as a nasal spray or aerosol for inhalation), nasal, parenteral (e.g., by an injectable form), gastrointestinal, intraspinal, intraperitoneal, intramuscular, intravenous, intrauterine, intraocular, intradermal, intracranial, intrathecal, intratracheal, intravaginal, intracerebroventricular, intracerebral, subcutaneous, ophthalmic (including intravitreal or intracameral), transdermal, rectal, buccal, epidural and sublingual. The compositions of the invention may be especially formulated for any of those administration routes. Preferably, the pharmaceutical compositions of the invention are formulated in a form that is suitable for oral delivery.

There may be different composition/formulation requirements depending on the different delivery systems. It is to be understood that not all of the compounds need to be administered by the same route. Likewise, if the composition comprises more than one active component, then those components may be administered by different routes. By way of example, the pharmaceutical composition of the invention may be formulated to be delivered using a mini-pump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be delivered by multiple routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile. For example, the compound of formula I, IA or IB may be coated with an enteric coating layer. The enteric coating layer material may be dispersed or dissolved in either water or in a suitable organic solvent. As enteric coating layer polymers, one or more, separately or in combination, of the following can be used; e.g., solutions or dispersions of methacrylic acid copolymers, cellulose acetate phthalate, cellulose acetate butyrate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating layer polymer(s). For environmental reasons, an aqueous coating process may be preferred. In such aqueous processes methacrylic acid copolymers are most preferred.

When appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For buccal or sublingual administration, the compositions may be administered in the form of tablets or lozenges, which can be formulated in a conventional manner.

When the composition of the invention is to be administered parenterally, such administration includes one or more of: intravenously, intraarterially, intraperitoneally, intrathecally, intraventricularly, intraurethrally, intrasternally, intracranially, intramuscularly or subcutaneously administering the agent; and/or by using infusion techniques.

Pharmaceutical compositions of the invention can be administered parenterally, e.g., by infusion or injection. Pharmaceutical compositions suitable for injection or infusion may be in the form of a sterile aqueous solution, a dispersion or a sterile powder that contains the active ingredient, adjusted, if necessary, for preparation of such a sterile solution or dispersion suitable for infusion or injection. This preparation may optionally be encapsulated into liposomes. In all cases, the final preparation must be sterile, liquid, and stable under production and storage conditions. To improve storage stability, such preparations may also contain a preservative to prevent the growth of microorganisms. Prevention of the action of micro-organisms can be achieved by the addition of various antibacterial and antifungal agents, e.g., paraben, chlorobutanol, sodium acetate, sodium lactate, sodium citrate or acsorbic acid. In many cases isotonic substances are recommended, e.g., sugars, buffers and sodium chloride to assure osmotic pressure similar to those of body fluids, particularly blood. Prolonged absorption of such injectable mixtures can be achieved by introduction of absorption-delaying agents, such as aluminium monostearate or gelatin.

Dispersions can be prepared in a liquid carrier or intermediate, such as glycerin, liquid polyethylene glycols, triacetin oils, and mixtures thereof. The liquid carrier or intermediate can be a solvent or liquid dispersive medium that contains, for example, water, ethanol, a polyol (e.g., glycerol, propylene glycol or the like), vegetable oils, non-toxic glycerine esters and suitable mixtures thereof. Suitable flowability may be maintained, by generation of liposomes, administration of a suitable particle size in the case of dispersions, or by the addition of surfactants.

For parenteral administration, the compound is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Sterile injectable solutions can be prepared by mixing a compound of formula I, IA or IB with an appropriate solvent and one or more of the aforementioned carriers, followed by sterile filtering. In the case of sterile powders suitable for use in the preparation of sterile injectable solutions, preferable preparation methods include drying in vacuum and lyophilization, which provide powdery mixtures of the aldosterone receptor antagonists and desired excipients for subsequent preparation of sterile solutions.

The compounds according to the invention may be formulated for use in human or veterinary medicine by injection (e.g., by intravenous bolus injection or infusion or via intramuscular, subcutaneous or intrathecal routes) and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilizing, solubilizing and/or dispersing agents. Alternatively, the active ingredient may be in sterile powder form for reconstitution with a suitable vehicle, e.g., sterile, pyrogen-free water, before use.

The compounds of the invention can be administered (e.g., orally or topically) in the form of tablets, capsules, ovules, elixirs, solutions or suspensions, which may contain flavouring or colouring agents, for immediate-, delayed-, modified-, sustained-, pulsed- or controlled-release applications.

The compounds of the invention may also be presented for human or veterinary use in a form suitable for oral or buccal administration, for example in the form of solutions, gels, syrups, mouth washes or suspensions, or a dry powder for constitution with water or other suitable vehicle before use, optionally with flavouring and colouring agents. Solid compositions such as tablets, capsules, lozenges, pastilles, pills, boluses, powder, pastes, granules, bullets or premix preparations may also be used. Solid and liquid compositions for oral use may be prepared according to methods well-known in the art. Such compositions may also contain one or more pharmaceutically acceptable carriers and excipients which may be in solid or liquid form.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate, stearic acid, glyceryl behenate and talc may be included.

The compositions may be administered orally, in the form of rapid or controlled release tablets, microparticles, mini tablets, capsules, sachets, and oral solutions or suspensions, or powders for the preparation thereof. In addition to the new solid-state forms of pantoprazole of the invention as the active substance, oral preparations may optionally include various standard pharmaceutical carriers and excipients, such as binders, fillers, buffers, lubricants, glidants, dyes, disintegrants, odourants, sweeteners, surfactants, mold release agents, antiadhesive agents and coatings. Some excipients may have multiple roles in the compositions, e.g., act as both binders and disintegrants.

Examples of pharmaceutically acceptable disintegrants for oral compositions include starch, pre-gelatinized starch, sodium starch glycolate, sodium carboxymethylcellulose, croscarmellose sodium, microcrystalline cellulose, alginates, resins, surfactants, effervescent compositions, aqueous aluminum silicates and cross-linked polyvinylpyrrolidone.

Examples of pharmaceutically acceptable binders for oral compositions include acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthane resin, alginates, magnesium-aluminum silicate, polyethylene glycol or bentonite.

Examples of pharmaceutically acceptable fillers for oral compositions include lactose, anhydrolactose, lactose monohydrate, sucrose, dextrose, mannitol, sorbitol, starch, cellulose (particularly microcrystalline cellulose), dihydro- or anhydro-calcium phosphate, calcium carbonate and calcium sulphate.

Examples of pharmaceutically acceptable lubricants useful in the compositions of the invention include magnesium stearate, talc, polyethylene glycol, polymers of ethylene oxide, sodium lauryl sulphate, magnesium lauryl sulphate, sodium oleate, sodium stearyl fumarate, and colloidal silicon dioxide.

Examples of suitable pharmaceutically acceptable odourants for the oral compositions include synthetic aromas and natural aromatic oils such as extracts of oils, flowers, fruits (e.g., banana, apple, sour cherry, peach) and combinations thereof, and similar aromas. Their use depends on many factors, the most important being the organoleptic acceptability for the population that will be taking the pharmaceutical compositions.

Examples of suitable pharmaceutically acceptable dyes for the oral compositions include synthetic and natural dyes such as titanium dioxide, beta-carotene and extracts of grapefruit peel.

Examples of useful pharmaceutically acceptable coatings for the oral compositions, typically used to facilitate swallowing, modify the release properties, improve the appearance, and/or mask the taste of the compositions include hydroxypropylmethylcellulose, hydroxypropylcellulose and acrylate-methacrylate copolymers.

Examples of pharmaceutically acceptable sweeteners for the oral compositions include aspartame, saccharin, saccharin sodium, sodium cyclamate, xylitol, mannitol, sorbitol, lactose and sucrose.

Examples of pharmaceutically acceptable buffers include citric acid, sodium citrate, sodium bicarbonate, dibasic sodium phosphate, magnesium oxide, calcium carbonate and magnesium hydroxide.

Examples of pharmaceutically acceptable surfactants include sodium lauryl sulphate and polysorbates.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

The compounds of the invention may also, for example, be formulated as suppositories e.g., containing conventional suppository bases for use in human or veterinary medicine or as pessaries e.g., containing conventional pessary bases.

The compounds according to the invention may be formulated for topical administration, for use in human and veterinary medicine, in the form of ointments, creams, gels, hydrogels, lotions, solutions, shampoos, powders (including spray or dusting powders), pessaries, tampons, sprays, dips, aerosols, drops (e.g., eye ear or nose drops) or pour-ons.

For application topically to the skin, the agent of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax, sorbitan monostearate, a polyethylene glycol, liquid paraffin, polysorbate 60, cetyl esters wax, cetearyl alcohol, 2-octyldodecanol, benzyl alcohol, and water. Such compositions may also contain other pharmaceutically acceptable excipients, such as polymers, oils, liquid carriers, surfactants, buffers, preservatives, stabilizers, antioxidants, moisturizers, emollients, colourants, and odourants.

Examples of pharmaceutically acceptable polymers suitable for such topical compositions include acrylic polymers; cellulose derivatives, such as carboxymethylcellulose sodium, methylcellulose or hydroxypropylcellulose; natural polymers, such as alginates, tragacanth, pectin, xanthan and cytosan.

Examples of suitable pharmaceutically acceptable oils which are so useful include mineral oils, silicone oils, fatty acids, alcohols, and glycols.

Examples of suitable pharmaceutically acceptable liquid carriers include water, alcohols or glycols such as ethanol, isopropanol, propylene glycol, hexylene glycol, glycerol and polyethylene glycol, or mixtures thereof in which the pseudopolymorph is dissolved or dispersed, optionally with the addition of non-toxic anionic, cationic or non-ionic surfactants, and inorganic or organic buffers.

Examples of pharmaceutically acceptable preservatives include sodium benzoate, ascorbic acid, esters of p-hydroxybenzoic acid and various antibacterial and antifungal agents such as solvents, for example ethanol, propylene glycol, benzyl alcohol, chlorobutanol, quaternary ammonium salts, and parabens (such as methyl paraben, ethyl paraben and propyl paraben).

Examples of pharmaceutically acceptable stabilizers and antioxidants include ethylenediaminetetraacetic acid (EDTA), thiourea, tocopherol and butyl hydroxyanisole.

Examples of pharmaceutically acceptable moisturizers include glycerine, sorbitol, urea and polyethylene glycol.

Examples of pharmaceutically acceptable emollients include mineral oils, isopropyl myristate, and isopropyl palmitate.

The compounds may also be dermally or transdermally administered, for example, by use of a skin patch.

For ophthalmic use, the compounds can be formulated as micronized suspensions in isotonic, pH adjusted, sterile saline, or, preferably, as solutions in isotonic, pH adjusted, sterile saline, optionally in combination with a preservative such as a benzylalkonium chloride.

As indicated, the compounds of the invention can be administered intranasally or by inhalation and is conveniently delivered in the form of a dry powder inhaler or an aerosol spray presentation from a pressurized container, pump, spray or nebulizer with the use of a suitable propellant, e.g., dichlorodifluoromethane, trichlorofluoromethane, dichlorotetrafluoroethane, a hydrofluoroalkane such as 1,1, 1,2-tetrafluoroethane (HFA 134AT) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g., using a mixture of ethanol and the propellant as the solvent, which may additionally contain a lubricant, e.g., sorbitan trioleate.

Capsules and cartridges (made, for example, from gelatin) for use in an inhaler or insufflator may be formulated to contain a powder mix of the compound and a suitable powder base such as lactose or starch.

For topical administration by inhalation the compounds according to the invention may be delivered for use in human or veterinary medicine via a nebulizer.

The pharmaceutical compositions of the invention may contain from 0.01 to 99% weight per volume of the active material. For topical administration, for example, the composition will generally contain from 0.01-10%, more preferably 0.01-1% of the active material.

The active agents can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The pharmaceutical composition or unit dosage form of the invention may be administered according to a dosage and administration regimen defined by routine testing in the light of the guidelines given above in order to obtain optimal activity while minimizing toxicity or side effects for a particular patient. However, such fine tuning of the therapeutic regimen is routine in the light of the guidelines given herein.

The dosage of the active agents of the invention may vary according to a variety of factors such as underlying disease conditions, the individual's condition, weight, gender and age, and the mode of administration. An effective amount for treating a disorder can easily be determined by empirical methods known to those of ordinary skill in the art, for example by establishing a matrix of dosages and frequencies of administration and comparing a group of experimental units or subjects at each point in the matrix. The exact amount to be administered to a patient will vary depending on the state and severity of the disorder and the physical condition of the patient. A measurable amelioration of any symptom or parameter can be determined by a person skilled in the art or reported by the patient to the physician.

The amount of the agent to be administered can range between about 0.01 and about 25 mg/kg/day, preferably between about 0.1 and about 10 mg/kg/day and most preferably between 0.2 and about 5 mg/kg/day. It will be understood that the pharmaceutical formulations of the invention need not necessarily contain the entire amount of the agent that is effective in treating the disorder, as such effective amounts can be reached by administration of a plurality of doses of such pharmaceutical formulations. In general, an "effective amount" refers to the amount of a pharmaceutical composition administered to improve, inhibit, or ameliorate a disease or disorder or condition of a subject, or a symptom of a disease or disorder, in a clinically relevant manner. Any clinically relevant improvement in the subject is considered sufficient to achieve treatment. Preferably, an amount sufficient to treat is an amount that prevents the occurrence or one or more symptoms of the infection or is an amount that reduces the severity of, or the length of time during which a subject suffers from, or develops, one or more symptoms of the infection relative to a control subject that is not treated with a composition of the invention).

Preferred compounds of the invention according to formula I, IA or IB are formulated in capsules or tablets, preferably containing 10 to 200 mg of the compounds of the invention, and are preferably administered to a patient at a total daily dose of 10 to 300 mg, preferably 20 to 150 mg and most preferably about 50 mg.

A pharmaceutical composition for parenteral administration contains from about 0.01% to about 100% by weight of the active agents of the invention, based upon 100% weight of total pharmaceutical composition.

Generally, transdermal dosage forms contain from about 0.01% to about 100% by weight of the active agents versus 100% total weight of the dosage form.

The pharmaceutical composition or unit dosage form may be administered in a single daily dose, or the total daily dosage may be administered in divided doses. In addition, co-administration or sequential administration of another compound for the treatment of the disorder may be desirable. To this purpose, the combined active principles are formulated into a simple dosage unit.

For combination treatment where the compounds are in separate dosage formulations, the compounds can be administered concurrently, or each can be administered at staggered intervals. For example, the compound of the invention may be administered in the morning and the antimuscarinic compound may be administered in the evening, or vice versa. Additional compounds may be administered at specific intervals too. The order of administration will depend upon a variety of factors including age, weight, gender and medical condition of the patient; the severity and etiology of the disorders to be treated, the route of administration, the renal and hepatic function of the patient, the treatment history of the patient, and the responsiveness of the patient. Determination of the order of administration may be fine-tuned and such fine-tuning is routine in the light of the guidelines given herein.

Synthesis

Compounds of formula I, IA or IB, and enantiomers, diastereomers, N-oxides, and pharmaceutically acceptable salts or combinations thereof, may be prepared by the general methods outlined hereinafter, said methods constituting a further aspect of the invention.

The compounds of this invention can be prepared by employing reactions as shown in the following schemes, in addition to other standard manipulations that are known in the literature, exemplified in the experimental section or clear to one skilled in the art. The starting materials which are not described herein are either commercially available or may be prepared by employing reactions described in the literature or are clear to one skilled in the art. The following examples are provided so that the invention might be more fully understood, are illustrative only, and should not be construed as limiting.

It will be appreciated by those skilled in the art that it may be desirable to use protected derivatives of intermediates used in the preparation of the compounds according to formula I, IA or IB. Protection and deprotection of functional groups may be performed by methods known in the art (see, for example, Green and Wuts *Protective Groups in Organic Synthesis*. John Wiley and Sons, New York, 1999).

The abbreviation PG describes a "protecting group" which is introduced to a reactive group before a certain manipulation is carried out, and which is later removed.

Examples of PG's for protecting a reactive group include: acetyl-, trifluoracetyl-, benzoyl-, ethoxycarbonyl-, N-tert-butoxycarbonyl- (BOC), N-benzyloxycarbonyl- (Cbz), benzyl-, methoxybenzyl-, 2,4-dimethoxybenzyl- and for amino groups additionally the phthalyl-group for amino-alkylamino or imino groups; N-methoxynethyl- (MOM), N-benzyloxymethyl-(BOM), N-(trimethylsilyl)ethoxymethyl- (SEM), N-tert-butyl-dimethylsiloxymethyl-, N-tert-butyl-dimethylsilyl- (TBDMS), N-triisopropylsilyl- (TIPS), N-benzyl-, N-4-methoxybenzyl (PMB), N-triphenylmethyl- (Tr), N-tert-butoxycarbonyl-(BOC), N-benzyloxycarbonyl-(Cbz) or N-trimethylsilylethylsulfonyl- (SES) for amide groups; methoxy-, benzyloxy-, trimethylsilyl- (TMS), acetyl-, benzoyl-, tert-butyl-, trityl-, benzyl-, or tetrahydropyranyl (THP) groups for hydroxy groups; or trimethylsilyl- (TMS), methyl-ethyl-, tert-butyl-, benzyl-, or tetrahydropyranyl (THP) groups for carboxyl groups.

The compounds of the invention are generally prepared according to the following schemes.

In some cases, the final product may be further modified, for example by manipulation of substituents. These manipulations may include, but are not limited to, reduction, oxidation, alkylation, acylation, and hydrolysis reactions which are commonly known to those skilled in the art. In some cases, the order of carrying out the foregoing reaction schemes may be varied in order to facilitate the reaction or to avoid unwanted reaction products. The following examples are provided so that the invention might be more fully understood. These examples are illustrative only and should not be constructed as limiting the invention in any way.

As shown in Scheme 1, an N-protected substituted piperidone or pyrrolidinone 1 is reacted with an alkynyl protected dialkyl propargylphosphonate following standard Wadsworth-Horner-Emmons procedure generating almost exclusively the (E)-ene-yne derivative 2. 2 is on turn directly reacted using Sonogashira-Heck coupling methodologies with the proper aryl, alkyl or heteroaryliodide/bromide in the presence of tetrabutylammonium fluoride to produce 4. Alternatively, the alkynyl derivatives 2 could be previously deprotected to afford 3 (using e.g., NaOH or $Na_2CO_3$ in MeOH, or tetrabutylammonium fluoride in THF or other methods very well known to those skilled in the art). This last intermediate could be converted into 4 with Sonogashira or Sonogashira-Heck procedures. N-protected compounds 4 may be unprotected with consolidated methodologies to afford 5. The cyclic amines 5 formed therefrom can be then reacted with an $R_5$—B—$R_4$-LG compound directly. LG represents a leaving group such as halogen, mesylate, tosylate, alkylsulphonate, triflate or other without limitation. This last derivatization procedure can be done using standard methods such us e.g. Buchwald reactions, acylation reactions, reaction with alkyl/arylisocyanates, alkyl/arylchloroformate, chloroformamides, reductive amination, alkylation or any kind of N-derivatization reaction useful to the aim of forming compounds according to formula I, IA or IB and very well known to people skilled in the art. This last reaction can be carried out also by the previous formation of suitable intermediates e.g. a chlorosulphonyl or chlorocarbonyl 1-imidazolylcarbonyl N-derivatives of intermediate 5.

Scheme 1.

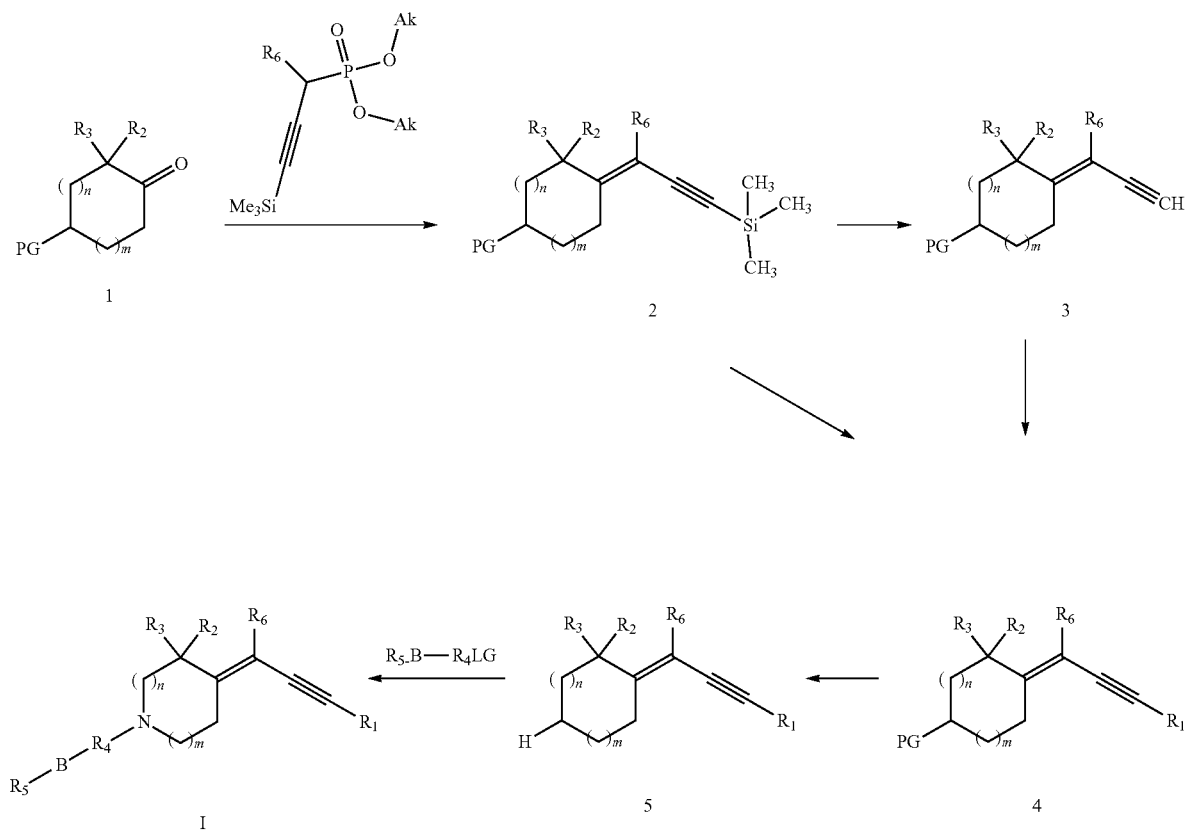

Alternatively, compounds of the invention can be prepared according to Scheme 2:

intermediate could be converted into I using the Sonogashira or Sonogashira-Heck procedure as above described.

Scheme 2.

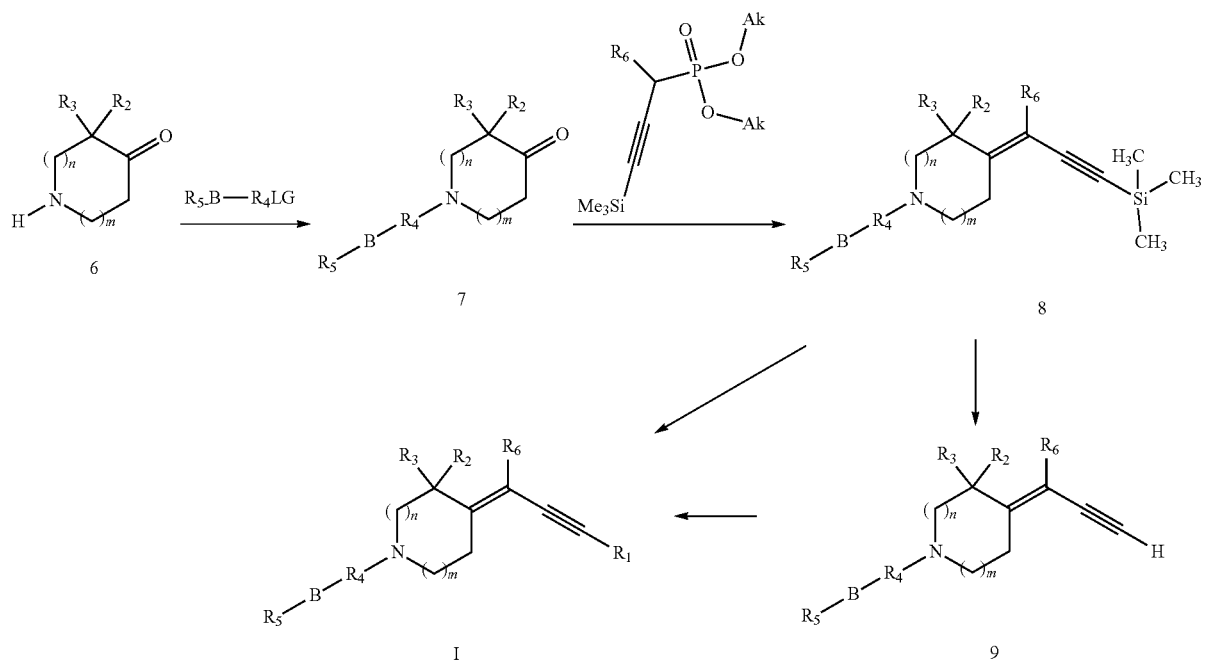

Following Scheme 2, the $R_5$ group is introduced at the beginning of the synthetic pathway by a Buchwald, Sonogashira or Sonogashira-like reaction of the dialkyl or cyclic acetal of propiolaldehyde with the proper alkylating, arylating or derivatising reagent $R_5$—B—$R_4$-LG where LG is a leaving group as defined above.

As per Scheme 2, the $R_5$—B—$R_4$ group can be introduced at the beginning of the synthetic pathway using the proper alkylating, arylating or derivatizing reagent R—B—$R_4$-LG where LG is a leaving group as defined above. For example, LG can be halogen, mesylate, tosylate, alkylsulphonate, triflate or other leaving group without limitation. The starting material 6 can be derivatized using standard methods, e.g., Buchwald reactions, acylation reactions, reaction with alkyl/arylisocyanates, alkyl/arylchloroformate, chloroformamides, aminosulphonyl chloride or by reductive amination, alkylation, or any N-derivatization reaction designed to form compounds according to Formula 7 and very well known to those skilled in the art. This last reaction can be carried out also by the previous formation of suitable intermediates e.g. a chlorosulphonyl or chlorocarbonyl 1-imidazolylcarbonyl N-derivatives of compound 6.

The so obtained intermediate 7 is then reacted with an alkynyl protected dialkyl propargylphosphonate following the standard Wadsworth-Horner-Emmons procedure yielding almost exclusively the (E)-ene-yne derivative 8. Derivative 8 is in turn directly reacted using Sonogashira-Heck coupling methodologies with the proper aryl, alkyl or heteroaryliodide/bromide in the presence of tetrabutylammonium fluoride to produce Compound I. Alternatively, the alkynyl derivative 8 could be previously deprotected to afford Compound 9 (using e.g., NaOH or $Na_2CO_3$ in MeOH, or tetrabutylammonium fluoride in THF or other methods very well known to those skilled in the art). This last The syntheses of other compounds not currently described in the general description above are well documented inside the experimental part of this invention which follows.

The free bases of compounds according to formula I, IA or IB, their diastereomers or enantiomers can be converted to the corresponding pharmaceutically acceptable salts under standard conditions well known in the art. For example, the free base is dissolved in a suitable organic solvent, such as methanol, treated with, for example one equivalent of maleic or oxalic acid, one or two equivalents of hydrochloric acid or methanesulphonic acid, and then concentrated under vacuum to provide the corresponding pharmaceutically acceptable salt. The residue can then be purified by recrystallization from a suitable organic solvent or organic solvent mixture, such as methanol/diethyl ether.

The N-oxides of compounds according to formula I, IA or IB can be synthesized by simple oxidation procedures well known to those skilled in the art.

Preparation of Compounds of the General Formula I, IA or IB

Unless otherwise stated, one or more tautomeric forms of compounds of the examples described hereinafter may be prepared in situ and/or isolated. All tautomeric forms of compounds of the examples described hereinafter should be considered to be disclosed.

The invention is illustrated by way of the following examples, in which the following abbreviations may be employed:
AcOH acetic acid
ACN acetonitrile
Aq. aqueous
BOC tert-butyloxycarbonyl
conc. concentrated
DCM dichloromethane DCE 1,2-dichloroethane
DIPEA N,N-diisopropylethylamine
DMF N,N-dimethylformamide
DMSO dimethyl sulfoxide
DPPF 1,1'-bis(diphenyl-phosphino)ferrocene
EI electron ionisation
ESI electrospray ionisation
EtOAc ethyl acetate
EtOH ethanol
HATU 2-(7-aza-1H-benzotriazole-1-yl)-1,1,3,3-tetramethyluronium hexafluorophosphate
HCl hydrochloric acid
HCOOH formic acid
HPLC high performance liquid chromatography
HPLC-MS HPLC coupled with mass spectrometry
i.vac. under vacuum
MeOH methanol
MS mass spectrometry
MW molecular weight
NaOH sodium hydroxide
NH$_4$OH ammonium hydroxide (30% ammonia in water)
PE petroleum ether
R$_f$ retention value (from thin layer chromatography)
RT or r.t. room temperature
R.sub.t retention time (from HPLC)
TBTU 2-(1H-benzotriazole-1-yl)-1,1,3,3-tetramethyluronium tetrafluoroborate
THF tetrahydrofurane
TEA triethylamine
TFA trifluoroacetic acid
THF tetrahydrofurane.

The following examples illustrate some of the compounds of general formula I, IA or IB as described above. These examples are illustrative only and are not intended to limit the scope of the invention. The reagents and starting materials are readily available to those skilled in the art.

Example 1 tert-Butyl (4E)-3,3-dimethyl-4-[3-(6-methylpyridin-2-yl)prop-2-yn-1-ylidene]piperidine-1-carboxylate tert-butyl (4E)-3,3-dimethyl-4-(3-trimethylsilylprop-2-ynylidene)piperidine-1-carboxylate (Compound 1a)

To a solution of 3-diethoxyphosphorylprop-1-ynyl(trimethyl)silane (4.26 g, 17.158 mmol) in dry THF (40 mL) stirred at −60° C. under nitrogen atm, was added dropwise lithium [bis(trimethylsilyl)amide] sol. 1M in THF (LiHMDS, 17.158 mL, 17.158 mmol) and the solution was stirred at −60° C. for 1 hour. To this solution tert-butyl 3,3-dimethyl-4-oxo-piperidine-1-carboxylate (3 g, 13.20 mmol) in dry THF (20 mL) was added dropwise and the mixture was stirred at −60° C. for 20 min, heated to r.t. in 2 hours, quenched with water and extracted with EtOAc (3×). The organic layer was dried over Na$_2$SO$_4$ and the solvent was evaporated to dryness to give a crude, which was purified via automated flash chromatography (Isolera Dalton® Biotage, SNAP100 Cartridge), eluting with a EtOAc-Petroleum Ether gradient from 2:98 to 15:85 to give the title product (2.68 g; 63%) as a white powder.

tert-Butyl (4E)-3,3-dimethyl-4-[3-(6-methylpyridin-2-yl)prop-2-yn-1-ylidene]piperidine-1-carboxylate A mixture of Compound 1a (55 mg, 0.171 mmol) 2-bromo-6-methylpyridine (23.4 ul, 0.205 mmol), tetrakis(triphenylphosphine)palladium (7.89 mg, 0.007 mmol), sodium acetate (28 mg, 0.342 mmol) and tetrabutylammonium fluoride (44.7 mg, 0.171 mmol)) in anhydrous DMF (3 mL) was heated at 110° C. into a microwave oven (Biotage Smith Creator®) for 10 min then cooled at r.t. The reaction mixture was poured into water and extracted with EtOAc (3×). The organic layer was dried over Na$_2$SO$_4$ and the solvent was evaporated to dryness to give a crude which was purified via automated flash chromatography (SP1® Biotage, SNAP25 Cartridge), eluting with a EtOAc-Petroleum Ether gradient from 75:25 to 1:1 to give mg 51 (87.6%) of the title compound.

UPLC-MS [M+H]$^+$=341.52

$^1$H NMR (400 MHz, DMSO-d6) δ ppm 7.68 (t, 1H), 7.31 (d, 1H), 7.22 (d, 1H), 5.66 (s, 1H), 3.43 (br t, 2H), 3.15 (s, 2H), 2.62 (br t, 2H), 2.45 (s, 3H), 1.42 (s, 9H), 1.08 (s, 6H)

Example 2 tert-Butyl (4E)-4-[3-(3-chlorophenyl)prop-2-ynylidene]-3,3-dimethyl-piperidine-1-carboxylate Compound 1a was reacted with 1-chloro-3-iodo-benzene instead of 2-bromo-6-methylpyridine following the procedure described for the compound of Example 1. After the usual work-up, the crude residue was purified via automated flash chromatography (Isolera Dalton® Biotage, SNAP25 Cartridge) eluting with a PE-EtOAc gradient from 99:1 to 8:2 to give the title compound (99%).

UPLC-MS [M+H]$^+$=360.60

$^1$H NMR (400 MHz, DMSO-d6) δ ppm 7.52 (s, 1H), 7.36-7.47 (m, 3H), 5.65 (s, 1H), 3.42 (t, 2H), 3.14 (s, 2H), 2.61 (t, 2H), 1.42 (s, 9H), 1.07 (s, 6H)

Example 3

Ethyl (4E)-3,3-dimethyl-4-[3-(6-methylpyridin-2-yl)prop-2-yn-1-ylidene]piperidine-1-carboxylate 2-[(3E)-3-(3,3-Dimethylpiperidin-4-ylidene)prop-1-yn-1-yl]-6-methylpyridine (Compound 3a)

To a solution of the Compound of Example 1 (51 mg, 0.15 mmol) in 4 mL of 1,2-dichloroethane was added trifluoroacetic acid (0.23 mL, 3 mmol) and the reaction mixture was stirred at reflux for 4 h, then was diluted with 1,2-DCE and washed with aq. K$_2$CO$_3$ (2×). Evaporation of the solvent afforded 36 mg of the title compound, which was used for the next reaction step without further purification.

Ethyl (4E)-3,3-dimethyl-4-[3-(6-methylpyridin-2-yl)prop-2-yn-1-ylidene]piperidine-1-carboxylate A solution of Compound 3a (19 mg, 0.080 mmol), triethylamine (TEA, 56.8 ul, 0.396 mmol), ethyl chloroformate (22.7 ul, 0.237 mmol) in 2 mL of 1,2-DCE was stirred at r.t. for 4 h. The reaction was washed with water alkaline by K$_2$CO$_3$, water then dried over Na$_2$SO$_4$ and evaporated to dryness in vacuo to give a crude residue, which was purified via automated flash chromatography (SP1® Biotage, SNAP25 Cartridge), eluting with a PE-EtOAc gradient from 8:2 to 6:4 to afford 22 mg of the title compound (89%).

UPLC-MS [M+H]$^+$=313.61

$^1$H NMR (400 MHz, CHLOROFORM-d) δ ppm 7.54 (t, 1H), 7.24 (d, 1H), 7.08 (d, 1H), 5.63 (s, 1H), 4.19 (q, 2H), 3.56 (t, 2H), 3.24 (br s, 2H), 2.75 (t, 2H), 2.57 (s, 3H), 1.30 (t, 3H), 1.14 (s, 6H)

Example 4

Ethyl (4E)-4-[3-(3-chlorophenyl)prop-2-yn-1-ylidene]-3,3-dimethylpiperidine-1-carboxylate

(4E)-4-[3-(3-Chlorophenyl)prop-2-ynylidene]-3,3-dimethyl-piperidine (Compound 4a)

Following the method reported above for Compound 3a the tile compound was prepared starting from the compound of Example 2 instead of the compound of Example 1 and using chloroform instead of 1,2-DCE. Used in the next step without further purification.

Ethyl (4E)-4-[3-(3-chlorophenyl)prop-2-yn-1-ylidene]-3,3-dimethylpiperidine-1-carboxylate The title compound was prepared following the procedure described for the compound of Example 3 replacing Compound 4a for Compound 3a. Purification via automated flash chromatography (SP1® Biotage, SNAP25 Cartridge), eluting with a PE-EtOAc gradient from 10:0 to 8.5:1.5 afforded the title compound (44.5%).

UPLC-MS $[M+H]^+$=332.46

$^1$H NMR (400 MHz, CHLOROFORM-d) δ ppm 7.42 (s, 1H), 7.22-7.34 (m, 3H), 5.61 (s, 1H), 4.19 (q, 2H), 3.57 (br s, 2H), 3.25 (t, 2H), 2.71 (t, 2H), 1.30 (t, 3H), 1.15 (s, 6H)

Example 5 tert-Butyl (4E)-4-[3-(2-chloropyridin-4-yl)prop-2-yn-1-ylidene]-3,3-dimethylpiperidine-1-carboxylate Compound 1a was reacted with 2-chloro-4-iodopyridine instead of 2-bromo-6-methylpyridine following the procedure described above for the compound of Example 1. After the usual work-up, the crude residue was purified via automated flash chromatography (Isolera Dalton® Biotage, SNAP25 Cartridge) eluting with a PE-EtOAc gradient from 1:0 to 9:1 to give the title compound (79.8%).

UPLC-MS $[M+H]^+$=361.54

$^1$H NMR (400 MHz, CHLOROFORM-d) δ ppm 8.48 (dd, 1H), 7.43 (d, 1H), 7.23 (dd, 1H), 5.61 (s, 1H), 3.53 (t, 2H), 3.21 (s, 2H), 2.73 (t, 2H), 1.50 (s, 9H), 1.14 (s, 6H)

Example 6 tert-Butyl (4E)-3,3-dimethyl-4-[3-(3-methylphenyl)prop-2-yn-1-ylidene]piperidine-1-carboxylate Compound 1a was reacted with 1-iodo-3-methyl-benzene instead of 2-bromo-6-methylpyridine following the procedure described for the compound of Example 1. After the usual work-up, the crude residue was purified via automated flash chromatography (Isolera Dalton® Biotage, SNAP25 Cartridge) eluting with a PE-EtOAc gradient from 95:5 to 6:4 to give the title compound (75.8%) as a pale yellow oil.

UPLC-MS $[M+H]^+$=340.65

$^1$H NMR (400 MHz, DMSO-d6) δ ppm 7.20-7.30 (m, 3H), 7.14-7.20 (m, 1H), 5.63 (s, 1H), 3.42 (t, 2H), 3.14 (s, 2H), 2.60 (t, 2H), 2.30 (s, 3H), 1.42 (s, 9H), 1.07 (s, 6H)

Example 7 tert-Butyl (4E)-3,3-difluoro-4-[3-(6-methylpyridin-2-yl)prop-2-yn-1-ylidene]piperidine-1-carboxylate tert-Butyl (4E)-3,3-difluoro-4-[3-(trimethylsilyl)prop-2-yn-1-ylidene]piperidine-1-carboxylate (Compound 7a)

The title compound was synthesised following the procedure reported above for Compound 1a and replacing tert-butyl 3,3-difluoro-4-oxo-piperidine-1-carboxylate for tert-butyl 3,3-dimethyl-4-oxo-piperidine-1-carboxylate. After the usual work-up the crude was purified via automated flash chromatography (SP1® Biotage), eluting with a PE-EtOAc gradient from 8:2 to 3:7 to give the title product (47.4%) as a white solid.

tert-Butyl (4E)-3,3-difluoro-4-[3-(6-methylpyridin-2-yl)prop-2-yn-1-ylidene]piperidine-1-carboxylate Compound 7a (instead of Compound 1a) was reacted with 2-bromo-6-methylpyridine following the procedure described for the compound of Example 1. After the usual work-up, the crude was purified via automated flash chromatography (SP1® Biotage) eluting with a PE-EtOAc gradient from 8:2 to 3:7 to give the title compound (51.3%) as a brownish oil.

UPLC-MS $[M+H]^+$=349.50

$^1$H NMR (400 MHz, CHLOROFORM-d) δ ppm 7.59 (t, 1H), 7.31 (d, 1H), 7.15 (d, 1H), 6.19 (s, 1H), 3.71-3.83 (m, 2H), 3.57 (t, 2H), 2.81 (t, 2H), 2.60 (s, 3H), 1.51 (s, 9H)

Example 8 tert-Butyl (4E)-4-[3-(3-chlorophenyl)prop-2-yn-1-ylidene]-3,3-difluoropiperidine-1-carboxylate Compound 7a (instead of Compound 1a) was reacted with 1-chloro-3-iodobenzene following the procedure described for the compound of Example 1. After the usual work-up, the crude was purified via automated flash chromatography (SP1® Biotage) eluting with a PE-EtOAc gradient from 8:2 to 3:7 to give the title compound (54.7%) as a brownish oil.

UPLC-MS $[M+H]^+$=368.58

$^1$H NMR (400 MHz, CHLOROFORM-d) δ ppm 7.46 (dd, 1H), 7.33-7.38 (m, 2H), 7.26-7.32 (m, 1H), 6.17 (s, 1H), 3.77 (t, 2H), 3.58 (t, 2H), 2.77 (t, 2H), 1.51 (s, 9H)

Example 9 tert-Butyl (4E)-4-[3-(4-chloropyridin-2-yl)prop-2-yn-1-ylidene]-3,3-difluoropiperidine-1-carboxylate Compound 7a (instead of Compound 1a) was reacted with 4-chloro-2-iodopyridine following the procedure described for the compound of Example 1. After the usual work-up, the crude was purified via automated flash chromatography (SP1® Biotage) eluting with a PE-EtOAc gradient from 8:2 to 3:7 to give the title compound (33.5%) as a brownish oil.
UPLC-MS [M+H]$^+$=369.59
$^1$H NMR (400 MHz, CHLOROFORM-d) δ ppm 8.53 (d, 1H), 7.51 (d, 1H), 7.32 (dd, 1H), 6.19 (s, 1H), 3.78 (t, 2H), 3.58 (t, 2H), 2.82 (t, 2H), 1.51 (s, 9H)

Example 10 tert-Butyl (4E)-3,3-difluoro-4-[3-(3-methylphenyl) prop-2-yn-1-ylidene]piperidine-1-carboxylate Compound 7a (instead of Compound 1a) was reacted with 3-methyliodobenzene following the procedure described for the compound of Example 1. After the usual work-up, the crude was purified via automated flash chromatography (SP1® Biotage) eluting with a PE-EtOAc gradient from 8:2 to 3:7 to give the title compound (52.7%) as a brownish oil.
UPLC-MS [M+H]$^+$=348.49
$^1$H NMR (400 MHz, CHLOROFORM-d) δ ppm 7.22-7.32 (m, 3H), 7.16-7.20 (m, 1H), 6.18 (s, 1H), 3.77 (t, 2H), 3.57 (t, 2H), 2.78 (t, 2H), 2.37 (s, 3H), 1.51 (s, 9H)

Example 11

Ethyl (4E)-3,3-difluoro-4-[3-(6-methylpyridin-2-yl) prop-2-yn-1-ylidene]piperidine-1-carboxylate
2-[(3E)-3-(3,3-difluoropiperidin-4-ylidene)prop-1-yn-1-yl]-6-methylpyridine (Compound 11a)

Following the method reported above for Compound 3a the title compound was prepared starting from the compound of Example 7 instead of compound of Example 1 by reacting overnight at r.t., and using chloroform instead of 1,2-DCE. Used in the next step without further purification. Brownish oil (93.7%).

Ethyl (4E)-3,3-difluoro-4-[3-(6-methylpyridin-2-yl) prop-2-yn-1-ylidene]piperidine-1-carboxylate The title compound was prepared following the procedure described for the compound of Example 3 replacing Compound 11a for Compound 3a. Purification via automated flash chromatography (SP1® Biotage, SNAP10 Cartridge), eluting with a PE-EtOAc gradient from 9:1 to 4:6 afforded the title compound (73%).
UPLC-MS [M+H]$^+$=321.44
$^1$H NMR (400 MHz, CHLOROFORM-d) δ ppm 7.61 (t, 1H), 7.32 (d, 1H), 7.16 (d, 1H), 6.21 (s, 1H), 4.22 (q, 2H), 3.83 (t, 2H), 3.63 (t, 2H), 2.83 (t, 2H), 2.61 (s, 3H), 1.32 (t, 3H)

Ethyl (4E)-4-[3-(3-chlorophenyl)prop-2-yn-1-ylidene]-3,3-difluoropiperidine-1-carboxylate (4E)-4-[3-(3-chlorophenyl)prop-2-ynylidene]-3,3-difluoro-piperidine (Compound 12a)

Following the method reported above for Compound 11a the tile compound was prepared starting from the compound of Example 8 instead of compound of Example 7. Used in the next step without further purification. Brownish oil (91.9%).

Ethyl (4E)-4-[3-(3-chlorophenyl)prop-2-yn-1-ylidene]-3,3-difluoropiperidine-1-carboxylate The title compound was prepared following the procedure described for the compound of Example 3 replacing Compound 11a for Compound 3a. Purification via automated flash chromatography (SP1® Biotage, SNAP10 Cartridge), eluting with a Petroleum Ether-EtOAc gradient from 9:1 to 4:6 afforded the title compound (73%).
UPLC-MS [M+H]$^+$=340.51
$^1$H NMR (400 MHz, CHLOROFORM-d) δ ppm 7.47 (dd, 1H), 7.33-7.38 (m, 2H), 7.26-7.33 (m, 1H), 6.19 (s, 1H), 4.22 (q, 2H), 3.83 (t, 2H), 3.63 (t, 2H), 2.78 (t, 2H), 1.32 (t, 3H)

Example 13

Ethyl (4E)-4-[3-(4-chloropyridin-2-yl)prop-2-yn-1-ylidene]-3,3-difluoropiperidine-1-carboxylate 4-Chloro-2-[(3E)-3-(3,3-difluoro-4-piperidylidene) prop-1-ynyl]pyridine (Compound 13a)

Following the method reported above for Compound 11a the tile compound was prepared starting from the compound of Example 9 instead of the compound of Example 7. Used in the next step without further purification. Brownish oil (91.6%).

Ethyl (4E)-4-[3-(4-chloropyridin-2-yl)prop-2-yn-1-ylidene]-3,3-difluoropiperidine-1-carboxylate The title compound was prepared following the procedure described for the compound of Example 3 replacing Compound 13a for Compound 3a. Purification via automated flash chromatography (SP1® Biotage, SNAP10 Cartridge), eluting with a Petroleum Ether-EtOAc gradient from 9:1 to 4:6 afforded the title compound (39. %). Brownish oil.
UPLC-MS [M+H]$^+$=341.52
$^1$H NMR (400 MHz, CHLOROFORM-d) δ ppm 8.52 (d, 1H), 7.49 (d, 1H), 7.30 (dd, 1H), 6.20 (s, 1H), 4.21 (q, 2H), 3.83 (t, 2H), 3.63 (t, 2H), 2.82 (t, 2H), 1.31 (t, 3H)

Example 14

Ethyl (4E)-3,3-difluoro-4-[3-(3-methylphenyl)prop-2-yn-1-ylidene]piperidine-1-carboxylate (4E)-3,3-difluoro-4-[3-(3-methylphenyl)prop-2-yn-1-ylidene]piperidine (Compound 14a)

Following the method reported above for Compound 11a the tile compound was prepared starting from the compound of Example 10 instead of the compound of Example 7. Used in the next step without further purification. Brownish oil (98.3%).

Ethyl (4E)-3,3-difluoro-4-[3-(3-methylphenyl)prop-2-yn-1-ylidene]piperidine-1-carboxylate The title compound was prepared following the procedure described for the compound of Example 3 replacing Compound 14a for Compound 3a. Purification via automated flash chromatography (SP1® Biotage, SNAP10 Cartridge), eluting with a Petroleum Ether-EtOAc gradient from 9:1 to 4:6 afforded the title compound (62%). Brownish oil.
UPLC-MS [M+H]$^+$=320.48
$^1$H NMR (400 MHz, CHLOROFORM-d) δ ppm 7.22-7.33 (m, 3H), 7.16-7.21 (m, 1H), 6.19 (s, 1H), 4.22 (q, 2H), 3.82 (t, 2H), 3.63 (t, 2H), 2.79 (t, 2H), 2.37 (s, 3H), 1.32 (t, 3H)

Example 15

Ethyl (4E)-4-[3-(2-chloropyridin-4-yl)prop-2-yn-1-ylidene]-3,3-dimethylpiperidine-1-carboxylate 2-Chloro-4-[(3E)-3-(3,3-dimethylpiperidin-4-ylidene)prop-1-yn-1-yl]pyridine (Compound 15a)

Following the method reported above for Compound 3a the tile compound was prepared starting from the compound of Example 5 instead of compound of Example 1. Used in the next step without further purification. Brownish oil (98.2%).

Ethyl (4E)-4-[3-(2-chloropyridin-4-yl)prop-2-yn-1-ylidene]-3,3-dimethylpiperidine-1-carboxylate The title compound was prepared following the procedure described for the compound of Example 3 replacing Compound 15a for Compound 3a. Purification via automated flash chromatography (SP1® Biotage, SNAP10 Cartridge), eluting with a Petroleum Ether-EtOAc gradient from 75:25 to 1:1 afforded the title compound (43.8%).

UPLC-MS [M+H]$^+$=333.55

$^1$H NMR (400 MHz, CHLOROFORM-d) δ ppm 8.49 (d, 1H), 7.44 (d, 1H), 7.25 (dd, 1H), 5.63 (s, 1H), 4.19 (q, 2H), 3.57 (t, 2H), 3.25 (s, 2H), 2.76 (t, 2H), 1.30 (t, 3H), 1.16 (s, 6H)

Example 16

Ethyl (4E)-3,3-dimethyl-4-[3-(3-methylphenyl)prop-2-yn-1-ylidene]piperidine-1-carboxylate (4E)-3,3-Dimethyl-4-[3-(m-tolyl)prop-2-ynylidene]piperidine (Compound 16a)

Following the method reported above for Compound 3a the tile compound was prepared starting from the compound of Example 10 instead of compound of Example 1. Used in the next step without further purification. Brownish oil (94.54%).

Ethyl (4E)-3,3-dimethyl-4-[3-(3-methylphenyl)prop-2-yn-1-ylidene]piperidine-1-carboxylate The title compound was prepared following the procedure described for the compound of Example 3 replacing Compound 16a for Compound 3a. Purification via automated flash chromatography (SP1® Biotage, SNAP10 Cartridge), eluting with a Petroleum Ether-EtOAc gradient from 1:0 to 9:1 afforded the title compound.

UPLC-MS [M+H]$^+$=312.67

$^1$H NMR (400 MHz, CHLOROFORM-d) δ ppm 7.18-7.28 (m, 3H), 7.09-7.18 (m, 1H), 5.62 (s, 1H), 4.19 (q, 2H), 3.57 (t, 2H), 3.24 (br s, 2H), 2.73 (t, 2H), 2.35 (s, 3H), 1.30 (t, 3H), 1.15 (s, 6H)

Example 17

Ethyl (4E)-3,3-dimethyl-4-(3-phenylprop-2-yn-1-ylidene)piperidine-1-carboxylate

Ethyl (4E)-3,3-dimethyl-4-[3-(trimethylsilyl)prop-2-yn-1-ylidene]piperidine-1-carboxylate (Compound 17a)

Prepared following the procedure reported above for Compound 1a using ethyl 3,3-dimethyl-4-oxo-piperidine-1-carboxylate instead of tert-butyl 3,3-dimethyl-4-oxo-piperidine-1-carboxylate Purification via automated flash chromatography (Isolera Dalton Biotage, SNAP50 Cartridge), eluting with a Petroleum Ether-EtOAc-gradient from 97:3 to 15:85 afforded the title product (77%) as a clear oil.

Ethyl (4E)-3,3-dimethyl-4-(3-phenylprop-2-yn-1-ylidene)piperidine-1-carboxylate

Compound 17a (instead of Compound 1a) was reacted with iodobenzene following the procedure described for the compound of Example 1. After the usual work-up, the crude was purified via automated flash chromatography (SP1® Biotage; SNAP 10 cartridge) eluting with a EtOAc-Petroleum Ether gradient from 1:0 to 8:2 to give the title compound (93%) as a clear oil.

UPLC-MS [M+H]$^+$=298.48

$^1$H NMR (400 MHz, DMSO-d$_6$) δ ppm 7.42-7.47 (m, 2H), 7.35-7.39 (m, 3H), 5.66 (s, 1H), 4.07 (q, 2H), 3.46 (t, 2H), 3.18 (s, 2H), 2.63 (t, 2H), 1.20 (t, 3H), 1.08 (s, 6H)

By the same procedure described for the compound of Example 17 using 17a and the proper haloaromatic(heteroaromatic) ring, the following compounds were prepared.

Example 18

Ethyl (4E)-4-[3-(4-chloropyridin-2-yl)prop-2-yn-1-ylidene]-3,3-dimethylpiperidine-1-carboxylate From 2-bromo-4-chloropyridine. Purification: SP1® Biotage; SNAP 10 cartridge; gradient PE-EtOAc from 95:5 to 6:4. Yield: 86.4%; clear oil.

UPLC-MS [M+H]$^+$=333.43

$^1$H NMR (400 MHz, DMSO-d$_6$) δ ppm 8.53 (d, 1H), 7.71 (d, 1H), 7.52 (dd, 1H), 5.70 (s, 1H), 4.08 (q, 2H), 3.48 (t, 2H), 3.20 (s, 2H), 2.66 (t, 2H), 1.20 (t, 3H), 1.09 (s, 6H)

Example 19

Ethyl (4E)-4-[3-(2,5-difluorophenyl)prop-2-yn-1-ylidene]-3,3-dimethylpiperidine-1-carboxylate From 2,5-difluoroiodobenzene. Purification: SP1® Biotage; SNAP 10 cartridge; gradient PE-EtOAc—95:5 to 6:4. Yield: 56.5%; clear oil.

UPLC-MS [M+H]$^+$=334.49

$^1$H NMR (400 MHz, DMSO-d$_6$) δ ppm 7.42 (ddd, 1H), 7.23-7.39 (m, 2H), 5.70 (s, 1H), 4.07 (q, 2H), 3.47 (t, 2H), 3.19 (s, 2H), 2.64 (t, 2H), 1.20 (t, 3H), 1.08 (s, 6H)

Ethyl (4E)-3,3-dimethyl-4-{3-[6-(trifluoromethyl)pyridin-2-yl]prop-2-yn-1-ylidene}piperidine-1-carboxylate From 2-bromo-6-(trifluoromethyl)pyridine. Purification: SP1® Biotage; SNAP 10 cartridge; gradient PE-EtOAc—1:0 to 6:4. Yield: 72.2%; clear oil that tends to solidify.

UPLC-MS [M+H]$^+$=367.44

$^1$H NMR (400 MHz, DMSO-d$_6$) δ ppm 8.11 (dd, 1H), 7.87 (d, 1H), 7.84 (d, 1H), 5.74 (s, 1H), 4.08 (q, 2H), 3.49 (t, 2H), 3.21 (s, 2H), 2.67 (t, 2H), 1.20 (t, 3H), 1.10 (s, 6H)

Example 21

Ethyl (4E)-4-[3-(3-fluorophenyl)prop-2-yn-1-ylidene]-3,3-dimethylpiperidine-1-carboxylate

Ethyl (4E)-3,3-dimethyl-4-prop-2-ynylidene-piperidine-1-carboxylate (Compound 21a)

To a solution of Compound 17a (1.6 g, 5.45 mmol) in THF (20 mL) was added under stirring a solution of tetrabutylammonium fluoride (1.6 g, 5.75 mmol) in THF (20 mL), stirring was continued for 30 min. at r.t. The reaction mixture was poured into water and extracted with EtOAc (3×), washing the combined organic layers with brine, drying ($Na_2SO_4$) and evaporating to dryness in vacuo. The crude residue was purified by automated flash column chromatography (SP1® Biotage; SNAP 60 RP) eluting with 40% acetonitrile to afford 892 mg of the title compound (74%).

Ethyl (4E)-4-[3-(3-fluorophenyl)prop-2-yn-1-ylidene]-3,3-dimethylpiperidine-1-carboxylate A mixture of Compound 21a (40 mg, 0.181 mmol), 1-fluoro-3-iodobenzene (25.5 □ (25.5 o-3-iodo, tetrakis(triphenylphosphine)palladium (8.37 mg, 0.007 mmol), sodium acetate (29.7 mg, 0.362 mmol) in anhydrous DMF (4 mL) was heated at 120° C. into a microwave oven (Biotage Smith Creator®) for 10 min then cooled at r.t. The reaction mixture was poured into water and extracted with EtOAc (3×). The organic layer was dried over $Na_2SO_4$ and the solvent was evaporated to dryness to give a crude which was purified via automated flash chromatography (SP1® Biotage, SNAP10 Cartridge), eluting with a EtOAc-Petroleum Ether gradient from 1:0 to 8:2 to give 37 mg of the title compound as a reddish oil (64.8%).

UPLC-MS $[M+H]^+$=316.51

$^1$H NMR (400 MHz, DMSO-$d_6$) δ ppm 7.39-7.48 (m, 1H), 7.26-7.34 (m, 2H), 7.19-7.26 (m, 1H), 5.66 (s, 1H), 4.08 (q, 2H), 3.46 (t, 2H), 3.19 (s, 2H), 2.63 (t, 2H), 1.20 (t, 3H), 1.08 (s, 6H)

By the same procedure described for the compound of Example 21 using 21a and the proper haloaromatic(heteroaromatic) reagent, the following compounds were prepared:

Example 22

Ethyl (4E)-3,3-dimethyl-4-{3-[3-(trifluoromethyl)phenyl]prop-2-yn-1-ylidene}piperidine-1-carboxylate From 1-iodo-3-trifluoromethylbenzene. Purification: SP1® Biotage; SNAP 10 cartridge; gradient PE-EtOAc—1:0 to 8:2. Yield: 80.5%; clear reddish oil.

UPLC-MS $[M+H]^+$=366.47

$^1$H NMR (400 MHz, DMSO-$d_6$) δ ppm 7.69-7.80 (m, 3H), 7.59-7.67 (m, 1H), 5.68 (s, 1H), 4.08 (q, 2H), 3.47 (br t, 2H), 3.19 (s, 2H), 2.66 (t, 2H), 1.20 (t, 3H), 1.08 (s, 6H)

Example 23

Ethyl (4E)-4-[3-(6-methoxypyridin-2-yl)prop-2-yn-1-ylidene]-3,3-dimethylpiperidine-1-carboxylate From 2-bromo-6-methoxy-pyridine. Purification: SP1® Biotage; SNAP 10 cartridge; gradient PE-EtOAc—1:0 to 8:2. Yield: 65.6%; pale yellow oil.

UPLC-MS $[M+H]^+$=329.49

$^1$H NMR (400 MHz, DMSO-$d_6$) δ ppm 7.69 (dd, 1H), 7.13 (d, 1H), 6.81 (d, 1H), 5.69 (s, 1H), 4.08 (q, 2H), 3.84 (s, 3H), 3.47 (t, 2H), 3.19 (s, 2H), 2.64 (t, 2H), 1.20 (t, 3H), 1.08 (s, 6H)

Example 24

Ethyl (4E)-4-[3-(3-methoxyphenyl)prop-2-yn-1-ylidene]-3,3-dimethylpiperidine-1-carboxylate From 3-iodoanisole. Purification: SP1® Biotage; SNAP 10 cartridge; gradient PE-EtOAc—1:0 to 8:2. Yield: 75.9%; yellowish oil.

UPLC-MS $[M+H]^+$=328.47

$^1$H NMR (400 MHz, DMSO-$d_6$) δ ppm 7.29 (dd, 1H), 7.01 (d, 1H), 6.91-6.99 (m, 2H), 5.65 (s, 1H), 4.07 (q, 2H), 3.77 (s, 3H), 3.46 (br t, 2H), 3.18 (s, 2H), 2.63 (t, 2H), 1.20 (t, 3H), 1.08 (s, 6H)

Example 25

Ethyl (4E)-4-[3-(4-methoxypyridin-2-yl)prop-2-yn-1-ylidene]-3,3-dimethylpiperidine-1-carboxylate From 2-bromo-4-methoxypyridine. Purification: SP1® Biotage; SNAP 10 cartridge; gradient PE-EtOAc—8:2 to 1:1. Yield: 57.2%; pale yellow oil.

UPLC-MS $[M+H]^+$=329.49

$^1$H NMR (400 MHz, DMSO-$d_6$) δ ppm 8.35 (d, 1H), 7.09 (d, 1H), 6.95 (dd, 1H), 5.67 (s, 1H), 4.08 (q, 2H), 3.85 (s, 3H), 3.47 (t, 2H), 3.19 (s, 2H), 2.65 (t, 2H), 1.20 (t, 3H), 1.08 (s, 6H)

Example 26

Ethyl (4E)-3,3-dimethyl-4-[3-(pyridin-2-yl)prop-2-yn-1-ylidene]piperidine-1-carboxylate From 2-iodopyridine. Purification: SP1® Biotage; SNAP 10 cartridge; gradient PE-EtOAc from 8:2 to 1:1. Yield: 68.5%; clear reddish oil.

UPLC-MS $[M+H]^+$=299.47

$^1$H NMR (400 MHz, DMSO-$d_6$) δ ppm 8.56 (dd, 1H), 7.80 (ddd, 1H), 7.52 (dd, 1H), 7.36 (ddd, 1H), 5.69 (s, 1H), 4.08 (q, 2H), 3.48 (t, 2H), 3.20 (s, 2H), 2.65 (t, 2H), 1.20 (t, 3H), 1.09 (s, 6H)

Example 27

Ethyl (4E)-4-[3-(3-cyanophenyl)prop-2-yn-1-ylidene]-3,3-dimethylpiperidine-1-carboxylate From 3-cyanoiodobenzene. Purification: SP1® Biotage; SNAP 10 cartridge; gradient PE-EtOAc—1:0 to 8:2 followed by RP purification with SNAP 12 cartridge eluting with acetonitrile 55:45 to acetonitrile 3:7. Yield: 65.1% %; yellow oil.

UPLC-MS [M+H]$^+$=323.42

$^1$H NMR (400 MHz, DMSO-d$_6$) δ ppm 7.95 (dd, 1H), 7.83 (ddd, 1H), 7.77 (ddd, 1H), 7.59 (dd, 1H), 5.67 (s, 1H), 4.08 (q, 2H), 3.47 (t, 2H), 3.19 (s, 2H), 2.65 (t, 2H), 1.20 (t, 3H), 1.08 (s, 6H)

Example 28

Ethyl (4E)-4-{3-[3-(cyanomethyl)phenyl]prop-2-yn-1-ylidene}-3,3-dimethylpiperidine-1-carboxylate From 3-cyanomethyliodobenzene. Purification: SP1® Biotage; SNAP 10 cartridge; gradient PE-EtOAc—1:0 to 8:2. Yield: 60.8% %; reddish oil.

UPLC-MS [M+H]$^+$=337.47

$^1$H NMR (400 MHz, DMSO-d$_6$) δ ppm 7.38-7.48 (m, 3H), 7.32-7.38 (m, 1H), 5.67 (s, 1H), 4.05 (s, 2H), 4.07 (q, 2H), 3.47 (t, 2H), 3.19 (s, 2H), 2.64 (t, 2H), 1.20 (t, 3H), 1.08 (s, 6H)

Example 29

Ethyl (4E)-4-[3-(6-methoxypyridin-3-yl)prop-2-yn-1-ylidene]-3,3-dimethylpiperidine-1-carboxylate From 5-iodo-2-methoxypyridine. Purification: SP1® Biotage; SNAP 10 cartridge; gradient PE-EtOAc from 8:2 to 1:1. Yield: 15.4%; pale yellow oil.

UPLC-MS [M+H]$^+$=329.41

$^1$H NMR (400 MHz, CHLOROFORM-d) δ ppm 8.26 (d, 1H), 7.59 (dd, 1H), 6.71 (d, 1H), 5.61 (s, 1H), 4.19 (q, 2H), 3.96 (s, 3H), 3.57 (t, 2H), 3.24 (s, 2H), 2.70 (t, 2H), 1.29 (t, 3H), 1.14 (s, 6H)

Example 30

Ethyl (4E)-3,3-dimethyl-4-{3-[6-(methylamino)pyridin-2-yl]prop-2-yn-1-ylidene}piperidine-1-carboxylate From 6-bromopyridin-2-ylmethyamine. Purification: SP1® Biotage; SNAP 10 cartridge; gradient PE-EtOAc from 8:2 to 1:1. Yield: 57.4% %; pale yellow solid.

UPLC-MS [M+H]$^+$=328.77

$^1$H NMR (400 MHz, DMSO-d$_6$) δ ppm 7.35 (dd, 1H), 6.63 (d, 1H), 6.58 (q, 1H), 6.41 (d, 1H), 5.65 (s, 1H), 4.07 (q, 2H), 3.46 (t, 2H), 3.18 (s, 2H), 2.74 (d, 3H), 2.61 (t, 2H), 1.20 (t, 3H), 1.08 (s, 6H)

Example 31

Ethyl (4E)-4-[3-(4-cyanopyridin-2-yl)prop-2-yn-1-ylidene]-3,3-dimethylpiperidine-1-carboxylate From 2-iodoisonicotinonitrile. Purification: SP1® Biotage; SNAP 10 cartridge; gradient PE-EtOAc from 8:2 to 4:6. Yield: 56.4% %; pale yellow oil.

UPLC-MS [M+H]$^+$=324.27

$^1$H NMR (400 MHz, DMSO-d$_6$) δ ppm 8.80 (dd, 1H), 8.04-8.08 (dd, 1H), 7.82 (dd, 1H), 5.72 (s, 1H), 4.08 (q, 2H), 3.48 (t, 2H), 3.20 (s, 2H), 2.67 (t, 2H), 1.20 (t, 3H), 1.09 (s, 6H)

Example 32

Ethyl (4E)-4-[3-(3-cyano-5-fluorophenyl)prop-2-yn-1-ylidene]-3,3-dimethylpiperidine-1-carboxylate From 5-fluoro-3-iodobenzonitrile. Purification: SP1® Biotage; SNAP 10 cartridge; gradient PE-EtOAc from 1:0 to 7:3. Yield: 57.2%; pale yellow solid.

UPLC-MS [M+H]$^+$=341.40

$^1$H NMR (400 MHz, DMSO-d$_6$) δ ppm 7.82-7.90 (m, 2H), 7.70-7.77 (m, 1H), 5.67 (s, 1H), 4.08 (q, 2H), 3.47 (t, 2H), 3.19 (s, 2H), 2.66 (t, 2H), 1.20 (t, 3H), 1.08 (s, 6H)

Example 33

2-{(4E)-3,3-Dimethyl-4-[3-(6-methylpyridin-2-yl)prop-2-yn-1-ylidene]piperidin-1-yl}-6-methyl-3-nitropyridine A solution of Compound 3a (32 mg, 0.133 mmol), 2-chloro-3-nitro-6-picoline (25.2 mg, 0.146 mmol) and triethylamine (23.1 ml, 0.166 mmol) in 1.5 mL of DMAC (dimethylacetamide) was stirred at r.t. for 2 h. After overnight resting, was poured into water and extracted with EtOAc (3×), which was dried (Na$_2$SO$_4$) and evaporated to dryness in vacuo to give a crude which was purified via automated flash chromatography (SP1® Biotage, SNAP10 Cartridge), eluting with a EtOAc-Petroleum Ether gradient from 85:5 to 70:30 to give 50 mg of the title compound. Oil (89.9%).

UPLC-MS [M+H]$^+$=377.50

$^1$H NMR (400 MHz, DMSO-d$_6$) δ ppm 7.82-7.90 (m, 2H), 7.70-7.77 (m, 1H), 5.67 (s, 1H), 4.08 (q, 2H), 3.47 (t, 2H), 3.19 (s, 2H), 2.66 (t, 2H), 1.20 (t, 3H), 1.08 (s, 6H)

Example 34

(3-Chlorophenyl)-{(4E)-4-[3-(3-chlorophenyl)prop-2-yn-1-ylidene]-3,3-dimethylpiperidin-1-yl}methanone A solution of (4E)-4-[3-(3-chlorophenyl)prop-2-ynylidene]-3,3-dimethyl-piperidine (Compound 4a, 0.203 g, 0.781 mmol), triethylamine (0.316 g, 3.125 mmol, 0.433 mL) and 3-chlorobenzoyl chloride (0.274 g, 1.563 mmol, 0.1999 mL) in CHCl$_3$ stabilized with amylene (15 mL) was stirred at r.t. for 1 hour, diluted with CHCl$_3$ and washed with aq. K$_2$C$_{O3}$ water. The organic layer was washed again with water, dried over Na$_2$SO$_4$ and the solvent was evaporated to give a crude which was purified twice via automated flash chromatography (Isolera-Dalton® Biotage, Snap25 Cartridge), eluting with a gradient PE-EtOAc from 8:2 to 3:7 to give the title compound (mg 257, 83%).

UPLC-MS [M+H]$^+$=398.17

$^1$H NMR (400 MHz, CHLOROFORM-d) δ ppm 7.35-7.49 (m, 4H), 7.24-7.35 (m, 4H), 5.65 (s, 1H), 3.08-3.99 (m, 4H), 2.62-2.95 (m, 2H), 1.24 (s, 3H), 1.11 (s, 3H)

Using the proper reagent and Compound 4a and using the same method reported above for the compound of Example 34, the following compounds were prepared:

Example 35

{(4E)-4-[3-(3-Chlorophenyl)prop-2-yn-1-ylidene]-3,3-dimethylpiperidin-1-yl}(piperidin-1-yl)methanone From 1-piperidinecarbonyl chloride using 1,2-DCE (instead of CHCl$_3$) stirring 6 h at r.t. Purification: SP1® Biotage; SNAP 10 cartridge; gradient PE-EtOAc from 75:25 to 1:1. Yield: 70.7%.

UPLC-MS [M+H]$^+$=371.48

$^1$H NMR (400 MHz, DMSO-d$_6$) δ ppm 7.50-7.56 (m, 1H), 7.36-7.47 (m, 3H), 5.62 (s, 1H), 3.22 (t, 2H), 3.08-3.17 (m, 4H), 2.96 (s, 2H), 2.68 (t, 2H), 1.42-1.61 (m, 6H), 1.08 (s, 6H)

Example 36

{(4E)-4-[3-(3-Chlorophenyl)prop-2-yn-1-ylidene]-3,3-dimethylpiperidin-1-yl}(pyrrolidin-1-yl)methanone From 1-pyrrolidinecarbonyl chloride using 1,2-DCE (instead of CHCl$_3$) stirring 6 h at r.t. Purification: SP1® Biotage; SNAP 10 cartridge; gradient PE-EtOAc from 75:25 to 1:1. Yield: 70.7%.

UPLC-MS [M+H]$^+$=357.48

$^1$H NMR (400 MHz, DMSO-d$_6$) δ ppm 7.50-7.55 (m, 1H), 7.35-7.47 (m, 3H), 5.63 (s, 1H), 3.27-3.36 (m, 4H), 3.24 (t, 2H), 2.99 (s, 2H), 2.67 (t, 2H), 1.70-1.84 (m, 4H), 1.10 (s, 6H)

Example 37

(4E)-4-[3-(3-Chlorophenyl)prop-2-yn-1-ylidene]-N,N,3,3-tetramethylpiperidine-1-carboxamide From N,N-dimethylcarbamoyl chloride using 1,2-DCE (instead of CHCl$_3$) stirring 6 h at r.t. Purification: SP1® Biotage; SNAP 10 cartridge; gradient PE-EtOAc from 80:20 to 1:1. Yield: 70.8%.

UPLC-MS [M+H]$^+$=331.45

$^1$H NMR (400 MHz, CHLOROFORM-d) δ ppm 7.39-7.46 (m, 1H), 7.22-7.34 (m, 3H), 5.60 (s, 1H), 3.33 (t, 2H), 3.04 (s, 2H), 2.88 (s, 6H), 2.74-2.80 (t, 2H), 1.17 (s, 6H)

Example 38

(4E)-4-[3-(3-Chlorophenyl)prop-2-yn-1-ylidene]-N,N-diethyl-3,3-dimethylpiperidine-1-carboxamide From N,N-diethylcarbamoyl chloride using 1,2-DCE (instead of CHCl$_3$) stirring 6 h at r.t. Purification: SP1® Biotage; SNAP 10 cartridge; gradient PE-EtOAc from 80:20 to 1:1. Yield: 54.1%.

UPLC-MS [M+H]$^+$=359.91

$^1$H NMR (400 MHz, CHLOROFORM-d) δ ppm 7.40-7.46 (m, 1H), 7.22-7.35 (m, 3H), 5.59 (s, 1H), 3.34 (t, 2H), 3.24 (q, 4H), 3.04 (s, 2H), 2.77 (t, 2H), 1.17 (s, 6H), 1.16 (t, 6H)

Example 39

{(4E)-4-[3-(3-Chlorophenyl)prop-2-yn-1-ylidene]-3,3-dimethylpiperidin-1-yl}(furan-2-yl)methanone From 2-furoyl chloride stirring 6 h at r.t. Purification: SP1® Biotage; SNAP 50 cartridge; gradient PE-EtOAc from 9:1 to 7:3. Yield: 74.8%.

UPLC-MS [M+H]$^+$=354.10

$^1$H NMR (400 MHz, CHLOROFORM-d) δ ppm 7.52 (dd, 1H), 7.41-7.46 (m, 1H), 7.23-7.36 (m, 3H), 7.06 (dd, 1H), 6.52 (dd, 1H), 5.66 (s, 1H), 3.85 (t, 2H), 3.57 (s, 2H), 2.83 (t, 2H), 1.19 (s, 6H)

Example 40

Methyl (4E)-4-[3-(3-Chlorophenyl)prop-2-yn-1-ylidene]-3,3-dimethylpiperidine-1-carboxylate From methyl chloroformate stirring 6 h at r.t. and overnight resting. Purification: SP1® Biotage; SNAP 10 cartridge; gradient PE-EtOAc from 8:2 to 1:1. Yield: 45.8%.

UPLC-MS [M+H]$^+$=318.14

$^1$H NMR (400 MHz, CHLOROFORM-d) δ ppm 7.43 (dd, 1H), 7.22-7.35 (m, 3H), 5.61 (s, 1H), 3.75 (s, 3H), 3.57 (br t, 2H), 3.25 (s, 2H), 2.71 (t, 2H), 1.15 (s, 6H)

Example 41

{(4E)-4-[3-(3-Chlorophenyl)prop-2-yn-1-ylidene]-3,3-dimethylpiperidin-1-yl}(morpholin-4-yl)methanone From 4-morpholinecarbonyl chloride stirring 2 h at r.t. Purification: SP1® Biotage; SNAP 10 cartridge; gradient PE-EtOAc from 8:2 to 6:4. Yield: 45.8%.

UPLC-MS [M+H]$^+$=373.44

$^1$H NMR (400 MHz, CHLOROFORM-d) δ ppm 7.42 (dd, 1H), 7.22-7.35 (m, 3H), 5.61 (s, 1H), 3.68-3.78 (m, 4H), 3.38 (t, 2H), 3.25-3.33 (m, 4H), 3.08 (s, 2H), 2.77 (t, 2H), 1.16 (s, 6H)

Example 42

(4E)-4-[3-(3-Chlorophenyl)prop-2-yn-1-ylidene]-N-methoxy-N,3,3-trimethylpiperidine-1-carboxamide From N-methoxy-N-methylcarbamoyl chloride stirring 6 h at r.t. Purification: SP1® Biotage; SNAP 10 cartridge; gradient PE-EtOAc from 8:2 to 1:1. Yield: 61.6%.

UPLC-MS [M+H]$^+$=347.40

$^1$H NMR (400 MHz, CHLOROFORM-d) δ ppm 7.43 (dd, 1H), 7.23-7.34 (m, 3H), 5.62 (s, 1H), 3.64 (s, 3H), 3.54 (t, 2H), 3.27 (s, 2H), 3.01 (s, 3H), 2.77 (t, 2H), 1.17 (s, 6H)

Example 43

{(4E)-4-[3-(3-Chlorophenyl)prop-2-yn-1-ylidene]-3,3-dimethylpiperidin-1-yl}(3-methylphenyl)methanone From 3-methylbenzoyl chloride stirring 6 h at r.t. Purification: SP1® Biotage; SNAP 10 cartridge; gradient PE-EtOAc from 8:2 to 3:7. Yield: 73%.
UPLC-MS [M+H]$^+$=378.16
$^1$H NMR (400 MHz, DMSO-d$_6$) δ ppm 7.12-7.59 (m, 8H), 5.68 (s, 1H), 3.10-3.78 (m, 4H), 2.70 (br t, 2H), 2.36 (s, 3H), 0.90-1.22 (m, 6H)

Example 44

2-{(3E)-3-[1-(3-Chlorobenzol)-3,3-dimethylpiperidin-4-ylidene]prop-1-yn-1-yl}pyridine-4-carbonitrile tert-Butyl (4E)-4-[3-(4-cyano-2-pyridyl)prop-2-ynylidene]-3,3-dimethyl-piperidine-1-carboxylate (Compound 44a)

The title compound was prepared by the same procedure described for the compound of Example 1 using 2-iodopyridine-4-carbonitrile. After the usual work-up procedure the crude was purified via automated flash chromatography (Biotage Isolera®, SNAP25 column) eluting with PE/AcOEt gradient from 95:5 to 60:40. The desired product was isolated as a pale yellow oil (68.62%).

(4E)-4-[3-(3-chlorophenyl)prop-2-ynylidene]-3,3-dimethyl-piperidine (Compound 44b)

Prepared as described for Compound 4a starting from Compound 44a, using chloroform as solvent and refluxing 20 min. Yellow oil (81.75%) used for the next step without further purification.

2-{(3E)-3-[1-(3-Chlorobenzoyl)-3,3-dimethylpiperidin-4-ylidene]prop-1-yn-1-yl}pyridine-4-carbonitrile Prepared from compound 44b using the method described for Compound 34. The crude residue was purified twice via automated flash chromatography (Isolera® Biotage, SNAP10) eluted with PE/AcOEt gradient from 9:1 to 45:55 and isolate as a pale yellow solid (64.45%).
UPLC-MS [M+H]$^+$=390.29
$^1$H NMR (400 MHz, DMSO-d$_6$) δ ppm 8.68-8.88 (br d, 1H), 8.06 (br d, 1H), 7.81 (br d, 1H), 7.25-7.60 (m, 4H), 5.75 (s, 1H), 3.61-3.86 (m, 1H), 3.34-3.55 (m, 2H), 3.15 (m, 1H), 2.75 (br t, 2H), 0.76-1.34 (m, 6H)

Example 45

(3-Chlorophenyl){(4E)-3,3-dimethyl-4-[3-(3-methylphenyl)prop-2-yn-1-ylidene]piperidin-1-yl}methanone tert-Butyl (4E)-3,3-dimethyl-4-[3-(m-tolyl)prop-2-ynylidene]piperidine-1-carboxylate (Compound 45a)

The title compound was prepared by the same procedure described for the compound of Example 1 using 1-iodo-3-methyl-benzene. After the usual work-up procedure the crude was purified via automated flash chromatography (Biotage Isolera®, SNAP25 column) eluting with PE/AcOEt gradient from 95:5 to 60:40. The desired product was isolated as a pale yellow oil (75.76%).

(4E)-3,3-Dimethyl-4-[3-(m-tolyl)prop-2-ynylidene]piperidine (Compound 45b)

Prepared as described for Compound 4a starting from Compound 45a, using chloroform as solvent and refluxing 20 min. Yellow oil (94.54%) used for the next step without further purification.

(3-Chlorophenyl)(4E)-3,3-dimethyl-4-[3-(3-methylphenyl)prop-2-yn-1-ylidene]piperidin-1-yl methanone Prepared from compound 45b using the method described for Compound 34. The crude residue was purified twice via automated flash chromatography (Isolera® Biotage, SNAP10) eluted with PE/AcOEt gradient from 9:1 to 45:55 and isolate as a pale yellow solid (47%).
UPLC-MS [M+H]$^+$=378.28
$^1$H NMR (400 MHz, DMSO-d$_6$) δ ppm 7.12-7.61 (m, 8H), 5.67 (s, 1H), 3.07-3.76 (m, 4H), 2.71 (br t, 2H), 2.29 (s, 3H), 0.89-1.27 (m, 6H)

Example 46

(2,5-dimethylfuran-3-yl)[(4E)-4-{3-[3-(hydroxymethyl)phenyl]prop-2-yn-1-ylidene]-3,3-dimethylpiperidin-1-yl}methanone tert-Butyl (4E)-4-[3-[3-(hydroxymethyl)phenyl]prop-2-ynylidene]-3,3-dimethyl-piperidine-1-carboxylate (Compound 46a)

The title compound was prepared by the same procedure described for the compound of Example 1 using (3-iodophenyl)methanol. After the usual work-up procedure the crude was purified via automated flash chromatography (Biotage Isolera®, SNAP25 column) eluting with PE/AcOEt gradient from 99:1 to 40:60 (86%).

[3-[(3E)-3-(3,3-dimethyl-4-piperidylidene)prop-1-ynyl]phenyl]methanol (46b)

Prepared as described for Compound 4a starting from Compound 46a, using chloroform as solvent and refluxing 20 min. Yellow oil used for the next step without further purification.

(2,5-dimethylfuran-3-yl)[(4E)-4-{3-[3-(hydroxymethyl)phenyl]prop-2-yn-1-ylidene}-3,3-dimethylpiperidin-1-yl]methanone Prepared from compound 46b using the method described for Compound 34 and replacing and 2,5-dimethylfuran-3-carbonyl chloride for 3-chlorobenzoyl chloride. The crude residue was purified twice via automated flash chromatography (Isolera® Biotage, SNAP10) eluted with PE/AcOEt gradient from 8:2 to 3:7 (65%).
UPLC-MS [M+H]$^+$=378.31
$^1$H NMR (400 MHz, DMSO-d$_6$) δ ppm 7.38 (dd, 1H), 7.27-7.36 (m, 3H), 6.13 (s, 1H), 5.67 (s, 1H), 5.22 (t, 1H), 4.49 (d, 2H), 3.57 (br t, 2H), 3.31 (s, 2H), 2.68 (br t, 2H), 2.25 (d, 6H), 0.90-1.21 (br s, 6H)

Example 47

[(4E)-3,3-Dimethyl-4-(3-{3-[(pyrrolidin-1-yl) methyl]phenyl}prop-2-yn-1-ylidene)piperidin-1-yl] (5-methylfuran-2-yl)methanone tert-butyl (4E)-3,3-dimethyl-4-[3-[3-(pyrrolidin-1-ylmethyl)phenyl]prop-2-ynylidene]piperidine-1-carboxylate (Compound 47a)

The title compound was prepared by the same procedure described for the compound of Example 1 using 1-[(3-iodophenyl)methyl]pyrrolidine. After the usual work-up procedure the crude was purified via automated flash chromatography (Biotage Isolera®, SNAP25 column) eluting with PE/AcOEt gradient from 95:5:1 to 60:40 (72%). Pale yellow oil.

(4E)-3,3-dimethyl-4-[3-[3-(pyrrolidin-1-ylmethyl) phenyl]prop-2-ynylidene]piperidine (47b)

Prepared as described for Compound 4a starting from Compound 47a, using chloroform as solvent and refluxing 20 min. Yellow oil used for the next step without further purification.

[(4E)-3,3-dimethyl-4-(3-{3-[(pyrrolidin-1-yl)methyl] phenyl}prop-2-yn-1-ylidene)piperidin-1-yl](5-methylfuran-2-yl)methanone Prepared from compound 47b using the method described for Compound 34 and replacing and 5-methylfuran-2-carbonyl chloride for 3-chlorobenzoyl chloride. The crude residue was purified twice via automated flash chromatography (Isolera® Biotage, SNAP10) eluted with AcOEt/MeOH gradient from 1:0 to 7:3 (12%).

UPLC-MS [M+H]$^+$=417.48

$^1$H NMR (400 MHz, DMSO-d$_6$) δ ppm 7.36-7.43 (m, 1H), 7.25-7.36 (m, 3H), 6.92 (d, 1H), 6.26 (d, 1H), 5.69 (s, 1H), 3.73 (t, 2H), 3.61 (s, 2H), 3.47 (br s, 2H), 2.73 (br t, 2H), 2.43-2.48 (m, 4H), 2.35 (d, 3H), 1.66-1.79 (m, 4H), 1.10 (s, 6H)

Example 48

Ethyl (3E)-2,2-dimethyl-3-[3-(6-methylpyridin-2-yl) prop-2-yn-1-ylidene]pyrrolidine-1-carboxylate Ethyl (3E)-2,2-dimethyl-3-[3-(trimethylsilyl)prop-2-yn-1-ylidene]pyrrolidine-1-carboxylate (Compound 48a)

Prepared by following the procedure reported above for Compound 1a and substituting ethyl 2,2-dimethyl-3-oxopyrrolidine-1-carboxylate for tert-butyl 3,3-dimethyl-4-oxo-piperidine-1-carboxylate. After the usual work-up procedure, the crude residue was purified via automated flash chromatography (Isolera® Biotage, SNAP25 Cartridge), eluting with a PE-EtOAc gradient from 95:5 to 5:5 to give the title product (68.9%) as a colourless oil.

Ethyl (3E)-2,2-dimethyl-3-[3-(6-methylpyridin-2-yl) prop-2-yn-1-ylidene]pyrrolidine-1-carboxylate Prepared by following the procedure reported above for the compound of Example 1 and substituting Compound 48a for Compound 1a. After the usual work-up procedure, the crude residue was purified via automated flash chromatography (Horizon SP1® Biotage, SNAP50 Cartridge), eluting with a PE-EtOAc gradient from 75:25 to 5:5 affording an oil which spontaneously crystallize to give the title product (79.2%).

UPLC-MS [M+H]$^+$=299.54

$^1$H NMR (400 MHz, DMSO-d$_6$) δ ppm 7.69 (dd, 1H), 7.33 (d, 1H), 7.24 (d, 1H), 5.85 (t, 1H), 4.04 (br s, 2H), 3.49 (t, 2H), 2.82 (td, 2H), 2.46 (s, 3H), 1.47 (s, 6H), 1.20 (t, 3H)

Example 49 tert-Butyl (3E)-2,2-dimethyl-3-[3-(6-methylpyridin-2-yl)prop-2-yn-1-ylidene]pyrrolidine-1-carboxylate Tert-butyl (3E)-2,2-dimethyl-3-[3-(trimethylsilyl) prop-2-yn-1-ylidene]pyrrolidine-1-carboxylate (Compound 49a)

Prepared by following the procedure reported above for Compound 1a and substituting tert-butyl 2,2-dimethyl-3-oxopyrrolidine-1-carboxylate for tert-butyl 3,3-dimethyl-4-oxo-piperidine-1-carboxylate. After the usual work-up procedure, the crude residue was purified via automated flash chromatography (Horizon SP1® Biotage, SNAP50 Cartridge), eluting with a PE-EtOAc gradient from 97:3 to 5:15 to give the title product (64.3%).

tert-Butyl (3E)-2,2-dimethyl-3-[3-(6-methylpyridin-2-yl)prop-2-yn-1-ylidene]pyrrolidine-1-carboxylate Prepared by following the procedure reported above for the compound of Example 1 and substituting Compound 49a for Compound 1a. After the usual work-up procedure, the crude residue was purified via automated flash chromatography (Horizon SP1® Biotage, SNAP50 Cartridge), eluting with a PE-EtOAc gradient from 80:20 to 3:7 affording the title product as a brownish solid (62.8%).

UPLC-MS [M+H]$^+$=327.38

$^1$H NMR (400 MHz, CHLOROFORM-d) δ ppm 7.57 (dd, 1H), 7.26 (d, 1H), 7.11 (d, 1H), 5.61 (s, 1H), 3.54 (br s, 2H), 2.83-2.95 (t, 2H), 2.59 (s, 3H), 1.39-1.68 (m, 15H)

Example 50

Propyl (3E)-2,2-dimethyl-3-[3-(6-methylpyridin-2-yl)prop-2-yn-1-ylidene]pyrrolidine-1-carboxylate 2-[(3E)-3-(2,2-dimethylpyrrolidin-3-ylidene)prop-1-yn-1-yl]-6-methylpyridine (Compound 50a)

Following the method reported above for Compound 3a the tile compound was prepared starting from the compound of Example 49 instead of the compound of Example 1 and using chloroform instead of 1,2-DCE. Brownish solid (98.9%). Used in the next step without further purification.

Propy (3E)-2,2-dimethyl-3-[3-(6-methylpyridin-2-yl)prop-2-yn-1-ylidene]pyrrolidine-1-carboxylate Following the procedure reported above for the compound of Example 3 but substituting Compound 50a for Compound 3a and propyl chloroformate for ethyl chloroformate. After the usual work-up procedure, the crude residue was purified via automated flash chromatography (Horizon SP1® Biotage, HP10 Cartridge), eluting with a PE-EtOAc gradient from 1:0 to 5:5 affording the title product as a pale yellow solid (48.4%).

UPLC-MS [M+H]$^+$=313.12

$^1$H NMR (400 MHz, DMSO-$d_6$) δ ppm 7.69 (dd, 1H), 7.32 (d, 1H), 7.23 (d, 1H), 5.85 (t, 1H), 3.95 (br s, 2H), 3.50 (br t, 2H), 2.83 (td, 2H), 2.46 (s, 3H), 1.53-1.68 (m, 2H), 1.48 (s, 6H), 0.92 (t, 3H)

Example 51

2-Methoxyethyl (3E)-2,2-dimethyl-3-[3-(6-methylpyridin-2-yl)prop-2-yn-1-ylidene]pyrrolidine-1-carboxylate Following the procedure reported above for the compound of Example 3 but replacing Compound 50a for Compound 3a and 2-methoxyethylchloroformate for ethyl chloroformate. After the usual work-up procedure, the crude residue was purified via automated flash chromatography (Horizon SP1® Biotage, HP10 Cartridge), eluting with a PE-EtOAc gradient from 1:0 to 5:5 affording the title product as a colourless oil (85.9%).

UPLC-MS [M+H]$^+$=329.49

$^1$H NMR (400 MHz, DMSO-$d_6$) δ ppm 7.69 (dd, 1H), 7.33 (d, 1H), 7.23 (d, 1H), 5.85 (t, 1H), 4.10 (br s, 2H), 3.40-3.60 (m, 4H), 3.28 (s, 3H), 2.83 (td, 2H), 2.46 (s, 3H), 1.48 (s, 6H)

Example 52

2-Methylpropyl (3E)-2,2-dimethyl-3-[3-(6-methylpyridin-2-yl)prop-2-yn-1-ylidene]pyrrolidine-1-carboxylate Following the procedure reported above for the compound of Example 3 but substituting Compound 50a for Compound 3a and isobutyl chloroformate for ethyl chloroformate. After the usual work-up procedure, the crude residue was purified via automated flash chromatography (Horizon SP1® Biotage, HP10 Cartridge), eluting with a PE-EtOAc gradient from 1:0 to 5:5 affording the title product as a white solid (83.2%).

UPLC-MS [M+H]$^+$=327.53

$^1$H NMR (400 MHz, DMSO-$d_6$) δ ppm 7.69 (dd, 1H), 7.33 (d, 1H), 7.23 (d, 1H), 5.85 (t, 1H), 3.78 (brs, 2H), 3.41-3.59 (m, 2H), 2.83 (td, 2H),2.46 (s, 3H), 1.78-1.97 (m, 1H), 1.48 (s, 6H), 0.92 (br s, 6H)

Example 53

Propan-2-yl (3E)-2,2-dimethyl-3-[3-(6-methylpyridin-2-yl)prop-2-yn-1-ylidene]pyrrolidine-1-carboxylate Following the procedure reported above for the compound of Example 3 but substituting Compound 50a for Compound 3a and isobutyl chloroformate isopropyl chloroformate (1 M in Toluene) for ethyl chloroformate. After the usual work-up procedure, the crude residue was purified via automated flash chromatography (Horizon SP1® Biotage, HP10 Cartridge), eluting with a PE-EtOAc gradient from 1:0 to 5:5 affording the title product as a yellow oil that tends to solidify at 0° C. (66.6%).

UPLC-MS [M+H]$^+$=313.43

$^1$H NMR (400 MHz, DMSO-$d_6$) δ ppm 7.69 (dd, 1H), 7.32 (d, 1H), 7.23 (d, 1H), 5.84 (t, 1H), 4.67-5.01 (m, 1H), 3.47 (t, 2H), 2.81 (td, 2H), 2.46 (s, 3H), 1.47 (s, 6H), 1.19 (br s, 6H)

Example 54

(3E)-N,N,2,2-Tetramethyl-3-[3-(6-methylpyridin-2-yl)prop-2-yn-1-ylidene]pyrrolidine-1-carboxamide Following the procedure reported above for the compound of Example 3 but substituting Compound 50a for Compound 3a and dimethylcarbamoyl chloride for ethyl chloroformate and heating at reflux for 4 h. After the usual work-up procedure, the crude residue was purified via automated flash chromatography (Horizon SP1® Biotage, SNAP10 Cartridge), eluting with a PE-EtOAc gradient from 9:1 to 4:6 affording the title product as a brownish oil (60.9%).

UPLC-MS [M+H]$^+$=298.34

$^1$H NMR (400 MHz, CHLOROFORM-d) δ ppm 7.55 (dd, 1H), 7.25 (d, 1H), 7.10 (d, 1H), 5.62 (t, 1H), 3.49 (t, 2H), 2.91 (td, 2H), 2.81 (s, 6H), 2.58 (s, 3H), 1.55 (s, 6H)

Example 55

{(3E)-2,2-dimethyl-3-[3-(6-methylpyridin-2-yl)prop-2-yn-1-ylidene]pyrrolidin-1-yl}(furan-2-yl)methanone Following the procedure reported above for the compound of Example 3 but substituting Compound 50a for Compound 3a and 2-furoyl chloride for ethyl chloroformate. After the usual work-up procedure, the crude residue was purified via automated flash chromatography (Horizon SP1® Biotage, SNAP10 Cartridge), eluting with a PE-EtOAc gradient from 9:1 to 4:6 affording the title product as a white solid (70.6%).

UPLC-MS [M+H]$^+$=321.40

$^1$H NMR (400 MHz, CHLOROFORM-d) δ ppm 7.60 (br s, 1H), 7.51 (br s, 1H), 7.28 (d, 1H), 7.14 (d, 1H), 7.06 (d, 1H), 6.50 (dd, 1H), 5.71 (t, 1H), 4.05 (t, 2H), 3.07 (t, 2H), 2.62 (s, 3H), 1.72 (s, 6H)

Example 56

(3-Chlorophenyl){(3E)-2,2-dimethyl-3-[3-(6-methylpyridin-2-yl)prop-2-yn-1-ylidene]pyrrolidin-1-yl}methanone Following the procedure reported above for the compound of Example 3 but substituting Compound 50a for Compound 3a and 3-chlorobenzoyl chloride for ethyl chloroformate. After the usual work-up procedure, the crude residue was purified via automated flash chromatography (Horizon SP1® Biotage, SNAP10 Cartridge), eluting with a PE-EtOAc gradient from 9:1 to 4:6 affording the title product as a brownish oil (79.4%). UPLC-MS [M+H]$^+$=365.34

$^1$H NMR (400 MHz, CHLOROFORM-d) δ ppm 7.60-7.89 (m, 1H), 7.33-7.46 (m, 4H), 7.26-7.32 (m, 1H), 7.14-7.25 (m, 1H), 5.71 (t, 1H), 3.52 (br t, 2H), 3.02 (br s, 2H), 2.69 (br s, 3H), 1.73 (s, 6H)

Example 57

{(3E)-2,2-Dimethyl-3-[3-(6-methylpyridin-2-yl)
prop-2-yn-1-ylidene]pyrrolidin-1-yl}(piperidin-1-yl)
methanone Following the procedure reported above for the compound of Example 3 but substituting Compound 50a for Compound 3a and piperidine-1-carbonyl chloride for ethyl chloroformate. After the usual work-up procedure, the crude residue was purified via automated flash chromatography (Horizon SP1® Biotage, SNAP10 Cartridge), eluting with a PE-EtOAc gradient from 8:2 to 2:8 affording the title product as a white solid (67%).
UPLC-MS [M+H]$^+$=338.48
$^1$H NMR (400 MHz, CHLOROFORM-d) δ ppm 7.57 (t, 1H), 7.24 (d, 1H), 7.10 (d, 1H), 5.60 (t, 1H), 3.47 (t, 2H), 3.14 (m, 4H), 2.89 (t, 2H), 2.59 (s, 3H), 1.54-1.64 (m, 6H), 1.53 (s, 6H)

Example 58

{(3E)-2,2-dimethyl-3-[3-(6-methylpyridin-2-yl)prop-
2-yn-1-ylidene]pyrrolidin-1-yl}(pyrrolidin-1-yl)
methanone Following the procedure reported above for the compound of Example 3 but substituting Compound 50a for Compound 3a and pyrrolidine-1-carbonyl chloride for ethyl chloroformate. After the usual work-up procedure, the crude residue was purified via automated flash chromatography (Horizon SP1® Biotage, SNAP10 Cartridge), eluting with a PE-EtOAc gradient from 8:2 to 2:8 affording the title product as a brownish oil (43.7%).
UPLC-MS [M+H]$^+$=324.48
$^1$H NMR (400 MHz, CHLOROFORM-d) δ ppm 7.55 (dd, 1H), 7.25 (d, 1H), 7.09 (d, 1H), 5.62 (t, 1H), 3.52 (t, 2H), 3.30-3.39 (m, 4H), 2.92 (td, 2H), 2.57 (s, 3H), 1.84 (dt, 4H), 1.58 (s, 6H)

Example 59

Methyl (3E)-2,2-dimethyl-3-[3-(6-methylpyridin-2-
yl)prop-2-yn-1-ylidene]pyrrolidine-1-carboxylate Following the procedure reported above for the compound of Example 3 but substituting Compound 50a for Compound 3a and methyl chloroformate for ethyl chloroformate. After the usual work-up procedure, the crude residue was purified via automated flash chromatography (Horizon SP1® Biotage, SNAP10 Cartridge), eluting with a PE-EtOAc gradient from 8:2 to 2:8 affording the title product as a white solid (69.5%).
UPLC-MS [M+H]$^+$=285.41
$^1$H NMR (400 MHz, CHLOROFORM-d) δ ppm 7.57 (dd, 1H), 7.28 (d, 1H), 7.11 (d, 1H), 5.63 (br s, 1H), 3.71 (s, 3H), 3.57 (br s, 2H), 2.93 (t, 2H), 2.60 (s, 3H), 1.55 (s, 6H)

Example 60 tert-Butyl (3E)-2,2-dimethyl-3-[3-(4-methylpyrimi-
din-2-yl)prop-2-yn-1-ylidene]pyrrolidine-1-carboxy-
late Prepared by following the procedure reported above for the compound of Example 1 and substituting Compound 49a for Compound 1a and 2-bromo-4-methylpyrimidine for 2-bromo-6-methylpyridine. After the usual work-up procedure, the crude residue was purified via automated flash chromatography (Horizon SP1® Biotage, SNAP50 Cartridge), eluting with a PE-EtOAc gradient from 80:20 to 2:8 affording the title product (48%).
UPLC-MS [M+H]$^+$=328.28
$^1$H NMR (400 MHz, DMSO-d$_6$) δ ppm 8.63 (d, 1H), 7.34 (d, 1H), 5.87 (t, 1H), 3.44 (t, 2H), 2.80 (td, 2H), 2.46 (s, 3H), 1.46 (s, 6H), 1.41 (s, 9H)

Example 61

Ethyl (3E)-2,2-dimethyl-3-[3-(4-methylpyrimidin-2-
yl)prop-2-yn-1-ylidene]pyrrolidine-1-carboxylate 2-[(3E)-3-(2,2-Dimethylpyrrolidin-3-ylidene)prop-1-
yn-1-yl]-4-methylpyrimidine Compound 61a)

Following the method reported above for Compound 3a, the tile compound was prepared starting from the compound of Example 60 instead of the compound of Example 1 and using DCM instead of 1,2-DCE (100%). Used in the next step without further purification.

Ethyl (3E)-2,2-dimethyl-3-[3-(4-methylpyrimidin-2-
yl)prop-2-yn-1-ylidene]pyrrolidine-1-carboxylate Prepared by following the procedure reported above for the compound of Example 3 but substituting Compound 61a for Compound 3a. After the usual work-up procedure, the crude residue was purified via automated flash chromatography (Horizon SP1® Biotage, HP10 Cartridge), eluting with a PE-EtOAc gradient from 1:0 to 5:5 affording the title product as a pale yellow solid (48.4%).
UPLC-MS [M+H]$^+$=300.21
$^1$H NMR (400 MHz, DMSO-d$_6$) δ ppm 8.63 (d, 1H), 7.34 (d, 1H), 5.89 (t, 1H), 4.04 (br q, 2H), 3.50 (t, 2H), 2.84 (td, 2H), 2.46 (s, 3H), 1.48 (s, 6H), 1.20 (t, 3H)

Example 62

2-Methoxyethyl (3E)-2,2-dimethyl-3-[3-(4-meth-
ylpyrimidin-2-yl)prop-2-yn-1-ylidene]pyrrolidine-1-
carboxylate 2-Methoxyethyl (3E)-2,2-dimethyl-3-[3-(4-meth-
ylpyrimidin-2-yl)prop-2-yn-1-ylidene]pyrrolidine-1-
carboxylate Following the procedure reported above for the compound of Example 3 but substituting Compound 61a for Compound 3a and 2-methoxyethyl chloroformate for ethyl chloroformate. After the usual work-up procedure, the crude residue was purified via automated flash chromatography (Horizon SP1® Biotage, HP10 Cartridge), eluting with a PE-EtOAc gradient from 8:2 to 0:1 affording the title product as a dense yellowish oil (64.4%).
UPLC-MS [M+H]$^+$=330.16
$^1$H NMR (400 MHz, DMSO-d$_6$) δ ppm 8.63 (d, 1H), 7.34 (d, 1H), 5.89 (t, 1H), 4.11 (br s, 2H), 3.45-3.60 (m, 4H), 3.28 (s, 3H), 2.85 (td, 2H), 2.46 (s, 3H), 1.48 (s, 6H)

Example 63

Propan-2-yl (3E)-2,2-dimethyl-3-[3-(4-methylpy-
rimidin-2-yl)prop-2-yn-1-ylidene]pyrrolidine-1-car-
boxylate Following the procedure reported above for the compound of Example 3 but substituting Compound 61a for Compound 3a and isopropyl chloroformate 1M in Toluene for ethyl chloroformate. After the usual work-up procedure, the crude residue was purified via automated flash chromatography (Horizon SP1® Biotage, HP10 Cartridge), eluting with a PE-EtOAc gradient from 8:2 to 0:1 affording the title product (69.3%).

UPLC-MS [M+H]$^+$=314.21

$^1$H NMR (400 MHz, DMSO-d$_6$) δ ppm 8.63 (d, 1H), 7.34 (d, 1H), 5.88 (t, 1H), 4.71-4.96 (m, 1H), 3.48 (t, 2H), 2.83 (td, 2H), 2.46 (s, 3H), 1.48 (s, 6H), 1.19 (s, 6H)

Example 64

Methyl (3E)-2,2-dimethyl-3-[3-(4-methylpyrimidin-2-yl)prop-2-yn-1-ylidene]pyrrolidine-1-carboxylate Following the procedure reported above for the compound of Example 3 but substituting Compound 61a for Compound 3a and methyl chloroformate for ethyl chloroformate. After the usual work-up procedure, the crude residue was purified via automated flash chromatography (Horizon SP1® Biotage, HP10 Cartridge), eluting with a PE-EtOAc gradient from 8:2 to 0:1 affording the title product (69.3%).

UPLC-MS [M+H]$^+$=286.18

$^1$H NMR (400 MHz, DMSO-d$_6$) δ ppm 8.63 (d, 1H), 7.34 (d, 1H), 5.89 (t, 1H), 3.60 (s, 3H), 3.50 (t, 2H), 2.84 (td, 2H), 2.46 (s, 3H), 1.48 (s, 6H)

tert-Butyl (3E)-2,2-dimethyl-3-{3-[6-(methylamino)pyridin-2-yl]prop-2-yn-1-ylidene}pyrrolidine-1-carboxylate Prepared by following the procedure reported above for the compound of Example 1 and substituting Compound 49a for Compound 1a and 2-bromo-4-methylpyrimidine for 2-bromo-6-methylpyridine. After the usual work-up procedure, the crude residue was purified via automated flash chromatography (Horizon SP1® Biotage, SNAP25 Cartridge), eluting with a PE-EtOAc gradient from 9:1 to 1:1 affording the title product as a white solid (83.4%).

UPLC-MS [M+H]$^+$=342.21

$^1$H NMR (400 MHz, DMSO-d$_6$) δ ppm 7.35 (dd, 1H), 6.63 (d, 1H), 6.59 (q, 1H), 6.42 (dd, 1H), 5.79 (t, 1H), 3.42 (t, 2H), 2.70-2.80 (m, 5H), 1.45 (s, 6H), 1.43 (s, 9H)

Example 66

Ethyl (3E)-2,2-dimethyl-3-{3-[6-(methylamino)pyridin-2-yl]prop-2-yn-1-ylidene}pyrrolidine-1-carboxylate 6-[(3E)-3-(2,2-dimethylpyrrolidin-3-ylidene)prop-1-yn-1-yl]-N-methylpyridin-2-amine (Compound 66a)

Following the method reported above for Compound 3a, the tile compound was prepared starting from the compound of Example 66 instead of the compound of Example 1 and using chloroform instead of 1,2-DCE (100%). Used in the next step without further purification.

Ethyl (3E)-2,2-dimethyl-3-{3-[6-(methylamino)pyridin-2-yl]prop-2-yn-1-ylidene}pyrrolidine-1-carboxylate Prepared by following the procedure reported above for the compound of Example 3 but substituting Compound 66a for Compound 3a. After the usual work-up procedure, the crude residue was purified via automated flash chromatography (Horizon SP1® Biotage, SNAP10 Cartridge), eluting with a PE-EtOAc gradient from 8:2 to 5:5 affording the title product as a pale beige solid (90.4%).

UPLC-MS [M+H]$^+$=314.21

$^1$H NMR (400 MHz, DMSO-d$_6$) δ ppm 7.35 (dd, 1H), 6.64 (d, 1H), 6.60 (q, 1H), 6.42 (d, 1H), 5.81 (t, 1H), 4.03 (br q, 2H), 3.48 (t, 2H), 2.79 (td, 2H), 2.74 (d, 3H), 1.47 (s, 6H), 1.20 (t, 3H)

Example 67

Propyl (3E)-2,2-dimethyl-3-{3-[6-(methylamino)pyridin-2-yl}prop-2-yn-1-ylidene]pyrrolidine-1-carboxylate Prepared by following the procedure reported above for the compound of Example 3 but substituting Compound 66a for Compound 3a and n-propyl chloroformate instead of ethyl chloroformate. After the usual work-up procedure, the crude residue was purified via automated flash chromatography (Horizon SP1® Biotage, SNAP10 Cartridge), eluting with a PE-EtOAc gradient from 8:2 to 5:5 affording the title product as a white solid (58.9%).

UPLC-MS [M+H]$^+$=328.20

$^1$H NMR (400 MHz, CHLOROFORM-d) δ ppm 7.45 (dd, 1H), 6.78 (d, 1H), 6.39 (d, 1H), 5.61 (t, 1H), 5.05 (q, 1H), 4.04 (q, 2H), 3.59 (t, 2H), 2.88-2.98 (m, 5H), 1.62-1.77 (m, 2H), 1.54 (s, 6H), 0.99 (t, 3H)

Example 68

2-Methoxyethyl (3E)-2,2-dimethyl-3-{3-[6-(methylamino)pyridin-2-yl]prop-2-yn-1-ylidene}pyrrolidine-1-carboxylate Prepared by following the procedure reported above for the compound of Example 3 but substituting Compound 66a for Compound 3a and 2-methoxyethyl chloroformate instead of ethyl chloroformate. After the usual work-up procedure, the crude residue was purified via automated flash chromatography (Horizon SP1® Biotage, SNAP10 Cartridge), eluting with a PE-EtOAc gradient from 6:4 to 2:8 affording the title product as a yellowish solid (80.9%).

UPLC-MS [M+H]$^+$=344.23

$^1$H NMR (400 MHz, DMSO-d$_6$) δ ppm 7.35 (dd, 1H), 6.64 (d, 1H), 6.60 (q, 1H), 6.42 (d, 1H), 5.81 (t, 1H), 4.10 (br s, 2H), 3.53 (t, 2H), 3.49 (t, 2H), 3.28 (s, 3H), 2.80 (td, 2H), 2.75 (d, 3H), 1.47 (s, 6H)

Example 69

2-Methylpropyl (3E)-2,2-dimethyl-3-{3-[6-(methylamino)pyridin-2-yl]prop-2-yn-1-ylidene}pyrrolidine-1-carboxylate Prepared by following the procedure reported above for the compound of Example 3 but substituting Compound 66a for Compound 3a and isobutyl chloroformate instead of ethyl chloroformate. After the usual work-up procedure, the crude residue was purified via automated flash chromatography (Horizon SP1® Biotage, SNAP10 Cartridge), eluting with a PE-EtOAc gradient from 9:1 to 1:1 affording the title product as a white solid (84.8%).

UPLC-MS [M+H]$^+$=342.28

$^1$H NMR (400 MHz, CHLOROFORM-d) δ ppm 7.44 (dd, 1H), 6.78 (d, 1H), 6.37 (d, 1H), 5.61 (t, 1H), 4.85 (q, 1H), 3.77-4.05 (m, 2H), 3.58 (t, 2H), 2.94 (d, 3H), 2.91 (td, 2H), 1.86-2.05 (m, 1H), 1.54 (s, 6H), 0.98 (s, 6H)

Example 70

Propan-2-yl (3E)-2,2-dimethyl-3-{3-[6-(methylamino)pyridin-2-yl]prop-2-yn-1-ylidene}pyrrolidine-1-carboxylate Prepared by following the procedure reported above for the compound of Example 3 but substituting Compound 66a for Compound 3a and isopropyl chloroformate 1N in toluene instead of ethyl chloroformate. After the usual work-up procedure, the crude residue was purified via automated flash chromatography (Horizon SP1® Biotage, SNAP10 Cartridge), eluting with a PE-EtOAc gradient from 95:5 to 1:1 affording the title product as a yellowish solid (79.3%).

UPLC-MS [M+H]$^+$=328.18

$^1$H NMR (400 MHz, CHLOROFORM-d) δ ppm 7.44 (dd, 1H), 6.77 (d, 1H), 6.38 (d, 1H), 5.61 (t, 1H), 4.95 (q, 2H), 3.44-3.70 (m, 2H), 2.95 (d, 3H), 2.90 (td, 2H), 1.53 (s, 6H), 1.28 (br s, 6H)

Example 71

Methyl (3E)-2,2-dimethyl-3-{3-[6-(methylamino)pyridin-2-yl]prop-2-yn-1-ylidene}pyrrolidine-1-carboxylate Prepared by following the procedure reported above for the compound of Example 3 but substituting Compound 66a for Compound 3a and methyl chloroformate instead of ethyl chloroformate. After the usual work-up procedure, the crude residue was purified via automated flash chromatography (Horizon SP1® Biotage, SNAP10 Cartridge), eluting with a PE-EtOAc gradient from 8:2 to 1:1 affording the title product as a yellowish solid (67.9%).

UPLC-MS [M+H]$^+$=300.48

$^1$H NMR (400 MHz, CHLOROFORM-d) δ ppm 7.43 (dd, 1H), 6.77 (d, 1H), 6.37 (d, 1H), 5.61 (t, 1H), 4.80 (q, 1H), 3.66-3.84 (m, 3H), 3.49-3.66 (m, 2H), 2.94 (d, 3H), 2.91 (td, 2H), 1.54 (s, 6H)

Example 72 tert-Butyl (3E)-3-[3-(4-cyanopyridin-2-yl)prop-2-yn-1-ylidene]-2,2-dimethylpyrrolidine-1-carboxylate Prepared by following the procedure reported above for the compound of Example 1 and substituting Compound 49a for Compound 1a and 2-iodo-4-methylpyridine for 2-bromo-6-methylpyridine. After the usual work-up procedure, the crude residue was purified via automated flash chromatography (Horizon SP1® Biotage, HP50 Cartridge), eluting with a PE-EtOAc gradient from 1:0 to 1:1 affording the title product as a dark brown solid (69.2%).

UPLC-MS [M+H]$^+$=338.41

$^1$H NMR (400 MHz, CHLOROFORM-d) δ ppm 8.77 (dd, 1H), 7.62 (dd, 1H), 7.43 (dd, 1H), 5.62 (t, 1H), 3.56 (br s, 2H), 2.89 (td, 2H), 1.51 (s, 15H)

Example 73

Ethyl (3E)-3-[3-(4-cyanopyridin-2-yl)prop-2-yn-1-ylidene]-2,2-dimethylpyrrolidine-1-carboxylate 2-[(3E)-3-(2,2-Dimethylpyrrolidin-3-ylidene)prop-1-yn-1-yl]pyridine-4-carbonitrile (Compound 73a)

Following the method reported above for Compound 3a, the tile compound was prepared starting from the compound of Example 72 instead of the compound of Example 1 and using dichloromethane instead of 1,2-DCE and stirring at r.t. (100%). Used in the next step without further purification.

Ethyl (3E)-3-[3-(4-cyanopyridin-2-yl)prop-2-yn-1-ylidene]-2,2-dimethylpyrrolidine-1-carboxylate Prepared by following the procedure reported above for the compound of Example 3 but substituting Compound 73a for Compound 3a. After the usual work-up procedure, the crude residue was purified via automated flash chromatography (Horizon SP1® Biotage, SNAP10 Cartridge), eluting with a PE-EtOAc gradient from 8:2 to 0:1 affording the title product as a pale yellow solid (71.9%).

UPLC-MS [M+H]$^+$=310.42

$^1$H NMR (400 MHz, DMSO-d$_6$) δ ppm 8.81 (dd, 1H), 8.07 (d, 1H), 7.83 (dd, 1H), 5.91 (t, 1H), 4.04 (q, 2H), 3.50 (t, 2H), 2.86 (td, 2H), 1.48 (s, 6H), 1.20 (t, 3H)

Example 74

2-Methoxyethyl (3E)-3-[3-(4-cyanopyridin-2-yl)prop-2-yn-1-ylidene]-2,2-dimethylpyrrolidine-1-carboxylate Prepared by following the procedure reported above for the compound of Example 3 but substituting Compound 73a for Compound 3a and 2-methoxyethyl chloroformate instead of ethyl chloroformate. After the usual work-up procedure, the crude residue was purified via automated flash chromatography (Horizon SP1® Biotage, HP10 Cartridge), eluting with a PE-EtOAc gradient from 8:2 to 0:1 affording the title product as a brownish oil (69.1%).

UPLC-MS [M+H]$^+$=340.44

$^1$H NMR (400 MHz, DMSO-d$_6$) δ ppm 8.81 (dd, 1H), 8.06 (s, 1H), 7.83 (dd, 1H), 5.92 (t, 1H), 4.07-4.23 (m, 2H), 3.46-3.61 (m, 4H), 3.28 (s, 3H), 2.87 (td, 2H), 1.49 (s, 6H)

Example 75

2-Methylpropyl (3E)-3-[3-(4-cyanopyridin-2-yl)prop-2-yn-1-ylidene]-2,2-dimethylpyrrolidine-1-carboxylate Prepared by following the procedure reported above for the compound of Example 3 but substituting Compound 73a for Compound 3a and isobutyl chloroformate instead of ethyl chloroformate. After the usual work-up procedure, the crude residue was purified via automated flash chromatography (Horizon SP1® Biotage, SNAP10 Cartridge), eluting with a PE-EtOAc gradient from 1:0 to 3:7 affording the title product as a brownish oil (65.4%).
UPLC-MS [M+H]$^+$=338.41

Example 76

Propan-2-yl (3E)-3-[3-(4-cyanopyridin-2-yl)prop-2-yn-1-ylidene]-2,2-dimethylpyrrolidine-1-carboxylate Prepared by following the procedure reported above for the compound of Example 3 but substituting Compound 73a for Compound 3a and isopropyl chloroformate 1N in toluene instead of ethyl chloroformate. After the usual work-up procedure, the crude residue was purified via automated flash chromatography (Horizon SP1® Biotage, SNAP10 Cartridge), eluting with a PE-EtOAc gradient from 1:0 to 1:1 affording the title product as a yellowish oil (50.5%).
UPLC-MS [M+H]$^+$=324.41
$^1$H NMR (400 MHz, DMSO-d$_6$) δ ppm 8.81 (dd, 1H), 8.06 (dd, 1H), 7.83 (dd, 1H), 5.91 (t, 1H), 4.64-4.99 (m, 1H), 3.48 (t, 2H), 2.85 (td, 2H), 1.48 (s, 6H), 1.19 (s, 6H)

Example 77

Methyl (3E)-3-[3-(4-cyanopyridin-2-yl)prop-2-yn-1-ylidene]-2,2-dimethylpyrrolidine-1-carboxylate Prepared by following the procedure reported above for the compound of Example 3 but substituting Compound 73a for Compound 3a and methyl chloroformate instead of ethyl chloroformate. After the usual work-up procedure, the crude residue was purified via automated flash chromatography (Horizon SP1® Biotage, SNAP10 Cartridge), eluting with a PE-EtOAc gradient from 8:2 to 0:1 affording the title product as a yellowish oil (68.3%).
UPLC-MS [M+H]$^+$=296.38
$^1$H NMR (400 MHz, DMSO-d$_6$) δ ppm 8.81 (dd, 1H), 8.07 (dd, 1H), 7.83 (dd, 1H), 5.92 (t, 1H), 3.55-3.69 (m, 3H), 3.51 (t, 2H), 2.87 (td, 2H), 1.48 (s, 6H)

Example 78 tert-Butyl (3E)-3-[3-(3-cyano-5-fluorophenyl)prop-2-yn-1-ylidene]-2,2-dimethylpyrrolidine-1-carboxylate Prepared by following the procedure reported above for the compound of Example 1 and substituting Compound 49a for Compound 1a and 5-fluoro-3-iodobenzonitrile for 2-bromo-6-methylpyridine. After the usual work-up procedure, the crude residue was purified via automated flash chromatography (Horizon SP1® Biotage, SNAP50 Cartridge), eluting with a PE-EtOAc gradient from 1:0 to 75:25 affording the title product as a yellowish solid (62.1%).
UPLC-MS [M+H]$^+$=355.45
$^1$H NMR (400 MHz, DMSO-d$_6$) δ ppm 7.88 (ddd, 1H), 7.85 (dd, 1H), 7.73 (ddd, 1H), 5.84 (t, 1H), 3.43 (t, 2H), 2.81 (td, 2H), 1.46 (s, 6H), 1.43 (s, 9H)

Example 79

Ethyl (3E)-3-[3-(3-cyano-5-fluorophenyl)prop-2-yn-1-ylidene]-2,2-dimethylpyrrolidine-1-carboxylate 3-[(3E)-3-(2,2-dimethylpyrrolidin-3-ylidene)prop-1-yn-1-yl]-5-fluorobenzonitrile (Compound 79a)

Following the method reported above for Compound 3a, the tile compound was prepared starting from the compound of Example 78 instead of the compound of Example 1 and using chloroform instead of 1,2-DCE and stirring at r.t. (91.5%). Used in the next step without further purification.

Ethyl (3E)-3-[3-(3-cyano-5-fluorophenyl)prop-2-yn-1-ylidene]-2,2-dimethylpyrrolidine-1-carboxylate Prepared by following the procedure reported above for the compound of Example 3 but substituting Compound 79a for Compound 3a. After the usual work-up procedure, the crude residue was purified via automated flash chromatography (Horizon SP1® Biotage, SNAP10 Cartridge), eluting with a PE-EtOAc gradient from 1:0 to 8:2 affording the title product as a white solid (71.9%).
UPLC-MS [M+H]$^+$=327.38
$^1$H NMR (400 MHz, DMSO-d$_6$) δ ppm 7.83-7.92 (m, 2H), 7.70-7.78 (m, 1H), 5.86 (t, 1H), 3.96-4.16 (m, 2H), 3.49 (t, 2H), 2.85 (td, 2H), 1.47 (s, 6H), 1.20 (t, 3H)

Example 80

1-Propyl (3E)-3-[3-(3-cyano-5-fluorophenyl)prop-2-yn-1-ylidene]-2,2-dimethylpyrrolidine-1-carboxylate Prepared by following the procedure reported above for the compound of Example 3 but substituting Compound 79a for Compound 3a and n-propyl chloroformate instead of ethyl chloroformate. After the usual work-up procedure, the crude residue was purified via automated flash chromatography (Horizon SP1® Biotage, HP10 Cartridge), eluting with a PE-EtOAc gradient from 1:0 to 8:2 affording the title product as a clear oil (72.2%).
UPLC-MS [M+H]$^+$=341.20
$^1$H NMR (400 MHz, DMSO-d$_6$) δ ppm 7.89 (ddd, 1H), 7.85 (dd, 1H), 7.74 (ddd, 1H), 5.87 (t, 1H), 3.85-4.10 (m, 2H), 3.50 (t, 2H), 2.85 (td, 2H), 1.52-1.73 (m, 2H), 1.48 (s, 6H), 0.92 (t, 3H)

Example 81

2-Methoxyethyl (3E)-3-[3-(3-cyano-5-fluorophenyl)prop-2-yn-1-ylidene]-2,2-dimethylpyrrolidine-1-carboxylate Prepared by following the procedure reported above for the compound of Example 3 but substituting Compound 79a for Compound 3a and 2-methoxyethyl chloroformate instead of ethyl chloroformate. After the usual work-up procedure, the crude residue was purified via automated flash chromatography (Horizon SP1® Biotage, HP10 Cartridge), eluting with a PE-EtOAc gradient from 95:5 to 6:4 affording the title product as a yellow oil (56.1%).
UPLC-MS [M+H]$^+$=357.40
$^1$H NMR (400 MHz, DMSO-d$_6$) δ ppm 7.88 (ddd, 1H), 7.86 (dd, 1H), 7.74 (ddd, 1H), 5.87 (t, 1H), 4.06-4.20 (m, 2H), 3.43-3.59 (m, 4H), 3.28 (s, 3H), 2.86 (td, 2H), 1.48 (s, 6H)

Example 82

2-Methylpropyl (3E)-3-[3-(3-cyano-5-fluorophenyl)prop-2-yn-1-ylidene]-2,2-dimethylpyrrolidine-1-carboxylate Prepared by following the procedure reported above for the compound of Example 3 but substituting Compound 79a for Compound 3a and isobutyl chloroformate instead of ethyl chloroformate. After the usual work-up procedure, the crude residue was purified via automated flash chromatography (Horizon SP1® Biotage, SNAP10 Cartridge), eluting with a PE-EtOAc gradient from 1:0 to 8:2 affording the title product as a white solid (42.4%).

UPLC-MS [M+H]$^+$=355.43

$^1$H NMR (400 MHz, DMSO-d$_6$) δ ppm 7.88 (ddd, 1H), 7.85 (dd, 1H), 7.74 (ddd, 1H), 5.87 (t, 1H), 3.71-3.93 (m, 2H), 3.51 (t, 2H), 2.86 (td, 2H), 1.80-1.99 (m, 1H), 1.48 (s, 6H), 0.92 (d, 6H)

Example 83

Propan-2-yl (3E)-3-[3-(3-cyano-5-fluorophenyl)prop-2-yn-1-ylidene]-2,2-dimethylpyrrolidine-1-carboxylate Prepared by following the procedure reported above for the compound of Example 3 but substituting Compound 79a for Compound 3a and isopropyl chloroformate 1N in toluene instead of ethyl chloroformate. After the usual work-up procedure, the crude residue was purified via automated flash chromatography (Horizon SP1® Biotage, SNAP10 Cartridge), eluting with a PE-EtOAc gradient from 1:0 to 1:1 affording the title product as a yellowish oil (50.5%).

UPLC-MS [M+H]$^+$=341.38

$^1$H NMR (400 MHz, DMSO-d$_6$) δ ppm 7.87 (ddd, 1H), 7.85 (dd, 1H), 7.74 (ddd, 1H), 5.86 (t, 1H), 4.67-4.94 (m, 1H), 3.47 (dd, 2H), 2.84 (td, 2H), 1.47 (s, 6H), 1.21 (d, 6H)

Example 84

Methyl (3E)-3-[3-(3-cyano-5-fluorophenyl)prop-2-yn-1-ylidene]-2,2-dimethylpyrrolidine-1-carboxylate Prepared by following the procedure reported above for the compound of Example 3 but substituting Compound 73a for Compound 3a and methyl chloroformate instead of ethyl chloroformate. After the usual work-up procedure, the crude residue was purified via automated flash chromatography (Horizon SP1® Biotage, SNAP10 Cartridge), eluting with a PE-EtOAc gradient from 8:2 to 0:1 affording the title product as a white solid (76%).

UPLC-MS [M+H]$^+$=313.38

$^1$H NMR (400 MHz, DMSO-d$_6$) δ ppm 7.83-7.93 (m, 2H), 7.74 (ddd, 1H), 5.86 (t, 1H), 3.59 (s, 3H), 3.50 (t, 2H), 2.86 (td, 2H), 1.47 (s, 6H)

Example 85 tert-Butyl (3E)-3-[3-(4-chloropyridin-2-yl)prop-2-yn-1-ylidene]-2,2-dimethylpyrrolidine-1-carboxylate Prepared by following the procedure reported above for the compound of Example 1 and substituting Compound 49a for Compound 1a and 2-bromo-4-chloropyridine for 2-bromo-6-methylpyridine. After the usual work-up procedure, the crude residue was purified via automated flash chromatography (Horizon SP1® Biotage, SNAP50 Cartridge), eluting with a PE-EtOAc gradient from 8:2 to 6:4 affording the title product. (64.5%).

UPLC-MS [M+H]$^+$=347.43

$^1$H NMR (400 MHz, CHLOROFORM-d) δ ppm 8.49 (d, 1H), 7.45 (d, 1H), 7.26 (dd, 1H), 5.60 (t, 1H), 3.54 (br s, 2H), 2.89 (td, 2H), 1.51 (br s, 15H)

Example 86

{(3E)-3-[3-(4-Chloropyridin-2-yl)prop-2-yn-1-ylidene]-2,2-dimethylpyrrolidin-1-yl}(furan-2-yl)methanone 4-Chloro-2-[(3E)-3-(2,2-dimethylpyrrolidin-3-ylidene)prop-1-ynyl]pyridine (Compound 86a)

Following the method reported above for Compound 3a, the title compound was prepared starting from the compound of Example 85 instead of the compound of Example 1 and using chloroform instead of 1,2-DCE (93.9%). Used in the next step without further purification.

{(3E)-3-[3-(4-Chloropyridin-2-yl)prop-2-yn-1-ylidene]-2,2-dimethylpyrrolidin-1-yl}(furan-2-yl)methanone Prepared by following the procedure reported above for the compound of Example 3 but substituting Compound 86a for Compound 3a and furoyl chloride instead of ethyl chloroformate. After the usual work-up procedure, the crude residue was purified via automated flash chromatography (Horizon SP1® Biotage, SNAP10 Cartridge), eluting with a PE-EtOAc gradient from 8:2 to 1:1 affording the title product (48.7%).

UPLC-MS [M+H]$^+$=341.38

$^1$H NMR (400 MHz, CHLOROFORM-d) δ ppm 8.52 (d, 1H), 7.52 (dd, 1H), 7.49 (d, 1H), 7.31 (dd, 1H), 7.07 (dd, 1H), 6.51 (dd, 1H), 5.71 (t, 1H), 4.06 (t, 2H), 3.08 (td, 2H), 1.73 (s, 6H)

Example 87

(3E)-3-[3-(4-Chloropyridin-2-yl)prop-2-yn-1-ylidene]-N,N-diethyl-2,2-dimethylpyrrolidine-1-carboxamide Prepared by following the procedure reported above for the compound of Example 3 but substituting Compound 86a for Compound 3a and N,N-diethylcarbamoyl chloride (3 eq.) instead of ethyl chloroformate and stirring at 60° C. for 4 h. After the usual work-up procedure, the crude residue was purified via automated flash chromatography (Horizon SP1® Biotage, SNAP10 Cartridge), eluting with a PE-EtOAc gradient from 8:2 to 1:1 affording the title product (22.9%).

UPLC-MS [M+H]$^+$=346.46

$^1$H NMR (400 MHz, CHLOROFORM-d) δ ppm 8.50 (d, 1H), 7.47 (d, 1H), 7.29 (dd, 1H), 5.62 (t, 1H), 3.52 (t, 2H), 3.18 (q, 4H), 2.95 (td, 2H), 1.56 (s, 6H), 1.15 (t, 6H)

Example 88

{(3E)-3-[3-(4-Chloropyridin-2-yl)prop-2-yn-1-ylidene]-2,2-dimethylpyrrolidin-1-yl}(pyrrolidin-1-yl)methanone Prepared by following the procedure reported above for the compound of Example 3 but substituting Compound 86a for Compound 3a and 1-pyrrolidinecarbonyl chloride (2.5 eq.) instead of ethyl chloroformate and stirring at 60° C. for 2 h. After the usual work-up procedure, the crude residue was purified via automated flash chromatography (Horizon SP1® Biotage, SNAP10 Cartridge), eluting with a PE-EtOAc gradient from 6:4 to 4:6 affording the title product (35.1%).

UPLC-MS [M+H]⁺=344.50

$^1$H NMR (400 MHz, CHLOROFORM-d) δ ppm 8.50 (d, 1H), 7.47 (d, 1H), 7.29 (dd, 1H), 5.63 (t, 1H), 3.55 (t, 2H), 3.29-3.44 (m, 4H), 2.97 (td, 2H), 1.80-1.92 (m, 4H), 1.59 (s, 6H)

Example 89

{(3E)-3-[3-(4-Chloropyridin-2-yl)prop-2-yn-1-ylidene]-2,2-dimethylpyrrolidin-1-yl}(piperidin-1-yl)methanone Prepared by following the procedure reported above for the compound of Example 3 but substituting Compound 86a for Compound 3a and 1-piperidinecarbonyl chloride (1.5 eq.) instead of ethyl chloroformate and stirring at 60° C. for 2 h. After the usual work-up procedure, the crude residue was purified via automated flash chromatography (Horizon SP1® Biotage, SNAP10 Cartridge), eluting with a PE-EtOAc gradient from 8:2 to 6:4 affording the title product (40.6%).

UPLC-MS [M+H]⁺=358.50

$^1$H NMR (400 MHz, DMSO-d$_6$) δ ppm 8.53 (d, 1H), 7.70 (d, 1H), 7.53 (dd, 1H), 5.81 (t, 1H), 3.44 (t, 2H), 3.04 (br d, 4H), 2.81 (td, 2H), 1.46-1.59 (m, 6H), 1.45 (s, 6H)

Example 90

(3E)-3-[3-(4-chloropyridin-2-yl)prop-2-yn-1-ylidene]-N,N,2,2-tetramethylpyrrolidine-1-carboxamide Prepared by following the procedure reported above for the compound of Example 3 but substituting Compound 86a for Compound 3a and N,N-dimethylcarbamoyl chloride (3 eq.) instead of ethyl chloroformate and stirring overnight. After the usual work-up procedure, the crude residue was purified via automated flash chromatography (Horizon SP1® Biotage, SNAP10 Cartridge), eluting with a PE-EtOAc gradient from 8:2 to 1:1 affording the title product (57.7%).

UPLC-MS [M+H]⁺=318.39

$^1$H NMR (400 MHz, CHLOROFORM-d) δ ppm 8.50 (d, 1H), 7.46 (d, 1H), 7.27 (dd, 1H), 5.62 (t, 1H), 3.51 (t, 2H), 2.93 (td, 2H), 2.81 (s, 6H), 1.56 (s, 6H)

Example 91

Ethyl (3E)-3-[3-(4-chloropyridin-2-yl)prop-2-yn-1-ylidene]-2,2-dimethylpyrrolidine-1-carboxylate Prepared by following the procedure reported above for the compound of Example 3 but substituting Compound 86a for Compound 3a and stirring overnight. After the usual work-up procedure, the crude residue was purified via automated flash chromatography (Horizon SP1® Biotage, SNAP10 Cartridge), eluting with a PE-EtOAc gradient from 8:2 to 6:4 affording the title product (47.9%).

UPLC-MS [M+H]⁺=319.39

$^1$H NMR (400 MHz, CHLOROFORM-d) δ ppm 8.50 (d, 1H), 7.45 (d, 1H), 7.25 (dd, 1H), 5.62 (t, 1H), 4.17 (br s, 2H), 3.59 (t, 2H), 2.92 (td, 2H), 1.55 (s, 6H), 1.30 (t, 3H)

Example 92

Methyl (3E)-3-[3-(4-chloropyridin-2-yl)prop-2-yn-1-ylidene]-2,2-dimethylpyrrolidine-1-carboxylate Prepared by following the procedure reported above for the compound of Example 3 but substituting Compound 86a for Compound 3a and methyl chloroformate (2 eq.) instead of ethyl chloroformate and stirring overnight. After the usual work-up procedure, the crude residue was purified via automated flash chromatography (Horizon SP1® Biotage, SNAP10 Cartridge), eluting with a PE-EtOAc gradient from 95:5 to 85:15 affording the title product (45.7%).

UPLC-MS [M+H]⁺=305.37

$^1$H NMR (400 MHz, CHLOROFORM-d) δ ppm 8.50 (d, 1H), 7.45 (d, 1H), 7.27 (dd, 1H), 5.63 (t, 1H), 3.71 (br s, 3H), 3.58 (t, 2H), 2.93 (td, 2H), 1.56 (s, 6H)

Example 93

(3-Chlorophenyl){(3E)-3-[3-(4-chloropyridin-2-yl)prop-2-yn-1-ylidene]-2,2-dimethylpyrrolidin-1-yl}methanone Prepared by following the procedure reported above for the compound of Example 3 but substituting Compound 86a for Compound 3a and 3-chlorobenzoyl chloride (2 eq.) instead of ethyl chloroformate and stirring overnight. After the usual work-up procedure, the crude residue was purified twice via automated flash chromatography (Horizon SP1® Biotage, SNAP10 Cartridge), eluting with a PE-EtOAc gradient from 7:3 to 40:60 affording the title product (48.9%).

UPLC-MS [M+H]⁺=385.33

$^1$H NMR (400 MHz, CHLOROFORM-d) δ ppm 8.50 (d, 1H), 7.32-7.48 (m, 4H), 7.25-7.32 (m, 2H), 5.71 (t, 1H), 3.52 (t, 2H), 2.94 (td, 2H), 1.74 (s, 6H)

Example 94

Ethyl (3E)-3-[3-(6-aminopyridin-2-yl)prop-2-yn-1-ylidene]-2,2-dimethylpyrrolidine-1-carboxylate Prepared by following the procedure reported above for the compound of Example 1 and substituting Compound 48a for Compound 1a and 2-amino-6-bromopyridine for 2-bromo-6-methylpyridine. After the usual work-up procedure, the crude residue was purified via automated flash chromatography (Horizon SP1® Biotage, SNAP10 Cartridge), eluting with a PE-EtOAc gradient from 80:20 to 30:70 affording an oil which spontaneously crystallize to give the title product as a brownish oil (45.4%).

UPLC-MS [M+H]⁺=300.48

$^1$H NMR (400 MHz, CHLOROFORM-d) δ ppm 7.42 (dd, 1H), 6.83 (d, 1H), 6.48 (d, 1H), 5.61 (t, 1H), 4.69 (br s, 2H), 4.01-4.31 (m, 2H), 3.57 (t, 2H), 2.91 (td, 2H), 1.53 (s, 6H), 1.30 (br t, 3H)

Example 95

(3E)-3-[3-(6-Aminopyridin-2-yl)prop-2-yn-1-ylidene]-N,N-diethyl-2,2-dimethylpyrrolidine-1-carboxamide

[(3E)-3-(2,2-dimethylpyrrolidin-3-ylidene)prop-1-ynyl]-trimethylsilane (Compound 95a)

To a solution of Compound 49a (1 g, 3.25 mmol) in acetonitrile was added dropwise iodotrimethylsilane at 0° C.

The reaction mixture was stirred at r.t. for 40 min. Then further 0.5 eq. of iodotrimethylsilane was added. After 20 min. the reaction mixture was quenched with 2 mL of MeOH and taken up with a saturated aq. solution of NaHCO$_3$, extracted with DCM (3×), dried over anhydrous sodium sulphate and evaporated to dryness affording the title compound use in the next step without any further purification.

(3E)-N,N-diethyl-2,2-dimethyl-3-[3-(trimethylsilyl)prop-2-yn-1-ylidene]pyrrolidine-1-carboxamide (Compound 95b)

Prepared by following the procedure reported above for the compound of Example 3 but substituting Compound 95a for Compound 3a and using N,N-diethylcarbamoyl chloride (3 eq.) instead of ethyl chloroformate and stirring at 50° C. for 4 h. After the usual work-up procedure, the crude residue was purified via automated flash chromatography (Horizon SP1® Biotage, SNAP10 Cartridge), eluting with a PE-EtOAc gradient from 95:5 to 1:1 affording the title product as a colourless oil (32.5%).

(3E)-3-[3-(6-Aminopyridin-2-yl)prop-2-yn-1-ylidene]-N,N-diethyl-2,2-dimethylpyrrolidine-1-carboxamide Prepared by following the procedure reported above for the compound of Example 1 but substituting Compound 95b for Compound 1a and 2-amino-6-bromopyridine for 2-bromo-6-methylpyridine. After the usual work-up procedure, the crude residue was purified via automated flash chromatography (Horizon SP1® Biotage, SNAP10 Cartridge), eluting with a PE-EtOAc gradient from 8:2 to 3:7 affording the title product as a brownish solid (31.3%).

UPLC-MS [M+H]$^+$=327.53

$^1$H NMR (400 MHz, CHLOROFORM-d) δ ppm 7.41 (dd, 1H), 6.82 (d, 1H), 6.46 (d, 1H), 5.59 (t, 1H), 4.66 (s, 2H), 3.47 (t, 2H), 3.16 (q, 4H), 2.89 (td, 2H), 1.54 (s, 6H), 1.13 (t, 6H)

Example 96

Methyl (3E)-3-[3-(6-aminopyridin-2-yl)prop-2-yn-1-ylidene]-2,2-dimethylpyrrolidine-1-carboxylate

Methyl (3E)-2,2-dimethyl-3-(3-trimethylsilylprop-2-ynylidene)pyrrolidine-1-carboxylate (Compound 96a)

Prepared by following the procedure reported above for the compound of Example 3 but substituting Compound 95a for Compound 3a and using methyl chloroformate (1.2 eq.) instead of ethyl chloroformate and stirring at 50° C. for 4 h. Used in the next step without further purification (78.2%).

Methyl (3E)-3-[3-(6-aminopyridin-2-yl)prop-2-yn-1-ylidene]-2,2-dimethylpyrrolidine-1-carboxylate Prepared by following the procedure reported above for the compound of Example 1 but substituting Compound 96a for Compound 1a and 2-amino-6-bromopyridine for 2-bromo-6-methylpyridine. After the usual work-up procedure, the crude residue was purified via automated flash chromatography (Horizon SP1® Biotage, SNAP10 Cartridge), eluting with a PE-EtOAc gradient from 8:2 to 3:7 affording the title product as a brownish solid (13.9%).

UPLC-MS [M+H]$^+$=286.39

$^1$H NMR (400 MHz, CHLOROFORM-d) δ ppm 7.48 (dd, 1H), 6.83 (d, 1H), 6.53 (d, 1H), 5.62 (s, 1H), 5.32 (br s, 2H), 3.71 (s, 3H), 3.58 (br s, 2H), 2.95 (t, 2H), 1.54 (s, 6H)

Example 97

(3E)-3-[3-(6-aminopyridin-2-yl)prop-2-yn-1-ylidene]-N,N,2,2-tetramethylpyrrolidine-1-carboxamide

(3E)-N,N,2,2-tetramethyl-3-(3-trimethylsilylprop-2-ynylidene)pyrrolidine-1-carboxamide (Compound 97a)

Prepared by following the procedure reported above for the compound of Example 3 but substituting Compound 95a for Compound 3a and using dimethylcarbamoyl chloride (1.2 eq.) instead of ethyl chloroformate and stirring at 50° C. for 4 h. After the usual work-up procedure, the crude residue was purified via automated flash chromatography (Horizon SP1® Biotage, SNAP10 Cartridge), eluting with a PE-EtOAc gradient from 95:5 to 1:1 affording the title product as a colourless oil (48.2%).

(3E)-3-[3-(6-Aminopyridin-2-yl)prop-2-yn-1-ylidene]-N,N-diethyl-2,2-dimethylpyrrolidine-1-carboxamide Prepared by following the procedure reported above for the compound of Example 1 but substituting Compound 97a for Compound 1a and 2-amino-6-bromopyridine for 2-bromo-6-methylpyridine. After the usual work-up procedure, the crude residue was purified via automated flash chromatography (Horizon SP1® Biotage, SNAP10 NH Cartridge), eluting with a PE-EtOAc gradient from 8:2 to 3:7 affording the title product as a brownish oil (28.1%).

UPLC-MS [M+H]$^+$=299.27

$^1$H NMR (400 MHz, CHLOROFORM-d) δ ppm 7.51 (dd, 1H), 6.82 (d, 1H), 6.54 (d, 1H), 5.59 (t, 1H), 5.41 (br s, 2H), 3.50 (t, 2H), 2.96 (t, 2H), 2.80 (s, 6H), 1.53 (s, 6H)

Example 98 tert-Butyl (3E)-3-[3-(3-chlorophenyl)prop-2-yn-1-ylidene]-2,2-dimethylpyrrolidine-1-carboxylate Prepared by following the procedure reported above for the compound of Example 1 and substituting Compound 49a for Compound 1a and 1-chloro3-iodobenzene for 2-bromo-6-methylpyridine. After the usual work-up procedure, the crude residue was purified via automated flash chromatography (Horizon SP1® Biotage, SNAP50 Cartridge), eluting with a PE-EtOAc gradient from 75:250 to 1:1 affording the title product (81.3%).

UPLC-MS [M+H]$^+$=346.38

$^1$H NMR (400 MHz, CHLOROFORM-d) δ ppm 7.43 (dd, 1H), 7.22-7.35 (m, 3H), 5.58 (t, 1H), 3.55 (br s, 2H), 2.84 (td, 2H), 1.51 (s, 15H)

Example 99

{(3E)-3-[3-(3-Chlorophenyl)prop-2-yn-1-ylidene]-2,2-dimethylpyrrolidin-1-yl}(piperidin-1-yl)methanone (3E)-3-[3-(3-Chlorophenyl)prop-2-ynylidene]-2,2-dimethyl-pyrrolidine (Compound 99a)

Following the method reported above for Compound 3a, the title compound was prepared starting from the compound of Example 98 instead of the compound of Example 1 and using chloroform instead of 1,2-DCE refluxing for 20 min (98.1%). Used in the next step without further purification. {(3E)-3-[3-(3-Chlorophenyl)prop-2-yn-1-ylidene]-2,2-dimethylpyrrolidin-1-yl}(piperidin-1-yl)methanone Prepared by following the procedure reported above for the compound of Example 3 but substituting Compound 99a for Compound 3a and 1-piperidinecarbonyl chloride instead of ethyl chloroformate heating at 60° C. for 2 h. After the usual work-up procedure, the crude residue was purified via automated flash chromatography (Horizon SP1® Biotage, SNAP10 Cartridge), eluting with a PE-EtOAc gradient from 9:1 to 6:4 affording the title product (84%).

UPLC-MS [M+H]$^+$=357.48

$^1$H NMR (400 MHz, DMSO-d$_6$) δ ppm 7.49-7.54 (m, 1H), 7.36-7.49 (m, 3H), 5.76 (t, 1H), 3.43 (t, 2H), 2.97-3.10 (m, 4H), 2.78 (td, 2H), 1.46-1.59 (m, 6H), 1.44 (s, 6H)

Example 100

{(3E)-3-[3-(3-Chlorophenyl)prop-2-yn-1-ylidene]-2,2-dimethylpyrrolidin-1-yl}(pyrrolidin-1-yl)methanone Prepared by following the procedure reported above for the compound of Example 3 but substituting Compound 99a for Compound 3a and 1-pyrrolidinecarbonyl chloride (1.5 eq.) instead of ethyl chloroformate heating at 60° C. for 2 h. After the usual work-up procedure, the crude residue was purified via automated flash chromatography (Horizon SP1® Biotage, SNAP10 Cartridge), eluting with a PE-EtOAc gradient from 6:4 to 4:6 affording the title product (98.6%).

UPLC-MS [M+H]$^+$=343.40

$^1$H NMR (400 MHz, DMSO-d$_6$) δ ppm 7.52 (br s, 1H), 7.38-7.48 (m, 3H), 5.76 (t, 1H), 3.48 (t, 2H), 3.20-3.27 (m, 4H), 2.82 (td, 2H), 1.69-1.79 (m, 4H), 1.48 (s, 6H)

Example 101

Ethyl (3E)-3-[3-(3-chlorophenyl)prop-2-yn-1-ylidene]-2,2-dimethylpyrrolidine-1-carboxylate Prepared by following the procedure reported above for the compound of Example 3 but substituting Compound 99a for Compound 3a and ethyl chloroformate (1.5 eq.) instead of ethyl chloroformate heating at r.t. for 2 h. After the usual work-up procedure, the crude residue was purified via automated flash chromatography (Horizon SP1® Biotage, SNAP10 Cartridge), eluting with a PE-EtOAc gradient from 95:5 to 8:2 affording the title product (61.5%).

UPLC-MS [M+H]$^+$=318.32

Example 102

(3E)-3-[3-(3-Chlorophenyl)prop-2-yn-1-ylidene]-N-ethyl-2,2-dimethyl-N-(propan-2-yl)pyrrolidine-1-carboxamide Prepared by following the procedure reported above for the compound of Example 3 but substituting Compound 99a for Compound 3a and 1-[ethyl(propan-2-yl)carbamoyl]-3-methyl-1H-imidazol-3-ium iodide (1.5 eq.) instead of ethyl chloroformate heating at reflux for 4 h. After the usual work-up procedure, the crude residue was purified via automated flash chromatography (Horizon SP1® Biotage, SNAP10 Cartridge), eluting with a PE-EtOAc gradient from 95:5 to 75:25 affording the title product (14.9%).

UPLC-MS [M+H]$^+$=359.41

$^1$H NMR (400 MHz, CHLOROFORM-d) δ ppm 7.43 (br s, 1H), 7.22-7.35 (m, 3H), 5.59 (t, 1H), 3.83 (spt, 1H), 3.52 (t, 2H), 3.08 (q, 2H), 2.87 (td, 2H), 1.56 (s, 6H), 1.18 (d, 6H), 1.10 (t, 3H)

Example 103

(3E)-3-[3-(3-Chlorophenyl)prop-2-yn-1-ylidene]-N,N,2,2-tetramethylpyrrolidine-1-carboxamide Prepared by following the procedure reported above for the compound of Example 3 but substituting Compound 99a for Compound 3a and 1dimethylcarbamoyl chloride (1.5 eq.) instead of ethyl chloroformate stirring for 6 h at r.t. After the usual work-up procedure, the crude residue was purified via automated flash chromatography (Horizon SP1® Biotage, SNAP10 Cartridge), eluting with a PE-EtOAc gradient from 8:2 to 1:1 affording the title product (61.7%).

UPLC-MS [M+H]$^+$=317.36

$^1$H NMR (400 MHz, CHLOROFORM-d) δ ppm 7.43 (br s, 1H), 7.22-7.35 (m, 3H), 5.59 (t, 1H), 3.52 (t, 2H), 2.86 (td, 2H), 2.82 (s, 6H), 1.56 (s, 6H)

Example 104

{(3E)-3-[3-(3-Chlorophenyl)prop-2-yn-1-ylidene]-2,2-dimethylpyrrolidin-1-yl}(furan-2-yl)methanone Prepared by following the procedure reported above for the compound of Example 3 but substituting Compound 99a for Compound 3a and 2-furoyl chloride (1.5 eq.) instead of ethyl chloroformate stirring for 6 h at r.t. After the usual work-up procedure, the crude residue was purified twice via automated flash chromatography (Horizon SP1® Biotage, SNAP10 Cartridge), eluting with a PE-EtOAc gradient from 95:5 to 75:25 affording the title product (39.25%).

UPLC-MS [M+H]$^+$=340.35

$^1$H NMR (400 MHz, CHLOROFORM-d) δ ppm 7.52 (d, 1H), 7.45 (dd, 1H), 7.24-7.37 (m, 3H), 7.07 (d, 1H), 6.51 (dd, 1H), 5.68 (t, 1H), 4.06 (t, 2H), 2.99 (td, 2H), 1.73 (s, 6H)

Example 105

Methyl (3E)-3-[3-(3-chlorophenyl)prop-2-yn-1-ylidene]-2,2-dimethylpyrrolidine-1-carboxylate Prepared by following the procedure reported above for the compound of Example 3 but substituting Compound 99a for Compound 3a and methyl chloroformate (1.5 eq.) instead of ethyl chloroformate stirring for 2 h at r.t. After the usual work-up procedure, the crude residue was purified twice via automated flash chromatography (Horizon SP1® Biotage, SNAP10 Cartridge), eluting with a PE-EtOAc gradient from 95:5 to 85:15 affording the title product (66.2%).
UPLC-MS [M+H]$^+$=304.40

Example 106

(3-Chlorophenyl){(3E)-3-[3-(3-chlorophenyl)prop-2-yn-1-ylidene]-2,2-dimethylpyrrolidin-1-yl}methanone Prepared by following the procedure reported above for the compound of Example 3 but substituting Compound 99a for Compound 3a and 3-chlorobenzoyl chloride (1.5 eq.) instead of ethyl chloroformate stirring for 2 h at r.t. After the usual work-up procedure, the crude residue was purified twice via automated flash chromatography (Horizon SP1® Biotage, SNAP10 Cartridge), eluting with a PE-EtOAc gradient from 95:5 to 75:25 affording the title product (89%).
UPLC-MS [M+H]$^+$=384.24
$^1$H NMR (400 MHz, CHLOROFORM-d) δ ppm 7.39-7.44 (m, 3H), 7.36 (dd, 1H), 7.24-7.34 (m, 4H), 5.68 (t, 1H), 3.52 (t, 2H), 2.87 (td, 2H), 1.74 (s, 6H)

Example 107

(3-Chlorophenyl)-[(4E)-4-[[5-(3-chlorophenyl)-1H-pyrazol-3-yl]methylene]-3,3-dimethyl-1-piperidyl]methanone tert-Butyl (4E)-3,3-dimethyl-4-prop-2-ynylidene-piperidine-1-carboxylate (Compound 107a To a solution of Compound 1a (0.092 g, 0.2862 mmol) in THF anhydrous (7 mL) was added a solution of tetrabutylammonium fluoride (0.374 g, 1.43 mmol, 5 equiv.) in THF (5 mL). The reaction mixture was stirred for 1 hour at r.t., poured into water and extracted with EtOAc. After the usual work-up procedure, the title product was obtained as a yellow oil (99%) and used for the next step without further purification.

tert-Butyl-(4E)-4-[4-(3-chlorophenyl)-4-oxo-but-2-ynylidene]-3,3-dimethyl-piperidine-1-carboxylate (Compound 107b)

To a solution of Compound 107a (0.075 g, 0.3007 mmol, 75 mg), 3-chlorobenzoyl chloride (0.07894 g, 0.4511 mmol, 0.058 mL) in THF anhydrous (5 mL, 5 mL) bis(triphenylphosphine)palladium dichloride (0.011 g, 0.015 mmol), copper iodide (0.0012 g, 0.006 mmol) and triethylamine (0.091 g, 0.902 mmol, 0.13 mL) were added. The resulting mixture was stirred at r.t. for 4 hours and after overnight resting was poured into water and extracted with EtOAc. After the usual work-up procedure, the crude residue was purified via automated flash chromatography (Biotage Isolera-Dalton®), eluting with a gradient PE/EtOAc from 9:1 to 7:3 affording the title product as a yellow oil (82%).

(4E)-1-(3-Chlorophenyl)-4-(3,3-dimethyl-4-piperidylidene)but-2-yn-1-one (Compound 107c)

A solution of Compound 107b (0.1 g, 0.2578 mmol) and 2,2,2-trifluoroacetic acid (0.588 g, 5.16 mmol, 20 equiv., 0.397 mL) in CHCl$_3$ (5 mL) was heated at reflux for 2 hours, cooled to r.t. and washed with 1M NaOH. The organic layer was dried over Na$_2$SO$_4$ and the solvent was evaporated to dryness affording to the title product (82%), used without further purification for the next step.

(4E)-1-(3-Chlorophenyl)-4-(3,3-dimethyl-4-piperidylidene)but-2-yn-1-one (Compound 107d)

A solution of Compound 107c (0.061 g, 0.2120 mmol), triethylamine (0.0858 g, 0.848 mmol, 0.118 mL) and 3-chlorobenzoyl chloride (0.05564 g, 0.3179 mmol, 1.50 equiv., 0.04070 mL) in CHCl$_3$ ethanol free (5 mL) was stirred at r,t, for 1 hour, diluted with CHCl$_3$ and washed with water. After the usual work-up procedure, the crude residue was purified via automated flash chromatography (Biotage Isolera-Dalton®), eluting with a gradient EtOAc/ETP from 1:9 to 3:7 affording the title product as a yellow oil (17%).

(3-Chlorophenyl)-[(4E)-4-[[5-(3-chlorophenyl)-1H-pyrazol-3-yl]methylene]-3,3-dimethyl-1-piperidyl]methanone A solution of Compound 107d (0.016 g, 0.03753 mmol) and hydrazine hydrate (0.0076 g, 0.15 mmol 0.0075 mL) in EtOH (3 mL) was stirred overnight at r.t., quenched with water and extracted with EtOAc. After the usual work-up procedure, the crude residue was purified via automated flash chromatography (Biotage Isolera-Dalton®), eluting with a gradient EtOAc/ETP from 2:8 to 1:1 affording the title product as a brownish solid (18%).
UPLC-MS [M+H]$^+$=440.55
$^1$H NMR (400 MHz, CHLOROFORM-d) δ ppm 7.71 (m, 2H), 7.30-7.48 (m, 6H), 6.53 (br s, 1H), 6.27 (br s, 1H), 3.09-3.97 (m, 4H), 2.57-2.96 (m, 2H), 1.28 (s, 6H)

Example 108

Ethyl 2,2,6,6-Tetramethyl-4-[3-(6-methylpyridin-2-yl)prop-2-yn-1-ylidene]piperidine-1-carboxylate Ethyl 2,2,6,6-tetramethyl-4-oxopiperidine-1-carboxylate (Compound 108a)

To a solution of 2,2,6,6-tetramethylpiperidin-4-one (817 mg, 5 mmol) in 5 mL of diethyl ether was added dropwise via syringe ethyl chloroformate (0.493 mL, 5 mmol). The reaction solution was stirred at 40° C. for 10 min, then at r.t. for 6 days. The precipitated solid was filtered and washed with diethyl ether; the filtrate was washed with HCl 0.5 N (3×7 mL), then with aq. Na$_2$CO$_3$ followed by brine (2×7 mL); afterwards it was dried over sodium sulphate and evaporated to dryness in vacuo to afford 56 mg (9%) of the title product as an orange semi-solid.

Ethyl 2,2,6,6-tetramethyl-4-[3-(trimethylsilyl)prop-2-yn-1-ylidene]piperidine-1-carboxylate (Compound 108b)

The title compound was prepared following the procedure reported above for Compound 1a replacing tert-butyl 3,3- dimethyl-4-oxo-piperidine-1-carboxylate with Compound 108a. After the usual work-up, the reaction crude was purified by automated flash chromatography (SP1® Biotage, 10 g HP column) eluting with PE-EtOAc 97:3 affording the title product as a colourless oil (35.1%).

Ethyl 2,2,6,6-tetramethyl-4-(prop-2-yn-1-ylidene) piperidine-1-carboxylate (Compound 108c)

The title compound was prepared following the procedure reported above for Compound 107a replacing Compound 1a with Compound 108b. After the usual work-up, the reaction crude was purified by automated flash chromatography (SP1® Biotage, 10 g HP column) eluting with PE-EtOAc 95:5 affording the title product (56.6%).

Ethyl 2,2,6,6-tetramethyl-4-[3-(6-methylpyridin-2-yl)prop-2-yn-1-ylidene]piperidine-1-carboxylate The title compound was prepared following the procedure reported above for Compound 107b replacing Compound 107a with Compound 108c and 3-chlorobenzoyl chloride with 2-iodo-6-methylpyridine. After the usual work-up, the reaction crude was purified by automated flash chromatography (SP1® Biotage, 10 g SNAP column) eluting with PE-EtOAc 85:15 affording the title product (100%).

UPLC-MS [M+H]$^+$=269.296

$^1$H NMR (400 MHz, CHLOROFORM-d) δ ppm 7.54 (dd, 1H), 7.25 (d, 1H), 7.07 (d, 1H), 5.66 (s, 1H), 2.58 (s, 3H), 2.43 (s, 2H), 2.14 (s, 2H), 1.24 (s, 6H), 1.21 (s, 6H)

Example 109

2-Methyl-6-[3-(2,2,6,6-tetramethylpiperidin-4-ylidene)prop1-yn-1-yl]pyridine 2,2,6,6-Tetramethyl-4-[3-(trimethylsilyl)prop-2-yn-1-ylidene]piperidine (Compound 109a)

The title compound was prepared following the procedure reported above for Compound 1a replacing tert-butyl 3,3-dimethyl-4-oxo-piperidine-1-carboxylate with 2,2,6,6-tetramethyl-4-piperidinone. After the usual work-up, the reaction crude was used without any further purification in the next step (58.6%).

2,2,6,6-Tetramethyl-4-(prop-2-yn-1-ylidene)piperidine (Compound 109b)

The title compound was prepared following the procedure reported above for Compound 107a replacing Compound 1a with Compound 109a. After the usual work-up, the reaction crude was purified by automated flash chromatography (SP1® Biotage, 50 g HP column) eluting with CHCl$_3$— 3.8 N methanolic ammonia gradient from 100:2 to 100:3 giving the title product as a brownish oil that tends to solidify (68%).

2-Methyl-6-[3-(2,2,6,6-tetramethylpiperidin-4-ylidene)prop1-yn-1-yl]pyridine

The title compound was prepared following the procedure reported above for Compound 107b replacing Compound 107a with Compound 109b and 3-chlorobenzoyl chloride with 2-iodo-6-methylpyridine. After the usual work-up, the reaction crude was purified by automated flash chromatography (SP1® Biotage, 10 g SNAP column) eluting with CHCl$_3$— 3.8 N methanolic ammonia gradient from 100:4 to 100:5 affording the title product (55.5%).

UPLC-MS [M+H]$^+$=341.195

$^1$H NMR (400 MHz, CHLOROFORM-d) δ ppm 7.60 (br s, 1H), 7.30 (br d, 1H), 7.12 (br d, 1H), 5.64 (quin, 1H), 4.15 (q, 2H), 2.86 (br s, 2H), 2.56-2.69 (m, 5H), 1.49 (s, 6H), 1.43 (s, 6H), 1.32 (t, 3H)

Example 110 tert-Butyl 8-[3-(6-methylpyridin-2-yl)prop-2-yn-1-ylidene]-5-azaspiro[3,5]nonane-5-carboxylate (E:Z Mixture)

tert-Butyl 8-[3-(trimethylsilyl)prop-2-yn-1-ylidene]-5-azaspiro[3,5]nonane-5-carboxylate (E:Z mixture) (Compound 110a)

The title compound was prepared following the procedure reported above for Compound 1a replacing tert-butyl 3,3-dimethyl-4-oxo-piperidine-1-carboxylate with tert-butyl 8-oxo-5-azaspiro[3,5]nonane-5-carboxylate. After the usual work-up, the reaction crude was purified by automated flash chromatography (SP1® Biotage, 25 g SNAP column) eluting with PE-EtOAc gradient from 1:0 to 8:2 affording the title product as a colourless oil (100%). E/Z mixture 55:45 ($^1$H-NMR).

tert-Butyl 8-[3-(6-methylpyridin-2-yl)prop-2-yn-1-ylidene]-5-azaspiro[3,5]nonane-5-carboxylate E/Z Mixture The title compound was prepared following the procedure reported above for the compound of Example 1 replacing Compound 110a for Compound 1a and 2-iodo-6-methylpyridine for 3-chlorobenzoyl chloride. After the usual work-up, the reaction crude was purified by automated flash chromatography (SP1® Biotage, 10 g SNAP column) eluting with PE-EtOAc gradient from 9:1 to 6:4 affording the title product as a dense colourless oil (77.8%). E/Z mixture 55:45 ($^1$H-NMR).

UPLC-MS [M+H]$^+$=353.16, 353.23

$^1$H NMR (400 MHz, CHLOROFORM-d) mix of isomers δ ppm 7.57 (br s, 2H), 7.20-7.27 (m, 2H), 7.10 (br d, 2H), 5.69 (s, 1H) and 5.62 (s, 1H), 3.26-3.41 (m, 4H), 2.82 (s, 2H), 2.59 (br s, 6H), 2.51 (s, 2H) and 2.53 (br s, 2H), 2.23-2.34 (m, 4H), 2.21 (m, 2H) and 1.94-2.12 (m, 4H), 1.62-1.81 (m, 4H), 1.49 (m, 18H)

Example 111

Methyl 8-[3-(6-methylpyridin-2-yl)prop-2-yn-1-ylidene]-5-azaspiro[3,5]nonane-5-carboxylate (E:Z Mixture)

tert-Butyl 8-[3-(6-methyl-2-pyridyl)prop-2-ynylidene]-5-azaspiro[3,5]nonane-5-carboxylate (E:Z Mixture) (Compound 111a)

The title compound was prepared following the procedure reported above for the Compound of Example 1 and replacing Compound 1a with Compound 110a. The title compound was obtained as a dense colourless oil from the usual work-up and purified by flash chromatography (77.8%).

8-[3-(6-Methylpyridin-2-yl)prop-2-yn-1-ylidene]-5-azaspiro[3,5]nonane (E:Z Mixture) (Compound 111b)

The title compound was prepared following the procedure reported above for Compound 3a replacing the compound of Example 1 with 111a and conducting the reaction at r.t. The title compound was obtained as a brownish dense oil from the usual work-up and used without any further purification in the next step (93%).

Methyl 8-[3-(6-methylpyridin-2-yl)prop-2-yn-1-ylidene]-5-azaspiro[3,5]nonane-5-carboxylate (E:Z Mixture)

Following the procedure reported above for the compound of Example 3 but substituting Compound 111b for Compound 3a and methyl chloroformate for ethyl chloroformate. After the usual work-up procedure, the crude residue was purified via automated flash chromatography (Horizon SP1® Biotage, SNAP10 Cartridge), eluting with a PE-EtOAc gradient from 9:1 to 5:5 affording the title product as a white solid (80.5%). E/Z mixture 55:45 (1H-NMR)
UPLC-MS [M+H]$^+$=311.26
$^1$H NMR (400 MHz, CHLOROFORM-d) mix of isomers δ ppm 7.51-7.61 (m, 2H), 7.23-7.28 (m, 2H), 7.10 (br d, 2H), 5.70 (s, 1H) and 5.62 (s, 1H), 3.71 (s, 6H), 3.30-3.44 (m, 4H), 2.81 (s, 2H), 2.59 (s, 6H), 2.51 (s, 2H), 2.46-2.55 (m, 2H), 2.24-2.37 (m, 4H), 2.22 (br t, 2H), 1.95-2.14 (m, 4H), 1.62-1.87 (m, 4H)

Example 112

4-[3-(3-Chlorophenyl)prop-2-yn-1-ylidene]-1,2,2,6,6-pentamethylpiperidine 1,2,2,6,6-Pentamethyl-4-[3-(trimethylsilyl)prop-2-yn-1-ylidene]piperidine (Compound 112a)

The title compound was prepared following the procedure reported above for Compound 1a replacing tert-butyl 3,3-dimethyl-4-oxo-piperidine-1-carboxylate with 1,2,2,6,6-pentamethyl-4-piperidone. The crude residue after work-up was purified via automated flash chromatography (Horizon SP1® Biotage, SNAP50 Cartridge), eluting with CHCl$_3$-MeOH gradient from 100:0 to 85:15 affording the title product as a colourless oil (82.5%).

4-[3-(3-Chlorophenyl)prop-2-yn-1-ylidene]-1,2,2,6,6-pentamethylpiperidine

Compound 112a was reacted with 1-bromo-3-chlorobenzene instead of 2-bromo-6-methylpyridine following the procedure described for the compound of Example 1. After the usual work-up, the crude residue was purified via automated flash chromatography (Horizon SP1® Biotage, SNAP25 Cartridge) eluting with EtOAc-3.8 N methanolic ammonia gradient from 99:1 to 97:3 to give the title compound as a brownish dense oil (45.9%).
UPLC-MS [M+H]$^+$=301.98
$^1$H NMR (400 MHz, CHLOROFORM-d) δ ppm 7.39-7.44 (m, 1H), 7.21-7.33 (m, 3H), 5.55 (s, 1H), 2.47 (s, 2H), 2.29 (s, 3H), 2.21 (s, 2H), 1.14 (s, 6H), 1.09 (s, 6H)

Example 113

2-Methyl-6-[3-(1,2,2,6,6-pentamethylpiperidin-4-ylidene)prop-1-yn-1-yl]pyridine

Compound 112a instead of Compound 1a was reacted following the procedure described for the compound of Example 1. After the usual work-up, the crude residue was purified via automated flash chromatography (Horizon SP1® Biotage, SNAP25 Cartridge) eluting with PE-EtOAc-3.8 N methanolic ammonia gradient from 8:2:0.2 to 0:10:1 to give the title compound as a brownish dense oil (91.5%).
UPLC-MS [M+H]$^+$=283.14
$^1$H NMR (400 MHz, CHLOROFORM-d) δ ppm 7.53 (t, 1H), 7.24 (d, 1H), 7.07 (d, 1H), 5.59 (s, 1H), 2.57 (s, 3H), 2.50 (s, 2H), 2.28 (s, 3H), 2.21 (s, 2H), 1.13 (s, 6H), 1.09 (s, 6H)

Example 114

Ethyl 3-[3-(6-methylpyridin-2-yl)prop-2-yn-1-ylidene]-8-azabicyclo[3.2.1]octane-8-carboxylate Ethyl 3-[3-(trimethylsilyl)prop-2-yn-1-ylidene]-8-azabicyclo[3.2.1]octane-8-carboxylate (Compound 114a)

The title compound was prepared following the procedure reported above for Compound 1a replacing tert-butyl 3,3-dimethyl-4-oxo-piperidine-1-carboxylate with 1-ethoxycarbonyltropanone. After the usual work-up, the reaction crude was purified via automated flash chromatography (SP1® Biotage, 25 g SNAP column) eluting with PE-EtOAc gradient from 95:5 to 8:2 affording the title product as a colourless oil (63.5%).

Ethyl 3-[3-(6-methylpyridin-2-yl)prop-2-yn-1-ylidene]-8-azabicyclo[3.2.1]octane-8-carboxylate Compound 114a was reacted instead of compound 1a following the procedure described for the compound of Example 1. After the usual work-up, the crude residue was purified via automated flash chromatography (Horizon SP1® Biotage, SNAP25 Cartridge) eluting with PE-EtOAc gradient from 8:2 to 3:7 to give the title compound as a yellowish solid (83.7%).
UPLC-MS [M+H]$^+$=311.06

Example 115

8-(6-Methyl-3-nitropyridin-2-yl)-3-[3-(6-methylpyridin-2-yl)prop-2-yn-1-ylidene]-8-azabicyclo[3.2.1]octane 3-[3-(6-Methylpyridin-2-yl)prop-2-yn-1-ylidene]-8-azabicyclo[3.2.1]octane (Compound 115a To a solution of the compound of Example 114 (160 mg, 0.115 mmol) in 5 mL of CHCl$_3$ was added dropwise at r.t. iodo(trimethyl)silane (0.088 mL, 0.618 mmol) stirring at reflux for 4 h. The reaction mixture was quenched with methanol and evaporated to dryness. The residue was taken up with DCM and water, the organic layer was separated and dried over sodium sulphate. The so obtained brownish solid was used as it was in the next step. 8-(6-Methyl-3-nitropyridin-2-yl)-3-[3-(6-methylpyridin-2-yl)prop-2-yn-1-ylidene]-8-azabicyclo[3.2.1]octane The title compound was prepared as described for the compound of Example 3 using Compound 115a instead of Compound 3a. After the usual work-up, the crude residue was purified via automated flash chromatography (Horizon SP1® Biotage, SNAP25 Cartridge) eluting with PE-EtOAc gradient from 95:5 to 7:3 to give the title compound as a yellow solid (59.1%).

UPLC-MS [M+H]$^+$=375.44

$^1$H NMR (400 MHz, CHLOROFORM-d) δ ppm 8.04 (d, 1H), 7.56 (t, 1H), 7.25 (d, 1H), 7.09 (d, 1H), 6.56 (d, 1H), 5.67 (s, 1H), 4.57 (br. s., 1H), 4.50 (br. s., 1H), 3.00 (d, 1H), 2.75 (d, 1H), 2.63 (br. d, 1H), 2.59 (br. s., 3H), 2.46 (s, 3H), 2.24 (d, 1H), 1.90-2.03 (m, 2H), 1.65-1.78 (m, 2H)

Example 116

3-{(3E)-3-[1-(3-Chlorobenzol)-3,3-dimethylpiperidin-4-ylidene]prop-1-yn-1-yl}benzonitrile 3,3-Dimethylpiperidin-1-ium-4-one; 2,2,2-trifluoroacetate (Compound 116a)

To an ice bath cooled solution of tert-butyl 3,3-dimethyl-4-oxo-piperidine-1-carboxylate (2.4 g, 10.56 mmol) in CH$_2$Cl$_2$ (30 mL) was added dropwise 2,2,2-trifluoroacetic acid (12.04 g, 105.59 mmol, 10 equiv., 8.09 mL) and the reaction mixture was stirred at r.t. for 2 h. The solvent was evaporated and the residue was taken up with toluene and evaporated five times to give the title compound as trifluoroacetate (yellow oil). The latter was used for the next step without any further purification.

1-(3-Chlorobenzoyl)-3,3-dimethyl-piperidin-4-one (Compound 116b)

To an ice bath cooled solution of Compound 116a (2.54 g, 10.53 mmol) in dichloromethane (30 mL), triethylamine (52.65 mmol, 7.3 mL, 5.33 g) was added, followed by 3-chlorobenzoyl chloride (2.76 g, 15.80 mmol, 2.022 mL) and the resulting mixture was stirred at room temperature overnight. Afterwards, the reaction mixture was washed with water (2×) and brine (1x), the organic phase was separated and dried over Na$_2$SO$_4$, filtered and evaporated. The crude residue was purified by means of a Isolera One® Biotage, cartridge type SNAP50, using a gradient from petroleum ether-EtAcO 2:8 to petroleum ether:EtAcO 1:1. 2,720 g of the title compound (yellow oil) were collected.

(3-Chlorophenyl)-[(4E)-3,3-dimethyl-4-(3-trimethylsilylprop-2-ynylidene)-1-piperidyl]methanone (Compound 116c)

To a solution of 3-diethoxyphosphorylprop-1-ynyl(trimethyl)silane (3.300 g, 13 mmol) in dry THF (40 mL) stirred at −60° C. under nitrogen atmosphere, lithium [bis(trimethylsilyl)amide]. 1M sol. in THF (13 mmol, 1.3 equiv., 13 mL) was added dropwise and the reaction solution was stirred at −60° C. for 1 hour. A solution of Compound 116b (2.520 g, 7.0 mmol) in dry THF (20 mL) was added dropwise and the mixture was stirred at −60° C. for 20 min, warmed to r.t. in 2 hours, quenched with water and extracted with EtOAc. The organic layer was dried over Na$_2$SO$_4$, filtered and evaporated. The crude residue was purified by means of a Isolera One® Biotage, cartridge type SNAP50, using a gradient from petroleum ether 100% to Petroleum ether: EtAcO 8:2. 2.52 g of the title compound (light yellow powder) were collected.

3-{(3E)-3-[1-(3-chlorobenzoyl)-3,3-dimethylpiperidin-4-ylidene]prop-1-yn-1-yl}benzonitrile To a solution of Compound 116c (100 mg, 0.28 mmol) in DMF (1 mL), 3-iodobenzonitrile (B, 0.306 mmol, 70 mg) was added, followed by sodium acetate 3H$_2$O (0.56 mmol, 75.6 mg), TBAF (0.28 mmol, 72.64 mg) and Pd Tetrakis (0.01 mmol, 12.84 mg) and the mixture was heated at 110° C. under microwave irradiation for 10 min. After cooling at room temperature, water and EtAcO were added, the two phases were separated, the organic layer was washed with water and brine, dried over Na$_2$SO$_4$, filtered and evaporated. The crude residue was purified by means of a Isolera One® Biotage, cartridge type SNAP10, using a gradient from petroleum ether EtAcO 9:1 to Petroleum ether:EtAcO 6:4. 88 mg of the title compound as a light yellow powder were collected (81%).

UPLC-MS [M+H]$^+$=389.35

The following compounds were prepared starting from Compound 116c following the procedure described above for the Compound of Example 116 and replacing 3-iodobenzonitrile with the proper haloaromatic compound:

Example 117

3-{(3E)-3-[1-(3-Chlorobenzol)-3,3-dimethylpiperidin-4-ylidene]prop-1-yn-1-yl}-5-fluorobenzonitrile Prepared using 3-bromo-5-fluorobenzonitrile. Yellow powder (73%).

UPLC-MS [M+H]$^+$=407.36

Example 118

(3-Chlorophenyl){(4E)-4-[3-(3-methoxyphenyl)prop-2-yn-1-ylidene]-3,3-dimethylpiperidin-1-yl}methanone From 1-iodo-3-methoxybenzene. Yellow oil (73%).
UPLC-MS [M+H]$^+$=394.30

(3-Chlorophenyl)[(4E)-4-{3-[3-(hydroxymethyl)phenyl]prop-2-yn-1-ylidene]-3,3-dimethylpiperidin-1-yl}methanone From (3-iodophenyl)methanol. Yellow oil (75.8%)
UPLC-MS [M+H]$^+$=394.30

Example 120

(3-Chlorophenyl){(4E)-4-[3-(4-fluorophenyl)prop-2-yn-1-ylidene]-3,3-dimethylpiperidin-1-yl}methanone From 1-fluoro-4-iodobenzene. Yellow oil (48%).
UPLC-MS [M+H]$^+$=382.24

Example 121

(3-Chlorophenyl)[(4E)-3,3-dimethyl-4-(3-{3-[(pyrrolidin-1-Yl)methyl]phenyl]prop-2-yn-1-ylidene)piperidin-1-yl}methanone From 1-[(3-bromophenyl)methyl]pyrrolidine. Yellow oil (31.4%).
UPLC-MS [M+H]$^+$=477.33

Example 122

(3-Chlorophenyl){(4E)-3,3-dimethyl-4-[3-(6-methylpyridin-2-yl)prop-2-yn-1-ylidene]piperidin-1-yl}methanone From 2-bromo-6-methyl-pyridine. Yellow oil (83.61%).
UPLC-MS [M+H]$^+$=379.27

Example 123

5-{(3E)-3-[1-(3-Chlorobenzol)-3,3-dimethylpiperidin-4-ylidene]prop-1-yn-1-yl}pyridine-2-carbonitrile From 5-bromopyridine-2-carbonitrile. Light yellow powder (60.32%).
UPLC-MS [M+H]$^+$=390.25

Example 124

3-Chlorophenyl){(4E)-4-[3-(6-methoxypyridin-3-yl)prop-2-yn-1-ylidene]-3,3-dimethylpiperidin-1-yl}methanone From 5-iodo-2-methoxy-pyridine. Yellow oil (76.6%).
UPLC-MS [M+H]$^+$=395.29

Example 125

(3-Chlorophenyl){(4E)-4-[3-(3-fluoro-5-hydroxyphenyl)prop-2-yn-1-ylidene]-3,3-dimethylpiperidin-1-yl}methanone From 3-bromo-5-fluorophenol. Light yellow powder (58.81%).
UPLC-MS [M+H]$^+$=398.26

The following compounds were prepared by reacting Compound 4a with the proper derivatizing reagent as detailed in the text:

Example 126

{(4E)-4-[3-(3-Chlorophenyl)prop-2-yn-1-ylidene]-3,3-dimethylpiperidin-1-yl}(3-hydroxyphenyl)methanone A solution of Compound 4a.HCl (45 mg, 0.150 mmol), 3-hydroxybenzoic acid (27.28 mg, 0.20 mmol) and HATU (75.09 mg, 0.20 mmol) in DMF (1.3503 mL, 0.017 mol) was treated with TEA (0.04 mL, 0.30 mmol) then stirred at r.t. for 1 h. Afterwards, the reaction mixture was diluted with EtOAc, washed with 1N HCl sol, sat. aq. NaHCO$_3$ sol, brine, dried (Na$_2$SO$_4$) and concentrated to dryness in vacuo. The crude residue was purified by Biotage Isolera® (SiO$_2$, 10 g ULTRA, PE/EtOAc, 5% EtOAc 3 CV, 5-30% 20 CV, 30% 3 CV). 14.8 mg (25.1%) of the desired product as beige powder were obtained.
UPLC-MS [M+H]$^+$=380.2

Example 127

{(4E)-4-[3-(3-Chlorophenyl)prop-2-yn-1-ylidene]-3,3-dimethylpiperidin-1-yl}(4-methoxypyridin-2-yl)methanone Prepared as described for the compound of Example 126 but using 4-methoxypyridin-2-carboxylic acid instead of 3-hydroxybenzoic acid (Yield: 21%).
UPLC-MS [M+H]$^+$=395.3

Example 128

{(4E)-4-[3-(3-Chlorophenyl)prop-2-yn-1-ylidene]-3,3-dimethylpiperidin-1-yl}(6-methylpyridin-2-yl)methanone Prepared as described for the compound of Example 126 but using 6-methylpyridin-2-carboxylic acid instead of 3-hydroxybenzoic acid (Yield: 21%).
UPLC-MS [M+H]$^+$=379.5

Example 129

(4E)-4-[3-(3-Chlorophenyl)prop-2-yn-1-ylidene]-3,3-dimethyl-N-(6-methylpyridin-2-yl)piperidine-1-carboxamide A solution of 6-methylpyridin-2-amine (0.04 mL, 0.41 mmol) in DCE (1.5 mL) stirred at r.t. was treated with bis(trichloromethyl) carbonate (40.07 mg, 0.14 mmol), then TEA (0.11 mL, 0.81 mmol) was added dropwise. The reaction mixture was stirred at reflux for 1 h. Afterwards, it was cooled to r.t. and evaporated in vacuo. The residue was dissolved in THF (4 mL) and treated with a solution of (4E)-4-[3-(3-chlorophenyl)prop-2-ynylidene]-3,3-dimethyl-piperidine hydrochloride (Compound 4a, 80. mg, 0.27 mmol) and TEA (0.08 mL, 0.54 mmol) in THF (2 mL) and the reaction mixture was stirred at r.t. for 1 h, then at 50° C. for 15 h. The reaction mixture was diluted with DCM, washed with water, brine, dried (Na$_2$SO$_4$) and concentrated to dryness in vacuo. The crude product was purified by Biotage Isolera® (SiO$_2$, 10 g ULTRA, PE/EtOAc, 10% EtOAc 3 CV, 10-80% 30 CV, 800% 3 CV). 33.9 mg of the title product as white solid was obtained (Yield: 29.6%).
UPLC-MS [M+H]$^+$=394.2

Example 130

{(4E)-4-[3-(3-Chlorophenyl)prop-2-yn-1-ylidene]-3,3-dimethylpiperidin-1-yl}(2,2-dimethylmorpholin-4-yl)methanone Prepared from Compound 4a following the synthetic methodology reported above for the compound of Example 129 using 2,2-dimethylmorpholine instead of 6-methylpyridin-2-amine. The title product was obtained as a white powder (Yield: 6.4%).
UPLC-MS [M+H]$^+$=401.3

Example 131

(4E)-4-[3-(3-Chlorophenyl)prop-2-yn-1-ylidene]-N-(2,2-dimethyltetrahydro-2H-pyran-4-yl)-3,3-dimethylpiperidine-1-carboxamide Prepared from Compound 4a following the synthetic methodology reported above for the compound of Example 129 using 2,2-dimethyltetrahydropyran-4-amine instead of 6-methylpyridin-2-amine. The title product was obtained as a beige powder (Yield: 12.3%).
UPLC-MS [M+H]$^+$=415.3

Example 132

(4E)-4-[3-(3-Chlorophenyl)prop-2-yn-1-ylidene]-3,3-dimethyl-N-(pyridin-2-yl)piperidine-1-carboxamide Prepared from Compound 4a following the synthetic methodology reported above for the compound of Example 129 using pyridin-2-amine instead of 6-methylpyridin-2-amine. The title product was obtained as a brown oil (Yield: 18.3%).
UPLC-MS [M+H]$^+$=380.2

Example 133

2-({(4E)-4-[3-(3-Chlorophenyl)prop-2-yn-1-ylidene]-3,3-dimethylpiperidin-1-yl}carbonyl)pyridine-4-carbonitrile Prepared as described for the compound of Example 126 but using 4-cyanopyridine-2-carboxylic acid instead of 3-hydroxybenzoic acid. Beige oil (Yield: 37.5%).
UPLC-MS [M+H]$^+$=390.2

Example 134

1-{(4E)-4-[3-(3-Chlorophenyl)prop-2-yn-1-ylidene]-3,3-dimethylpiperidin-1-yl}-2-(2,2-dimethyltetrahydro-2H-pyran-4-yl)ethanone Prepared as described for the compound of Example 126 but using 2-(2,2-dimethyltetrahydropyran-4-yl)acetic acid instead of 3-hydroxybenzoic acid. Beige solid (Yield: 41.47%).
UPLC-MS [M+H]$^+$=414.3

Example 135

{(4E)-4-[3-(3-Chlorophenyl)prop-2-yn-1-ylidene]-3,3-dimethylpiperidin-1-yl}(4-chloropyridin-2-yl)methanone Prepared as described for the compound of Example 126 but using 4-chloropyridine-2-carboxylic acid instead of 3-hydroxybenzoic acid. Beige solid (Yield: 48.84%).
UPLC-MS [M+H]$^+$=399.1

Example 136

{(4E)-4-[3-(3-Chlorophenyl)prop-2-yn-1-ylidene]-3,3-dimethylpiperidin-1-yl}(4,5-dimethylfuran-2-yl)methanone Prepared as described for the compound of Example 126 but using 4,5-dimethyl-2-furoic acid instead of 3-hydroxybenzoic acid. Beige solid (Yield: 24.7%).
UPLC-MS [M+H]$^+$=382.2

Example 137

{(4E)-4-[3-(3-Chlorophenyl)prop-2-yn-1-ylidene]-3,3-dimethylpiperidin-1-yl}(3-methoxyphenyl)methanone Prepared as described for the compound of Example 126 but using 3-methoxybenzoic acid instead of 3-hydroxybenzoic acid. Brown solid (Yield: 63.82%).
UPLC-MS [M+H]$^+$=394.2

Example 138

3-({(4E)-4-[3-(3-Chlorophenyl)prop-2-yn-1-ylidene]-3,3-dimethylpiperidin-1-yl}carbonyl)benzonitrile Prepared as described for the compound of Example 126 but using 3-cyanobenzoic acid instead of 3-hydroxybenzoic acid. Brown solid (Yield: 62.7%).
UPLC-MS [M+H]$^+$=389.2

Example 139

(4E)-4-[3-(3-Chlorophenyl)prop-2-yn-1-ylidene]-N-(4-chloropyridin-2-yl)-3,3-dimethylpiperidine-1-carboxamide Prepared from Compound 4a following the synthetic methodology reported above for the compound of Example 129 using 4-chloropyridin-2-amine instead of 6-methylpyridin-2-amine. The title product was obtained as a beige solid (Yield: 5.3%).
UPLC-MS [M+H]$^+$=414.2

2,2-Dimethylpropyl (4E)-4-[3-(3-chlorophenyl)prop-2-yn-1-ylidene]-3,3-dimethylpiperidine-1-carboxylate Prepared from Compound 4a following the synthetic methodology reported above for the compound of Example 129 using 2,2-dimethylpropan-1-ol instead of 6-methylpyridin-2-amine. The title product was obtained as a beige solid (Yield: 14.1%).
UPLC-MS [M+H]$^+$=374.3

Example 141

(4E)-4-[3-(3-Chlorophenyl)prop-2-yn-1-ylidene]-3,3-dimethyl-N-(3-methylphenyl)piperidine-1-carboxamide Prepared from Compound 4a following the synthetic methodology reported above for the compound of Example 129 using 3-methylaniline instead of 6-methylpyridin-2-amine. The title product was obtained as a beige powder (Yield: 9.8%).
UPLC-MS [M+H]⁺=393.2

Example 142

2-Methylpyridin-4-yl (4E)-4-[3-(3-chlorophenyl)prop-2-yn-1-ylidene]-3,3-dimethylpiperidine-1-carboxylate Prepared from Compound 4a following the synthetic methodology reported above for the compound of Example 129 using 2-methylpyridin-4-ol instead of 6-methylpyridin-2-amine. The title product was obtained as a beige solid (Yield: 8.1%).
UPLC-MS [M+H]⁺=395.2

Example 143

(4E)-4-[3-(3-Chlorophenyl)prop-2-yn-1-ylidene]-N-(2,2-dimethylpropyl)-3,3-dimethylpiperidine-1-carboxamide Prepared from Compound 4a following the synthetic methodology reported above for the compound of Example 129 using 2,2-dimethylpropanamine instead of 6-methylpyridin-2-amine. The title product was obtained as a white powder (Yield: 31.3%).
UPLC-MS [M+H]⁺=373.3

Example 144

{(4E)-4-[3-(3-Chlorophenyl)prop-2-yn-1-ylidene]-3,3-dimethylpiperidin-1-yl}(4-hydroxypiperidin-1-yl)methanone Prepared from Compound 4a following the synthetic methodology reported above for the compound of Example 129 using piperidin-4-ol instead of 6-methylpyridin-2-amine. The title product was obtained as a brown solid (Yield: 11.9%).
UPLC-MS [M+H]⁺=387.3

Example 145

Ethyl 4-({(4E)-4-[3-(3-chlorophenyl)prop-2-yn-1-ylidene]-3,3-dimethylpiperidin-1-yl}sulfonyl)piperidine-1-carboxylate To a solution of Compound 4a (42 mg, 0.16 mmol) and TEA (0.32 mmol, 32.72 mg, 0.0451 mL) in $CH_2Cl_2$ (5 mL) cooled at 0° C., ethyl 4-chlorosulfonylpiperidine-1-carboxylate (0.24 mmol, 62.01 mg) was added and the mixture was stirred at r.t. overnight. Then water was added, the two phases were separated, the organic layer was dried over $Na_2SO_4$, filtered and evaporated. The crude residue was purified by means of Biotage Isolera One®, cartridge type SNAP10, using a gradient from Petroleum Ether:EtOAc 9:1 to Petroleum ether:EtOAc 6:4. 25 mg of the title compound (yellow oil) were recovered (32%).
UPLC-MS [M+H]⁺=479.24
¹H NMR (400 MHz, DMSO-d₆) δ ppm 7.50-7.55 (m, 1H), 7.37-7.47 (m, 3H), 5.68 (s, 1H), 4.04 (q, 4H), 3.34-3.44 (m, 3H), 3.06 (s, 2H), 2.73-2.92 (m, 2H), 2.69 (t, 2H), 1.89-2.02 (m, 2H), 1.46 (m, 2H), 1.18 (t, 3H), 1.13 (s, 6H)

The following compounds were prepared as reported above for Compound 145 replacing ethyl 4-chlorosulfonylpiperidine-1-carboxylate with the proper commercially available sulphonyl chloride:

TABLE 2

Example compounds prepared.

| Example | Chemical name | MW | UPLC-MS [M + H]+ |
|---|---|---|---|
| 146 | (4E)-4-[3-(3-chlorophenyl)prop-2-yn-1-ylidene]-3,3-dimethyl-1-[(tetrahydro-2H-pyran-2-ylmethyl)sulfonyl]piperidine | 421.98 | 422.34 |
| 147 | 5-({(4E)-4-[3-(3-chlorophenyl)prop-2-yn-1-ylidene]-3,3-dimethylpiperidin-1-yl}sulfonyl)-3-ethyl[1,2]oxazolo[5,4-b]pyridine | 469.98 | 470.23 |
| 148 | (4E)-4-[3-(3-chlorophenyl)prop-2-yn-1-ylidene]-3,3-dimethyl-1-{[(3-methyl-1,2-oxazol-5-yl)methyl]sulfonyl}piperidine | 418.94 | 419.28 |
| 149 | (4E)-4-[3-(3-chlorophenyl)prop-2-yn-1-ylidene]-N,3,3-trimethyl-N-(propan-2-yl)piperidine-1-sulfonamide | 394.96 | 395.33 |
| 150 | 4-({(4E)-4-[3-(3-chlorophenyl)prop-2-yn-1-ylidene]-3,3-dimethylpiperidin-1-yl}sulfonyl)-2,6-dimethylmorpholine | 437.00 | 437.26 |
| 151 | (4E)-4-[3-(3-chlorophenyl)prop-2-yn-1-ylidene]-3,3-dimethyl-1-(phenylsulfonyl)piperidine | 399.93 | 400.22 |
| 152 | (4E)-N-tert-butyl-4-[3-(3-chlorophenyl)prop-2-yn-1-ylidene]-3,3-dimethylpiperidine-1-sulfonamide | 394.96 | 395.27 |
| 153 | 4-({(4E)-4-[3-(3-chlorophenyl)prop-2-yn-1-ylidene]-3,3-dimethylpiperidin-1-yl}sulfonyl)morpholine | 408.94 | 409.22 |
| 154 | 4-({(4E)-4-[3-(3-chlorophenyl)prop-2-yn-1-ylidene]-3,3-dimethylpiperidin-1-yl}sulfonyl)-1-methyl-1H-benzotriazole | 454.97 | 455.20 |
| 155 | 3-({(4E)-4-[3-(3-chlorophenyl)prop-2-yn-1-ylidene]-3,3-dimethylpiperidin-1-yl}sulfonyl)-5-(propan-2-yloxy)pyridine | 459.00 | 459.33 |
| 156 | (4E)-4-[3-(3-chlorophenyl)prop-2-yn-1-ylidene]-N-(cyclopropylmethyl)-N,3,3-trimethylpiperidine-1-sulfonamide | 406.97 | 407.33 |
| 157 | 5-({(4E)-4-[3-(3-chlorophenyl)prop-2-yn-1-ylidene]-3,3-dimethylpiperidin-1-yl}sulfonyl)-2-methoxypyridine | 430.95 | 431.34 |
| 158 | 3-({(4E)-4-[3-(3-chlorophenyl)prop-2-yn-1-ylidene]-3,3-dimethylpiperidin-1-yl}sulfonyl)-6,7-dihydro-5H-pyrazolo[5,1-b][1,3]oxazine | 445.96 | 446.35 |
| 159 | (4E)-4-[3-(3-chlorophenyl)prop-2-yn-1-ylidene]-N-cyclohexyl-N,3,3-trimethylpiperidine-1-sulfonamide | 435.02 | 435.30 |
| 160 | (4E)-4-[3-(3-chlorophenyl)prop-2-yn-1-ylidene]-3,3-dimethyl-1-[(4-methylpiperidin-1-yl)sulfonyl]piperidine | 421.00 | 421.18 |
| 161 | (4E)-4-[3-(3-chlorophenyl)prop-2-yn-1-ylidene]-1-[(2,2-dimethylpropyl)sulfonyl]-3,3-dimethylpiperidine | 393.97 | 394.16 |
| 162 | (4E)-4-[3-(3-chlorophenyl)prop-2-yn-1-ylidene]-3,3-dimethyl-1-[(tetrahydro-2H-pyran-3-ylmethyl)sulfonyl]piperidine | 421.98 | 422.25 |

TABLE 2-continued

Example compounds prepared.

| Example | Chemical name | MW | UPLC-MS [M + H]+ |
|---|---|---|---|
| 163 | (4E)-4-[3-(3-chlorophenyl)prop-2-yn-1-ylidene]-1-[(3,5-dimethyl-1,2-oxazol-4-yl)sulfonyl]-3,3-dimethylpiperidine | 418.94 | 419.20 |
| 164 | 6-({(4E)-4-[3-(3-chlorophenyl)prop-2-yn-1-ylidene]-3,3-dimethylpiperidin-1-yl}sulfonyl)pyrazolo[1,5-a]pyrimidine-3-carbonitrile | 526.09 | 526.14 |
| 165 | (4E)-4-[3-(3-chlorophenyl)prop-2-yn-1-ylidene]-1-[(1-ethyl-3,5-dimethyl-1H-pyrazol-4-yl)sulfonyl]-3,3-dimethylpiperidine | 446.01 | 446.18 |

Example 166

{(4E)-4-[3-(3-Chlorophenyl)prop-2-yn-1-ylidene]-3,3-dimethylpiperidin-1-yl}(4,6-dimethoxypyrimidin-2-yl)methanone To a solution of (4E)-4-[3-(3-chlorophenyl)prop-2-ynylidene]-3,3-dimethyl-piperidine (Compound 4a, 37 mg, 0.14 mmol) and 4,6-dimethoxypyrimidine-2-carboxylic acid (1.1 equiv., 28.85 mg, 0.157 mmol) in anhydrous DMF, diethyl cyanophosphonate (1.1 equiv., 25.55 mg, 0.157 mmol) and TEA (1.1 equiv., 15.85 mg, 0.157 mmol) were added and the mixture was stirred at r.t. for 5 hours, poured into water and extracted with EtOAc. The collected organic layers were dried over $Na_2SO_4$ and the solvent was evaporated to dryness to give a crude which was purified via automated flash chromatography (Biotage Isolera Dalton®), SNAP 25 Cartridge, eluting with a EtOAc—Petroleum Ether gradient from 1:9 to 9:1 to give 54 mg of the title compound (89%).

UPLC-MS $[M+H]^+$=426.91

Example 167

{(4E)-4-[3-(3-Chlorophenyl)prop-2-yn-1-ylidene]-3,3-dimethylpiperidin-1-yl}(2-ethyl-5-methyl-2H-1,2,3-triazol-4-yl)methanone Prepared by the same procedure described for the compound of Example 166 but using 2-ethyl-5-methyltriazole-4-carboxylic acid instead of 4,6-dimethoxypyrimidine-2-carboxylic acid. Pale yellow solid (65%).

UPLC-MS $[M+H]^+$=397.26

Example 168

{(4E)-4-[3-(3-Chlorophenyl)prop-2-yn-1-ylidene]-3,3-dimethylpiperidin-1-yl}(4-methoxypyrimidin-2-yl)methanone Prepared by the same procedure described for the compound of Example 166 but using 4-methoxypyrimidine-2-carboxylic acid instead of 4,6-dimethoxypyrimidine-2-carboxylic acid (40.9%).

UPLC-MS $[M+H]^+$=396.23

Example 169

{(4E)-4-[3-(3-Chlorophenyl)prop-2-yn-1-ylidene]-3,3-dimethylpiperidin-1-yl}(6,7-dihydro-5H-pyrazolo[5,1-b][1,3]oxazin-3-yl)methanone Prepared by the same procedure described for the compound of Example 166 but using 6,7-dihydro-5H-pyrazolo[5,1-b][1,3]oxazine-3-carboxylic acid instead of 4,6-dimethoxypyrimidine-2-carboxylic acid. Pale yellow solid (63.4%).

UPLC-MS $[M+H]^+$=410.32

Example 170

{(4E)-4-[3-(3-Chlorophenyl)prop-2-yn-1-ylidene]-3,3-dimethylpiperidin-1-yl}([1,2,4]triazolo[1,5-a]pyridin-2-yl)methanone Prepared by the same procedure described for the compound of Example 166 but using triazolo[1,5-a]pyridine-2-carboxylic acid instead of 4,6-dimethoxypyrimidine-2-carboxylic acid. Pale yellow solid (63.4%).

UPLC-MS $[M+H]^+$=405.27

Example 171

{(4E)-4-[3-(3-Chlorophenyl)prop-2-yn-1-ylidene]-3,3-dimethylpiperidin-1-yl}(2,6-dimethoxypyrimidin-4-yl)methanone Prepared by the same procedure described for the compound of Example 166 but using 2,6-dimethoxypyrimidine-4-carboxylic acid instead of 4,6-dimethoxypyrimidine-2-carboxylic acid (80.78%).

UPLC-MS $[M+H]^+$=426.30

Example 172

4-({(4E)-4-[3-(3-Chlorophenyl)prop-2-yn-1-ylidene]-3,3-dimethylpiperidin-1-yl}carbonyl)pyridine-2-carbonitrile Prepared by the same procedure described for the compound of Example 166 but using 2-cyanopyridine-4-carboxylic acid instead of 4,6-dimethoxypyrimidine-2-carboxylic acid (68.43%).

UPLC-MS $[M+H]^+$=390.29

Example 173

{(4E)-4-[3-(3-Chlorophenyl)prop-2-yn-1-ylidene]-3,3-dimethylpiperidin-1-yl}(1,5-dimethyl-1H-1,2,3-triazol-4-yl)methanone Prepared by the same procedure described for the compound of Example 166 but using 1,5-dimethyltriazole-4-carboxylic acid instead of 4,6-dimethoxypyrimidine-2-carboxylic acid. Pale yellow solid (68.8%).

UPLC-MS $[M+H]^+$=383.25

Example 174

{(4E)-4-[3-(3-Chlorophenyl)prop-2-yn-1-ylidene]-3,
3-dimethylpiperidin-1-yl}(5,6-dihydro-8H-imidazo
[2,1-c][1,4]oxazin-3-yl)methanone Prepared by the same procedure described for the compound of Example 166 but using 5,6-dihydro-8H-imidazo[2,1-c][1,4]oxazine-3-carboxylic acid instead of 4,6-dimethoxypyrimidine-2-carboxylic acid. Pale yellow solid (50.7%).
UPLC-MS [M+H]$^+$=410.32

Example 175

6-({(4E)-4-[3-(3-Chlorophenyl)prop-2-yn-1-ylidene]-3,3-dimethylpiperidin-1-yl}carbonyl)pyridine-2-carbonitrile Prepared by the same procedure described for the compound of Example 166 but using 6-cyanopyridine-2-carboxylic acid instead of 4,6-dimethoxypyrimidine-2-carboxylic acid (55.53%).
UPLC-MS [M+H]$^+$=390.30

Example 176

{(4E)-4-[3-(3-Chlorophenyl)prop-2-yn-1-ylidene]-3,
3-dimethylpiperidin-1-yl}(3-methoxy-1-methyl-1H-
pyrazol-5-yl)methanone Prepared by the same procedure described for the compound of Example 166 but using 3-methoxy-1-methyl-1H-pyrazole-5-carboxylic acid instead of 4,6-dimethoxypyrimidine-2-carboxylic acid. Pale yellow solid (78.35%).
UPLC-MS [M+H]$^+$=398.31

Example 177

(3-Chlorophenyl){(4E)-4-[3-(4-methoxypyridin-2-
yl)prop-2-yn-1-ylidene]-3,3-dimethylpiperidin-1-
yl}methanone Prepared starting from Compound 116c following the procedure described above for the Compound of Example 116 and replacing 3-iodobenzonitrile with 2-bromo-4-methoxypyridine. Oil (yield: 27.23%).
UPLC-MS [M+H]$^+$=395.2

Example 178

(3-Chlorophenyl)[(4E)-4-{3-[5-(hydroxymethyl)
furan-2-yl]prop-2-yn-1-ylidene}-3,3-dimethylpiperi-
din-1-yl]methanone tert-Butyl (4E)-4-[3-[5-(hydroxymethyl)-2-furyl]
prop-2-ynylidene]-3,3-dimethylpiperidine-1-car-
boxylate (Compound 178a)

Prepared starting from Compound 1a following the procedure described above for the Compound of Example 1 and replacing 2-bromo-6-methylpyridine with 5-bromo-2-furylmethanol. Orange oil (yield: 31.8%).

[5-[(3E)-3-(3,3-dimethyl-4-piperidylidene)prop-1-
ynyl]-2-furyl]methanol (Compound 178b)

A solution of Compound 178a (106 mg, 0.307 mmol) in 1,4-dioxane (4.08 mL) cooled to 0° C. was treated with hydrogen chloride (0.77 mL, 3.07 mmol, 4N dioxane solution) then left in the fridge overnight. Afterwards, the reaction mixture was evaporated to dryness to afford 150 mg of a yellow residue used in the next step as it was.

(3-Chlorophenyl)[(4E)-4-{3-[5-(hydroxymethyl)
furan-2-yl]prop-2-yn-1-ylidene}-33-dimethylpiperi-
din-1-yl]methanone A solution of 3-chlorobenzoic acid (96.13 mg, 0.61 mmol) and 1,1'-carbonyldiimidazole (CDI) (99.56 mg, 0.61 mmol) in THF (3.08 mL) was stirred for 60 min at r.t., then a solution of Compound 178b (86 mg, 0.307 mmol) in THF (3.08 mL) was added. The reaction mixture was stirred at r.t. for 3 h. Then the reaction mixture was concentrated to dryness in vacuo. The crude residue was purified by Biotage Isolera® (SiO$_2$, 25 g Ultra, flow 30 mL/min, PE/EtOAc, 9/1 (1 CV), 9/1 to 1/1 (20 CV), 1/1 (5 CV)) affording the desired product (14 mg) as colorless oily residue. This compound was purified again by Biotage Isolera (C18, 12 g ultra, flow 30 mL/min, water/MeCN, 10% water (2 CV), 10-70% (20 CV), 70% (1 CV)) affording the desired product (4.99 mg) as white solid.
UPLC-MS [M+H]$^+$=384.1

Example 179

(3-Chlorophenyl)[(4E)-4-({3-[3-(hydroxymethyl)
phenyl]-1H-pyrazol-5-yl]methylidene)-3,3-dimeth-
ylpiperidin-1-yl}methanone Lithium: (Z)-1-(3-cyanophenyl)-4-ethoxy-3,4-dioxo-
but-1-en-1-olate (Compound 179a)

To a solution of 1M (THF) LHMDS (37.89 ml, 37.89 mmol) in THF (20 ml, 0.247 mol) was slowly added a solution of 3-acetylbenzonitrile (5 g, 34.4 mmol) in diethyl ether (25 ml) and diethyl ether (60 ml, 0.57 mol) in order to solubilize the substrate stirring at −78° C. After 45 min at −78° C. diethyl oxalate (5.15 ml, 37.89 mmol) was added dropwise and the reaction mixture was then stirred at room temperature for 16 h. The reaction mixture was concentrated and the crude title product so obtained was used in the next step without further purification considering a quantitative yield.

Ethyl 5-(3-cyanophenyl)-1H-pyrazole-3-carboxylate
(Compound 179b)

To a solution of Compound 179a (8.65 g, 34.45 mmol) in absolute ethanol (100 ml) was added hydrazine dihydrochloride (3.98 g, 37.89 mmol) at r.t. The reaction mixture was stirred at the same temperature for 24 h. Solvent was removed in vacuo; the mixture so obtained was portioned between water (200 ml) and EtOAc (150 ml), phase were separated and the aqueous layer extracted with EtOAc (150 ml). Combined organics were washed with brine (100 ml) and dried over sodium sulphate. Evaporation to dryness gave ethyl 5-(3-cyanophenyl)-1H-pyrazole-3-carboxylate (8.2 g, 33.99 mmol) as a yellow powder.

Ethyl 5-(3-cyanophenyl)-2-[(4-methoxyphenyl) methyl]pyrazole-3-carboxylate and ethyl 5-(3-cyanophenyl)-1-[(4-methoxyphenyl)methyl]pyrazole-3-carboxylate (Compound 179c and 179d)

A suspension of ethyl 5-(3-cyanophenyl)-1H-pyrazole-3-carboxylate (1 g, 4.15 mmol) and potassium iodide (825.7 mg, 4.97 mmol) in MeCN (30 mL) was treated with 1-(chloromethyl)-4-methoxybenzene (0.62 mL, 4.97 mmol) and stirred at 40° C. for 5 h. UPLC-MS showed mainly starting materials and formation of traces of a new peak. Potassium iodide (825.71 mg, 4.97 mmol) was added and stirring was continued at 40° C. till UPLC-MS showed completion of the title compounds formation with two major peaks. The reaction mixture was filtered off and evaporated to dryness. The residue was portioned between DCM and water. Organic phase was separated, dried (Na$_2$SO$_4$) and concentrated to dryness in vacuo. The crude product was purified by Biotage Isolera® (SiO$_2$, 100 g, PE/EA, 5% EA 3 CV, 5-50% 15 CV, 50% 3 CV) giving the two title compounds: product A (RT 2.25 min), g 1.03, white solid (unknown regioisomer); product B (RT: 1.9 min), g 0.33, yellow oil (unknown regioisomer). Products A and B were combined and used in the next step.

3-[5-(Hydroxymethyl)-1-[(4-methoxyphenyl)methyl] pyrazol-3-yl]benzaldehyde and 3-[5-(hydroxymethyl)-2-[(4-methoxyphenyl)methyl]pyrazol-3-yl] benzaldehyde (Compound 179e and 179_f)

A stirred solution of Compounds 179 c and 179d previously combined (1.07 g, 2.96 mmol) in THF (12.3 ml) cooled to −78° C. was slowly treated with 1 M LiAlH$_4$ in THF (5.92 mL, 5.92 mmol) then warmed to 0° C. and stirred at 0° C. for 30 min. The reaction mixture was quenched by addition of 1N HCl sol., then diluted with EtOAc. Organic phase was separated. The aqueous phase was extracted with EtOAc. Organic phases were dried (Na$_2$SO$_4$) and concentrated to dryness in vacuo. The crude product was purified by Biotage Isolera® (SiO$_2$, 50 g, PE/EtOAc, 10% EA 1 CV, 10-100% 15 CV, 100% 3 CV) giving two products: A (unknown regioisomer), RT 1.51, 227 mg, colourless sticky solid and B (unknown regioisomer) RT 1.37, 43 mg, yellow sticky solid. Products A and B were combined (270 mg) and used in the next step. 1H-NMR ratio 4/1.

3-[5-(Bromomethyl)-2-[(4-methoxyphenyl)methyl]-1H-pyrazol-3-yl]benzaldehyde and 3-[5-(bromomethyl)-1-[(4-methoxyphenyl)methyl]-1H-pyrazol-3-yl]benzaldehyde (Compound 179g and 179 h)

A solution of Compounds 179e and 179f previously combined (270 mg, 0.85 mmol) in DCM (15.1 mL, 0.236 mol) was treated with triphenylphosphine (243.93 mg, 0.93 mmol) and carbon tetrabromide (420.6 mg, 1.27 mmol). The reaction mixture was stirred at r.t. for 2 h. Then further 120 mg (0.55 eq) of triphenylphosphine and 210 mg (0.75 eq) of CBr$_4$ were added. The reaction mixture was stirred at r.t. for further 2 h. Monitoring by UPLC-MS showed that the reaction went to completion. The reaction mixture was concentrated to dryness and the crude residue was purified by Biotage Isolera® (SiO$_2$, 50 g, PE/EtOAc, 50% EtOAc 3 CV, 5-30% 15 CV, 30% 3 CV) giving two products respectively with RT 2.07 (A) and 1.96 (B) min, which were combined together giving 290 mg of a yellow sticky solid as a mixture of regioisomeric title compounds as ratio 9/1 ($^1$H-NMR-UPLC) used in the next step.

Diethyl {[3-(3-formylphenyl)-1-(4-methoxybenzyl)-1H-pyrazol-5-yl]methyl}phosphonate and-diethyl {[5-(3-formylphenyl)-1-(4-methoxybenzyl)-1H-pyrazol-3-yl]methyl}phosphonate (Compound 179i and 179l)

Triethyl phosphite (0.4 mL, 2.31 mmol) was added to a solution of 3-[5-(bromomethyl)-1-[(4-methoxyphenyl) methyl]pyrazol-3-yl]benzaldehyde and 3-[5-(bromomethyl)-2-[(4-methoxyphenyl)methyl]pyrazol-3-yl]benzaldehyde (Compounds 179i and 179j mixture, 650 mg, 1.7 mmol) in toluene (6.78 mL). Potassium iodide (70.6 mg, 0.43 mmol) was added and the resulting suspension was heated at 120° C. in an oil bath and the reaction was kept under stirring. After cooling down, the reaction mixture was evaporated to dryness and the resulting crude was purified by Biotage Isolera (SiO$_2$, 100 g, DCM/EtOAc, 0% EtOAc 1 CV, 0-100 20 CV, 100% 3 CV, then EtOAc/MeOH 0-10% MeOH, 5 CV, 10% 3 CV) affording 2 products: A (unknown regioisomer), 407 mg; B (unknown regioisomer), 33 mg. Products A and B were recombined (0.44 g) and used in the next step (90% pure, HPLC purity, ratio 75/25).

Diethyl ({3-[3-(hydroxymethyl)phenyl]-1-(4-methoxybenzyl)-1H-pyrazol-5-yl}methyl)phosphonate and diethyl ({5-[3-(hydroxymethyl)phenyl]-1-(4-methoxybenzyl)-1H-pyrazol-3-yl}methyl) phosphonate (Compound 179k and 179l)

A mixture of compound 179j and 179k (0.44 g, 0.990 mmol) in methanol (6.05 mL) was treated at 0° C. with NaBH$_4$ (0.06 g, 1.49 mmol) added in small portions. The reaction mixture was stirred at RT for 1 h. The reaction mixture was quenched by addition of sat. aq. NH$_4$Cl sol and diluted with EtOAc. The organic phase was separated, washed with brine, dried (Na$_2$SO$_4$) and concentrated to dryness in vacuo. The crude title compound (400 mg of white sticky solid) was used in the next step and was 88% pure by HPLC as a 75:25 regioisomer mixture.

Diethyl ({3-[3-({[tert-butyl(dimethyl)silyl] oxy}methyl)phenyl]-1-(4-methoxybenzyl)-1H-pyrazol-5-yl}methyl)phosphonate and diethyl ({5-[3-({[tert-butyl(dimethyl)silyl]oxy}methyl)phenyl]-1-(4-methoxybenzyl)-1H-pyrazol-3-yl}methyl) phosphonate (Compound 179m and 179n)

A solution of Compounds 179k and l; 440 mg, 0.99 mmol) in DCM (9 mL) was treated with imidazole (101.1 mg, 1.48 mmol) and then with tert-butyl-chloro-diphenylsilane (326.52 mg, 1.2 mmol). The reaction mixture was stirred at r.t. for 1 h. Further imidazole (101.1 mg, 1.5 mmol) and tert-butyl-chloro-diphenylsilane (326.52 mg, 1.2 mmol) was added and the reaction stirred for 1 h. UPLC showed still 20% of starting materials. Then imidazole (101.1 mg, 1.48 mmol) and tert-butyl-chloro-diphenylsilane (326.52 mg, 1.19 mmol) was added again and stirring continued for 3 h. The reaction mixture was concentrated to dryness, diluted with DCM and filtered off. The crude product was purified by Biotage Isolera® (SiO$_2$, 50 g ultra, PE/EtOAc, 20% EtOAc 2 CV, 20-100 10 CV, 100% 3 CV, then EtOAc/MeOH, 0-10% MeOH 5 CV, 10% 3 CV) giving the desired products as colourless oil (0.59 g). The title compounds ratio was 9:1 and used so far in the next step.

[(4E)-4-[[5-[3-[[tert-butyl(dimethyl)silyl]oxymethyl]
phenyl]-2-[(4-ethoxyphenyl)methyl]pyrazol-3-yl]
methylidene]-3,3-dimethyl-piperidin-1-yl]-(3-chlorophenyl)methanone and [(4E)-4-[[5-[3-[[tert-butyl
(dimethyl)silyl]oxymethyl]phenyl]-1-[(4-ethoxyphenyl)methyl]pyrazol-3-yl]methylidene]-3,
3-dimethyl-piperidin-1-yl]-(3-chlorophenyl)
methanone (Compound 179o and 179p)

LHMDS (0.44 mL, 0.440 mmol, 1 M solution in THF) was added dropwise to a solution of a Compounds 179m and 179 mixture (258.94 mg, 0.440 mmol) in THF (6 mL) cooled at −78° C. After stirring for 30 min the anion formation was checked by quenching the reaction mixture directly with $D_2O$ and analysing the sample by UPLC-MS. The reaction mixture was kept under stirring for 1 h at −78° C. The second check showed no progress of the reaction, so LHMDS (0.44 mL, 0.440 mmol) was added again and after 30 min a third check was done. Afterwards, a solution of 1-(3-chlorophenyl)carbonyl-3,3-dimethylpiperidin-4-one (90. mg, 0.340 mmol) in THF (2 mL) was added dropwise. Then, the reaction mixture was left warming to r.t. on. After quenching with water, the reaction mixture was diluted with EtOAc. The organic phase was separated, washed with brine, dried ($Na_2SO_4$) and solvent evaporated to give a crude yellow oil, which was purified by Biotage Isolera ($SiO_2$, 25 g, PE/EtOAc, 10% EtOAc 3 CV, 10-100% 20 CV, 100% 3 CV) giving the title products (150 mg of colourless sticky solid), mixture of desired products (purity 87%, ratio 87/13 by UPLC). used in the next step.

(3-Chlorophenyl)[(4E)-4-(3-[3-(hydroxymethyl)
phenyl]-1H-pyrazol-5-ylmethylidene)-3,3-dimethylpiperidin-1-yl]methanone A solution of Compounds 179o and 179 p (75 mg, 0.110 mmol) in DCE (1 mL) was cooled to 0° C. and treated with TFA (1. mL, 13.07 mmol). The reaction mixture was stirred at r.t. for 4 h. After UPLC-MS check, the reaction mixture was heated at 60° C. for 2 h. 0.5 mL of TFA were added and the reaction mixture was heated at reflux for 5 days. The reaction mixture was concentrated to dryness, diluted with DCM, cooled to 0° C. and 1N NaOH sol was added (2 mL). Organic phase was separated. Water phase was extracted with DCM (3×). Recombined organic phases were dried over $Na_2SO_4$ and evaporated to dryness to afford 64 mg of yellow solid which was purified by Biotage Isolera ($SiO_2$, 10 g ultra, PE/EtOAc, 10% EtOAc 3 CV, 10-100% 20 CV, 100% 3 CV) giving the desired product (22.6 mg of white solid).
UPLC-MS $[M+H]^+=436.3$ Example 180

3-(5-{(E)-[1-(3-Chlorobenzoyl)-3,3-dimethylpiperidin-4-ylidene]methyl}-1H-pyrazol-3-yl)benzonitrile 3-[5-(Hydroxymethyl)-2-[(4-methoxyphenyl)methyl]
pyrazol-3-yl]benzenecarbonitrile and 3-[5-(hydroxymethyl)-1-[(4-methoxyphenyl)methyl]pyrazol-
3-yl]benzenecarbonitrile (Compound 180a and
180b)

A solution of ethyl 5-(3-cyanophenyl)-1-[(4-methoxyphenyl)methyl]pyrazole-3-carboxylate and ethyl 5-(3-cyanophenyl)-2-[(4-methoxyphenyl)methyl]pyrazole-3-carboxylate (2 g, 5.53 mmol, Compounds 179c and 179d) in THF (39.53 mL, 0.487 mol) was treated with a solution of calcium chloride dihydrate (1.23 g, 11.07 mmol) in ethanol (39.53 mL), then $NaBH_4$ (0.84 g, 22.14 mmol) was added in 3 portions over a period of 30 min. The reaction mixture was stirred at r.t. for 6 h. The reaction mixture was quenched by addition of sat. aq. $NH_4Cl$ sol. and diluted with EtOAc. The reaction mixture was filtered off. Organic phase was washed with brine, dried ($Na_2SO_4$) and concentrated to dryness in vacuo. The crude product (1.4 g of white foamy solid) was used in the next step without further purification.
UPLC-MS: mixture of title products (91% pure, ratio 75/25) and 8% of starting material with RT=2.2 min; 1H-NMR: mixture of desired products (ratio 75/25) and starting material (8%).

3-[5-Bromomethyl)-2-[(4-methoxyphenyl)methyl]
pyrazol-3-yl]benzenecarbonitrile and 3-[5-(bromomethyl)-1-[(4-methoxyphenyl)methyl]pyrazol-3-yl]
benzenecarbonitrile (Compound 180c and 180 d)

A solution of pre-mixed Compounds 180a and 180 b (1.6 g, 5.01 mmol) in DCM (100 mL) was treated with triphenylphosphine (1.97 g, 7.52 mmol) and carbon tetrabromide (3.32 g, 10.02 mmol). The reaction mixture was stirred at r.t. Then further $PPh_3$ (1 g, 1 eq) and $CBr_4$ (1.7 g, 2 eq) were added and reaction stirred at r.t. for 4 h. The reaction mixture was concentrated to dryness in vacuo and the crude residue was purified by Biotage Isolera® ($SiO_2$, 100 g ultra, PE/EtOAc, 5% EtOAc 3 CV, 5-50% 15 CV, 50% 3 CV) giving two products with RT 2.07 (A) and 1.96 (B) min which were combined together. 1 g of white solid was obtained UPLC-MS: mixture of regioisomers ratio 75/25. $^1$H-NMR: title products (mixture of regioisomers ratio 72/28). These products mixture was used in the next step.

Diethyl {[3-(3-cyanophenyl)-1-(4-methoxybenzyl)-
1H-pyrazol-5-yl]methyl}phosphonate and diethyl
{[5-(3-cyanophenyl)-1-(4-methoxybenzyl)-1H-pyrazol-3-yl]methyl}phosphonate (Compound 180e and
180f)

Triethyl phosphite (0.61 mL, 3.56 mmol) was added to a solution of Compound 180c and 180d (1 g, 2.62 mmol) in toluene (10.46 mL). Potassium iodide (108.54 mg, 0.650 mmol) was added and the resulting suspension was heated at 120° C. in an oil bath (reagent got solubilized) and the reaction was stirred for 6 h then reagents (triethyl phosphite (0.61 mL, 3.56 mmol) and potassium iodide (108.54 mg, 0.650 mmol) were added again and stirring was continued till UPLC-MS check established reaction accomplishment. After cooling to r.t., the reaction mixture was evaporated to dryness in vacuo and the resulting crude was purified by Biotage Isolera® ($SiO_2$, 50 g, DCM/EtOAc 0% EtOAc 3 CV, 0-100 20 CV, 100% 3 CV) affording the 2 title compounds which were combined together affording 1.82 g of yellow oil containing the 2 regioisomers (UPLC-MS:ratio 7/3) and triethylphosphite. This product was purified again by Biotage Isolera ($SiO_2$, 100 g ultra, DCM/EtOAc, 0% EtOAc 1 CV, 0-100 15 CV, 100% 1 CV, then EtOAc/MeOH, 0-10% MeOH 5 CV, 10% 3 CV) affording 2 products which were re-combined together giving 0.41 g of yellow oil. UPLC-MS: mixture of title products (ratio 68/32). 1.1 g of colourless oil was also recovered. UPLC-MS: mixture of desired product with RT=1.79 and triethyl phosphite. The last product was re-purified by Biotage Isolera® ($SiO_2$, 100 g, PE/EtOAc, 0% EtOAc 3 CV, 0-100 20 CV, 100% 5 CV) affording the desired product as colorless oil. This product was combined with the previously obtained mixture (1.01 g of yellow oily residue) and used in the next step. UPLC-MS: mixture of title products (ratio 72/28); $^1$H-NMR: title products (ratio 72/28).

3-[5-[(E)-[1-(3-Chlorophenyl)carbonyl-3,3-dimethyl-piperidin-4-ylidene]methyl]-1-[(4-methoxyphenyl)methyl]pyrazol-3-yl]benzenecarbonitrile and 3-[5-[(E)-[1-(3-chlorophenyl)carbonyl-3,3-dimethylpiperidin-4-ylidene]methyl]-2-[(4-methoxyphenyl)methyl]pyrazol-3-yl]benzenecarbonitrile (Compound 180g and 180 h)

Prepared starting from Compounds 180e and 180 f mixture following the procedure described for Compounds 179o and p.
Purification by Biotage Isolera® (SiO$_2$, 25 g, PE/EtOAc, 10% EtOAc 3 CV, 10-100% 20 CV, 100% 3 CV) gave 98 mg (52%) of the title products as colourless sticky solid. UPLC-MS: mixture of desired products (ratio 55/45); $^1$H-NMR: mixture of desired products. Used in the next step.

3-[5-[(E)-[1-(3-Chlorophenyl)carbonyl-3,3-dimethyl-piperidin-4-ylidene]methyl]-1H-pyrazol-3-yl]benzenecarbonitrile Prepared following the procedure described for the compound of Example 179 but starting from Compounds 180g and 180 h pre-mixed. Crude purification by Biotage Isolera (SiO$_2$, 10 g ultra, PE/EtOAc, 10% EtOAc 3 CV, 10-80% 20 CV, 80% 3 CV) gave the title product (39.7 mg of white powder).
UPLC-MS [M+H]$^+$=431.2

Example 181

(3-Chlorophenyl)[(4E)-3,3-dimethyl-4-{[3-(6-methylpyridin-2-yl)-1H-pyrazol-5-yl]methylidene]piperidin-1-yl}methanone Ethyl 5-(6-methyl-2-pyridyl)-1H-pyrazole-3-carboxylate (Compound 181a)

The title compound was prepared from 1-acetyl-6-methylpyridine following steps a and b of the preparation of the compound of Example 179.

Ethyl 1-[(4-methoxyphenyl)methyl]-5-(6-methyl-2-pyridyl)pyrazole-3-carboxylate and ethyl 2-[(4-methoxyphenyl)methyl]-5-(6-methyl-2-pyridyl)pyrazole-3-carboxylate (Compound 181b and 181c)

The title compounds were prepared from Compound 181a following the synthetic methodology reported above for Compounds 179c and 179d. Colourless oil (92.1%), 2:1 mixture of regioisomer (UPLC-MS).

[1-[(4-Methoxyphenyl)methyl]-5-(6-methyl-2-pyridyl)pyrazol-3-yl]methanol and [2-[(4-methoxyphenyl)methyl]-5-(6-methyl-2-pyridyl)pyrazol-3-yl]methanol (Compound 181d and 181e)

The title compounds were prepared from the mixture of Compounds 181b and 181c following the synthetic methodology reported above for the synthesis of Compounds 180a and 180b. Colourless oil (92.8%), 2:1 mixture of regioisomer (UPLC-MS).

2-[5-(Bromomethyl)-1-[(4-methoxyphenyl)methyl]pyrazol-3-yl]-6-methyl-pyridine and 2-[5-(bromomethyl)-2-[(4-methoxyphenyl)methyl]pyrazol-3-yl]-6-methyl-pyridine (Compound 181f and 181 g)

The title compounds were prepared from the mixture of Compounds 181d and 181e following the synthetic methodology reported above for Compounds 180c and 180d. Yellow oil as unpurified mixture of regioisomers containing also triphenylphospine but used in the next step without further purification.

Diethyl {[1-(4-methoxybenzyl)-3-(6-methylpyridin-2-yl)-1H-pyrazol-5-yl]methyl}phosphonate and diethyl {[1-(4-methoxybenzyl)-5-(6-methylpyridin-2-yl)-1H-pyrazol-3-yl]methyl}phosphonate (Compound 181h and 181i)

The title compounds were prepared from the mixture of Compounds 181f and 181 g following the synthetic methodology reported above for Compounds 180e and 180f. Colourless oil. 4:3 mixture (UPLC-MS, 1H-NMR) of regioisomers (Yield: 25%).

(3-Chlorophenyl)-[(4E)-4-[[1-[(4-hydroxyphenyl)methyl]-5-(6-methyl-2-pyridyl)pyrazol-3-yl]methylene]-3,3-dimethyl-1-piperidyl]methanone and (3-chlorophenyl)-[(4E)-4-[[2-[(4-methoxyphenyl)methyl]-5-(6-methyl-2-pyridyl)pyrazol-3-yl]methylene]-3,3-dimethyl-1-piperidyl]methanone (Compound 181j and 181k)

The title compounds were prepared from the mixture of Compounds 181h and 181i following the synthetic methodology reported above for Compounds 180g and 180 h. Yield: 33%. 1:1 mixture (UPLC-MS, 1H-NMR) of regioisomers (25%).

(3-Chlorophenyl)[(4E)-3,3-dimethyl-4-{[3-(6-methylpyridin-2-yl)-1H-pyrazol-5-yl]methylidene}piperidin-1-yl]methanone The title compound was prepared from the mixture of Compounds 181j and 181k following the synthetic methodology reported above for the compound of example 180. White solid. Yield: 53%.
UPLC-MS [M+H]$^+$=421.3

Example 182

[(4E)-4-{[5-(3-Chlorophenyl)-1H-pyrazol-3-yl]methylidene}-3,3-dimethylpiperidin-1-yl](2,5-dimethylfuran-3-yl)methanone

[5-(3-Chlorophenyl)-1-[(4-methoxyphenyl)methyl]pyrazol-3-yl]methanol and [5-(3-chlorophenyl)-2-[(4-methoxyphenyl)methyl]pyrazol-3-yl]methanol (Compound 182a and 182b)

The title compounds were prepared from the methyl 5-(3-chlorophenyl)-1H-pyrazole-3-carboxylate (commercially available) following the synthetic methodology reported above for the synthesis of Compounds 180a and 180b. 182a and 182b were combined to be used in the next step. Yellow solid (89%), 78:21 mixture of regioisomers (UPLC-MS, $^1$H-NMR).

3-(Bromomethyl)-5-(4-chlorophenyl)-1-[(4-methoxyphenyl)methyl]pyrazole and 5-(bromomethyl)-3-(3-chlorophenyl)-1-[(4-methoxyphenyl)methyl]pyrazole (Compound 182c and 182d)

The title compounds were prepared from the mixture of Compounds 182a and 182b following the synthetic methodology reported above for Compounds 180c and 180d. Yellow sticky solid as 60:40 mixture of regioisomers (UPLC-MS). Used in the next step as it is.

Diethyl {[3-(3-chlorophenyl)-1-(4-methoxybenzyl)-1H-pyrazol-5-yl]methyl}phosphonate and diethyl {[5-(3-chlorophenyl)-1-(4-methoxybenzyl)-1H-pyrazol-3-yl]methyl}phosphonate (Compound 182e and 182f)

The title compounds were prepared from the mixture of Compounds 182c and 182d following the synthetic methodology reported above for Compounds 180e and 180f. Colourless oil as undetermined mixture of regioisomers used in the next step.

(3-Chlorophenyl)-[(4E)-4-[[5-(3-chlorophenyl)-1-[(4-hydroxyphenyl)methyl]pyrazol-3-yl]methylene]-3,3-dimethyl-1-piperidyl]methanone and (3-chlorophenyl)-[(4E)-4-[[5-(3-chlorophenyl)-2-[(4-methoxyphenyl)methyl]pyrazol-3-yl]methylene]-3,3-dimethyl-1-piperidyl]methanone (Compound 182g and 182 h)

The title compounds were prepared from the mixture of Compounds 182e and 182f following the synthetic methodology reported above for Compounds 180g and 180 h but using N-Boc-3,3-dimethyl-4-piperidone. Colourless oil. Yield: 33% as a 1:1 mixture of regioisomers (UPLC-MS).

(4E)-4-[[3-(3-Chlorophenyl)-1H-pyrazol-5-yl]methylene]-3,3-dimethylpiperidine (Compound 182i)

A solution of Compounds 182g and 182 h (116 mg, 0.222 mmol) in DCE/TFA 1/1 (4 ml) was heated at 100° C. under MW irradiation for 15 min. The reaction mixtures were diluted with DCM, cooled to 0° C. and 2N NaOH sol. was slowly added (10-15 ml). Organic phase was separated. Water phase was extracted with DCM (3×). Recombined organic phases were dried over Na$_2$SO$_4$ and evaporated to dryness to afford 68 mg of a yellow oily residue. Used in the next step.

(3-Chlorophenyl)[(4E)-3,3-dimethyl-4-{[3-(6-methylpyridin-2-yl)-1H-pyrazol-5-yl]methylidene}piperidin-1-yl]methanone The title compound was prepared from Compound 182i following the synthetic methodology reported above for the compound of Example 126 using 2,5-dimethylfuran-3-carboxylic acid. White solid. Yield: 53.89%.
UPLC-MS [M+H]$^+$=424.3

(3-Chlorophenyl){(4E)-3,3-dimethyl-4-[(5-phenyl-1,2-oxazol-3-yl)methylidene]piperidin-1-yl}methanone Diethyl [(5-phenyl-1,2-oxazol-3-yl)methyl]phosphonate (Compound 183a)

Triethyl phosphite (452.8 mg, 2.72 mmol) was added to 3-(chloromethyl)-5-phenyl-1,2-oxazole (388 mg, 2 mmol, commercially available), previously weighed in a 2 ml microwave vial. The resulting suspension was heated at 120° C. in an oil bath and the reaction was followed by UPLC-MS. After 5 h KI (83.1 mg, 0.501 mmol) was added and the reaction mixture heated to 150° C. After 30 min at this temperature the reaction mixture was cooled down, the resulting crude was purified by automated flash chromatography (Horizon—Biotage® SNAP 100 G column) eluting with DCM/EtOAc (100:0 to 75:25). Evaporation to dryness of the solvent afforded 503 mg of a colourless oil that solidifies in the fridge.

(3-Chlorophenyl){(4E)-3,3-dimethyl-4-[(5-phenyl-1,2-oxazol-3-yl)methylidene]piperidin-1-yl}methanone LHMDS (1 M solution in THF) was added dropwise to a solution of the phosphonate 183a (108 mg, 0.36 mmol) in THF (1.8 ml) cooled at −70° C. After stirring for 1 h and 20 min a solution of Compound 116b (75 mg, 0.28 mmol) in THF (0.9 ml) was added dropwise. Then the reaction mixture was stirred for 30 min at −70° C. and allowed to warm-up slowly. After 2 h the cooling bath was removed and the reaction was stirred at r.t. overnight and followed by UPLC-MS. After quenching with water (0.5 ml) the reaction was diluted with EtOAc (50 ml) and washed with water (2×50 ml). The organic phase was dried (Na$_2$SO$_4$) and solvent evaporated to give 149 mg of an oil. The crude was purified by automated flash chromatography (Horizon—Biotage® SNAP KP-Sil 10 G column) eluting with Petroleum ether/EtOAc (95:5 to 70:30). Evaporation of the solvent afforded 26 mg of a white powder.
UPLC-MS [M+H]$^+$=407.2

Example 184

(3-Chlorophenyl)[(4E)-4-{[5-(3-chlorophenyl)-1,3-oxazol-2-yl]methylidene]-3,3-dimethylpiperidin-1-yl}methanone Diethyl {[5-(3-chlorophenyl)-1,3-oxazol-2-yl]methyl}phosphonate (Compound 184a)

Prepared from commercial 2-chloromethyl-5-(3-chlorophenyl)-1,3-oxazole as described for Compound 183a. Purification by automated column chromatography afforded the title compound as colourless oil (73.8%).

(3-Chlorophenyl)[(4E)-4-{[5-(3-chlorophenyl)-1,3-oxazol-2-yl]methylidene}-33-dimethylpiperidin-1-yl]methanone Prepared following the synthetic method described above for the compound of Example 183. White powder (14.2%)
UPLC-MS [M+H]$^+$=441.2

Example 185

3-Chlorophenyl[(4E)-4-{[5-(3-chlorophenyl)-1,2,4-oxadiazol-3-yl]methylidene]-3,3-dimethylpiperidin-1-yl}methanone Diethyl {[5-(3-chlorophenyl)-1,2,4-oxadiazol-3-yl]methyl}phosphonate (Compound 185a)

Prepared from commercial 3-chloromethyl-5-(3-chlorophenyl)-1,2,4-oxadiazole as described for Compound 183a.

Purification by automated column chromatography afforded the title compound as colourless oil (85%).

3-Chlorophenyl[(4E)-4-{[5-(3-chlorophenyl)-1,3,4-oxadiazol-3-yl]methylidene}-3,3-dimethylpiperidin-1-yl]methanone Prepared following the synthetic method described above for the compound of Example 183. White powder (40.4%). UPLC-MS [M+H]$^+$=442.2

Example 186

3-Chlorophenyl[(4E)-4-{[5-(3-chlorophenyl)-1,3,4-oxadiazol-2-yl]methylidene}-3,3-dimethylpiperidin-1-yl}methanone Diethyl {[5-(3-chlorophenyl)-1,3,4-oxadiazol-2-yl]methyl}phosphonate (Compound 186a)

Prepared from commercial 2-chloromethyl-5-(3-chlorophenyl)-1,3,4-oxadiazole as described for Compound 183a. Purification by automated column chromatography afforded the title compound as colourless oil (68%).

3-Chlorophenyl[(4E)-4-{[5-(3-chlorophenyl)-1,3,4-oxadiazol-2-yl]methylidene}-3,3-dimethylpiperidin-1-yl]methanone Prepared following the synthetic method described above for the compound of Example 183. White powder (43.6%). UPLC-MS [M+H]$^+$=442.2

(3-Chlorophenyl)[(4E)-4-(3-cyclohexylprop-2-yn-1-ylidene)-3,3-dimethylpiperidin-1-yl]methanone tert-Butyl (4E)-4-(bromomethylene)-3,3-dimethylpiperidine-1-carboxylate (Compound 187a A stirred suspension of bromomethyl(triphenyl)phosphonium bromide (2.014 g, 4.62 mmol) in THF (12 ml) was cooled to −15° C. and treated with LHMDS (4.62 ml, 4.62 mmol). Stirring was continued for 15 min then a solution of tert-butyl 3,3-dimethyl-4-oxopiperidine-1-carboxylate (1 g, 4.4 mmol) in THF (10 ml) was added slowly. The reaction mixture was left warming to r.t. and stirred for 2 h. The reaction mixture was quenched with water, then diluted with EtOAc. Organic phase was separated, washed with water (3×), brine, dried (Na$_2$SO$_4$) and concentrated. The crude residue (1.6 g) was purified by Biotage Isolera® (SiO$_2$, 100 g, PE/EtOAc, 0% EtOAc 3 CV, 0-20% 15 CV, 20% 3 CV) giving 140 mg of the title product as colourless oil used in the next step.

tert-Butyl (4E)-4-(3-cyclohexylprop-2-ynylidene)-3,3-dimethyl-piperidine-1-carboxylate (Compound 187b)

A solution of ethynylcyclohexane (0.07 ml, 0.51 mmol) in DMF (2.5 ml, 0.032 mol) cooled to −78° C. was treated with n-Buli (0.37 ml, 0.590 mmol) and stirred at −78° C. for 1 h. Triisopropyl borate (0.13 ml, 0.55 mmol) was added and stirring was continued at −78° C. for 2 h. After warming to r.t. (30 min), this solution was added to a stirred solution of Compound 187a (120. mg, 0.39 mmol) and Pd Tetrakis (45.58 mg, 0.040 mmol) in diethyl ether (5 ml, 0.048 mol). CuI (7.5 mg, 0.040 mmol) was added and the reaction mixture was stirred at 80° C. for 4 h. After 3 h the reaction was diluted with EtOAc and water. Organic phase was separated. Water phase was back extracted with EtOAc. Recombined organic phases were dried (Na$_2$SO$_4$) and concentrated. The crude brown residue (183 mg) was purified by Biotage Isolera® (SiO$_2$, 25 g UlTRA, PE/EtOAc, 5% EtOAc 3 CV, 5-20% 20 CV, 20% 3 CV) giving 38 mg of the title product as sticky solid used in the next step.

(4E)-4-(3-cyclohexylprop-2-ynylidene)-3,3-dimethyl-piperidine (Compound 187c)

A solution of tert-butyl (4E)-4-(3-cyclohexylprop-2-ynylidene)-3,3-dimethyl-piperidine-1-carboxylate (Compound 187b, 38 mg, 0.110 mmol) in DCM (1 ml) cooled to 0° C. was treated with TFA (0.1 ml, 0.110 mmol) then stirred at r.t. for 1 h. Organic phase was separated. Aqueous layer was extracted with DCM. Combined organic layers were dried over Na$_2$SO$_4$ and evaporated to afford 22.6 mg of a yellow oil. Used in the next step.

(3-Chlorophenyl)[(4E)-4-(3-cyclohexylprop-2-yn-1-ylidene)-3,3-dimethylpiperidin-1-yl]methanone A solution of Compound 187c (26.61 mg, 0.120 mmol) and TEA (0.03 mL, 0.230 mmol) in DCM (1 mL) was treated with 3-chlorobenzoyl chloride (0.02 mL, 0.150 mmol) and stirred at r.t. for 1 h. The reaction mixture was diluted with DCM, washed with 1N HCl sol., brine, dried (Na$_2$SO$_4$) and concentrated. The crude residue (65 mg) was purified by Biotage Isolera® (SiO$_2$, 10 g, PE/EtOAc, 5% EtOAc 3 CV, 5-30% 15 CV, 30% 3 CV) giving the desired product as yellow sticky solid. UPLC-MS showed that the title product was not pure containing 5% of 3-chlorobenzoic acid. So it was dissolved with DCM and washed with sat. aq. NaHCO$_3$ sol. Organic phase was dried and concentrated affording 25 mg of the desired product as yellow sticky solid. Further UPLC-MS revealed that the sample was 75% pure. Then the compound was purified again by Biotage Isolera® (SiO$_2$, 10 g, PE/EtOAc, 5% EtOAc 3 CV, 5-30% 15 CV, 30% 3 CV). 9.3 mg of the desired product as yellow sticky solid were obtained.

UPLC-MS [M+H]$^+$=370.3

Example 188

(3-Chlorophenyl){(4E)-4-[3-(4-chloropyridin-2-yl)prop-2-yn-1-ylidene]-3,3-dimethylpiperidin-1-yl}methanone Prepared from Compound 116c following the method reported above for the compound of Example 116 replacing 2-iodo-4-chloropyridine for 3-iodobenzonitrile. Sticky solid (42.8%)

UPLC-MS [M+H]$^+$=399

Example 189

(3-Chlorophenyl)[(4E)-3,3-dimethyl-4-{3-[6-(trifluoromethyl)pyridin-2-yl]prop-2-yn-1-ylidene}piperidin-1-yl]methanone Prepared from Compound 116c following the method reported above for the compound of Example 116 replacing 2-iodo-6-trifluoromethylpyridine for 3-iodobenzonitrile. Off white solid (43.9%).
UPLC-MS [M+H]$^+$=433.2

(3-Chlorophenyl){(4E)-4-[3-(6-methoxypyridin-2-yl)prop-2-yn-1-ylidene]-3,3-dimethylpiperidin-1-yl}methanone Prepared from Compound 116c following the method reported above for the compound of Example 116 replacing 2-bromo-6-methoxypyridine for 3-iodobenzonitrile. Yellow oil (47%)
UPLC-MS [M+H]$^+$=395.3

Example 191

(3-Chlorophenyl){(4E)-4-[3-(3-hydroxyphenyl)prop-2-yn-1-ylidene]-3,3-dimethylpiperidin-1-yl}methanone tert-Butyl (4E)-4-[3-(3-hydroxyphenyl)prop-2-ynylidene]-3,3-dimethyl-piperidine-1-carboxylate (Compound 190a)

Prepared starting from Compound 1a following the procedure described above for the Compound of Example 1 and replacing 2-bromo-6-methylpyridine with 3-iodophenol. Orange oil (yield: 31.8%).

3-[(3E)-3-(3,3-Dimethyl-4-piperidylidene)prop-1-ynyl]phenol (Compound 191b)

Prepared starting from Compound 190a following the procedure described above for Compound 3a. Light brown solid used without further purification (3-Chlorophenyl){(4E)-4-[3-(3-hydroxyphenyl)prop-2-yn-1-ylidene]-3,3-dimethylpiperidin-1-yl}methanone Prepared starting from Compound 191b by acylation with 3-chlorobenzoyl chloride in DCM/TEA. Light yellow oil (57%).
UPLC-MS [M+H]$^+$=380.26

Example 192

[(4E)-3,3-Dimethyl-4-(3-phenylprop-2-yn-1-ylidene)piperidin-1-yl](phenyl)methanone

[(3E)-3-(3,3-Dimethyl-4-piperidylidene)prop-1-ynyl]-trimethylsilane (Compound 192a)

Prepared as reported for Compound 3a but starting from Compound 1a and heating at reflux for 2 h. Used in the next step without further purification after the usual work-up.

[(4E)-3,3-Dimethyl-4-(3-trimethylsilylprop-2-ynylidene)-1-piperidyl]-phenylmethanone (Compound 192b)

A solution of benzoyl chloride (171.7 mg, 1.22 mmol, 1.30 equiv., 0.1418 mL), Compound 192a (208 mg, 0.9395 mmol, 208 mg) and DIPEA (242.8 mg, 1.88 mmol, 2 equiv., 0.327 mL) in chloroform ethanol free (10 mL) was stirred for 3 hours. The reaction mixture was washed with water, dried over Na$_2$SO$_4$ and the solvent was evaporated to dryness to give a crude which was purified twice via automated flash chromatography (Isolera-Dalton®), SNAP25 Cartridge, eluting with a gradient EtOAc/PE from 0:1 to 3:7 to give mg 118 of the title compound containing also some desililated product, but used as it was for the next step.

[(4E)-3,3-Dimethyl-4-(3-phenylprop-2-yn-1-ylidene)piperidin-1-yl](phenyl)methanone Prepared as described for the compound of Example 116 but starting from Compound 192b and using iodobenzene instead of 3-iodobenzonitrile (60%).
UPLC-MS [M+H]$^+$=330.29

Example 193

3-[(3E)-3-{1-[(2,5-Dimethylfuran-3-yl)carbonyl]-3,3-dimethylpiperidin-4-ylidene]prop-1-yn-1-yl}benzonitrile (2,5-Dimethyl-3-furyl)-[(4E)-3,3-dimethyl-4-(3-trimethylsilylprop-2-ynylidene)-1-piperidyl]methanone (Compound 193a)

Prepared as described for Compound 192b but using 2,5-dimethylfuran-3-carbonyl chloride. Used in the next step after purification.

3-[(3E)-3-{1-[(2,5-Dimethylfuran-3-yl)carbonyl]-3,3-dimethylpiperidin-4-ylidene}prop-1-yn-1-yl]benzonitrile Prepared as described for the compound of Example 116 but starting from Compound 193a (58.7%).
UPLC-MS [M+H]$^+$=373.32

Example 194

{(4E)-4-[3-(3-Chlorophenyl)prop-2-yn-1-ylidene]-3,3-dimethylpiperidin-1-yl}(phenyl)methanone Prepared as described for the compound of Example 116 but starting from Compound 192b and replacing 3-iodobenzonitrile with 3-chloroiodobenzene (40%).
UPLC-MS [M+H]$^+$=364.32

Example 195

3-{(3E)-3-[3,3-Dimethyl-1-(3-methylbenzoyl)piperidin-4-ylidene]prop-1-yn-1-yl}benzonitrile tert-Butyl (4E)-4-[3-(3-cyanophenyl)prop-2-ynylidene]-3,3-dimethyl-piperidine-1-carboxylate (Compound 195a)

Prepared starting from Compound 1a following the procedure described above for the Compound of Example 1 and replacing 2-bromo-6-methylpyridine with 3-iodobenzonitrile. Yellow sticky solid (75%).

3-[(3E)-3-(3,3-Dimethyl-4-piperidylidene)prop-1-ynyl]benzonitrile (Compound 195b)

Prepared following the method reported above for Compound 3a and used in the next step without further purification. Yellow sticky solid.

3-{(3E)-3-[3,3-Dimethyl-1-(3-methylbenzoyl)piperidin-4-ylidene]prop-1-yn-1-yl}benzonitrile Synthesised as reported for the compound of Example 126 but starting from Compound 195b and using 3-methylbenzoic acid instead of 3-hydroxybenzoic acid. Colourless oil.
UPLC-MS [M+H]$^+$=369.3

Example 196

3-{(3E)-3-[1-(3-Methoxybenzol)-3,3-dimethylpiperidin-4-ylidene]prop-1-yn-1-yl}benzonitrile Synthesised by acylating with 3-methoxybenzoyl chloride Compound 195b. Yellow sticky solid.
UPLC-MS [M+H]$^+$=385.3

Example 197

(4E)-4-{3-[3-(Hydroxymethyl)phenyl]prop-2-yn-1-ylidene}-3,3-dimethyl-N-(6-methylpyridin-2-yl)piperidine-1-carboxamide tert-Butyl (4E)-4-[3-[3-hydroxymethyl)phenyl]prop-2-ynylidene]-3,3-dimethyl-piperidine-1-carboxylate (Compound 197a)

Prepared from Compound 1a following the method reported here for Compound 3a but using 3-iodo-2-hydroxymethylbenzene instead of 6-methyl-2-bromopyridine.

[3-[(3E)-3-(3,3-Dimethyl-4-piperidylidene)prop-1-ynyl]phenyl]methanol

From Compound 197a following the method reported for Compound 3a. Yellow oil. Used in the next step.

(4E)-4-{3-[3-(Hydroxymethyl)phenyl]prop-2-yn-1-ylidene}-3,3-dimethyl-N-(6-methylpyridin-2-yl)piperidine-1-carboxamide Prepared as described above for the Compound of Example 129 but starting from Compound 197b. White solid (19.8%).
UPLC-MS [M+H]$^+$=390.4

Example 198

(3-Chlorophenyl){(4E)-4-[4-(3-chlorophenyl)but-3-yn-2-ylidene]-3,3-difluoropiperidin-1-yl}methanone tert-Butyl 3,3-difluoro-4-[methoxy(methyl)carbamoyl]piperidine-1-carboxylate (Compound 198a)

A mixture of 3,3-difluoro-1-{[(2-methyl-2-propanyl)oxy]carbonyl}-4-piperidinecarboxylic acid (492 mg, 1.85 mmol), N-methoxymethanamine hydrochloride (416.12 mg, 4.27 mmol) and HATU (1058 mg, 2.78 mmol) in DMF (6.28 mL) was treated with DIPEA (1.55 mL, 8.9 mmol) and then stirred at r.t. for 1 h. Afterwards, it was diluted with EtOAc, washed with 1N HCl sol., sat. aq. NaHCO$_3$ sol, brine, dried (Na$_2$SO$_4$) and concentrated to dryness in vacuo. The crude was purified by Biotage Isolera (SiO$_2$, 50 g, PE/EtOAc, 5% EtOAc 3 CV, 5-50% 15 CV, 50% 3 CV) giving 540 mg (94.4%) of the desired product as a pale yellow oil, used in the next step.

tert-Butyl 4-acetyl-3,3-difluoro-piperidine-1-carboxylate (Compound 198b)

A solution of Compound 198a (540 mg, 1.58 mmol) in THF (5.2 mL) cooled to −78° C. was treated slowly with methylmagnesium bromide (6.76 mL, 9.46 mmol) (1.4 M sol in Toluene/THF). The reaction mixture was warmed to 0° C. and stirred for 30 min. The reaction mixture was diluted with EtOAc then poured into water. The organic phase was separated. Water phase was extracted with EtOAc. Recombined organic phases were dried (Na$_2$SO$_4$) and concentrated. The crude product was purified Biotage Isolera (SiO$_2$, 50 g, PE/EtOAc, 5% EtOAc 3 CV, 5-50% 15 CV, 50% 3 CV) giving the desired product as colourless oil. 410 mg (98.7%).

tert-Butyl 4-[3-(3-chlorophenyl)-1-hydroxy-1-methyl-prop-2-ynyl]-3,3-difluoro-piperidine-1-carboxylate (Compound 198c) Distereoisomers Mixture Ethylmagnesium bromide (1.14 ml, 3.43 mmol) (3M sol. in Et$_2$O) was treated with a solution of 1-chloro-3-ethynylbenzene (0.38 ml, 3.11 mmol) in THF (6 ml). The resulting mixture was stirred at 85-95° C. for 2 h. This solution was cooled to r.t. and added via syringe to a solution of Compound 198b (410 mg, 1.56 mmol) in THF (16 ml) cooled to −10° C. The reaction mixture was stirred at r.t. for 2 h. Afterwards, the reaction mixture was quenched by addition of sat. aq. NH$_4$C$_1$ sol and extracted with EtOAc. The combined organic layers were washed with brine, dried (Na$_2$SO$_4$) and concentrated. The crude product was purified by Biotage Isolera® (SiO$_2$, 100 g, PE/EtOAc, 10% EtOAc 3 CV, 10-50% 10 CV, 50% 3 CV) affording 396 mg of the title product as a mixture of diastereoisomers. Pale yellow sticky solid.

tert-Butyl 4-[3-(3-chlorophenyl)-1-methyl-prop-2-ynylidene]-3,3-difluoro-piperidine-1-carboxylate (Compound 198d) E/Z mixture A mixture of Compound 198c (544. mg, 1.36 mmol) and Burgess reagent (518.72 mg, 2.18 mmol) in THF (13.63 mL) was heated at 60° C. for 1.5 h, then 1 h at r.t. Further 260 mg of Burgess reagent were added (0.8 eq) and the reaction mixture was stirred at 60° C. for 30 min. The reaction mixture was cooled to r.t., poured into water and extracted with EtOAc. The combined organic phases were dried (Na$_2$SO$_4$) and concentrated. The crude product 830 mg was purified by Biotage Isolera (SiO$_2$, 50 g, PE/ETOAc, 0% EtOAc 3 CV, 0-20% 15 CV, 20% 3 CV) giving two fractions: product A, 33 mg of yellow oil, (RT 2.74 min) desired regioisomer, E diastereoisomer, used in the next step; product B, 112 mg of yellow oil (RT 2.56 and 2.61 min ratio 3/7) mixture of the Z-diastereomer. And of the undesired regioisomer that is tert-butyl 4-[3-(3-chlorophenyl)-1-methylene-prop-2-ynyl]-3,3-difluoro-piperidine-1-carboxylate.

(4E)-4-[3-(3-Chlorophenyl)-1-methyl-prop-2-ynylidene]-3,3-difluoropiperidine (Compound 198 e)

Prepared from Compound 198d E-isomer following the method reported above for Compound 3a.

(3-Chlorophenyl){(4E)-4-[4-(3-chlorophenyl)but-3-yn-2-ylidene]-3,3-difluoropiperidin-1-yl}methanone A solution of 3-chlorobenzoic acid (15.89 mg, 0.100 mmol), HOBT (13.72 mg, 0.100 mmol), EDC (15.76 mg, 0.100 mmol) and TEA (0.02 mL, 0.160 mmol) in DMF (0.5 mL) was stirred for 15 min at r.t. Then a solution of (4E)-4-[4-(3-chlorophenyl)but-3-yn-2-ylidene]-3,3-bis(fluoranyl)piperidine (Compound 198 e, 22. mg, 0.080 mmol) in DMF (0.5 mL) was added. The reaction mixture was stirred at r.t. for till UPLC-MS revealed that the reaction was complete. The reaction mixture was diluted with EtOAc and washed with 1N HCl sol, sat. aq. NaHCO$_3$ sol., brine, dried (Na$_2$SO$_4$) and concentrated. The crude product was purified by Biotage Isolera® (SiO$_2$, 10 g, PE/EtOC, 0% EtOAc 3 CV, 0-40% 10 CV, 40% 3 CV) giving the desired product as yellow sticky oil (18 mg).
UPLC-MS [M+H]$^+$=420.2

Example 199

(3-Chlorophenyl){(4Z)-4-[4-(3-chlorophenyl)but-3-yn-2-ylidene]-3,3-difluoropiperidin-1-yl}methanone The title compound was prepared following the method here described for the synthesis of the Compound of Example 198 over the last two steps, but starting from the mixture of Compound 198d Z isomer and tert-butyl 4-[3-(3-chlorophenyl)-1-methylene-prop-2-ynyl]-3,3-difluoro-piperidine-1-carboxylate. After purification a brown sticky solid was obtained (23 mg).
UPLC-MS [M+H]$^+$=420.2

Example 200

3-[(3E)-3-{1-[(2,5-Dimethylfuran-3-yl)carbonyl]-3,3-dimethylpiperidin-4-ylidene]prop-1-yn-1-yl}-5-fluorobenzonitrile Prepared as described for the compound of Example 116 but starting from Compound 193a by reacting it with 3-fluoro-5-iodobenzonitrile (57%).
UPLC-MS [M+H]$^+$=391.33

Example 201

(3-Chlorophenyl){(4E)-4-[3-(3-chlorophenyl)prop-2-yn-1-ylidene]-3,3-difluoropiperidin-1-yl}methanone (4E)-4-[3-(3-Chlorophenyl)prop-2-ynylidene]-3,3-difluoro-piperidine (Compound 201a)

By reacting the compound of Example 8 as described for compound 3a the title compound was obtained and used without further purification in the next step. Yellow oil.

(3-Chlorophenyl){(4E)-4-[3-(3-chlorophenyl)prop-2-yn-1-ylidene]-3,3-difluoropiperidin-1-yl}methanone Prepared from Compound 201a following the method described for the compound of Example 126 but reacting 3-chlorobenzoic acid with Compound 201a. beige solid. Yield: 17.17%.
UPLC-MS [M+H]$^+$=406.1

Example 202

{(4E)-4-[3-(3-Chlorophenyl)prop-2-yn-1-ylidene]-3,3-difluoropiperidin-1-yl}(4-methoxypyridin-2-yl)methanone Prepared from Compound 201a following the method described for the compound of Example 126 but reacting 4-methoxypyridine-2-carboxylic acid with Compound 201a. Yield: 68%.
UPLC-MS [M+H]$^+$=403.2

Biological Assay

Cell lines stably transfected were generated using inducible expression vectors encoding human mGlu$_5$ receptor using the Tetracycline-Regulated Expression system (T-REx™ system, Invitrogen, Life Technologies). Human mGluR$_5$ open reading frame (ORF), comprehensive of the stop codon, were cloned into the pcDNA4/TO/myc-His™ A vector, carrying the TetO2. The insertion site was HindIII-PstI for mGluR$_5$ receptors. The obtained constructs were then transfected into the T-REx CHO™ cell line using the FuGENE protocol (Roche); the CHO T-REx™ cell line stably expresses the Tet repressor (from the pcDNA6/TR plasmid) under the selection of blasticidin, 10 µg/ml. Stable clones were obtained selecting with zeocin 1 mg/ml and maintaining in ULTRA CHO medium (LONZA) supplemented with dialyzed FBS, zeocin, blasticidine, at 37° C., in an atmosphere of 5% CO$_2$. The expression of h-mGluR$_5$ receptors was de-repressed with 1 µg/ml tetracycline for 18 h before binding experimentation, while the expression of h-mGluR$_5$ receptors was derepressed respectively with 3 ng/ml and 10 ng/ml tetracycline for 18 h before calcium fluorescence experimentation.

Radioligand Binding Assay at Cloned Human mGluR$_5$ Receptor Subtype

Affinity at transmembrane glutamate metabotropic cloned human mGluR$_5$ receptor was evaluated according to the methods of Anderson (Anderson et al., *J Pharmacol. Exp. Ther.*, (2002), Vol. 303(3), pp. 1044-51), with some modifications. Human cloned mGluR$_5$ was obtained by re-suspending CHO T-REx h-mGluR$_5$ cells (50 µg/well) in 20 mM HEPES, 2 mM MgCl$_2$, 2 mM CaCl$_2$, pH 7.4, that then were incubated in a final volume of 1 ml for 60 min at 25° C. with 4 nM [$^3$H]MPEP in the absence or presence of competing drugs. Non-specific binding was determined in the presence of 10 µM MPEP. The incubation was stopped by addition of cold Tris buffer pH 7.4 and rapid filtration through 0.2% polyethyleneimine pretreated Filtermat 1204-401 (Perkin Elmer) filters. The filters were then washed with cold buffer and the radioactivity retained on the filters was counted by liquid scintillation spectrometry (Betaplate 1204 BS-Wallac).

Results

The affinity Ki of the compounds of the invention for the human mGlu5 receptors is between 0.1 and 1000 nM. For instance, and in particular compounds 31, 34 and 48 have a Ki of 2.93, 0.99 and 2.44 nM, respectively.

Selected binding data expressed as Ki (nM) for some of the compounds of interest, prepared according to the invention, are shown below in Table 3.

TABLE 3

Binding data for selected compounds of the invention.

| Example | mGlu$_5$ Ki nM |
|---|---|
| 3 | 1.47 |
| 18 | 1.01 |
| 19 | 0.89 |
| 22 | 1.9 |
| 25 | 28.6 |
| 27 | 0.64 |
| 28 | 2.12 |
| 31 | 2.93 |
| 32 | 16.1 |
| 34 | 0.99 |
| 40 | 1.29 |
| 43 | 7.39 |
| 46 | 322.6 |
| 48 | 2.44 |
| 64 | 82.9 |
| 73 | 29.8 |
| 91 | 16.3 |
| 101 | 11.2 |
| 107 | 931.5 |
| 109 | 26.9 |
| 116 | 1.6 |
| 119 | 8.05 |
| 120 | 4.02 |
| 128 | 1.82 |
| 166 | 2.24 |
| 167 | 2.42 |
| 191 | 7.35 |
| 200 | 636.9 |
| 201 | 1.91 |

Calcium Fluorescence Measurements

Cells were seeded into black-walled, clear-bottom, 96-well plates at a density of 80000 cell/well, in RPMI (without Phenol Red, without L-glutamine; Gibco LifeTechnologies, CA) supplemented with 10% dialyzed FBS. Following 18-h incubation with tetracycline, the cells were loaded with 2 mM $Ca^{2+}$-sensitive fluorescent dye Fluo-4/AM (Molecular Probes) in Hanks' balanced saline solution (HBSS, Gibco LifeTechnologies, CA) with 20 µM Hepes (Sigma) and 2.5 mM probenecid (Sigma), for 1 h at 37° C. The cells were washed three times with HBSS to remove extracellular dye. Fluorescence signals were measured by using the fluorescence microplate reader Flexstation III (Molecular Devices) at sampling intervals of 1.5 s for 60 s.

The antagonist potency was determined using the $EC_{80}$ of the quisqualate used as agonist and the potentiation of mGlu$_5$ activation was determined using the $EC_{20}$ of the agonist (quisqualate or glutamate). The compounds were applied 10 minutes before the application of the agonist.

The negative allosteric modulator activity (expressed as IC50) and the positive allosteric modulator activity (expressed as EC50) of the compounds of the invention for the mGlu5 receptors is between 0.1 and 1000 nM. For instance, and in particular compounds 31 and 48 have an IC50 of 13.5 and 2.02 nM respectively, and compound 34 has an EC50 of 107.2 nM.

Fold Shift of Agonist Curve Determination

The PAM potency was evaluated by performing an agonist concentration response curve in the presence of the compounds. The compounds at fixed concentration (0.01 or 0.1 or 1 µM) were applied 10 minutes before the incubation of the agonist (quisqualate or glutamate) dose-response curve. The fold shift was determined as ratio of $EC_{50}$ agonist curves in presence and in absence of test compound. Selected folds shift for some of the compounds of interest, prepared according to the invention, are shown in Table 5 below. For instance, and in particular compound 34 has a fold shift of 2.7.

For binding, calcium assay and fold shift studies, the compounds were dissolved in DMSO or demineralized water according to their solubility. All the reported doses were those of the corresponding salts or bases.

Statistical Analysis.

The inhibition curves of the tested compounds at cloned mGluR$_5$ subtypes were determined by nonlinear regression analysis using software Prism 4.0 (Graphpad, San Diego, Calif.). The $IC_{50}$ values and pseudo-Hill slope coefficients were estimated by the program. The values for the inhibition constant, Ki, were calculated according to the equation $K_i=IC_{50}/(1+[L]/K_d)$, where [L] is the concentration of radioligand and $K_d$ is the equilibrium dissociation constant of the radioligand-receptor complex (Cheng et al., *Biochem. Pharmacol.* (1973), Vol. 22, pp. 3099-3108). Selected negative allosteric modulator activity expressed as $IC_{50}$ (nM) for some of the compounds of interest, prepared according to the invention, are shown below in Table 4.

TABLE 4

Negative allosteric modulator activity for selected compounds of the invention.

| Example | mGlu$_5$ IC$_{50}$ nM |
|---|---|
| 22 | 66.3 |
| 25 | 31.8 |
| 27 | 8.6 |
| 28 | 37.2 |
| 31 | 13.5 |
| 32 | 60 |
| 40 | 18.2 |
| 48 | 2.02 |
| 91 | 31.65 |
| 101 | 66.3 |

Selected positive allosteric modulator activity expressed as $EC_{50}$ (nM) and fold shift for some of the compounds of interest, prepared according to the invention, are shown below in the Table 5.

TABLE 5

Positive allosteric modulator activity for selected compounds of the invention.

| Examples | mGlu5 EC$_{50}$ nM | mGlu$_5$ Fold Shift @1 µM |
|---|---|---|
| 34 | 107.2 | 2.7 |
| 43 | 64.47 | 2.8 |
| 46 | 37.38 | 3.79 |
| 107 | 120.8 | 7.66 |
| 116 | 52.845 | 2.14 |
| 119 | 49.7 | 2.9 |
| 120 | 38.557 | 5.5 |
| 126 | 114.54 | 3.4 |
| 128 | 164.967 | 3.5 |
| 137 | 268.4 | 2.1 |
| 166 | 51.715 | 1.35 |
| 167 | 23.037 | 2.7 |
| 191 | 224.2 | 3.9 |
| 196 | 87.65 | 2.2 |
| 200 | 291.1 | 2.3 |
| 201 | 88.16 | 4.5 |

Effect on Cystometry in Conscious Rats

Male Sprague-Dawley rats [Crl:CD(SD) IGS BR] of 300-400 g b.w. supplied by Charles River Italia were used. The animals were housed with free access to food and water and maintained on a forced 12-hour-light/12-hour-dark cycle at 22-24° C. of temperature, except during the experiment. To quantify urodynamic parameters in conscious rats, cystometrographic studies were performed according to the procedure previously reported (Guarneri et al., Pharmacol. Res. Vol. 24, No. 2, pp. 175-187, 1991).

Briefly, the rats were anaesthetized by intraperitoneal administration of 3 ml/kg of Equithensin solution (pentobarbital 30 mg/kg and chloral hydrate 125 mg/kg) and placed in a supine position. An approximately 10 mm long midline incision was made in the shaved and cleaned abdominal wall. The urinary bladder was gently freed from adhering tissues, emptied and then cannulated via an incision in the bladder body, using a polyethylene cannula (0.58 mm internal diameter, 0.96 mm external diameter) which was permanently sutured with silk thread. The cannula was exteriorized through a subcutaneous tunnel in the retroscapular area, where it was connected to a plastic adapter in order to avoid the risk of removal by the animal. For drug testing, the rats were utilized one day after implantation.

On the day of the experiment, the rats were placed in modified Bollman cages, i.e., restraining cages that were large enough to permit the rats to adopt a normal crouched posture, but narrow enough to prevent turning around. After a stabilization period of about 20 minutes, the free tip of the bladder cannula was connected through a T-shaped tube to a pressure transducer (Statham P23XL) and to a peristaltic pump (Gilson Minipuls 2) for continuous infusion of a warm (37° C.) saline solution into the urinary bladder, at a constant rate of 0.1 ml/minute. The intraluminal-pressure signal during infusion of saline into the bladder (cystometrogram) was continuously recorded on a polygraph (Rectigraph-8K San-ei with BM614/2 amplifier from Biomedica Mangoni) or stored on PC by data acquisition system (PowerLab, Chart 4 software, AD Instruments). From the cystometrogram, bladder volume capacity (BVC) was evaluated. BVC (in ml) is defined as the volume of saline infused into the bladder necessary to induce detrusor contraction followed by micturition. Basal BVC value was evaluated as the mean of the values observed in the cystometrograms recorded in an initial period of 30-60 minutes. At this point in the assay, the infusion was interrupted and the test compounds were administered orally by a stomach tube. The bladder infusion restarted and changes in BVC were evaluated from the mean values obtained in the cystometrograms observed during 1, 2, and 3 hours after treatment. The compounds were administered in a volume of 2 ml/kg. Groups of control animals received the same amount of vehicle corresponding to a solution 0.5% methocel in water.

Under the given test conditions, measurement of BVC is equivalent to measurement of interval time between micturitions.

Statistical Analysis

Each experimental group was composed of 4-11 animals. All data were expressed as mean±standard error. The percent change of BVC versus the basal value, as well as A value (difference in ml) of BVC (BVC at time "x" minus basal value), were also evaluated for each rat/time.

Statistical analysis on BVC values, as well as on A values, was performed by S.A.S./STAT software, version 6.12. The difference between vehicle and active treatment effect was evaluated on A values of BVC, whereas the difference between the values at different times versus the basal values was evaluated on original BVC data.

Results

The activity of compounds of the invention and reference standard expressed as MED (i.e. Minimal Effective Dose that induces statistically significant increase of bladder volume capacity) is given in Table 6 below.

TABLE 6

MED for selected compounds of the invention.

| Examples | "In vivo" cystometry MED (mg/kg os) |
|---|---|
| Example 31 | 1 |
| Example 40 | 3 |
| Example 48 | 1 |

Novel Object Recognition Test in Mice

Novel object memory was assessed during three sessions. This task relies on the innate tendency of a mouse to explore unfamiliar objects vs. familiar objects. Testing was performed in an open-field arena. 24 h prior to training, C57/BL/6J 5-week male mice were habituated to the arena for 10 min (session 1).

During training, mice were administered by intraperitoneal route with the vehicle or the tested compound and after 30 min they were allowed for 5 min to explore two identical objects (A+A, session 2). Long-term object memory was assessed 24 h after the completion of training during which mice were given 5 min to explore the familiar (A) or the novel (B) object (A+B, session 3). The duration of exploration (defined as the mouse's snout or forelimbs physically touching or approaching within 1 cm of an object) of familiar and novel object was measured. The amount of time spent exploring the novel object over the total time exploring both novel and familiar object in each session was used to measure object memory.

Results

For instance, and in particular the activity of compound of Example 34, expressed as MED (Minimal Effective Dose that induces statistically significant difference of exploration of the two objects) is of 10 mg/kg. Statistical analysis of exploration time values, was performed by using a paired Student's test, which was calculated using GraphPad Prisma 4.

The invention claimed is:

1. A compound of formula IA:

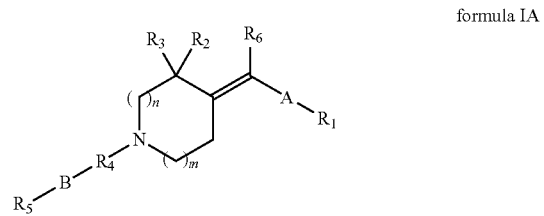

formula IA or an enantiomer, diastereomer, N-oxide, or a pharmaceutically acceptable salt or combinations thereof, wherein:

$R_1$ is an optionally substituted monocyclic 6-membered aryl group or an optionally substituted monocyclic 6-membered heteroaryl group containing 1 or 2 nitrogen atoms;
A is a carbon-carbon triple bond;
$R_2$ and $R_3$ each represent an alkyl;
n is 0 or 1 and m is 1;
$R_4$ is a carbonyl, a thiocarbonyl or a sulphonyl group, or a bond;
B is an oxygen or sulphur atom, a nitrogen atom optionally substituted by a $C_1$-$C_5$ alkyl group or a methoxy group, or B is absent;
$R_5$ is an optionally substituted mono-, bi- or tricyclic $C_6$-$C_{14}$ aryl group, an optionally substituted mono-, bi- or tricyclic $C_1$-$C_{13}$ heterocyclic group containing from 1 to 5 heteroatoms selected from N, O and S, an optionally substituted $C_3$-$C_6$ cycloalkyl group, an optionally substituted $C_3$-$C_6$ cycloalkenyl group or an optionally substituted $C_1$-$C_6$ alkyl group; and $R_6$ is a hydrogen atom, an optionally substituted C1-C4 alkyl group or a fluorine atom,
wherein the optional substituents are each independently selected from the group consisting of halogen atoms and $C_1$-$C_6$ alkyl, $C_1$-$C_6$ alkoxy, hydroxy, mercapto, nitro, cyano, oxo, halo(C1-C6)alkyl, halo(C1-C6) alkoxy, C1-C6 alkylthio, C1-C6 alkylsulphonyl, C1-C6 alkylcarbonyl, sulphamoyl, C1-C6 alkylsulphamoyl, di(C1-C6)alkylsulphamoyl, (C1-C6)alkoxycarbonyl and (C1-C6)alkylcarbonyl(C1-C6)alkyl groups, and from groups of the formulae —NR*R*, —C(=O)—NR*R*, -A, —O-A, —C(=O)-A, —(CH2)q-A, —NR-A, —C(=O)NR -A, —NR **C(=O)-A and —O—C(=O)-A wherein each R* independently represents a hydrogen atom or a C1-C6 alkyl, C1-C6 alkoxy, C1-C6 alkylcarbonyl, phenyl or benzyl group, R** represents a hydrogen atom or a C1-C6 alkyl group, q is an integer from 1 to 6 and A represents a phenyl group or a C1-C8 heterocyclic group containing from 1 to 3 heteroatoms selected from N, O and S; a C1-C6 cycloalkyl group; each group A being optionally substituted with from 1 to 3 groups independently selected from halo, hydroxy, cyano, nitro and C1-C6 alkyl.

2. A compound according to claim 1 wherein the optional substituents are selected from the groups consisting of halogen atoms and C1-C6 alkyl groups; and $R_6$ is a hydrogen atom, an optionally substituted $C_1$-$C_4$ alkyl group, or a fluorine atom.

3. A compound according to claim 1, wherein $R_1$ is selected from the group consisting of an optionally substituted phenyl, pyridinyl or pyrimidinyl moiety or derivative thereof.

4. A compound according to claim 1, wherein $R_5$ is selected from the group consisting of an optionally substituted methyl, ethyl, propyl, iso-propyl, tertiary-butyl, methoxyethyl, N,N-dimethyl, N-methoxy-N-methyl, N,N-diethyl, N-ethyl-N-isopropyl, cyclohexyl, benzotriazolyl, furanyl, isoxazolyl, morpholinyl, oxazolyl, phenyl, piperidinyl, pyranyl, pyrazolyl, pyridinyl, pyrimidinyl, pyrrolidinyl, triazinyl or triazolyl moiety or derivative thereof.

5. A compound according to claim 1, wherein $R_4$ is a carbonyl or sulphonyl group, B is absent and $R_5$ is an optionally substituted bicyclic $C_1$-$C_{13}$ heterocyclic group containing from 1 to 5 heteroatoms selected from N, O and S.

6. A compound according to claim 1, wherein B is an oxygen or nitrogen atom optionally substituted by a $C_1$-$C_5$ alkyl group or a methoxy group and $R_5$ is selected from the group consisting of an optionally substituted methyl, ethyl, propyl, iso-propyl, tertiary-butyl or methoxyethyl moiety or derivative thereof.

7. A compound according to claim 1, the compound being selected from the group consisting of:
1 tert-butyl (4E)-3,3-dimethyl-4-[3-(6-methylpyridin-2-yl)prop-2-yn-1-ylidene]piperidine-1-carboxylate;
1 tert-butyl (4E)-4-[3-(3-chlorophenyl)prop-2-yn-1-ylidene]-3,3-dimethylpiperidine-1-carboxylate;
ethyl (4E)-3,3-dimethyl-4-[3-(6-methylpyridin-2-yl) prop-2-yn-1-ylidene]piperidine-1-carboxylate;
ethyl (4E)-4-[3-(3-chlorophenyl)prop-2-yn-1-ylidene]-3,3-dimethylpiperidine-1-carboxylate;
tert-butyl (4E)-4-[3-(2-chloropyridin-4-yl)prop-2-yn-1-ylidene]-3,3-dimethylpiperidine-1-carboxylate;
1 tert-butyl (4E)-3,3-dimethyl-4-[3-(3-methylphenyl) prop-2-yn-1-ylidene]piperidine-1-carboxylate;
ethyl (4E)-4-[3-(2-chloropyridin-4-yl)prop-2-yn-1-ylidene]-3,3-dimethylpiperidine-1-carboxylate;
ethyl (4E)-3,3-dimethyl-4-[3-(3-methylphenyl)prop-2-yn-1-ylidene]piperidine-1-carboxylate;
ethyl (4E)-3,3-dimethyl-4-(3-phenylprop-2-yn-1-ylidene) piperidine-1-carboxylate;
ethyl (4E)-4-[3-(4-chloropyridin-2-yl)prop-2-yn-1-ylidene]-3,3-dimethylpiperidine-1-carboxylate;
ethyl (4E)-4-[3-(2,5-difluorophenyl)prop-2-yn-1-ylidene]-3,3-dimethylpiperidine-1-carboxylate;
ethyl (4E)-3,3-dimethyl-4-{3-[6-(trifluoromethyl)pyridin-2-yl]prop-2-yn-1-ylidene}piperidine-1-carboxylate;
ethyl (4E)-4-[3-(3-fluorophenyl)prop-2-yn-1-ylidene]-3,3-dimethylpiperidine-1-carboxylate;
ethyl (4E)-3,3-dimethyl-4-{3-[3-(trifluoromethyl)phenyl] prop-2-yn-1-ylidene}piperidine-1-carboxylate;
ethyl (4E)-4-[3-(6-methoxypyridin-2-yl)prop-2-yn-1-ylidene]-3,3-dimethylpiperidine-1-carboxylate;
ethyl (4E)-4-[3-(3-methoxyphenyl)prop-2-yn-1-ylidene]-3,3-dimethylpiperidine-1-carboxylate;
ethyl (4E)-4-[3-(4-methoxypyridin-2-yl)prop-2-yn-1-ylidene]-3,3-dimethylpiperidine-1-carboxylate;
ethyl (4E)-3,3-dimethyl-4-[3-(pyridin-2-yl)prop-2-yn-1-ylidene]piperidine-1-carboxylate;
ethyl (4E)-4-[3-(3-cyanophenyl)prop-2-yn-1-ylidene]-3,3-dimethylpiperidine-1-carboxylate;
ethyl (4E)-4-{3-[3-(cyanomethyl)phenyl]prop-2-yn-1-ylidene}-3,3-dimethylpiperidine-1-carboxylate;
ethyl (4E)-4-[3-(6-methoxypyridin-3-yl)prop-2-yn-1-ylidene]-3,3-dimethylpiperidine-1-carboxylate;
ethyl (4E)-3,3-dimethyl-4-{3-[6-(methylamino)pyridin-2-yl]prop-2-yn-1-ylidene}piperidine-1-carboxylate;
ethyl (4E)-4-[3-(4-cyanopyridin-2-yl)prop-2-yn-1-ylidene]-3,3-dimethylpiperidine-1-carboxylate;
ethyl (4E)-4-[3-(3-cyano-5-fluorophenyl)prop-2-yn-1-ylidene]-3,3-dimethylpiperidine-1-carboxylate;
2-{(4E)-3,3-dimethyl-4-[3-(6-methylpyridin-2-yl)prop-2-yn-1-ylidene]piperidin-1-yl}-6-methyl-3-nitropyridine;
(3-chlorophenyl){(4E)-4-[3-(3-chlorophenyl)prop-2-yn-1-ylidene]-3,3-dimethylpiperidin-1-yl}methanone;
{(4E)-4-[3-(3-chlorophenyl)prop-2-yn-1-ylidene]-3,3-dimethylpiperidin-1-yl}(piperidin-1-yl)methanone;
{(4E)-4-[3-(3-chlorophenyl)prop-2-yn-1-ylidene]-3,3-dimethylpiperidin-1-yl}(pyrrolidin-1-yl)methanone;
(4E)-4-[3-(3-chlorophenyl)prop-2-yn-1-ylidene]-N,N,3,3-tetramethylpiperidine-1-carboxamide;
(4E)-4-[3-(3-chlorophenyl)prop-2-yn-1-ylidene]-N,N-diethyl-3,3-dimethylpiperidine-1-carboxamide;

{(4E)-4-[3-(3-chlorophenyl)prop-2-yn-1-ylidene]-3,3-dimethylpiperidin-1-yl}(furan-2-yl)methanone;
methyl (4E)-4-[3-(3-chlorophenyl)prop-2-yn-1-ylidene]-3,3-dimethylpiperidine-1-carboxylate;
{(4E)-4-[3-(3-chlorophenyl)prop-2-yn-1-ylidene]-3,3-dimethylpiperidin-1-yl}(morpholin-4-yl)methanone;
(4E)-4-[3-(3-chlorophenyl)prop-2-yn-1-ylidene]-N-methoxy-N,3,3-trimethylpiperidine-1-carboxamide;
{(4E)-4-[3-(3-chlorophenyl)prop-2-yn-1-ylidene]-3,3-dimethylpiperidin-1-yl}(3-methylphenyl)methanone;
2-{(3E)-3-[1-(3-chlorobenzoyl)-3,3-dimethylpiperidin-4-ylidene]prop-1-yn-1-yl}pyridine-4-carbonitrile;
(3-chlorophenyl){(4E)-3,3-dimethyl-4-[3-(3-methylphenyl)prop-2-yn-1-ylidene]piperidin-1-yl}methanone;
(2,5-dimethylfuran-3-yl)[(4E)-4-{3-[3-(hydroxymethyl)phenyl]prop-2-yn-1-ylidene}-3,3-dimethylpiperidin-1-yl]methanone;
[(4E)-3,3-dimethyl-4-(3-{3-[(pyrrolidin-1-yl)methyl]phenyl}prop-2-yn-1-ylidene)piperidin-1-yl](5-methylfuran-2-yl)methanone;
ethyl (3E)-2,2-dimethyl-3-[3-(6-methylpyridin-2-yl)prop-2-yn-1-ylidene]pyrrolidine-1-carboxylate;
tert-butyl (3E)-2,2-dimethyl-3-[3-(6-methylpyridin-2-yl)prop-2-yn-1-ylidene]pyrrolidine-1-carboxylate;
propyl (3E)-2,2-dimethyl-3-[3-(6-methylpyridin-2-yl)prop-2-yn-1-ylidene]pyrrolidine-1-carboxylate;
2-methoxyethyl (3E)-2,2-dimethyl-3-[3-(6-methylpyridin-2-yl)prop-2-yn-1-ylidene]pyrrolidine-1-carboxylate;
2-methylpropyl (3E)-2,2-dimethyl-3-[3-(6-methylpyridin-2-yl)prop-2-yn-1-ylidene]pyrrolidine-1-carboxylate;
propan-2-yl (3E)-2,2-dimethyl-3-[3-(6-methylpyridin-2-yl)prop-2-yn-1-ylidene]pyrrolidine-1-carboxylate;
(3E)-N,N,2,2-tetramethyl-3-[3-(6-methylpyridin-2-yl)prop-2-yn-1-ylidene]pyrrolidine-1-carboxamide;
{(3E)-2,2-dimethyl-3-[3-(6-methylpyridin-2-yl)prop-2-yn-1-ylidene]pyrolidin-1-yl}(furan-2-yl)methanone;
(3-chlorophenyl){(3E)-2,2-dimethyl-3-[3-(6-methylpyridin-2-yl)prop-2-yn-1-ylidene]pyrrolidin-1-yl}methanone;
{(3E)-2,2-dimethyl-3-[3-(6-methylpyridin-2-yl)prop-2-yn-1-ylidene]pyrrolidin-1-yl}(piperidin-1-yl)methanone;
{(3E)-2,2-dimethyl-3-[3-(6-methylpyridin-2-yl)prop-2-yn-1-ylidene]pyrrolidin-1-yl}(pyrrolidin-1-yl)methanone;
methyl (3E)-2,2-dimethyl-3-[3-(6-methylpyridin-2-yl)prop-2-yn-1-ylidene]pyrrolidine-1-carboxylate;
tert-butyl (3E)-2,2-dimethyl-3-[3-(4-methylpyrimidin-2-yl)prop-2-yn-1-ylidene]pyrrolidine-1-carboxylate;
ethyl (3E)-2,2-dimethyl-3-[3-(4-methylpyrimidin-2-yl)prop-2-yn-1-ylidene]pyrrolidine-1-carboxylate;
2-methoxyethyl (3E)-2,2-dimethyl-3-[3-(4-methylpyrimidin-2-yl)prop-2-yn-1-ylidene]pyrrolidine-1-carboxylate;
propan-2-yl (3E)-2,2-dimethyl-3-[3-(4-methylpyrimidin-2-yl)prop-2-yn-1-ylidene]pyrrolidine-1-carboxylate;
methyl (3E)-2,2-dimethyl-3-[3-(4-methylpyrimidin-2-yl)prop-2-yn-1-ylidene]pyrrolidine-1-carboxylate;
tert-butyl (3E)-2,2-dimethyl-3-{3-[6-(methylamino)pyridin-2-yl]prop-2-yn-1-ylidene}pyrrolidine-1-carboxylate;
ethyl (3E)-2,2-dimethyl-3-{3-[6-(methylamino)pyridin-2-yl]prop-2-yn-1-ylidene}pyrrolidine-1-carboxylate;
propyl (3E)-2,2-dimethyl-3-{3-[6-(methylamino)pyridin-2-yl]prop-2-yn-1-ylidene}pyrrolidine-1-carboxylate;
2-methoxyethyl (3E)-2,2-dimethyl-3-{3-[6-(methylamino)pyridin-2-yl]prop-2-yn-1-ylidene}pyrrolidine-1-carboxylate;
2-methylpropyl (3E)-2,2-dimethyl-3-{3-[6-(methylamino)pyridin-2-yl]prop-2-yn-1-ylidene}pyrrolidine-1-carboxylate;
propan-2-yl (3E)-2,2-dimethyl-3-{3-[6-(methylamino)pyridin-2-yl]prop-2-yn-1-ylidene}pyrrolidine-1-carboxylate;
methyl (3E)-2,2-dimethyl-3-{3-[6-(methylamino)pyridin-2-yl]prop-2-yn-1-ylidene}pyrrolidine-1-carboxylate;
tert-butyl (3E)-3-[3-(4-cyanopyridin-2-yl)prop-2-yn-1-ylidene]-2,2-dimethylpyrrolidine-1-carboxylate;
ethyl (3E)-3-[3-(4-cyanopyridin-2-yl)prop-2-yn-1-ylidene]-2,2-dimethylpyrrolidine-1-carboxylate;
2-methoxyethyl (3E)-3-[3-(4-cyanopyridin-2-yl)prop-2-yn-1-ylidene]-2,2-dimethylpyrrolidine-1-carboxylate;
2-methylpropyl (3E)-3-[3-(4-cyanopyridin-2-yl)prop-2-yn-1-ylidene]-2,2-dimethylpyrrolidine-1-carboxylate;
propan-2-yl (3E)-3-[3-(4-cyanopyridin-2-yl)prop-2-yn-1-ylidene]-2,2-dimethylpyrrolidine-1-carboxylate;
methyl (3E)-3-[3-(4-cyanopyridin-2-yl)prop-2-yn-1-ylidene]-2,2-dimethylpyrrolidine-1-carboxylate;
tert-butyl (3E)-3-[3-(3-cyano-5-fluorophenyl)prop-2-yn-1-ylidene]-2,2-dimethylpyrrolidine-1-carboxylate;
ethyl (3E)-3-[3-(3-cyano-5-fluorophenyl)prop-2-yn-1-ylidene]-2,2-dimethylpyrrolidine-1-carboxylate;
propyl (3E)-3-[3-(3-cyano-5-fluorophenyl)prop-2-yn-1-ylidene]-2,2-dimethylpyrrolidine-1-carboxylate;
2-methoxyethyl (3E)-3-[3-(3-cyano-5-fluorophenyl)prop-2-yn-1-ylidene]-2,2-dimethylpyrrolidine-1-carboxylate;
2-methylpropyl (3E)-3-[3-(3-cyano-5-fluorophenyl)prop-2-yn-1-ylidene]-2,2-dimethylpyrrolidine-1-carboxylate;
propan-2-yl (3E)-3-[3-(3-cyano-5-fluorophenyl)prop-2-yn-1-ylidene]-2,2-dimethylpyrrolidine-1-carboxylate;
methyl (3E)-3-[3-(3-cyano-5-fluorophenyl)prop-2-yn-1-ylidene]-2,2-dimethylpyrrolidine-1-carboxylate;
tert-butyl (3E)-3-[3-(4-chloropyridin-2-yl)prop-2-yn-1-ylidene]-2,2-dimethylpyrrolidine-1-carboxylate;
{(3E)-3-[3-(4-chloropyridin-2-yl)prop-2-yn-1-ylidene]-2,2-dimethylpyrrolidin-1-yl}(furan-2-yl)methanone;
(3E)-3-[3-(4-chloropyridin-2-yl)prop-2-yn-1-ylidene]-N,N-diethyl-2,2-dimethylpyrrolidine-1-carboxamide;
{(3E)-3-[3-(4-chloropyridin-2-yl)prop-2-yn-1-ylidene]-2,2-dimethylpyrrolidin-1-yl}(pyrrolidin-1-yl)methanone;
{(3E)-3-[3-(4-chloropyridin-2-yl)prop-2-yn-1-ylidene]-2,2-dimethylpyrrolidin-1-yl}(piperidin-1-yl)methanone;
(3E)-3-[3-(4-chloropyridin-2-yl)prop-2-yn-1-ylidene]-N,N,2,2-tetramethylpyrrolidine-1-carboxamide;
ethyl (3E)-3-[3-(4-chloropyridin-2-yl)prop-2-yn-1-ylidene]-2,2-dimethylpyrrolidine-1-carboxylate;
methyl (3E)-3-[3-(4-chloropyridin-2-yl)prop-2-yn-1-ylidene]-2,2-dimethylpyrrolidine-1-carboxylate;
(3-chlorophenyl){(3E)-3-[3-(4-chloropyridin-2-yl)prop-2-yn-1-ylidene]-2,2-dimethylpyrrolidin-1-yl}methanone;
ethyl (3E)-3-[3-(6-aminopyridin-2-yl)prop-2-yn-1-ylidene]-2,2-dimethylpyrrolidine-1-carboxylate;
(3E)-3-[3-(6-aminopyridin-2-yl)prop-2-yn-1-ylidene]-N,N-diethyl-2,2-dimethylpyrrolidine-1-carboxamide;
methyl (3E)-3-[3-(6-aminopyridin-2-yl)prop-2-yn-1-ylidene]-2,2-dimethylpyrrolidine-1-carboxylate;

(3E)-3-[3-(6-aminopyridin-2-yl)prop-2-yn-1-ylidene]-N,N,2,2-tetramethylpyrrolidine-1-carboxamide;
tert-butyl (3E)-3-[3-(3-chlorophenyl)prop-2-yn-1-ylidene]-2,2-dimethylpyrrolidine-1-carboxylate;
{(3E)-3-[3-(3-chlorophenyl)prop-2-yn-1-ylidene]-2,2-dimethylpyrrolidin-1-yl}(piperidin-1-yl)methanone;
{(3E)-3-[3-(3-chlorophenyl)prop-2-yn-1-ylidene]-2,2-dimethylpyrrolidin-1-yl}(pyrrolidin-1-yl)methanone;
ethyl (3E)-3-[3-(3-chlorophenyl)prop-2-yn-1-ylidene]-2,2-dimethylpyrrolidine-1-carboxylate;
(3E)-3-[3-(3-chlorophenyl)prop-2-yn-1-ylidene]-N-ethyl-2,2-dimethyl-N-(propan-2-yl)pyrrolidine-1-carboxamide;
(3E)-3-[3-(3-chlorophenyl)prop-2-yn-1-ylidene]-N,N,2,2-tetramethylpyrrolidine-1-carboxamide;
{(3E)-3-[3-(3-chlorophenyl)prop-2-yn-1-ylidene]-2,2-dimethylpyrrolidin-1-yl}(furan-2-yl)methanone;
methyl (3E)-3-[3-(3-chlorophenyl)prop-2-yn-1-ylidene]-2,2-dimethylpyrrolidine-1-carboxylate;
(3-chlorophenyl){(3E)-3-[3-(3-chlorophenyl)prop-2-yn-1-ylidene]-2,2-dimethylpyrrolidin-1-yl}methanone;
(3-chlorophenyl)[(4E)-4-{[5-(3-chlorophenyl)-1H-pyrazol-3-yl]methylidene}-3,3-dimethylpiperidin-1-yl]methanone;
3-{(3E)-3-[1-(3-chlorobenzoyl)-3,3-dimethylpiperidin-4-ylidene]prop-1-yn-1-yl}benzonitrile;
3-{(3E)-3-[1-(3-chlorobenzoyl)-3,3-dimethylpiperidin-4-ylidene]prop-1-yn-1-yl}-5-fluorobenzonitrile;
(3-chlorophenyl){(4E)-4-[3-(3-methoxyphenyl)prop-2-yn-1-ylidene]-3,3-dimethylpiperidin-1-yl}methanone;
(3-chlorophenyl)[(4E)-4-{3-[3-(hydroxymethyl)phenyl]prop-2-yn-1-ylidene}-3,3-dimethylpiperidin-1-yl]methanone;
(3-chlorophenyl){(4E)-4-[3-(4-fluorophenyl)prop-2-yn-1-ylidene]-3,3-dimethylpiperidin-1-yl}methanone;
(3-chlorophenyl){(4E)-3,3-dimethyl-4-(3-β-[(pyrrolidin-1-yl)methyl]phenyl}prop-2-yn-1-ylidene)piperidin-1-yl]methanone;
(3-chlorophenyl){(4E)-3,3-dimethyl-4-[3-(6-methylpyridin-2-yl)prop-2-yn-1-ylidene]piperidin-1-yl}methanone;
5-{(3E)-3-[1-(3-chlorobenzoyl)-3,3-dimethylpiperidin-4-ylidene]prop-1-yn-1-yl}pyridine-2-carbonitrile;
(3-chlorophenyl){(4E)-4-[3-(6-methoxypyridin-3-yl)prop-2-yn-1-ylidene]-3,3-dimethylpiperidin-1-yl}methanone;
(3-chlorophenyl){(4E)-4-[3-(3-fluoro-5-hydroxyphenyl)prop-2-yn-1-ylidene]-3,3-dimethylpiperidin-1-yl}methanone;
{(4E)-4-[3-(3-chlorophenyl)prop-2-yn-1-ylidene]-3,3-dimethylpiperidin-1-yl}(3-hydroxyphenyl)methanone;
{(4E)-4-[3-(3-chlorophenyl)prop-2-yn-1-ylidene]-3,3-dimethylpiperidin-1-yl}(4-methoxypyridin-2-yl)methanone;
{(4E)-4-[3-(3-chlorophenyl)prop-2-yn-1-ylidene]-3,3-dimethylpiperidin-1-yl}(6-methylpyridin-2-yl)methanone;
(4E)-4-[3-(3-chlorophenyl)prop-2-yn-1-ylidene]-3,3-dimethyl-N-(6-methylpyridin-2-yl)piperidine-1-carboxamide;
{(4E)-4-[3-(3-chlorophenyl)prop-2-yn-1-ylidene]-3,3-dimethylpiperidin-1-yl}(2,2-dimethylmorpholin-4-yl)methanone;
(4E)-4-[3-(3-chlorophenyl)prop-2-yn-1-ylidene]-N-(2,2-dimethyltetrahydro-2H-pyran-4-yl)-3,3-dimethylpiperidine-1-carboxamide;
(4E)-4-[3-(3-chlorophenyl)prop-2-yn-1-ylidene]-3,3-dimethyl-N-(pyridin-2-yl)piperidine-1-carboxamide;
2-({(4E)-4-[3-(3-chlorophenyl)prop-2-yn-1-ylidene]-3,3-dimethylpiperidin-1-yl}carbonyl)pyridine-4-carbonitrile;
1-{(4E)-4-[3-(3-chlorophenyl)prop-2-yn-1-ylidene]-3,3-dimethylpiperidin-1-yl}-2-(2,2-dimethyltetrahydro-2H-pyran-4-yl)ethanone;
{(4E)-4-[3-(3-Chlorophenyl)prop-2-yn-1-ylidene]-3,3-dimethylpiperidin-1-yl}(4-chloropyridin-2-yl)methanone;
{(4E)-4-[3-(3-chlorophenyl)prop-2-yn-1-ylidene]-3,3-dimethylpiperidin-1-yl}(4,5-dimethylfuran-2-yl)methanone;
{(4E)-4-[3-(3-chlorophenyl)prop-2-yn-1-ylidene]-3,3-dimethylpiperidin-1-yl}(3-methoxyphenyl)methanone;
3-({(4E)-4-[3-(3-chlorophenyl)prop-2-yn-1-ylidene]-3,3-dimethylpiperidin-1-yl}carbonyl)benzonitrile;
(4E)-4-[3-(3-chlorophenyl)prop-2-yn-1-ylidene]-N-(4-chloropyridin-2-yl)-3,3-dimethylpiperidine-1-carboxamide;
2,2-dimethylpropyl (4E)-4-[3-(3-chlorophenyl)prop-2-yn-1-ylidene]-3,3-dimethylpiperidine-1-carboxylate;
(4E)-4-[3-(3-chlorophenyl)prop-2-yn-1-ylidene]-3,3-dimethyl-N-(3-methylphenyl)piperidine-1-carboxamide;
2-methylpyridin-4-yl (4E)-4-[3-(3-chlorophenyl)prop-2-yn-1-ylidene]-3,3-dimethylpiperidine-1-carboxylate;
(4E)-4-[3-(3-chlorophenyl)prop-2-yn-1-ylidene]-N-(2,2-dimethylpropyl)-3,3-dimethylpiperidine-1-carboxamide;
{(4E)-4-[3-(3-chlorophenyl)prop-2-yn-1-ylidene]-3,3-dimethylpiperidin-1-yl}(4-hydroxypiperidin-1-yl)methanone;
ethyl 4-({(4E)-4-[3-(3-chlorophenyl)prop-2-yn-1-ylidene]-3,3-dimethylpiperidin-1-yl}sulfonyl)piperidine-1-carboxylate;
(4E)-4-[3-(3-chlorophenyl)prop-2-yn-1-ylidene]-3,3-dimethyl-1-[(tetrahydro-2H-pyran-2-ylmethyl)sulfonyl]piperidine;
5-({(4E)-4-[3-(3-chlorophenyl)prop-2-yn-1-ylidene]-3,3-dimethylpiperidin-1-yl}sulfonyl)-3-ethyl[1,2]oxazolo[5,4-b]pyridine;
(4E)-4-[3-(3-chlorophenyl)prop-2-yn-1-ylidene]-3,3-dimethyl-1-{[(3-methyl-1,2-oxazol-5-yl)methyl]sulfonyl}piperidine;
(4E)-4-[3-(3-chlorophenyl)prop-2-yn-1-ylidene]-N,3,3-trimethyl-N-(propan-2-yl)piperidine-1-sulfonamide;
4-({(4E)-4-[3-(3-chlorophenyl)prop-2-yn-1-ylidene]-3,3-dimethylpiperidin-1-yl}sulfonyl)-2,6-dimethylmorpholine;
(4E)-4-[3-(3-chlorophenyl)prop-2-yn-1-ylidene]-3,3-dimethyl-1-(phenylsulfonyl)piperidine;
(4E)-N-tert-butyl-4-[3-(3-chlorophenyl)prop-2-yn-1-ylidene]-3,3-dimethylpiperidine-1-sulfonamide;
4-({(4E)-4-[3-(3-chlorophenyl)prop-2-yn-1-ylidene]-3,3-dimethylpiperidin-1-yl}sulfonyl)morpholine;
4-({(4E)-4-[3-(3-chlorophenyl)prop-2-yn-1-ylidene]-3,3-dimethylpiperidin-1-yl}sulfonyl)-1-methyl-1H-benzotriazole;
3-({(4E)-4-[3-(3-chlorophenyl)prop-2-yn-1-ylidene]-3,3-dimethylpiperidin-1-yl}sulfonyl)-5-(propan-2-yloxy)pyridine;
(4E)-4-[3-(3-chlorophenyl)prop-2-yn-1-ylidene]-N-(cyclopropylmethyl)-N,3,3-trimethylpiperidine-1-sulfonamide;
5-({{(4E)-4-[3-(3-chlorophenyl)prop-2-yn-1-ylidene]-3,3-dimethylpiperidin-1-yl}sulfonyl)-2-methoxypyridine;

3-({(4E)-4-[3-(3-chlorophenyl)prop-2-yn-1-ylidene]-3,3-dimethylpiperidin-1-yl}sulfonyl)-6,7-dihydro-5H-pyrazolo[5,1-b][1,3]oxazine;

(4E)-4-[3-(3-chlorophenyl)prop-2-yn-1-ylidene]-N-cyclohexyl-N,3,3-trimethylpiperidine-1-sulfonamide;

(4E)-4-[3-(3-chlorophenyl)prop-2-yn-1-ylidene]-3,3-dimethyl-1-[(4-methylpiperidin-1-yl)sulfonyl]piperidine;

(4E)-4-[3-(3-chlorophenyl)prop-2-yn-1-ylidene]-1-[(2,2-dimethylpropyl)sulfonyl]-3,3-dimethylpiperidine;

(4E)-4-[3-(3-chlorophenyl)prop-2-yn-1-ylidene]-3,3-dimethyl-1-[(tetrahydro-2H-pyran-3-ylmethyl)sulfonyl]piperidine;

(4E)-4-[3-(3-chlorophenyl)prop-2-yn-1-ylidene]-1-[(3,5-dimethyl-1,2-oxazol-4-yl)sulfonyl]-3,3-dimethylpiperidine;

6-({(4E)-4-[3-(3-chlorophenyl)prop-2-yn-1-ylidene]-3,3-dimethylpiperidin-1-yl}sulfonyl)pyrazolo[1,5-a]pyrimidine-3-carbonitrile;

(4E)-4-[3-(3-chlorophenyl)prop-2-yn-1-ylidene]-1-[(1-ethyl-3,5-dimethyl-1H-pyrazol-4-yl)sulfonyl]-3,3-dimethylpiperidine;

{(4E)-4-[3-(3-chlorophenyl)prop-2-yn-1-ylidene]-3,3-dimethylpiperidin-1-yl}(4,6-dimethoxypyrimidin-2-yl)methanone;

{(4E)-4-[3-(3-chlorophenyl)prop-2-yn-1-ylidene]-3,3-dimethylpiperidin-1-yl}(2-ethyl-5-methyl-2H-1,2,3-triazol-4-yl)methanone;

{(4E)-4-[3-(3-chlorophenyl)prop-2-yn-1-ylidene]-3,3-dimethylpiperidin-1-yl}(4-methoxypyrimidin-2-yl)methanone;

{(4E)-4-[3-(3-chlorophenyl)prop-2-yn-1-ylidene]-3,3-dimethylpiperidin-1-yl}(6,7-dihydro-5H-pyrazolo[5,1-b][1,3]oxazin-3-yl)methanone;

{(4E)-4-[3-(3-chlorophenyl)prop-2-yn-1-ylidene]-3,3-dimethylpiperidin-1-yl}([1,2,4]triazolo[1,5-a]pyridin-2-yl)methanone;

{(4E)-4-[3-(3-chlorophenyl)prop-2-yn-1-ylidene]-3,3-dimethylpiperidin-1-yl}(2,6-dimethoxypyrimidin-4-yl)methanone;

4-({(4E)-4-[3-(3-chlorophenyl)prop-2-yn-1-ylidene]-3,3-dimethylpiperidin-1-yl}carbonyl)pyridine-2-carbonitrile;

{(4E)-4-[3-(3-chlorophenyl)prop-2-yn-1-ylidene]-3,3-dimethylpiperidin-1-yl}(1,5-dimethyl-1H-1,2,3-triazol-4-yl)methanone;

{(4E)-4-[3-(3-chlorophenyl)prop-2-yn-1-ylidene]-3,3-dimethylpiperidin-1-yl}(5,6-dihydro-8H-imidazo[2,1-c][1,4]oxazin-3-yl)methanone;

6-({(4E)-4-[3-(3-chlorophenyl)prop-2-yn-1-ylidene]-3,3-dimethylpiperidin-1-yl}carbonyl)pyridine-2-carbonitrile;

{(4E)-4-[3-(3-chlorophenyl)prop-2-yn-1-ylidene]-3,3-dimethylpiperidin-1-yl}(3-methoxy-1-methyl-1H-pyrazol-5-yl)methanone;

(3-chlorophenyl){(4E)-4-[3-(4-methoxypyridin-2-yl)prop-2-yn-1-ylidene]-3,3-dimethylpiperidin-1-yl}methanone;

(3-chlorophenyl)[(4E)-4-{3-[5-(hydroxymethyl)furan-2-yl]prop-2-yn-1-ylidene}-3,3-dimethylpiperidin-1-yl]methanone;

(3-chlorophenyl)[(4E)-4-(3-cyclohexylprop-2-yn-1-ylidene)-3,3-dimethylpiperidin-1-yl]methanone;

(3-chlorophenyl){(4E)-4-[3-(4-chloropyridin-2-yl)prop-2-yn-1-ylidene]-3,3-dimethylpiperidin-1-yl}methanone;

(3-chlorophenyl)[(4E)-3,3-dimethyl-4-{3-[6-(trifluoromethyl)pyridin-2-yl]prop-2-yn-1-ylidene}piperidin-1-yl]methanone;

(3-chlorophenyl){(4E)-4-[3-(6-methoxypyridin-2-yl)prop-2-yn-1-ylidene]-3,3-dimethylpiperidin-1-yl}methanone;

(3-chlorophenyl){(4E)-4-[3-(3-hydroxyphenyl)prop-2-yn-1-ylidene]-3,3-dimethylpiperidin-1-yl}methanone;

[(4E)-3,3-dimethyl-4-(3-phenylprop-2-yn-1-ylidene)piperidin-1-yl](phenyl)methanone;

3-[(3E)-3-{1-[(2,5-dimethylfuran-3-yl)carbonyl]-3,3-dimethylpiperidin-4-ylidene}prop-1-yn-1-yl]benzonitrile;

{(4E)-4-[3-(3-chlorophenyl)prop-2-yn-1-ylidene]-3,3-dimethylpiperidin-1-yl}(phenyl)methanone;

3-{(3E)-3-[3,3-dimethyl-1-(3-methylbenzoyl)piperidin-4-ylidene]prop-1-yn-1-yl}benzonitrile;

3-{(3E)-3-[1-(3-methoxybenzoyl)-3,3-dimethylpiperidin-4-ylidene]prop-1-yn-1-yl}benzonitrile;

(4E)-4-{3-[3-(hydroxymethyl)phenyl]prop-2-yn-1-ylidene}-3,3-dimethyl-N-(6-methylpyridin-2-yl)piperidine-1-carboxamide; and 3-[(3E)-3-{1-[(2,5-dimethylfuran-3-yl)carbonyl]-3,3-dimethylpiperidin-4-ylidene}prop-1-yn-1-yl]-5-fluorobenzonitrile.

8. A pharmaceutical composition comprising a compound according to claim 1 and a pharmaceutically acceptable carrier or diluent.

9. A method for the treatment or prevention of a neurological or psychiatric disorder associated with glutamate dysfunction comprising administering to a subject in need of treatment an effective amount of a composition according to claim 8, wherein the disorder is selected from the group consisting of Fragile-X syndrome, Rett syndrome, Phelan-McDermid syndrome and tuberous sclerosis.

10. A method according to claim 9, wherein the disorder is treatable or preventable by positive allosteric modulation (PAM) or by negative allosteric modulation (NAM) of mGluR5.

11. A compound according to claim 2, wherein $R_1$ is selected from the group consisting of an optionally substituted phenyl, pyridinyl or pyrimidinyl moiety or derivative thereof.

12. A compound according to claim 1, wherein $R_1$ is selected from the group consisting of an optionally substituted phenyl, pyridinyl or pyrimidinyl moiety or derivative thereof.

13. A compound according to claim 2, wherein $R_5$ is selected from the group consisting of an optionally substituted methyl, ethyl, propyl, iso-propyl, tertiary-butyl, methoxyethyl, N,N-dimethyl, N-methoxy-N-methyl, N,N-diethyl, N-ethyl-N-isopropyl, cyclohexyl, benzotriazolyl, furanyl, isoxazolyl, morpholinyl, oxazolyl, phenyl, piperidinyl, pyranyl, pyrazolyl, pyridinyl, pyrimidinyl, pyrrolidinyl, triazinyl or triazolyl moiety or derivative thereof.

14. A compound according to claim 1, wherein $R_5$ is selected from the group consisting of an optionally substituted methyl, ethyl, propyl, iso-propyl, tertiary-butyl, methoxyethyl, N,N-dimethyl, N-methoxy-N-methyl, N,N-diethyl, N-ethyl-N-isopropyl, cyclohexyl, benzotriazolyl, furanyl, isoxazolyl, morpholinyl, oxazolyl, phenyl, piperidinyl, pyranyl, pyrazolyl, pyridinyl, pyrimidinyl, pyrrolidinyl, triazinyl or triazolyl moiety or derivative thereof.

15. A compound according to claim 2, wherein $R_4$ is a carbonyl or sulphonyl group, B is absent and $R_5$ is an optionally substituted bicyclic $C_1$-$C_{13}$ heterocyclic group containing from 1 to 5 heteroatoms selected from N, O and S.

16. A compound according to claim 1, wherein $R_4$ is a carbonyl or sulphonyl group, B is absent and R is an optionally substituted bicyclic $C_1$-$C_{13}$ heterocyclic group containing from to 5 heteroatoms selected from N, O and S.

17. A compound according to claim 2, wherein B is an oxygen or nitrogen atom optionally substituted by a $C_1$-$C_5$ alkyl group or a methoxy group and $R_5$ is selected from the group consisting of an optionally substituted methyl, ethyl, propyl, iso-propyl, tertiary-butyl or methoxyethyl moiety or derivative thereof.

18. A compound according to claim 1, wherein B is an oxygen or nitrogen atom optionally substituted by a $C_1$-$C_5$ alkyl group or a methoxy group and $R_5$ is selected from the group consisting of an optionally substituted methyl, ethyl, propyl, iso-propyl, tertiary-butyl or methoxyethyl moiety or derivative thereof.

* * * * *